(12) United States Patent
Gallego-Perez et al.

(10) Patent No.: US 11,578,107 B2
(45) Date of Patent: Feb. 14, 2023

(54) COMPOSITIONS AND METHODS FOR REPROGRAMMING SOMATIC CELLS INTO INDUCED VASCULOGENIC CELLS

(71) Applicant: Ohio State Innovation Foundation, Columbus, OH (US)

(72) Inventors: Daniel Gallego-Perez, Columbus, OH (US); Ly James Lee, Columbus, OH (US); Durba Pal, Kolkata (IN); Subhadip Ghatak, Columbus, OH (US); Chandan Sen, Upper Arlington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 317 days.

(21) Appl. No.: 16/471,808

(22) PCT Filed: Dec. 20, 2017

(86) PCT No.: PCT/US2017/067631
§ 371 (c)(1),
(2) Date: Jun. 20, 2019

(87) PCT Pub. No.: WO2018/119091
PCT Pub. Date: Jun. 28, 2018

(65) Prior Publication Data
US 2020/0115425 A1    Apr. 16, 2020

Related U.S. Application Data

(60) Provisional application No. 62/438,260, filed on Dec. 22, 2016, provisional application No. 62/530,132, filed on Jul. 8, 2017.

(51) Int. Cl.
| | | |
|---|---|---|
| C12N 15/79 | (2006.01) | |
| C07H 21/04 | (2006.01) | |
| C07K 14/47 | (2006.01) | |
| C12N 5/071 | (2010.01) | |
| C12N 15/85 | (2006.01) | |
| A61K 48/00 | (2006.01) | |
| C07H 21/02 | (2006.01) | |

(52) U.S. Cl.
CPC .......... *C07K 14/4702* (2013.01); *C12N 5/069* (2013.01); *C12N 15/85* (2013.01); *A61K 48/00* (2013.01); *C07H 21/02* (2013.01); *C07H 21/04* (2013.01); *C12N 2506/1307* (2013.01)

(58) Field of Classification Search
CPC .. C12N 15/79; C12N 15/85; C12N 2310/141; C07H 21/02; C07H 21/04
See application file for complete search history.

(56) References Cited

U.S. PATENT DOCUMENTS

2015/0307840 A1    10/2015    Yoon et al.

FOREIGN PATENT DOCUMENTS

| JP | 2015109833 A | 6/2015 |
|---|---|---|
| KR | 20150104049 A | 9/2015 |
| WO | 2005/013901 A2 | 2/2005 |
| WO | 2005/023986 A2 | 3/2005 |
| WO | 2006/093526 A2 | 9/2006 |
| WO | 2006/112872 A2 | 10/2006 |
| WO | 2007/021896 A2 | 2/2007 |
| WO | 2007/027775 A2 | 3/2007 |
| WO | 2007/027894 A2 | 3/2007 |
| WO | 2007/090073 A2 | 8/2007 |
| WO | 2007/112753 A2 | 10/2007 |
| WO | 2007/112754 A2 | 10/2007 |
| WO | 2008/046911 A2 | 4/2008 |
| WO | 2008/074328 A2 | 6/2008 |
| WO | 2008/091703 A2 | 7/2008 |
| WO | 2009/020771 A2 | 2/2009 |
| WO | 2012/006440 A2 | 1/2012 |
| WO | 2012006440 A2 | 1/2012 |
| WO | 2013/181326 A1 | 5/2013 |
| WO | 2015/133792 A1 | 11/2015 |

OTHER PUBLICATIONS

Ginsberg et al., 2012, Cell, vol. 151, p. 559-575.*
Yu et al., 2014, US 20140349398 A1.*
Robinson et al., An arterial-specific enhancer of the human Endothelin-converting enzyme 1 (ECE1) gene is synergistically activated by Sox17, FoxC2, and Etv2, Dev Biol., 395(2): 379-389, 2014.
International Search Report issued for PCT/US2017/067631, dated Apr. 30, 2018.
Office Action issued by the Japanese Patent Office for application 2019-533223, dated Jul. 19, 2021.
Liu et al., CCL5 promotes VEGF-dependent angiogenesis by downregulating miR-200b through PI3K/Akt signaling pathway in human chondrosarcoma cells, Oncotarget, 2014, vol. 5, pp. 10718-10731.
Clinical Therapeutics/New Technology—Pharmacologic Treatment of Complications, Diabetes, 2013, vol. 62, Supp.1, pp. A310.
Tonnesen, Marcia G., et al., "Angiogenesis in Wound Healing," The Society for Investigative Dermatology, Inc., vol. 5, No. 1 (2000), pp. 40-46.
Sen, Chandan K., et al., "miRNA Control of Tissue Repair and Regeneration," The American Journal of Pathology, vol. 185, No. 10 (2015) (12 pages).
Roy, Sashwati, et al., "Transcriptome-wide analysis of blood vessels laser captured from human skin and chronic vound-edge tissue," PNAS, vol. 104, No. 36, pp. 14472-14477.

(Continued)

*Primary Examiner* — Shin Lin Chen
(74) *Attorney, Agent, or Firm* — Thomas | Horstemeyer, LLP

(57) ABSTRACT

Disclosed herein are compositions and methods that involve using compositions containing one or more of ETV2, FOXC2, FLI1 and a miR-200b inhibitor for directly reprogramming somatic cells into induced vasculogenic cells both in vitro and in vivo. These compositions and methods are useful for a variety of purposes, including the development of pro-angiogenic therapies.

4 Claims, 163 Drawing Sheets

Specification includes a Sequence Listing.

(56) References Cited

OTHER PUBLICATIONS

Roy, Sashwati, et al, "Characterization of the acute temporal changes in excisional murine cutaneous wound inflammation by screening of the wound-edge transcriptome," Physiol Genomics, No. 34 (2008), pp. 162-184.

Rosova, Ivana, et al., "Hypoxic Preconditioning Results in Increased Motility and Improved Therapeutic Potential of Human Mesenchymal Stem Cells," Stem Cells, vol. 26 (2008), pp. 2173-2182.

Rink, Cameron, et al., "Oxygen-sensitive outcomes and gene expression in acute ischemic stroke," Journal of Cerebral Blood Flow & Metabolism, vol. 30, pp. 1275-1287.

Morita, Rimpei, et al., "ETS transcription factor ETV2 directly converts human fibroblasts into functional endothelial cells," PNAS, vol. 112, No. 1 (2015), pp. 160-165.

Marx, Vivien, "Cell biology: delivering tough cargo into cells," Nature Methods, vol. 13, No. 1 (2016), pp. 37-40.

Losordo, Douglas W., et al., "Therapeutic Angiogenesis and Vasculogenesis for Ischemic Disease Part II: Cell Based Therapies," Therapeutic Angiogenesis and Vasculogenesis, Part II (2004), pp. 2692-2697.

Khanna, Savita et al., "Loss of miR-29b following actute ischemic stroke contributes to neural cell death and infrarct size," Journal of Cerebral Blood Flow & Metabolism, vol. 33 (2013), pp. 1197-1206.

Hunt, David P.J., et al., "A Highly Enriched Niche of Precursor Cells with Neuronal and Glial Potential Within the Hair Follicle Dermal Papilla of Adult Skin," Stem Cells (2008), vol. 26, pp. 163-172.

Hughes, Brenda J., et al., "Monoclonal Antibody Targeting of Liposomes to Mouse Lung in Vivo," Cancer Research, vol. 49 (1989), pp. 6214-6220.

Higgins, Claire A., et al., "Reprogramming of Human Fair Follicle Dermal Papilla Cells into Induced Pluripotent Stem Cells," Journal of Investigative Dermatology, vol. 132 (2012), pp. 1725-1727.

Grande, Andrew, et al., "Environmental impact on direct neuronal reprogramming in vivo in the adult brain," Nature Communications, vol. 4 (2013) (12 pages).

Gnyawali, Surya C., et al., "High resolution ultrasound imaging for repeated measure of wound tissue morphometry, biomechanics and hemodynamics under fetal, adult and diabetic conditions," Plos One, (2020), (23 pages).

De Val, Sarah, et al., "Transcriptional Control of Endothelial Cell Development," Developmental Cell, vol. 16 (2009), pp. 180-195.

Chan, Kai M. A., et al., "Where are Cultural and Social in Ecosystem Services? A Framework for Constructive Engagement," BioScience, vol. 62, No. 8 (2012), pp. 744-756.

Brem, Harold, et al., "Cellular and molecular basis of wound healing in diabetes," The Journal of Clinical Investigation, vol. 117, No. 5 (2007), pp. 1219-1222.

Bagshawe, K.D., et al., "A cytotoxic agent can be generated selectively at cancer sites," Br. J. Cancer, vol. 58 (1988), pp. 700-703.

Bagshawe, K.D., "Towards generating cytotoxic agents at cancer sites," Br. J. Cancer, vol. 60 (1989), pp. 275-281.

\* cited by examiner

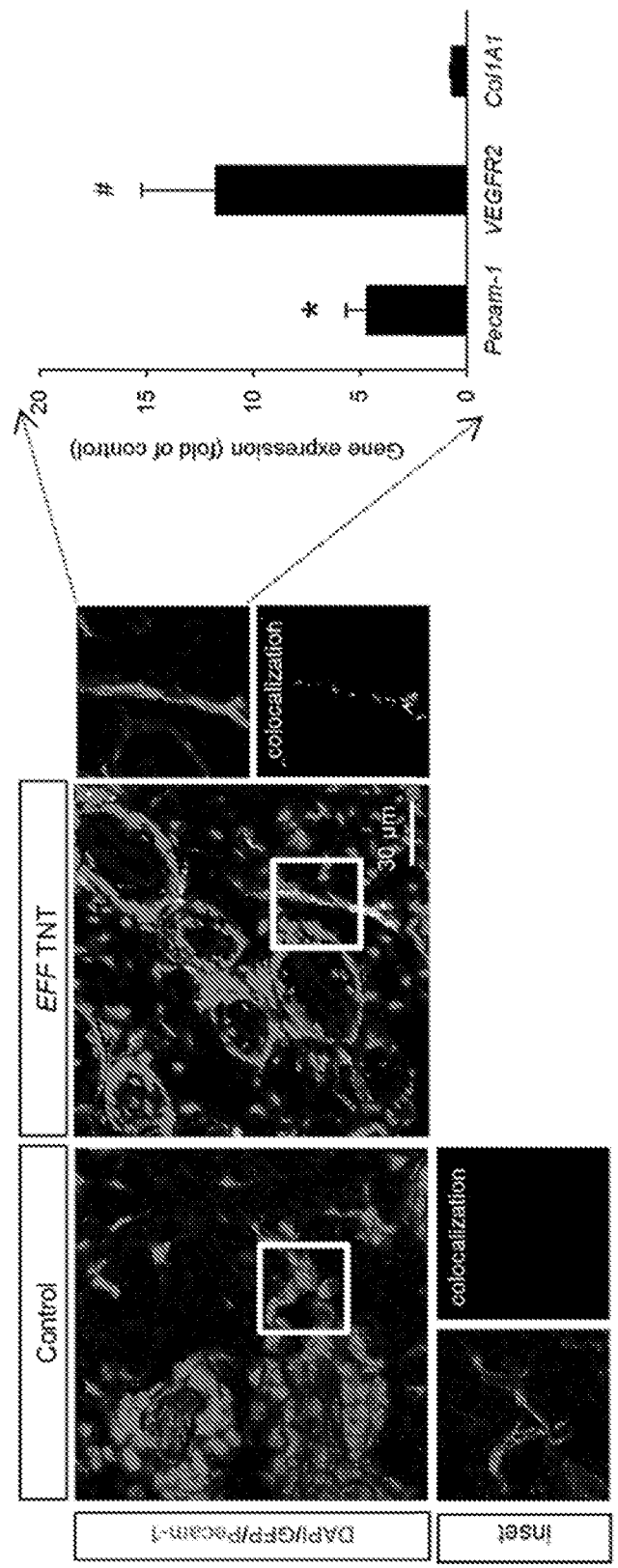

Position 879-886 of hFLI-1 3'-UTR (length: 2279) binding to hsa-miR-200b-3p  (SEQ ID NO:37)

5' ......UUUCCUAUAUCUCACAGUAUUA...
            |||||||
3'    AGUAGUAAUGGUCCGUCAUAAU

Position 900-907 of mFLI-1 3'-UTR (length:2274) binding to mmu-miR-200b-3p  (SEQ ID NO:38)

5' ......UUUCCUAUAUCUCACAGUAUUA...
            |||||||
3'    AGUAGUAAUGGUCCGUCAUAAU

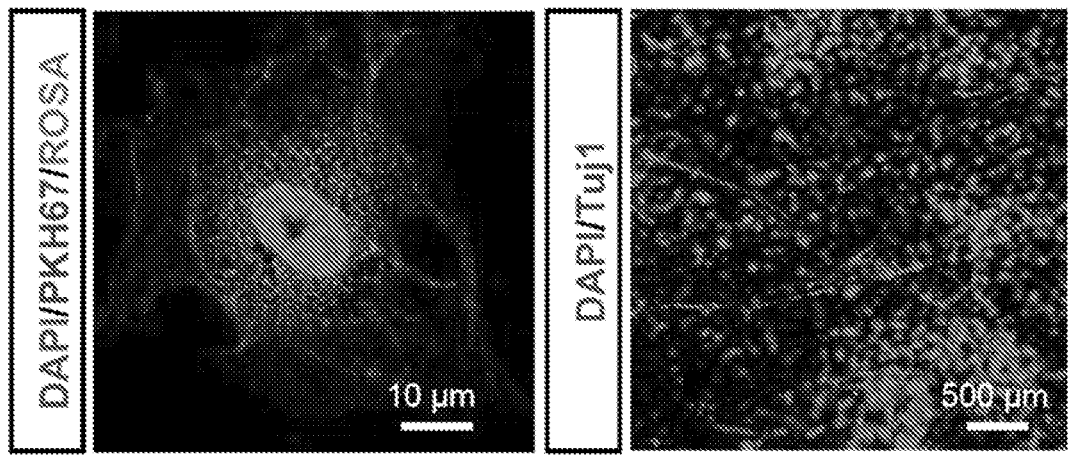
FIG. 17K
FIG. 17L
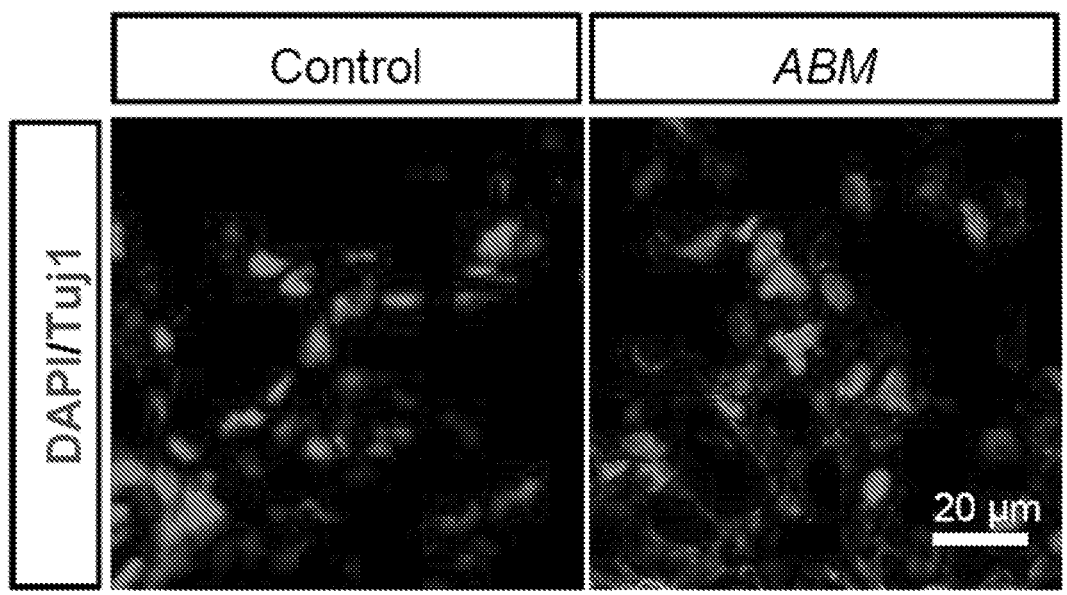
FIG. 17M

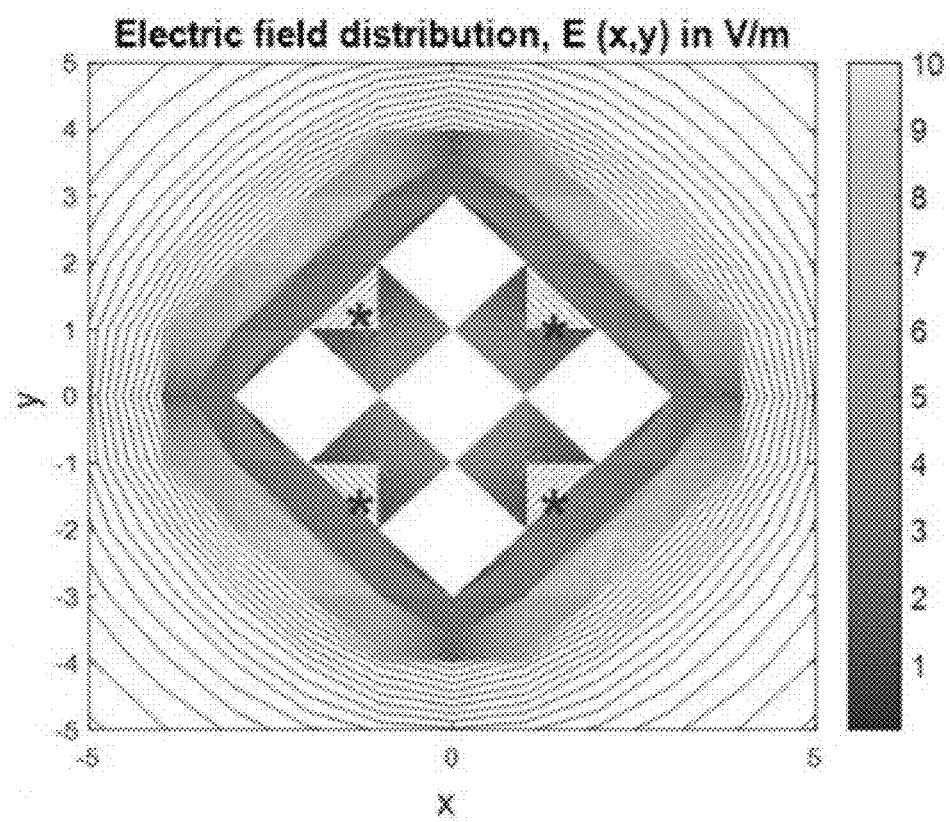
FIG. 20J1

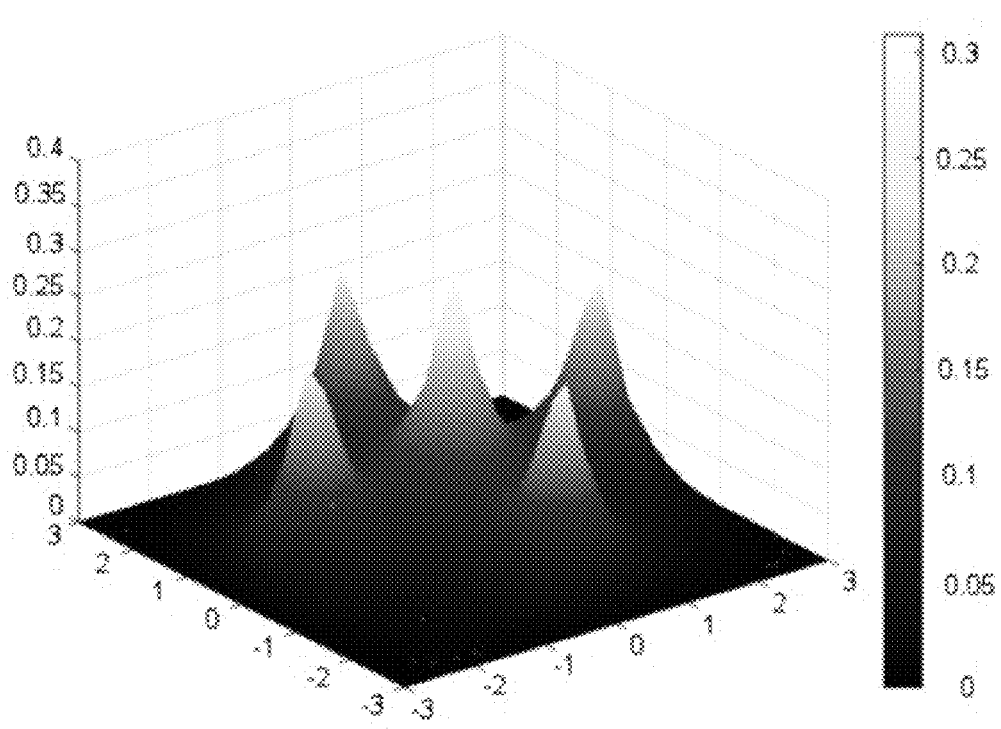
FIG. 20J2

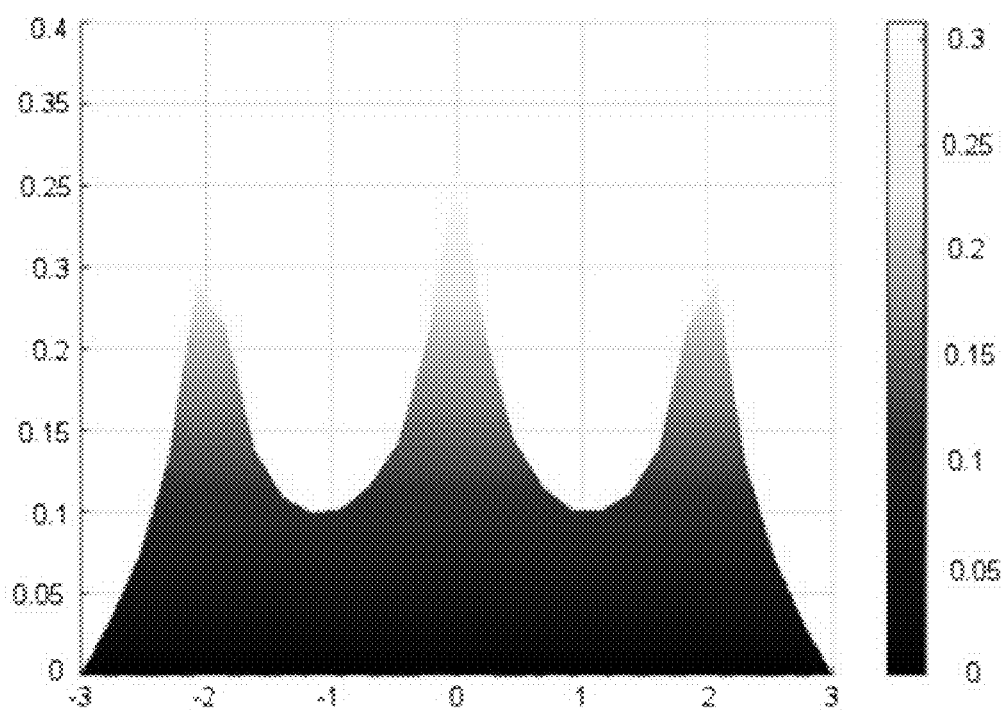
FIG. 20J3

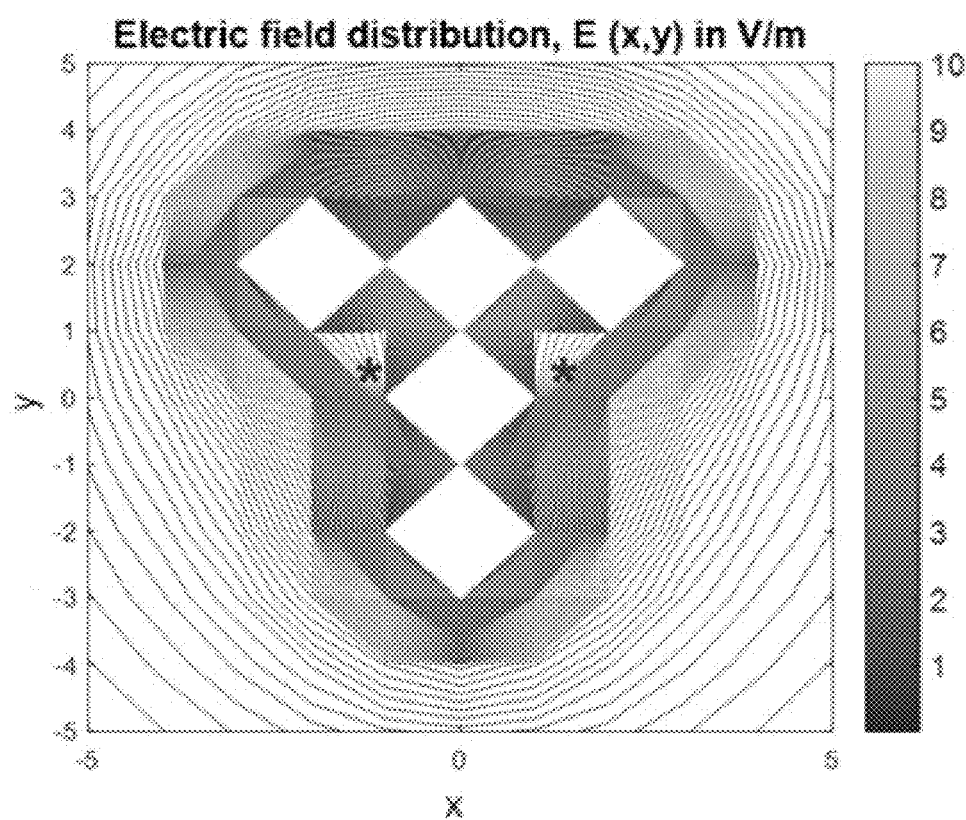
FIG. 20K1

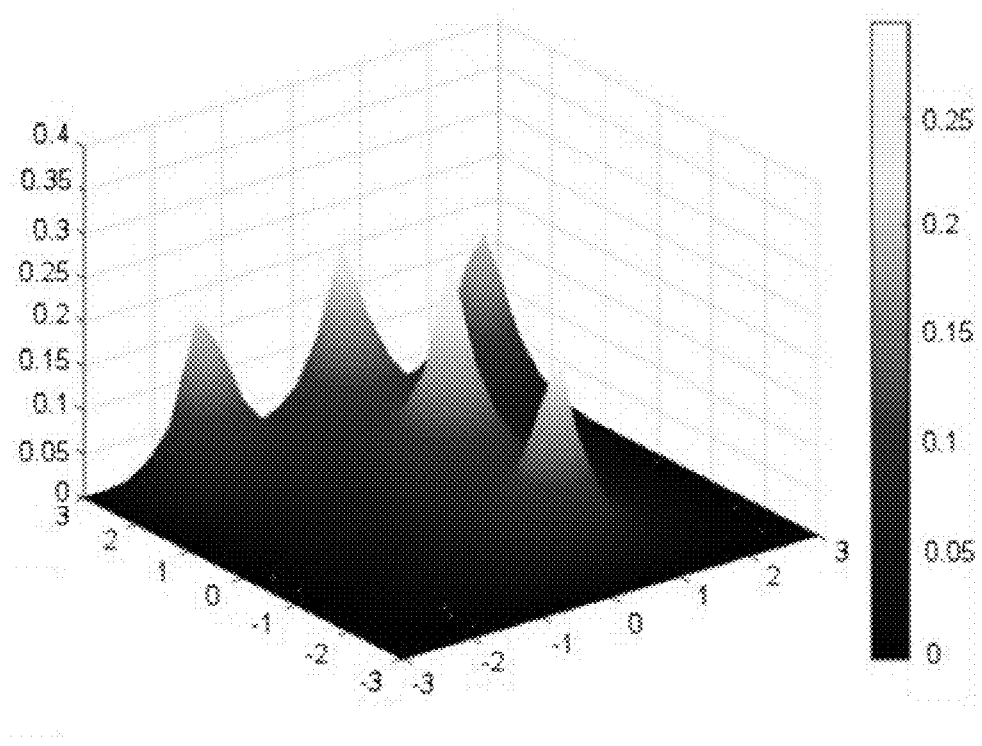
FIG. 20K2

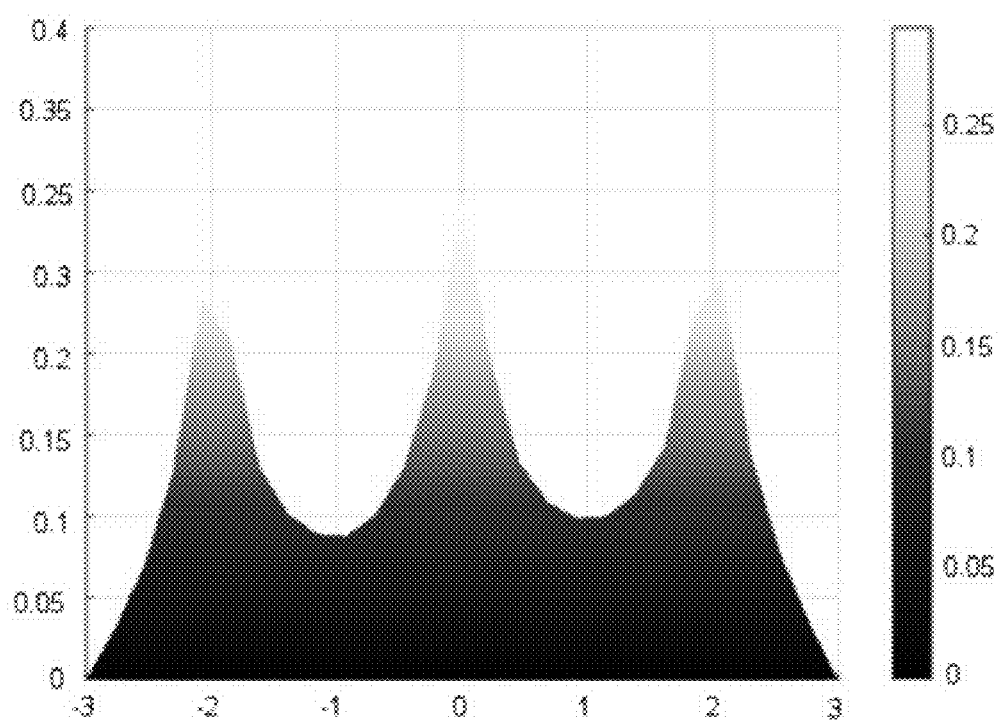
FIG. 20K3

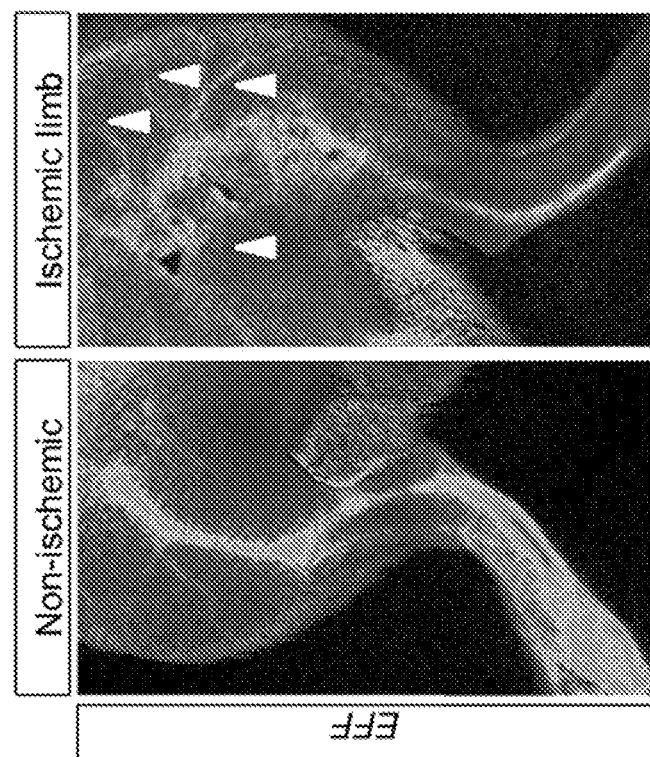
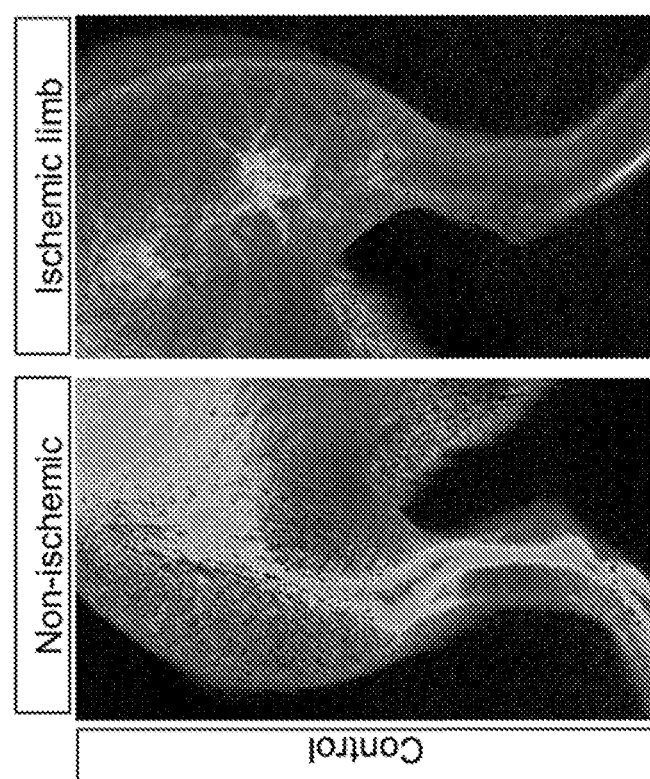
FIG. 32A

COMPOSITIONS AND METHODS FOR REPROGRAMMING SOMATIC CELLS INTO INDUCED VASCULOGENIC CELLS

CROSS-REFERENCE TO RELATED APPLICATIONS

This application claims benefit of U.S. Provisional Application No. 62/438,260, filed Dec. 22, 2016, and 62/530,132, filed Jul. 8, 2017, which are hereby incorporated herein by reference in their entireties.

STATEMENT REGARDING FEDERALLY FUNDED RESEARCH his invention was made with Government Support under grant numbers EB017539, GM077185, GM108014, NR015676, TR001070 awarded by the National Institutes of Health, and grant number EEC0914790 awarded by the National Science Foundation. The Government has certain rights in the invention.

BACKGROUND

Pro-angiogenic cell therapies offer a promising strategy for the treatment of a number of ischemic disorders. However, current approaches to pro-angiogenic cell therapies face major translational hurdles, including limited cell sources/donors, and the need for cumbersome and risky ex vivo cell pre-processing steps (e.g., induced pluripotency, expansion, differentiation). Thus, compositions and methods for the derivation of blood vessels through direct cell reprogramming in vivo are needed.

SUMMARY

Disclosed herein are compositions and methods for reprogramming somatic cells into vasculogenic cells and/or endothelial cells both in vitro and in vivo. One embodiment discloses a polynucleotide comprising two or more nucleic acid sequences encoding proteins selected from the group consisting of ETV2, FOXC2, and FLI1. In some embodiments, the ETV2, FOXC2, and FLI1 proteins are mammalian proteins, such as human proteins.

In some embodiments, the ETV2, FOXC2, and FLI1 proteins are expressed at approximately equal ratios. In some embodiments, the ETV2, FOXC2, and FLI1 proteins are expressed at ratios of about 1:1:1, 2:1:1, 1:2:1, 1:1:2, 2:1:1, 2:2:1, 2:1:2, 1:2:2, 3:1:1, 1:3:1, 1:1:3, 3:2:1, 1:2:3, 1:3:2, 2:1:3, 2:3:1, 3:1:2, 2:3:2, 3:2:2, 2:2:3, 3:3:1, 3:1:3, 1:3:3, 3:3:2, 3:2:3, or 2:3:3 (ETV2:FOXC2:FLI1).

Also disclosed a composition comprising a polynucleotide comprising one, two, or more nucleic acid sequences encoding proteins selected from the group consisting of ETV2, FOXC2, and FLI1 and a miR-200b inhibitor.

Also disclosed are non-viral vectors containing the disclosed polynucleotides. In particular embodiments, the vector is a recombinant bacterial plasmid. For example, in some embodiments, the non-viral vector has a pCDNA3 backbone. In some embodiments, the vector comprises an internal ribosome entry site (IRES).

Also disclosed is a method of reprogramming somatic cells into vasculogenic cells and/or endothelial cells that involves delivering intracellularly into the somatic cells a polynucleotide comprising two or more nucleic acid sequences encoding proteins selected from the group consisting of ETV2, FOXC2, and FLI1.

Another embodiment discloses a method of reprogramming somatic cells into vasculogenic cells and/or endothelial cells, comprising delivering intracellularly into the somatic cells a polynucleotide comprising one, two, or more nucleic acid sequences encoding proteins selected from the group consisting of ETV2, FOXC2, and FLI1 and a miR-200b inhibitor. In some embodiments, the method involves delivering intracellularly into the somatic cells a polynucleotide sequences encoding FLI1 alone. In some embodiments, the method involves delivering intracellularly into the somatic cells a polynucleotide sequences encoding an miR-200b inhibitor alone. In some embodiments, the method involves delivering intracellularly into the somatic cells a polynucleotide sequences encoding FLI1 and ETV2. In some embodiments, the method involves delivering intracellularly into the somatic cells a polynucleotide sequences encoding FLI1 and FOXC2.

Also disclosed is a method of reprogramming somatic cells, such as, but not limited to, skin cells or muscle cells, into vasculogenic cells and/or endothelial cells, comprising delivering intracellularly into the somatic cells a miR-200b inhibitor. For example, the miR-200b inhibitor can be an anti-miR-200b antagomir comprising the nucleic acid sequence UAAUACUGCCUGGUAAUGAUGA (SEQ ID NO:1), which can be purchased from Dharmacon (catalog #IH-300582-08-0005).

In some embodiments, after transfecting target cells with EFF, the cells can then pack the transfected genes (e.g. cDNA) into EVs, which can then induce endothelium in other somatic cells. Similarly, cells transfected with a miR-200b inhibitor will tend to exocytose part of that inhibitor in EVs, which could subsequently be used to induce endothelium in other/remote somatic cells. Therefore, also disclosed is a method of reprogramming somatic cells into vasculogenic cells and/or endothelial cells that involves exposing the somatic cell with an extracellular vesicle produced from a cell containing or expressing one or more proteins selected from the group consisting of ETV2, FOXC2, and FLI1. Also disclosed is a method of reprogramming somatic cells into vasculogenic cells and/or endothelial cells that involves exposing the somatic cell with an extracellular vesicle produced from a cell containing a miR-200b inhibitor.

In these embodiments, the polynucleotides and compositions may be delivered to the somatic cell, or the donor cell, intracellularly via a gene gun, a microparticle or nanoparticle suitable for such delivery, transfection by electroporation, three-dimensional nanochannel electroporation, a tissue nanotransfection device, a liposome suitable for such delivery, or a deep-topical tissue nanoelectroinjection device. In some of these embodiments, the polynucleotides can be incorporated into a non-viral vector, such as a bacterial plasmid. In some embodiments, a viral vector can be used. For example, the polynucleotides can be incorporated into a viral vector, such as an adenoviral vector. However, in other embodiments, the polynucleotides are not delivered virally.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic diagram showing treatment of mouse dorsal skin with EFF via tissue nanotransfection (TNT). FIG. 1B is a fluorescence micrograph showing increased angiogenesis, as evidenced by increased expression of the endothelial markers Pecam-1 and vWF. FIG. 1C shows gene expression analysis of Pecam-1 (approximately 450% control) and vWF (approximately 200% control, i.e. untreated skin) in EFF TNT-treated dorsal skin. FIG. 1D shows high resolution laser speckle imaging showing enhanced perfusion to the EFF TNT-treated area over time. FIG. 1E is a graph showing perfusion ratios of EFF TNT-treated skin (dashed line) and control skin (solid line). The EFF TNT-treated skin shows enhanced perfusion over time relative to the control skin. FIG. 1F is an ultrasound image of EFF TNT-treated skin confirming the presence of superficial blood vessels (dashed circle) with pulsatile behavior, which suggests successful anastomosis with the parent circulatory system. FIG. 1G shows the results of a monopedicle flap experiment showing increased flap necrosis for control tissue compared to EFF TNT-treated skin. FIG. 1H shows high resolution laser speckle imaging showing increased blood flow to the flapped EFF TNT-skin. FIG. 1I is a graph showing quantification of flap necrosis. The EFF TNT-treated skin showed decreased necrosis relative to control skin. *$p<0.05$ (Holm-Sidak method).

FIG. 2A is a schematic diagram showing HDAF cells being transfected with EFF via 3D Nanochannel Electroporation (NEP). FIG. 2B is a fluorescence micrograph showing strong expression of the endothelial marker Pecam-1 as well as reduced expression of the fibroblastic marker FSP 7 days post-transfection. FIG. 2C shows the results of gene expression analysis of endothelial markers for two different transfection conditions: Etv2 alone versus cotransfection of EFF. This analysis shows a marked difference in gene expression, with EFF resulting in significantly stronger endothelial gene expression at day 7 post-transfection compared to Etv2 alone. FIGS. 2D and 2E show results from a tube formation assay showing that EFF-transfected cells were able to form blood vessel-like structures when cultured in Matrigel comparable to endothelial cells (HMEC, positive control). Control HDAF cells, on the other hand, were not able to form tube-like structures when cultured in Matrigel. Tube length was: ~100 μm for control cells; ~450 μm for EFF-transfected cells; and ~375 μm for HMEC cells. FIG. 2F is a schematic diagram showing MEF cells being transfected with EFF via NEP (at day 0) and being injected into the flank of a mouse (at day 1). FIG. 2G is a fluorescence micrograph showing that MEF cells non-virally transfected with EFF show endothelial marker expression as early as 7 days post-transfection. FIG. 2H shows tdTomato-MEF cells non-virally transfected with EFF. Transfection foments blood vessel formation following flank injection in NSG mice. FIG. 2I is a fluorescence micrograph showing enhanced expression of Pecam-1. *$p<0.05$ (Holm-Sidak method).

FIG. 3A is a schematic diagram showing ligation and transection of a mouse femoral artery (at day 0) followed by EFF TNT (at day 3). FIG. 3B is laser speckle imaging showing that a one-time treatment of thigh skin lasting only a few seconds led to increased limb reperfusion following transection of the femoral artery. FIG. 3C is a graph showing the increase in limb reperfusion following EFF treatment (solid line) vs. the control (dotted line). Perfusion was calculated based on the ratio of the ischemic vs. normal/contralateral limb. FIG. 3D is an image of a control limb which shows more pronounced signs of tissue necrosis compared to EFF TNT-treated limbs (at day 14). FIG. 3E is an NMR spectrum. NMR-based measurements of muscle energetics confirmed increased ATP and $P_{Cr}$ levels for EFF TNT-treated limbs compared to controls. FIG. 3F is an immunofluorescence analysis of the gastrocnemius muscle showing enhanced angiogenesis (at day 14). *$p<0.05$ (Holm-Sidak method).

FIG. 4A shows laser speckle imaging of the limbs showing successful reperfusion after EFF TNT treatment. FIG. 4B shows macroscopic changes to the ischemic limb with and without TNT treatment.

FIG. 5A is a schematic diagram of injury/EV-mediated rescue. After ligation and transection of a mouse femoral (at day 0) artery followed by EFF TNT treatment (at day 1), EVs were isolated from the femur (at day 2) and then injected back into the femur (at day 3). FIG. 5B shows the results of qRT-PCR characterization of the EV content. Gene expression was measured relative to expression in control (untreated) mice. Etv2 was expressed at ~175× control levels; Fli1 was expressed at ~25× control levels; Foxc2 was expressed at ~50× control levels; VEGF (vascular endothelial growth factor) was expressed at ~26× control levels; and bFGF (basic fibroblast growth factor) was expressed at ~6× control levels. FIG. 5C shows laser speckle imagining showing enhanced lim reperfusion and rescue. FIG. 5D is a graph showing increased perfusion following EFF EV injection (dashed line) vs. the control (dotted line). Perfusion was calculated based on the ratio of the ischemic vs. normal/contralateral limb. FIG. 5D shows immunofluorescence analysis of the gastrocnemius muscle showing increased angiogenesis for the EV-treated limb. *$p<0.05$ (Holm-Sidak method).

FIGS. 6A and 6B show that iECs in the skin originate from Col1A1-expressing dermal sources. FIG. 6A shows fluorescence micrographs of EFF TNT-treated skin sections from the Col1A1-GFP mouse models showing skin cells of Col1A1 origin also expressing the Pecam-1 endothelial marker. FIG. 6B shows the results of LCM/qRT-PCR analysis. Cellular elements that were immunoreactive for both the GFP tracer and Pecam-1 were further analyzed by LCM/qRT-PCR. The results indicate that such double-positive elements had significantly high endothelial marker gene expression. Pecam-1 was expressed at ~5× control levels; VEGFR2 was expressed at ~12× control levels; and Col1A1 was expressed at ~1× control levels. *$p<0.05$ (Holm-Sidak method), #$0.05<p<0.07$ (one-tailed t-test). Experiments with the K14-Cre reporter and Col1A1-eGFP mouse models confirmed that the reprogrammed cell population had for the most part a dermal origin. Unlike the induced neurons model, there was no clear evidence of cells of K14 origin expressing endothelial markers. LCM/qRT-PCR measurements of GFP+/CD31+ cellular elements confirmed increased expression of endothelial markers.

As expected, a sizable amount of ABM copies was detected in the EV isolate, which fell within the lower range of gene copy numbers delivered directly through TNT. (c) Additional experiments in which MEF cells were exposed to skin-derived EVs in vitro further indicate that such copy number magnitude is conducive to positive reprogramming outcomes, as evidenced by the presence of iNs when exposed to ABM-loaded EVs.

Figure 23A:
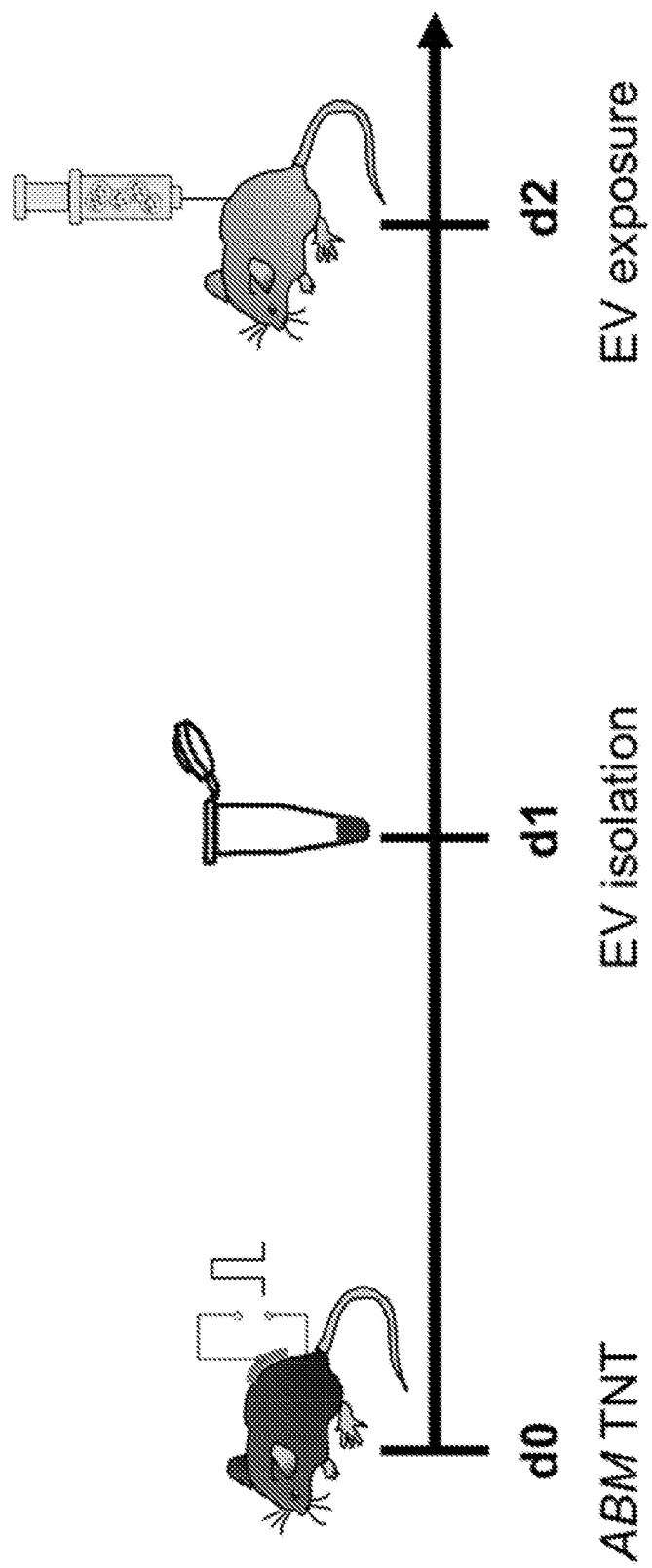
Figure 23B:
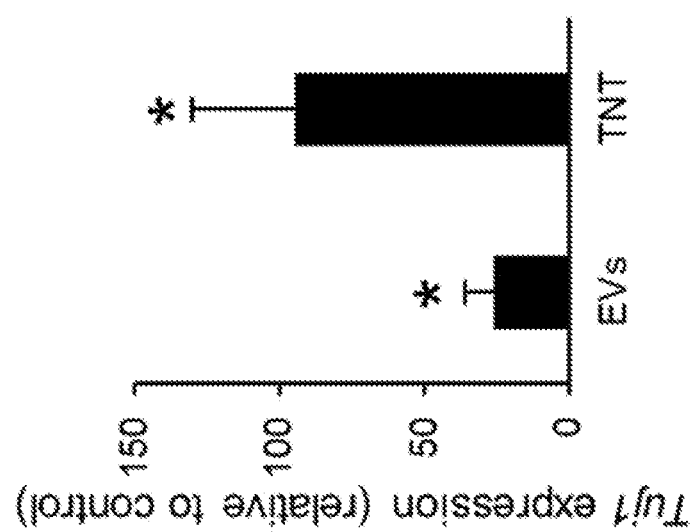

FIG. 23. Autologous ABM-loaded EVs isolated from TNT-treated dorsal skin exhibit neurotrophic-like characteristics when injected intradermally in naïve mice. (a) Schematic diagram illustrating the experimental set-up. EVs are collected from ABM TNT-treated dorsal skin and injected into naïve mice. (b) Tissue biopsies collected after 14 days show increase in Tuj1 expression compared to control (untreated) mice. ABM-loaded EVs led to a ~26-fold increase in Tuj1 expression. Comparatively, ABM TNT resulted in a ~94-fold increase in Tuj1 expression, which reflects the net effect of direct reprogramming factor injection combined with EV-mediated propagation. Control specimens in this case are untreated skin biopsies. n=3. *$p<0.05$ (Holm-Sidak method).

FIG. 24. Autologous ABM-loaded EVs isolated from TNT-treated dorsal skin exhibit neurotrophic-like characteristics in a MCAO stroke mouse (C57BL/6) model. (a) Schematic diagram illustrating the experimental set-up. MCAO stroke is first induced. This is then followed by ABM or control TNT treatment and EV isolation from dorsal skin prior to intracranial injection of EVs. (b, c) MRI imaging and quantification showing a significant reduction in the infarcted volume only 7 days after EV injection. (d) Immunofluorescence imaging 21 days after stroke induction showing DCX+ cells/processes projecting from the Subventricular (SVZ) zone towards the infarcted area (white arrows). DCX+ cells in control brains were found mostly lining the walls of the SVZ zone. Such preliminary findings suggest a potentially therapeutic effect for in vivo-derived EVs loaded with pro-neuronal factors. n=4-5. *$p<0.05$ (Holm-Sidak method).

Figure 25A:
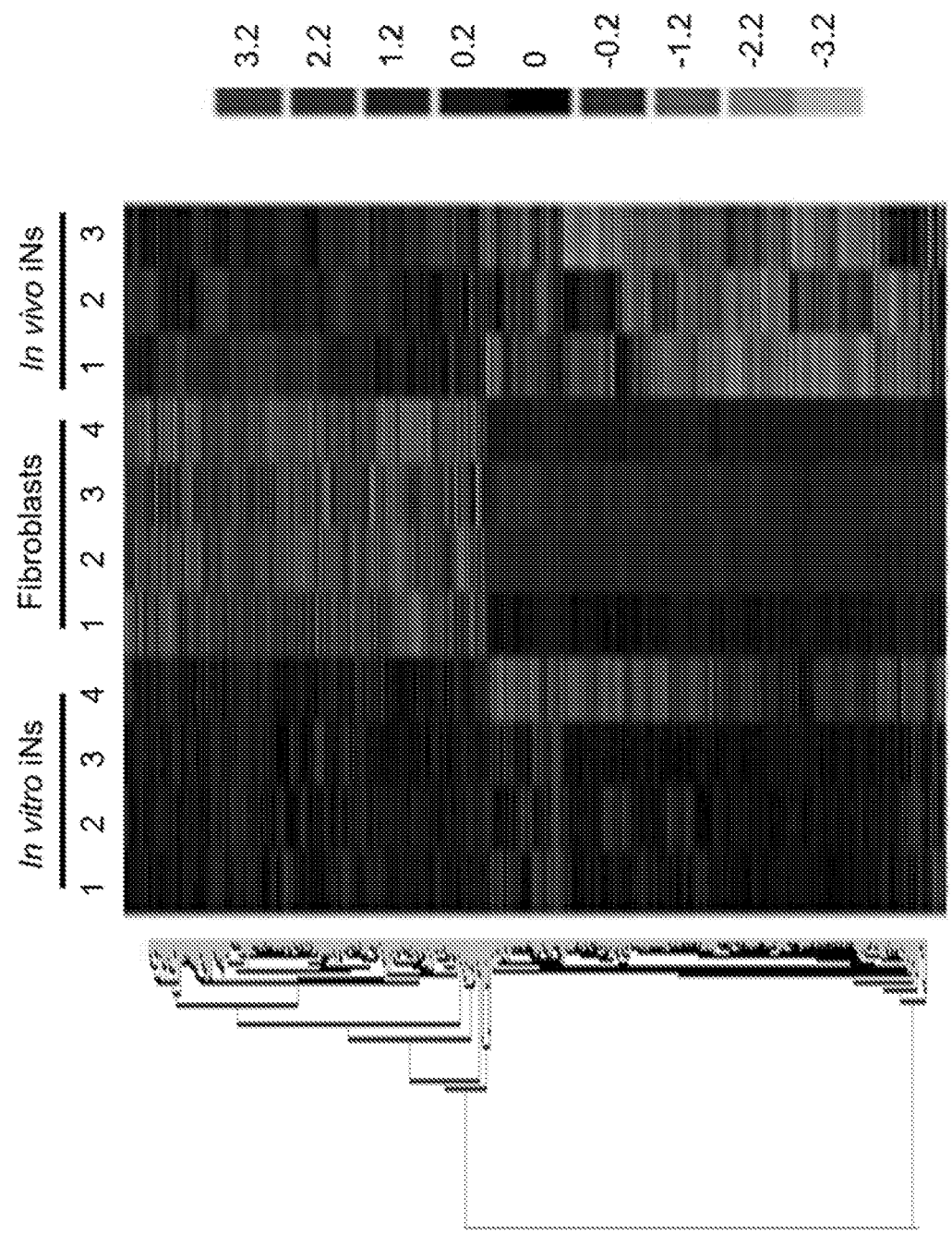
Figure 25B:
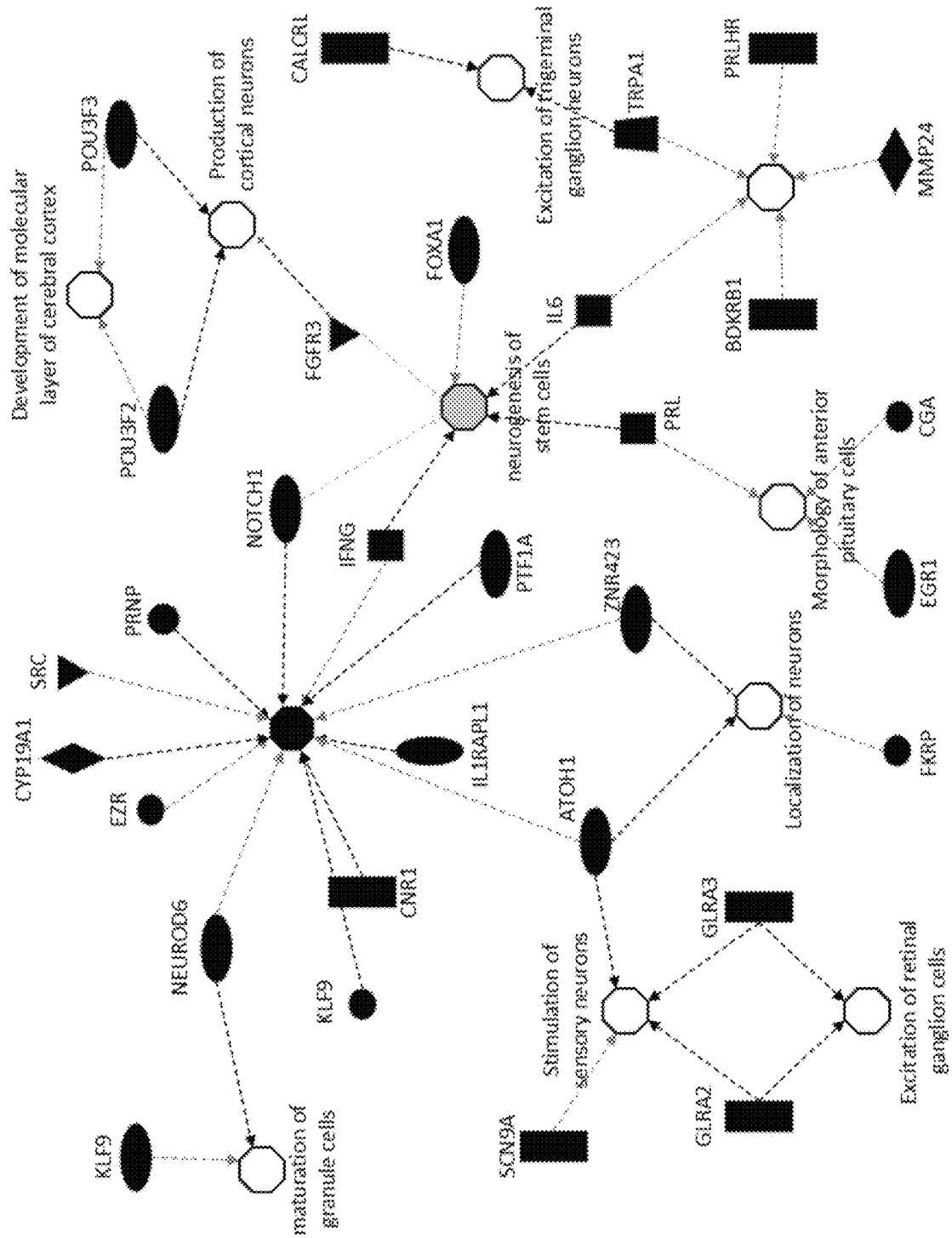

FIG. 25. Identification of gene expression profile homology between in vitro iNs versus in vivo iNs using GeneChip® microarray and IPA® analysis and clustering algorithms. iNs generated in vitro or laser-capture microdissected from ABM-transfected mouse skin (in vivo iNs) were subjected to murine transcriptome array (MTA 1.0) analysis followed by data mining using clustering algorithms. In vitro-derived iN cultures were obtained via non-viral, electroporation-based delivery of ABM6. To identify homology in expression patterns between in vitro iNs versus in vivo iNs, the 26225 annotated probe-sets were clustered into 16 groups using k-means unsupervised learning algorithm. A cluster of 3503 probe-sets that showed expression pattern homology between in vitro iN versus in vivo iN groups, was subjected to IPA® analysis and hierarchical clustering. (a) The heat map represents genes (528) that were significantly different as compared to the unreprogrammed fibroblast group. (b) IPA® analysis showing induction of gene expressions. For further details for (b) see Tables 1 & 2 below. Microarray-IPA® analysis identified induction of genes implicated in brain tissue development, including a large cluster of genes associated with the olfactory response (among others) in both in vitro- and in vivo-derived iNs. More robust induction was seen for the in vivo group.

Figure 26A:
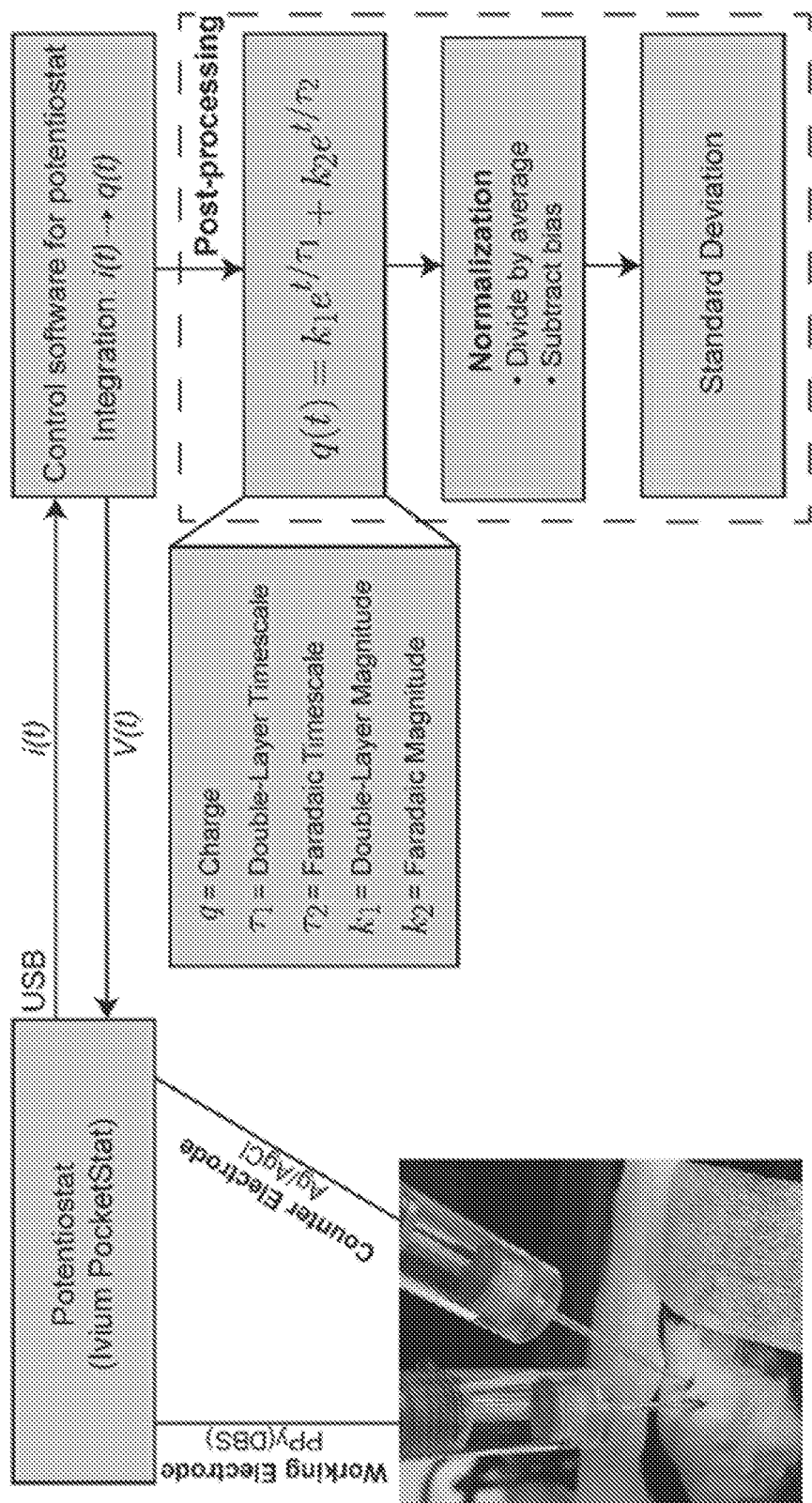
Figure 26B:
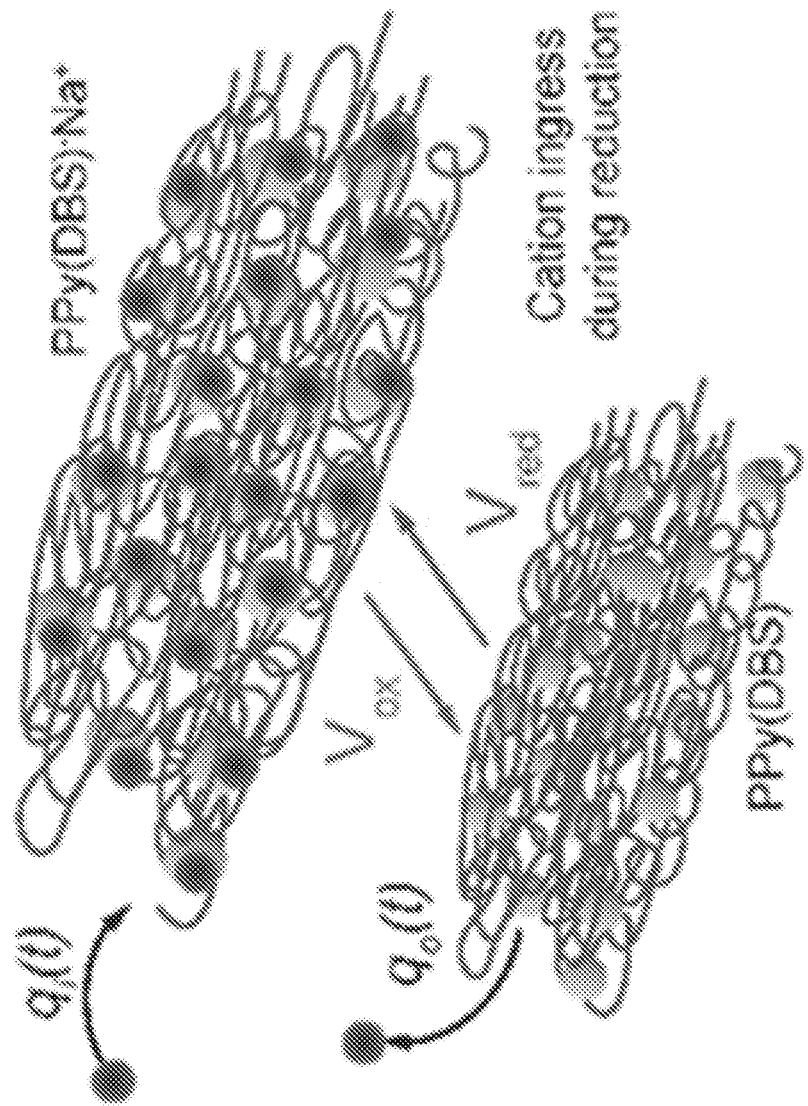
Figure 26C:
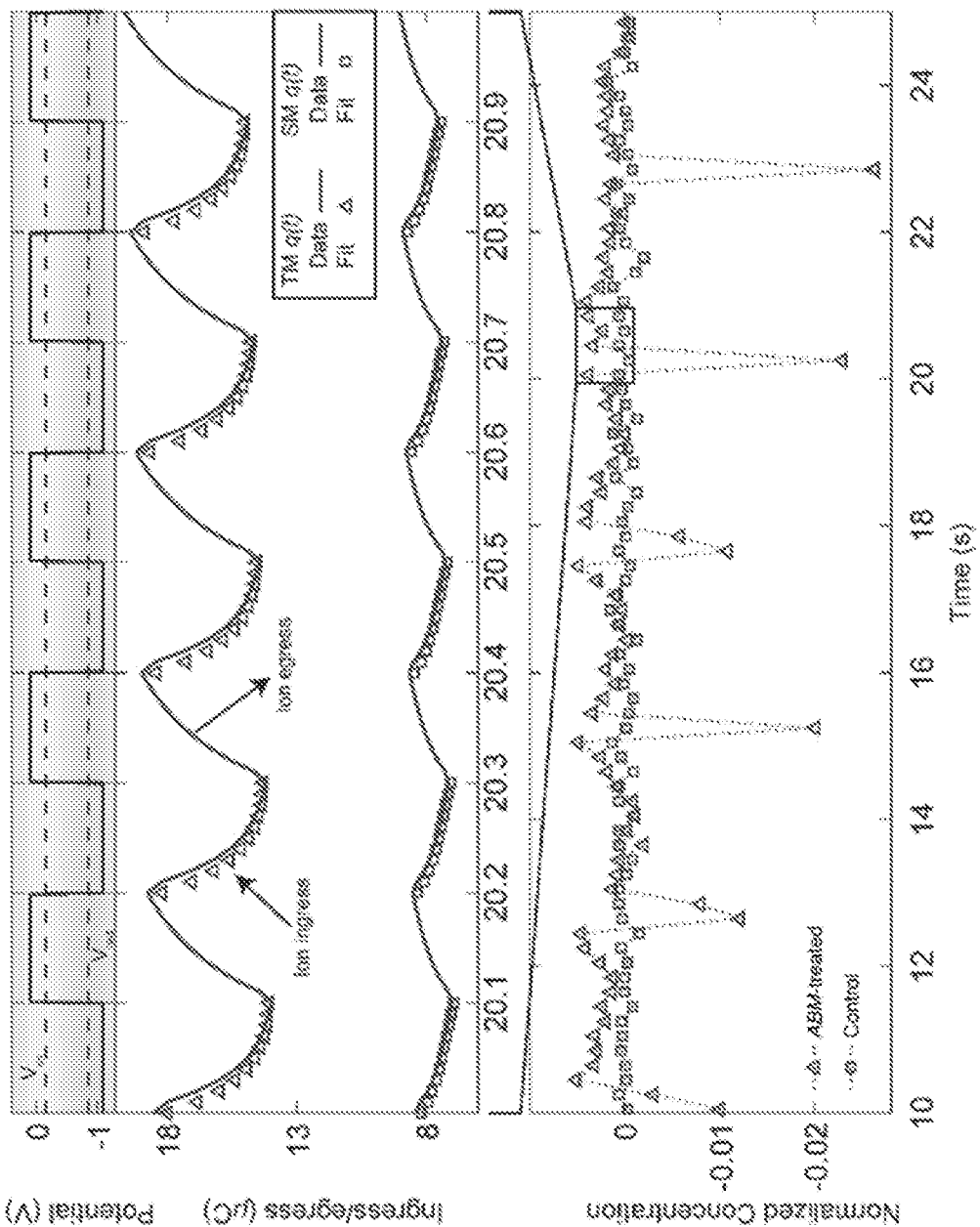

FIG. 26. In situ measurements of electrophysiological activity in the skin. (a) An information flow diagram detailing the in vivo action potential sensing process from experimental configuration (PPy(DBS) working electrode, Ag/AgCl counter electrode wires inserted with roughly 1-2 mm separation into the dermal layer and ionically connected with physiological saline during 5 Hz oxidation-reduction events over the course of 20 seconds, to data collection (input electrical potential causing rapid oxidation-reduction events and measuring resultant current), post processing (calculating the number of ions participating in the transport phenomena in the vicinity of the working electrode and deriving time-dependent changes in concentration through fitting the charge equation for electrically conductive faradaic materials, normalizing the data set by dividing the entire time dependent response by its average to remove experimental bias, and calculating a standard deviation to quantify excitability of local cells), and interpretation (determining if the resultant deviations from the normalized plots are in excess to the background electrical noise to determine if the cells near the PPy(DBS) tip are excitable cells), (b) a conceptual schematic depicting ion transport in the near field of a conducting polymer and demonstrating the concentration dependence on the rate of ion transfer as well as a conceptual schematic demonstrating the difference between how excitable and non-excitable cells regulate their surrounding media, (c) a plot of the input potential (V) between the working and counter/reference electrodes over 1 second, resultant charge calculated (μC) from the measured current (μA) response during the same 1 second, a fit of the charge equation to determine the value of the concentration-dependent K2 during reduction events, and a representative K2 vs time plot for a representative ABM-treated (excitable) and control sample.

Figure 27A:
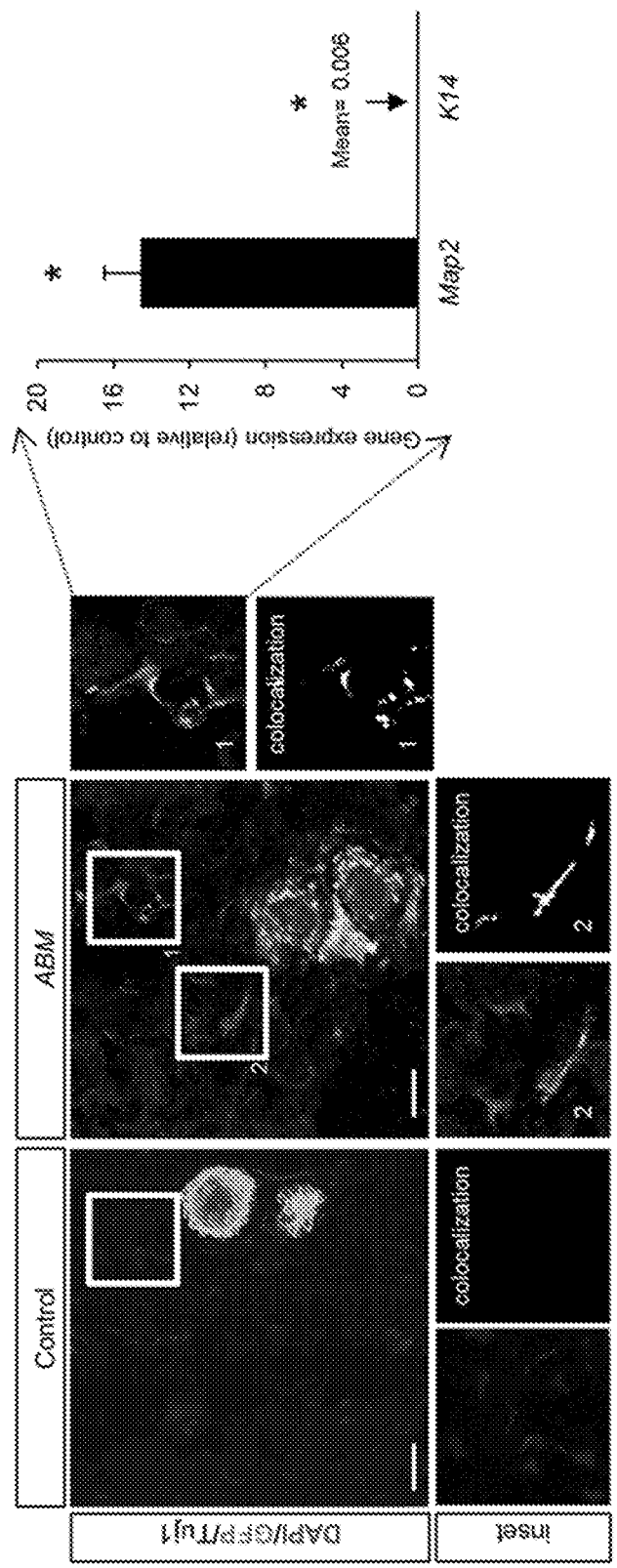
Figure 27B:
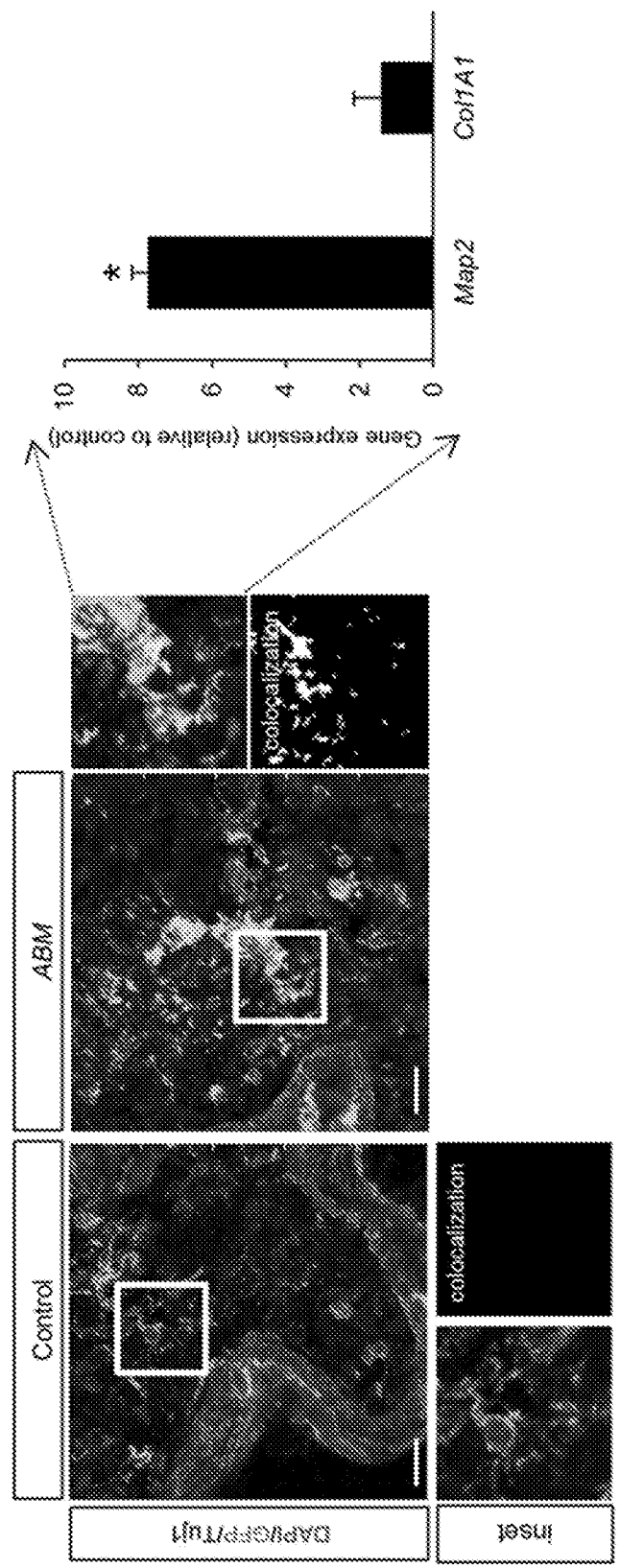
Figure 28A:
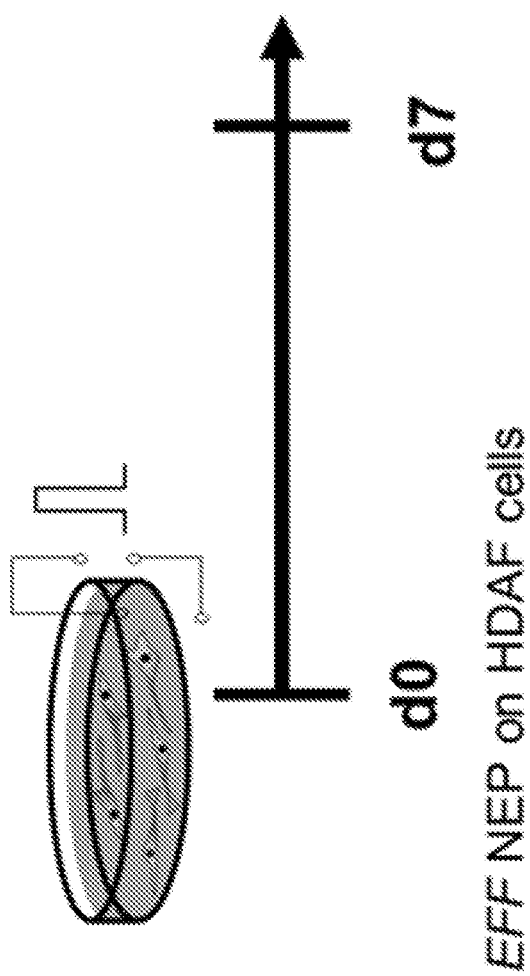
Figure 28B:
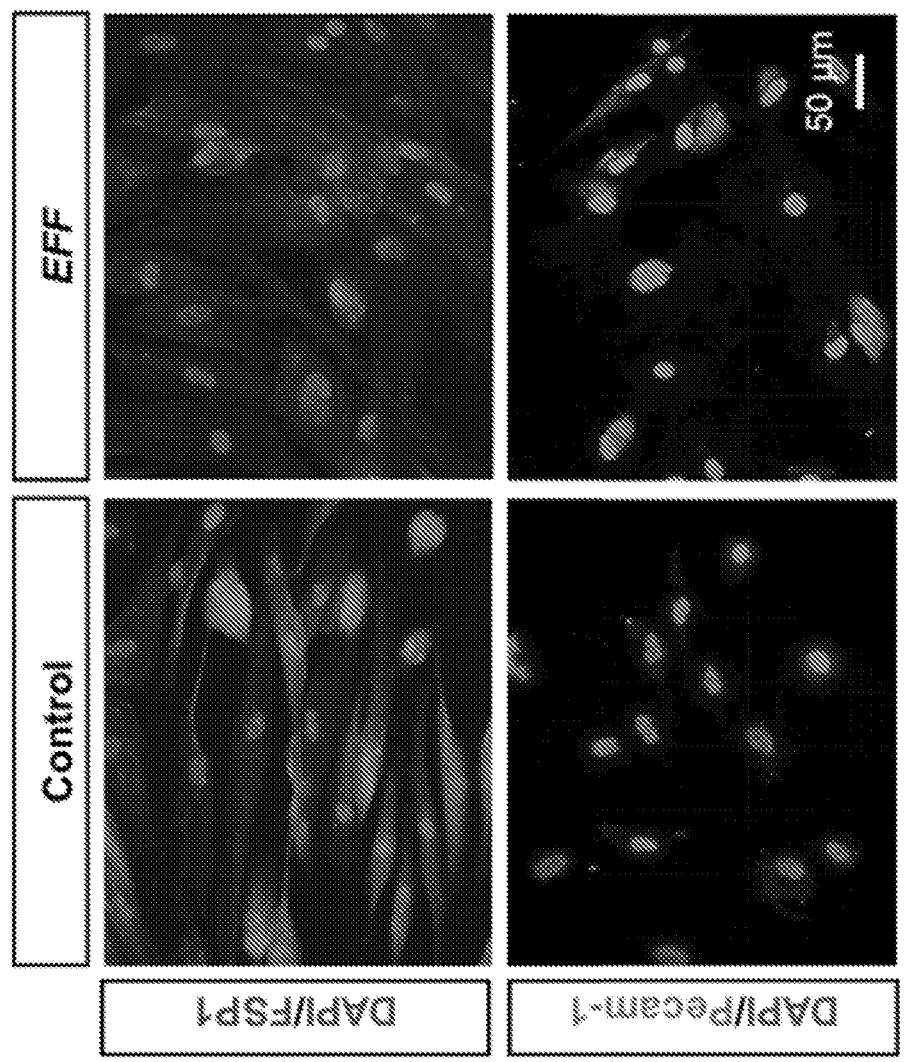
Figure 28C:
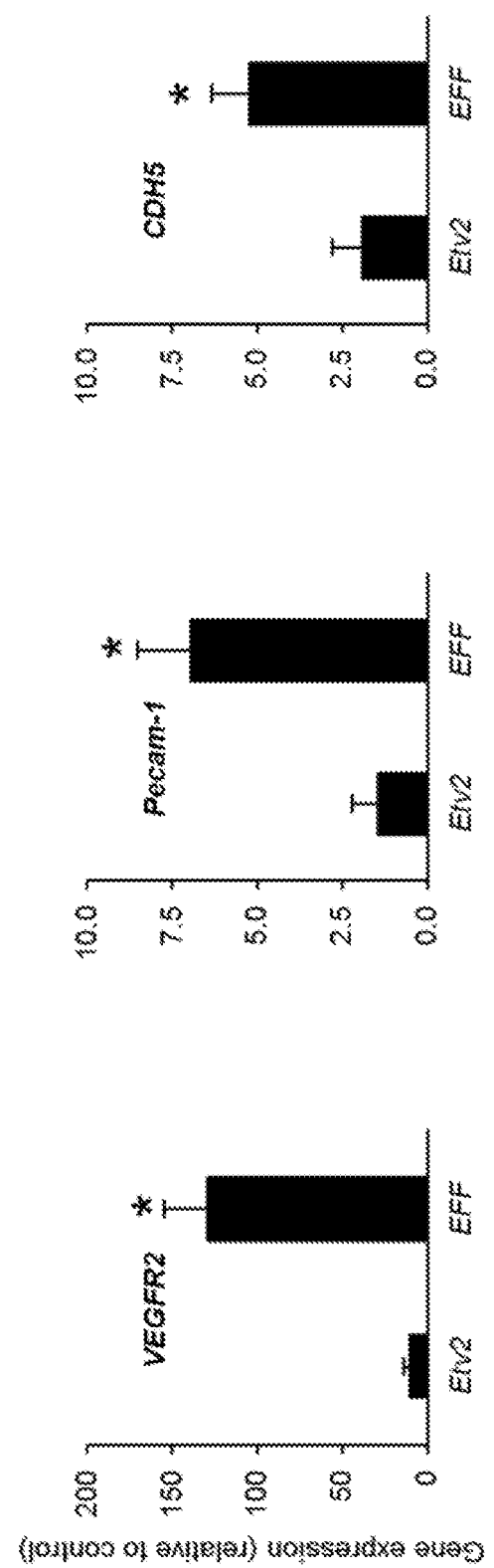
Figure 28D:
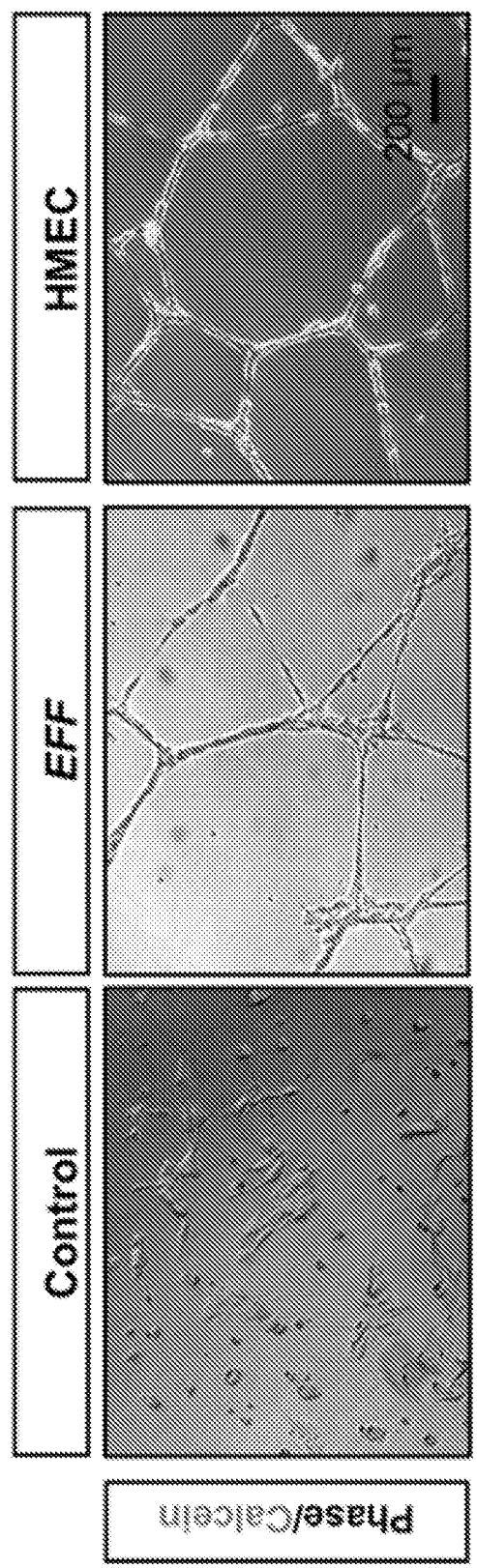
Figure 28E:
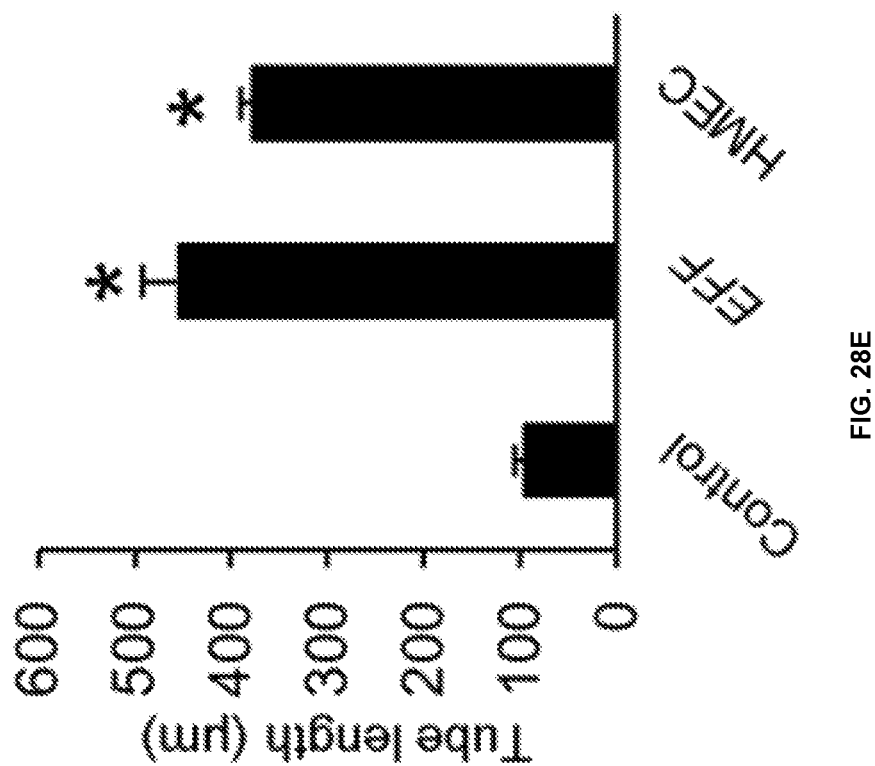
Figure 28F:
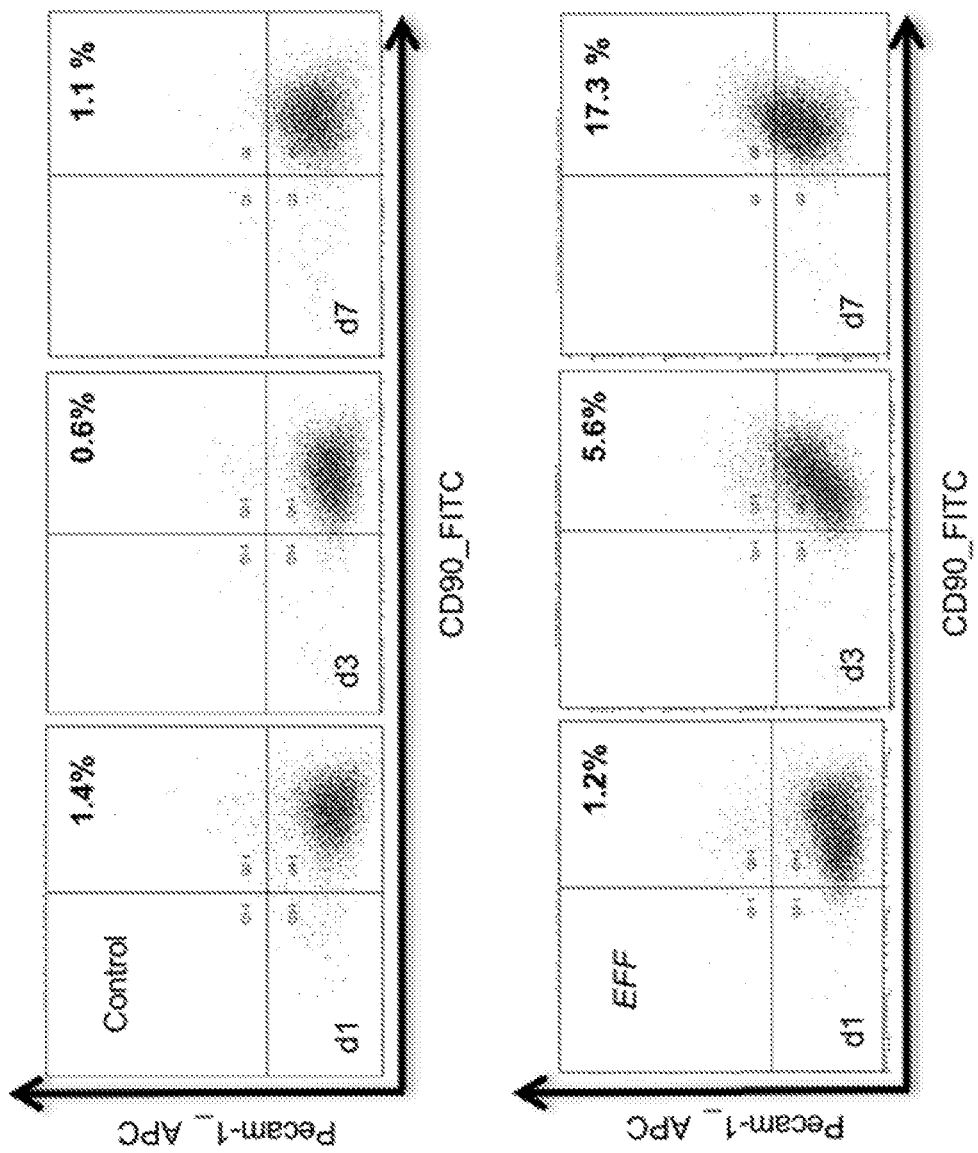
Figure 28G:
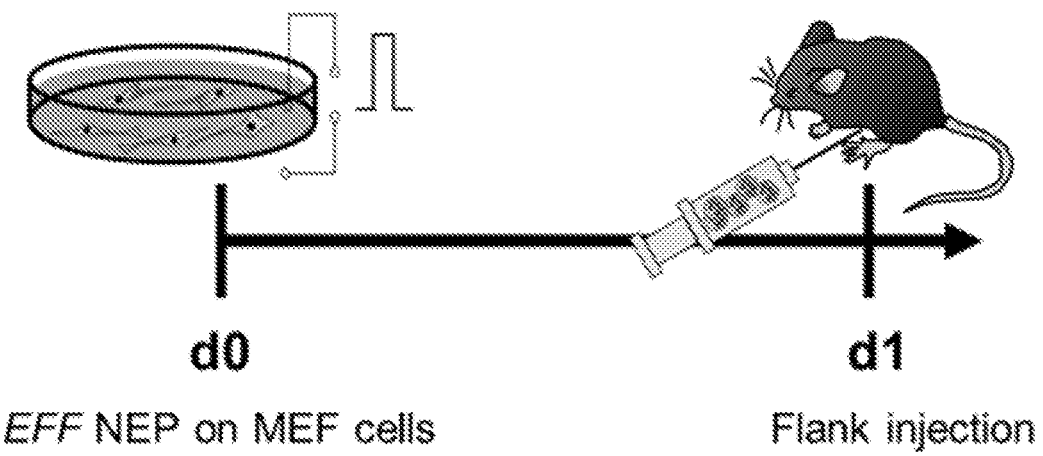
Figure 28H:
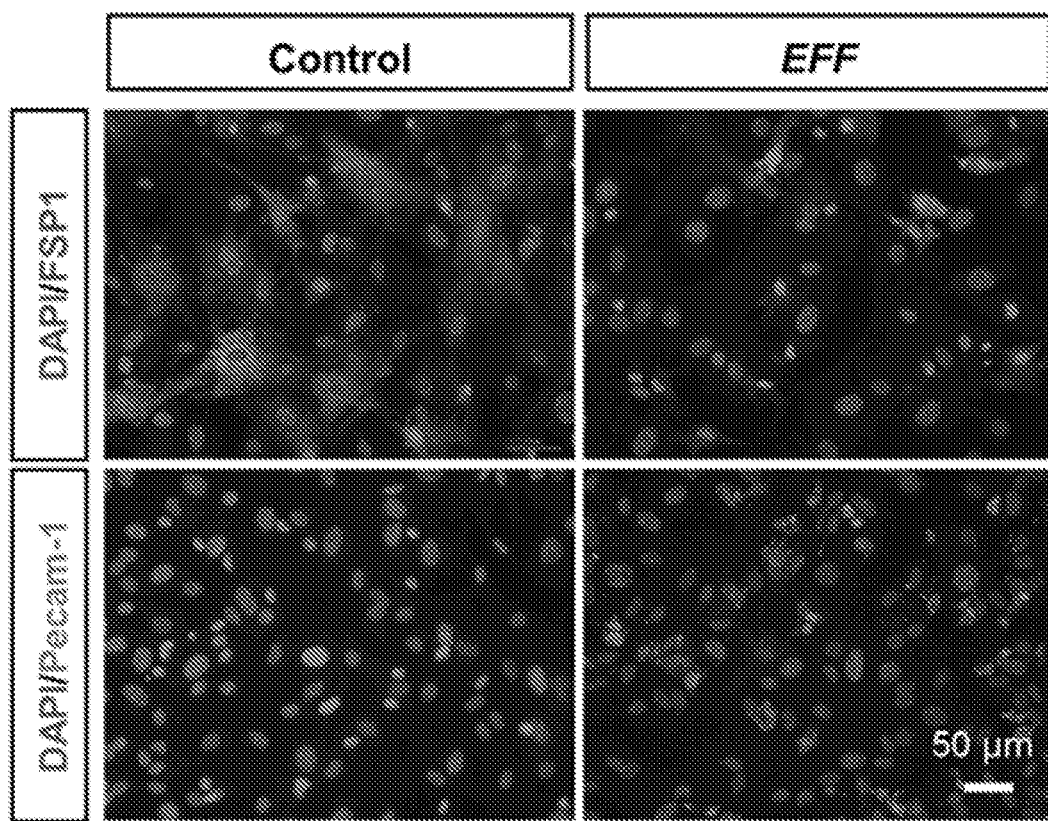
Figure 28I:
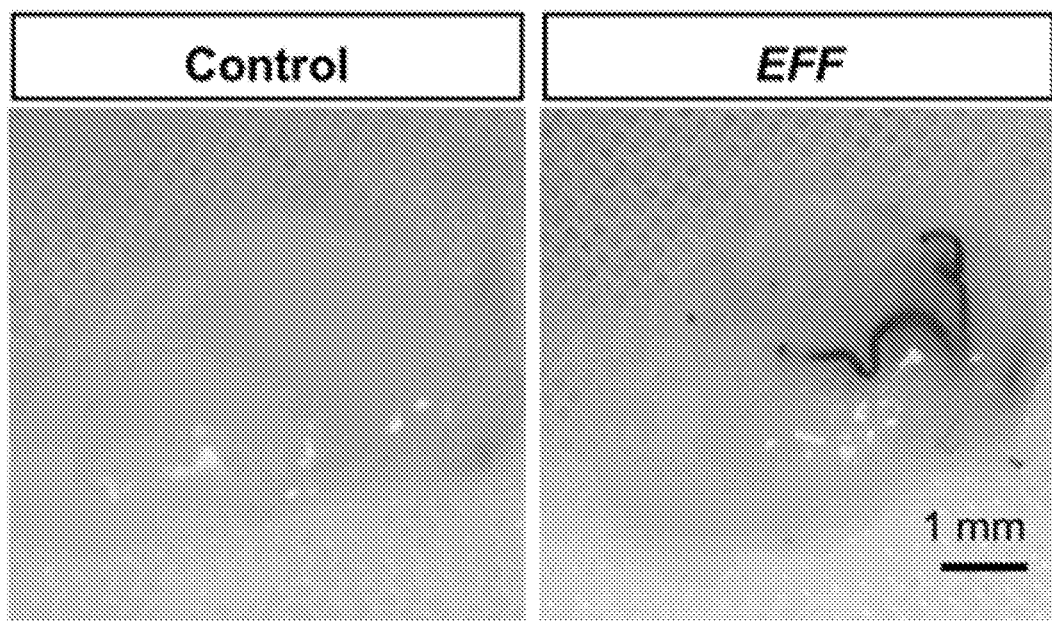
Figure 28J:
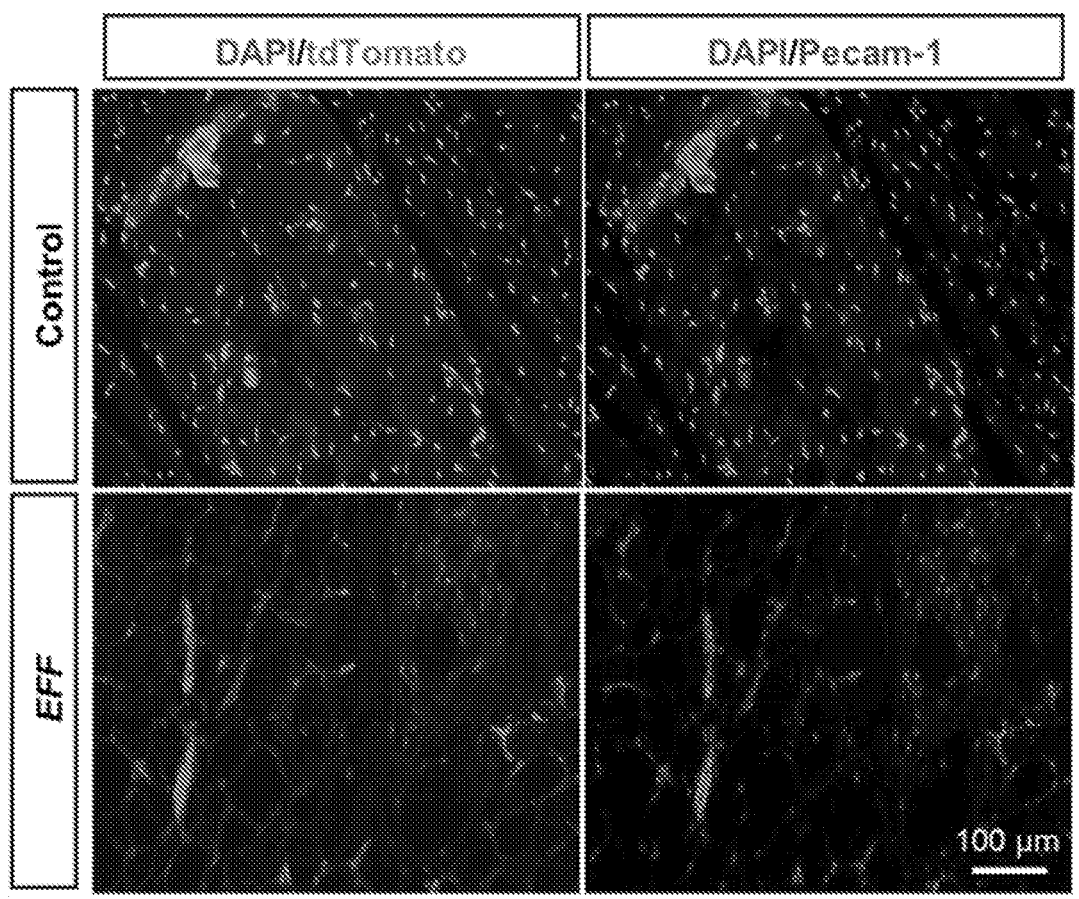

FIG. 27. iNs in the skin originate from epidermal and dermal sources. Fluorescence micrographs of ABM-treated skin sections from the (a) K14-Cre reporter mouse model and the (b) Col1A1-GFP mouse model showing skin cells of K14, or Col1A1 origin (green/GFP) also expressing the Tuj1 neuronal marker. The secondary antibody used for Tuj1 was CY5-tagged, and the emitting signal was pseudocolored red. The tdTomato background channel was excluded from the merged images. Scale=20 μm. (a.1, b.1) Cellular elements that were immunoreactive for both the GFP tracer and Tuj1 were further analyzed by LCM/qRT-PCR. The results indicate that such double-positive elements had significantly high neuronal marker gene expression and moderate to markedly reduced skin cell marker gene expression. n=3. *$p<0.05$ (Holm-Sidak method). Lineage tracing experiments with a K14-Cre reporter mouse model, where Keratin 14 positive (K14+) cells undergo cre-mediated recombination of the ROSA locus ultimately switching from tdTomato expression to eGFP, confirmed that the newly-induced neurons partly originated from K14+ skin cells. Experiments with a Col1A1-eGFP mouse model, where cells with an active Col1A1 promoter express eGFP, showed a number of Collagen/eGFP+ cells from the dermis in a transition phase to Tuj1+. Persistent Col1A1/GFP activity in these cells clearly reflects a gradual phenotypical shift between fibroblasts and induced neurons. LCM was used to capture and further characterize the gene expression profile of cellular elements from tissue sections of the transgenic mouse model that were both GFP+ and Tuj1+, which would correspond to cells that were of K14 origin but now express a neuronal marker, or cells that have an active collagen promoter (e.g., fibroblasts) transitioning to a neuronal fate. Our results indicated that such elements indeed exhibited increased expression of pro-neuronal markers, and reduced expression of the cell-of-origin marker (i.e., K14, Col1A1).

FIG. 28. The EFF gene cocktail drives faster and more efficient fibroblast reprogramming into an endothelial fate (iECs). (a) HDAF cells were non-virally transfected with EFF. (b) Fluorescence micrographs showing strong expression of the endothelial marker Pecam-1 as well as reduced expression of the fibroblastic marker FSP (t=7 days post transduction). (c) Gene expression analysis of endothelial markers for two different transduction conditions (Etv2 alone vs. co-transfection of EFF). Results show a marked difference in gene expression, with EFF resulting in significantly stronger endothelial gene expression at day 7 post-transduction compared to Etv2 alone. (d, e) Results from a tube formation assay showing that EFF-transduced cells were able to form blood vessel-like structures when cultured in matrigel comparable to endothelial cells (HMEC, positive control). Control HDAF cells, on the other hand, were not able to form tube-like structures when cultured in matrigel. (f) Flow cytometry-based analysis of endothelial and fibroblastic marker expression at days 1, 3 and 7 after EFF transfection. By days 3 and 7, approximately 6% and 17% of the population exhibited expression of Pecam-1, respectively, compared to control cells. Such dynamics agree with the timeline seen for increased perfusion following EFF TNT on dorsal skin (FIG. 19). Increased in vivo perfusion in response to EFF TNT, however, may not necessarily be entirely driven by reprogramming of stromal tissue into vascular tissue. Remodeling/sprouting of pre-existing vascular beds could be a contributing factor as well. (g, h) MEF cells non-virally transfected with EFF also show endothelial marker expression as early as 7 days post-transfection. (i, j) tdTomato-MEF cells non-virally transfected with EFF fomented blood vessel formation following flank injection in NSG mice. n=3-4. *p<0.05 (Holm-Sidak method).

Figure 29A:
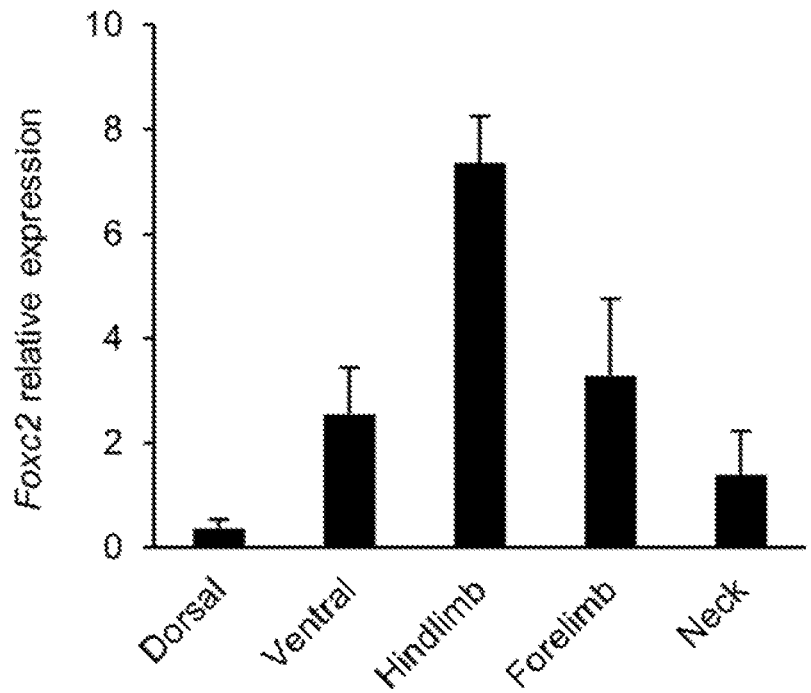
Figure 29B:
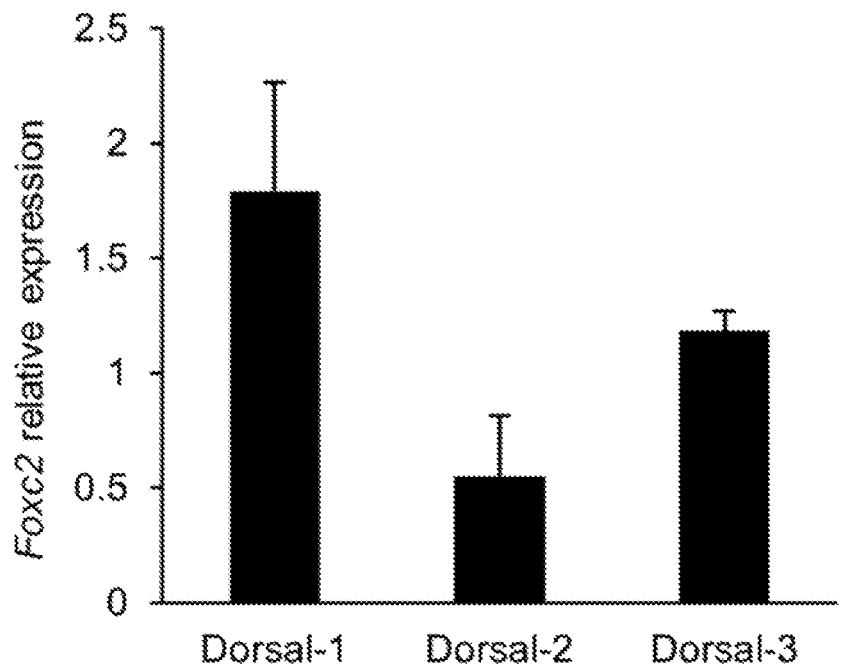

FIG. 29. Variations in endogenous Foxc2 expression. Relative Foxc2 expression in skin biopsied from (a) multiple locations or (b) different mice (same location). n=3. Although recent in vitro studies reported that genomic integration of lentiviral Etv2 vectors could induce direct endothelial reprogramming in cell lines with high levels of endogenous Foxc2, ubiquitous Foxc2 expression varied significantly in vivo (FIG. 25), thus implying that in some cases low levels of endogenous Foxc2 expression may hamper successful endothelial induction via non-viral episomal expression of Etv2 alone. As such, it a novel cocktail of transcription factors based on Etv2, Foxc2, and Fli1 (EFF) was proposed and tested. Fli1 is a known intronic enhancer, and thus could have the ability to potentiate the reprogramming cocktail efficacy17.

Figure 30A:
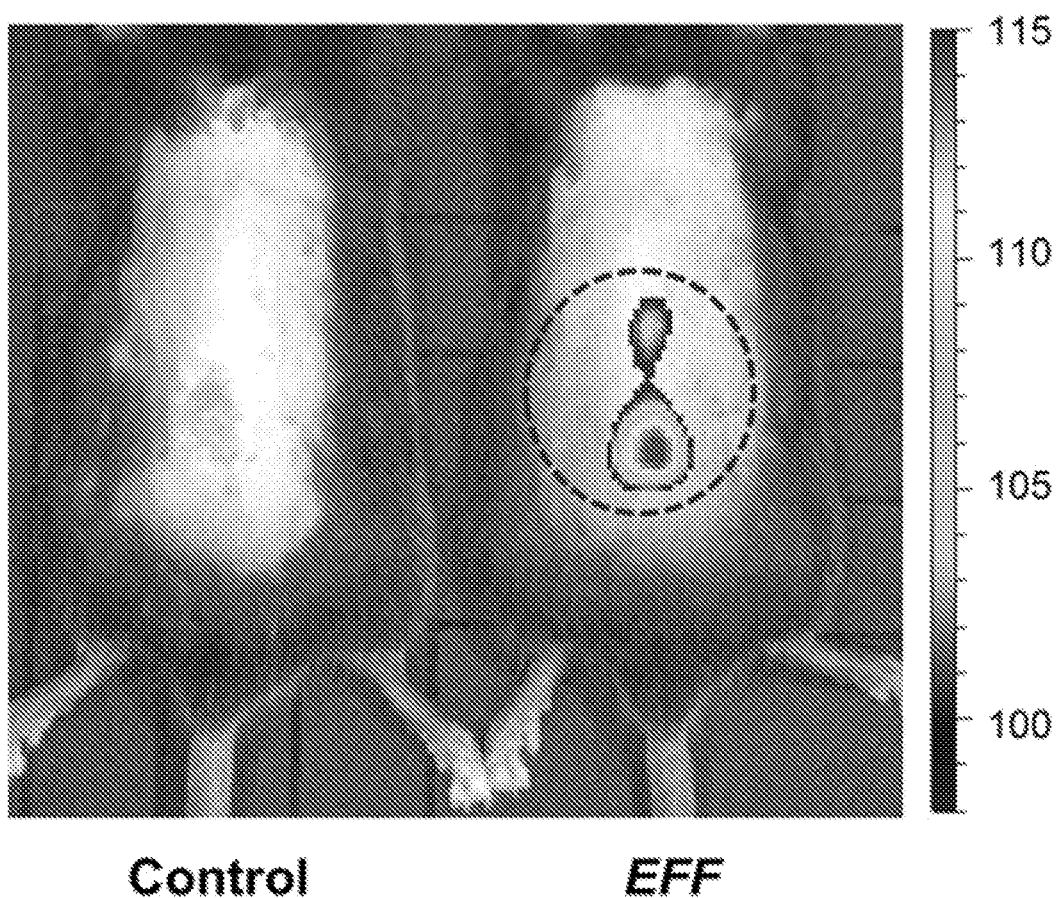
Figure 30B:
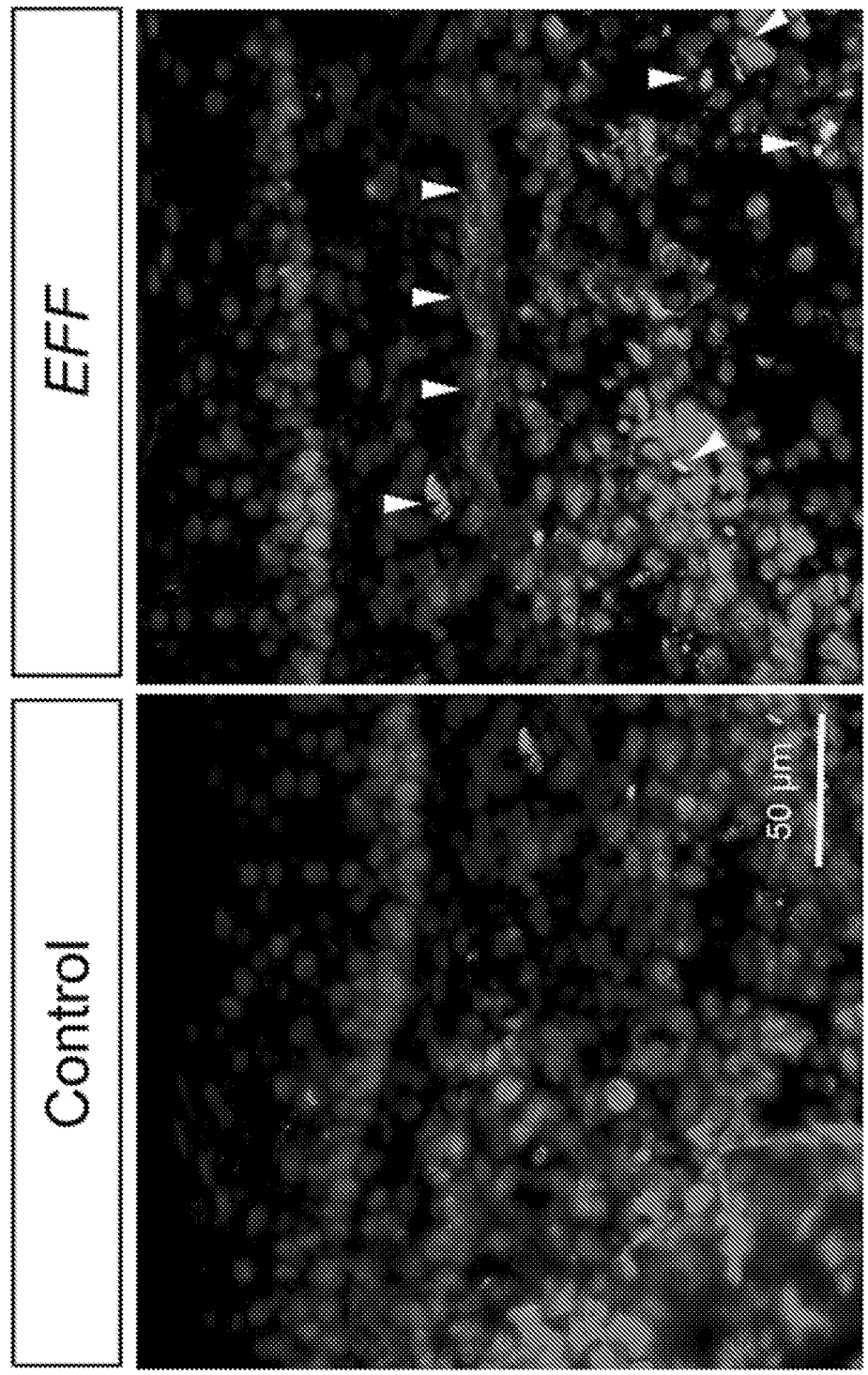

FIG. 30. EFF-treated skin shows signs of enhanced cell proliferation. (a) IVIS luminescence analysis in repTOP™ mitoIRE mice confirms proliferative activity on dorsal skin of EFF TNT-treated mice (dotted red line). These mice express a luciferase reporter under the control of an artificial promoter derived from the Cyclin B2 gene, which is specifically induced during cellular proliferation18. (b) Immunofluorescence analysis of dorsal skin showing colocalization of proliferation markers (Ki67) with endothelial markers (Pecam-1).

Figures 31A, 31B:
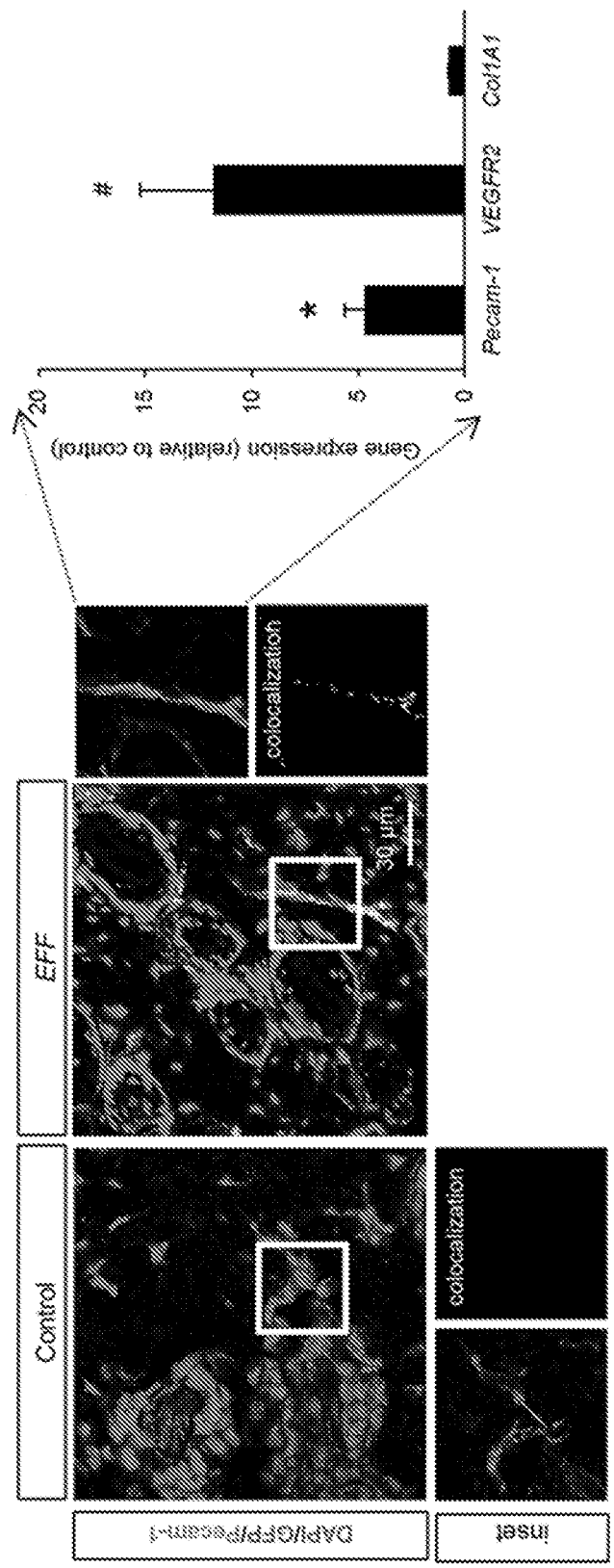

FIG. 31. iECs in the skin originate from Col1A1-expressing dermal sources. Fluorescence micrographs of EFF TNT-treated skin sections from the (a) Col1A1-GFP mouse models showing skin cells of Col1A1 origin (green) also expressing the Pecam1 endothelial marker, as they presumably transition from a fibroblast to an endothelial phenotype. (b) Cellular elements that were immunoreactive for both the GFP tracer and Pecam1 were further analyzed by LCM/qRT-PCR. The results indicate that such double-positive elements had significantly high endothelial marker gene expression. n=3. *p<0.05 (Holm-Sidak method), #0.05<p<0.07 (one-tailed t-test). Experiments with the K14-Cre reporter and Col1A1-eGFP mouse models confirmed that the reprogrammed cell population had for the most part a dermal origin. Unlike the induced neurons model, there was no clear evidence of cells of K14 origin expressing endothelial markers.

Figure 32B:
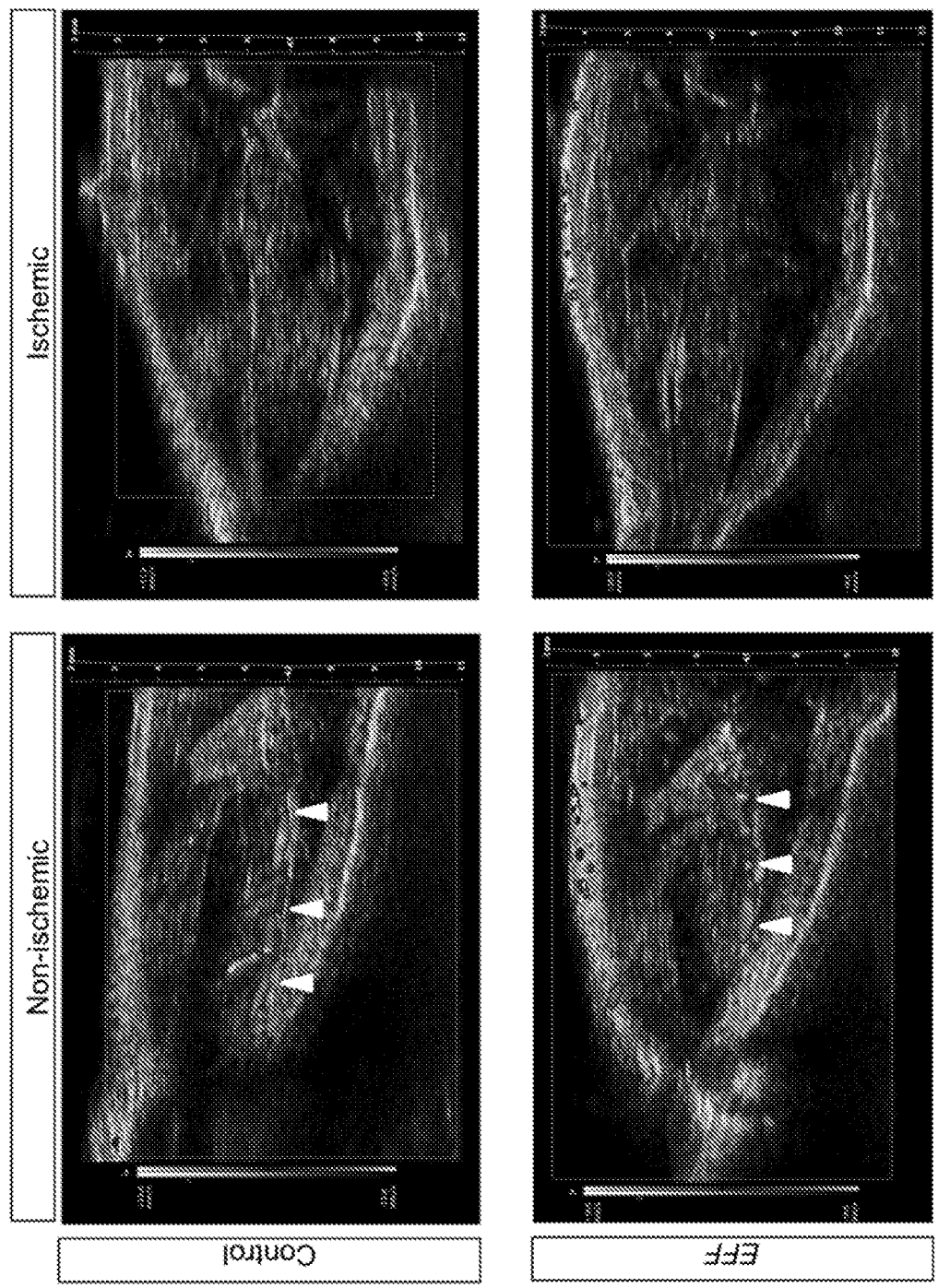

FIG. 32. HRLS and ultrasound imaging confirming transection of the femoral artery as well as increased incidence of collaterals in EFF-treated limbs. (a) HRLS imaging confirms the absence of a femoral artery in the ischemic limbs of both control and EFF-treated mice compared to their non-ischemic counterparts. Diffuse LS signal coming from the EFF-treated limbs (white arrows) suggest the presence of smaller caliber collateral vessels that presumably mediate limb reperfusion. (b) Ultrasound imaging also confirmed the absence of a femoral artery in the ischemic limbs, thus further suggesting that limb reperfusion is likely modulated by the development of new/smaller collaterals and not the repair of the severed femoral artery.

Figure 33A:
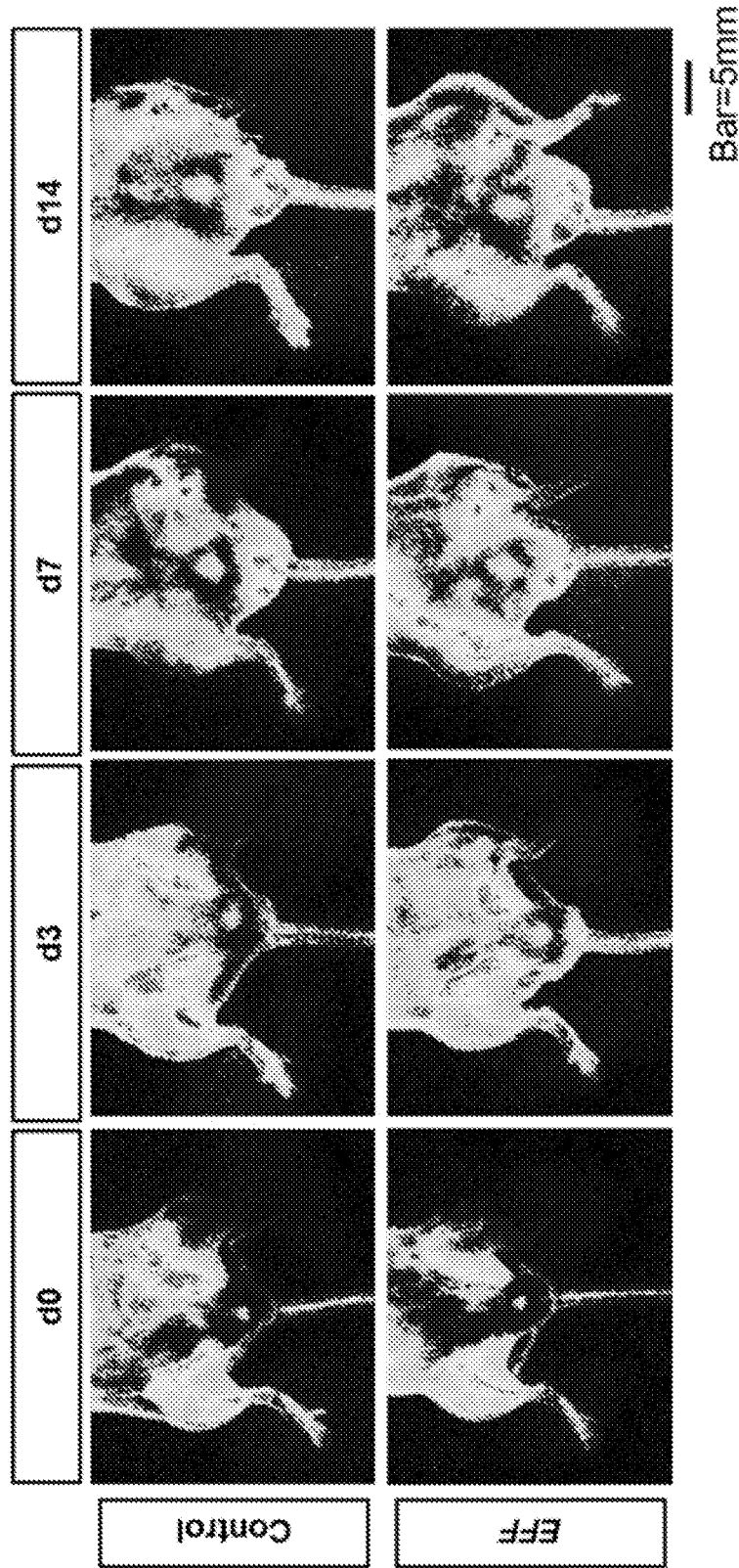
Figure 33B:
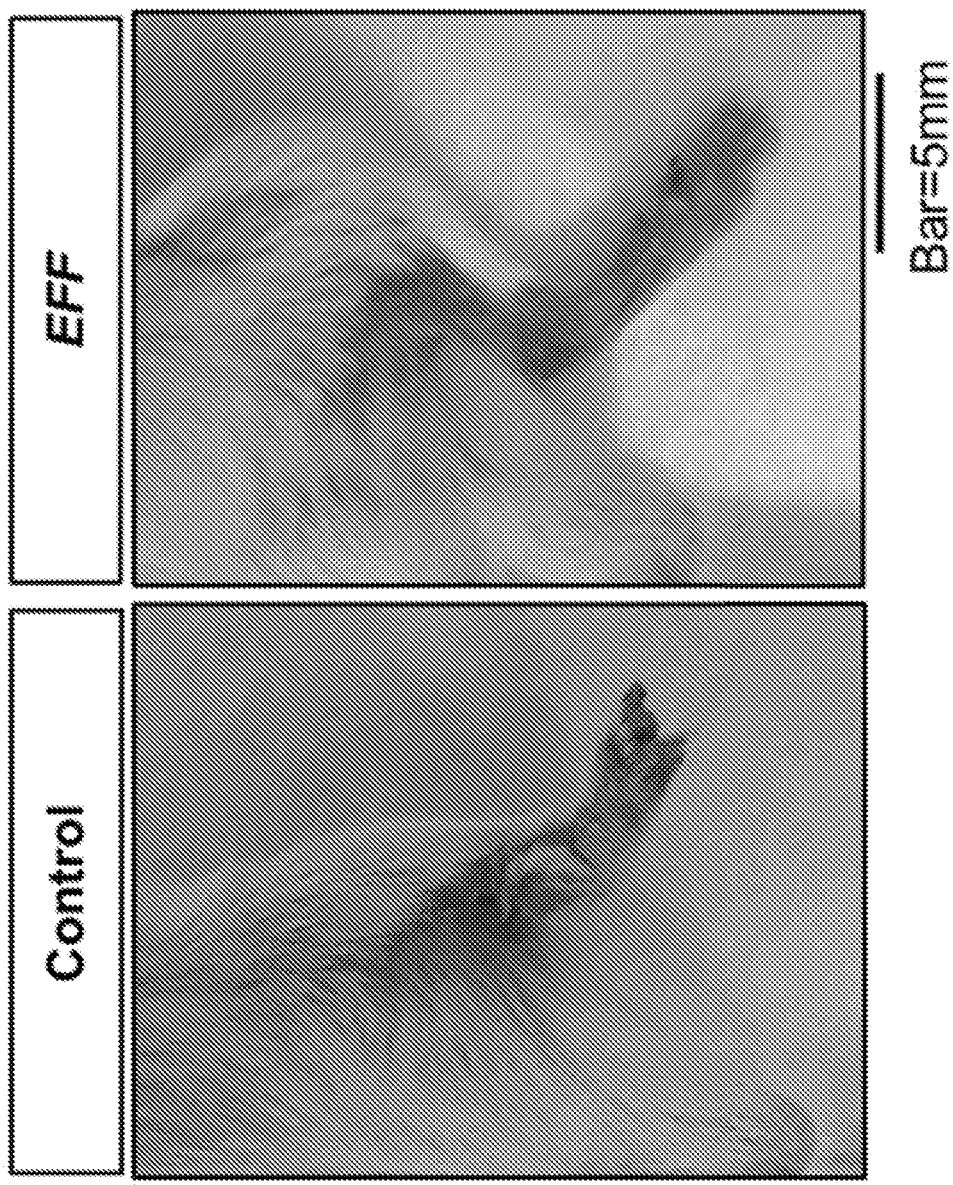

FIG. 33. EFF transfection helps to prevent necrosis in Balb/c hindlimb ischemia models. (a) Laser speckle imaging of the limbs showing successful reperfusion after EFF transfection. (b) Macroscopic changes to the ischemic limb with and without EFF treatment.

Figure 34:
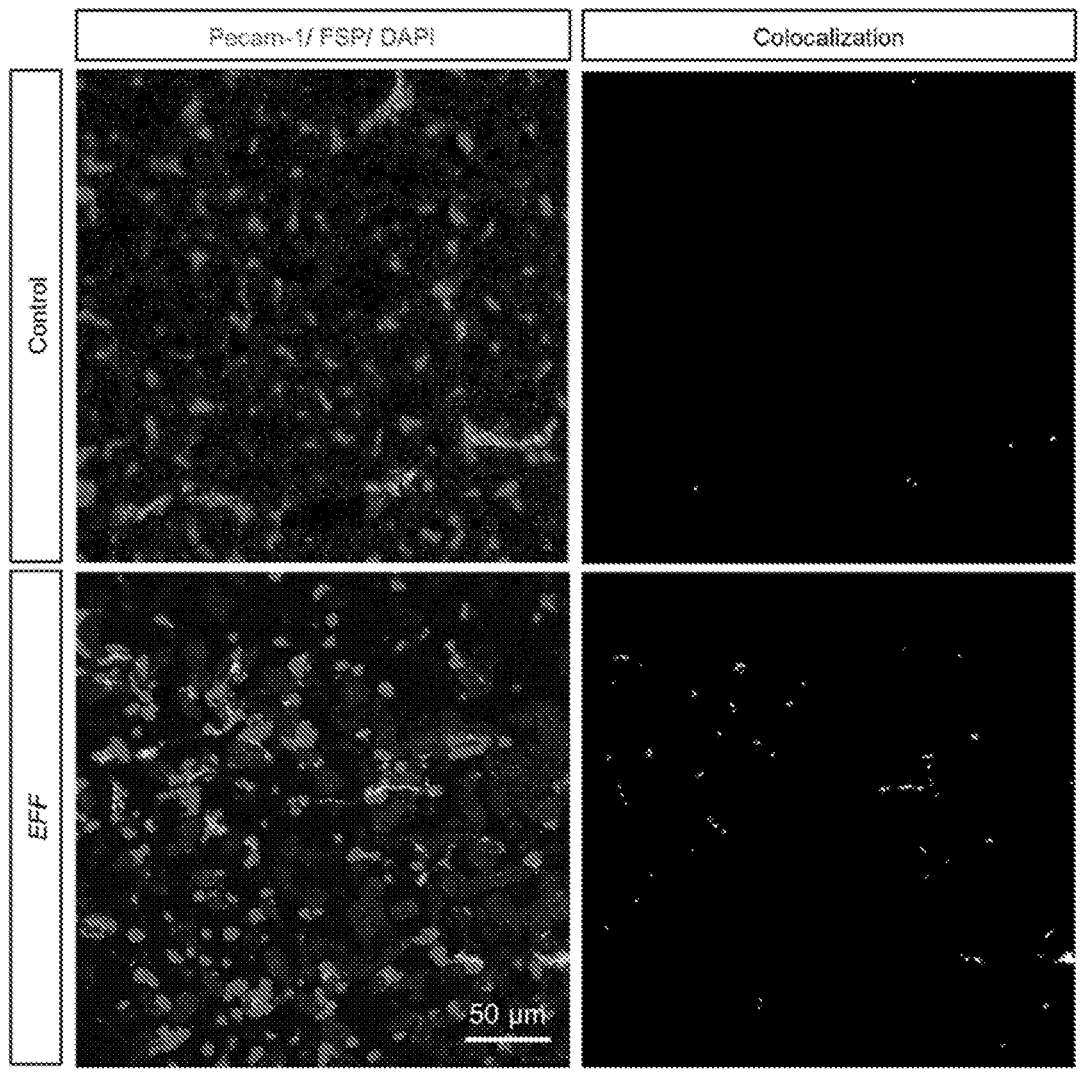
Figure 35A:
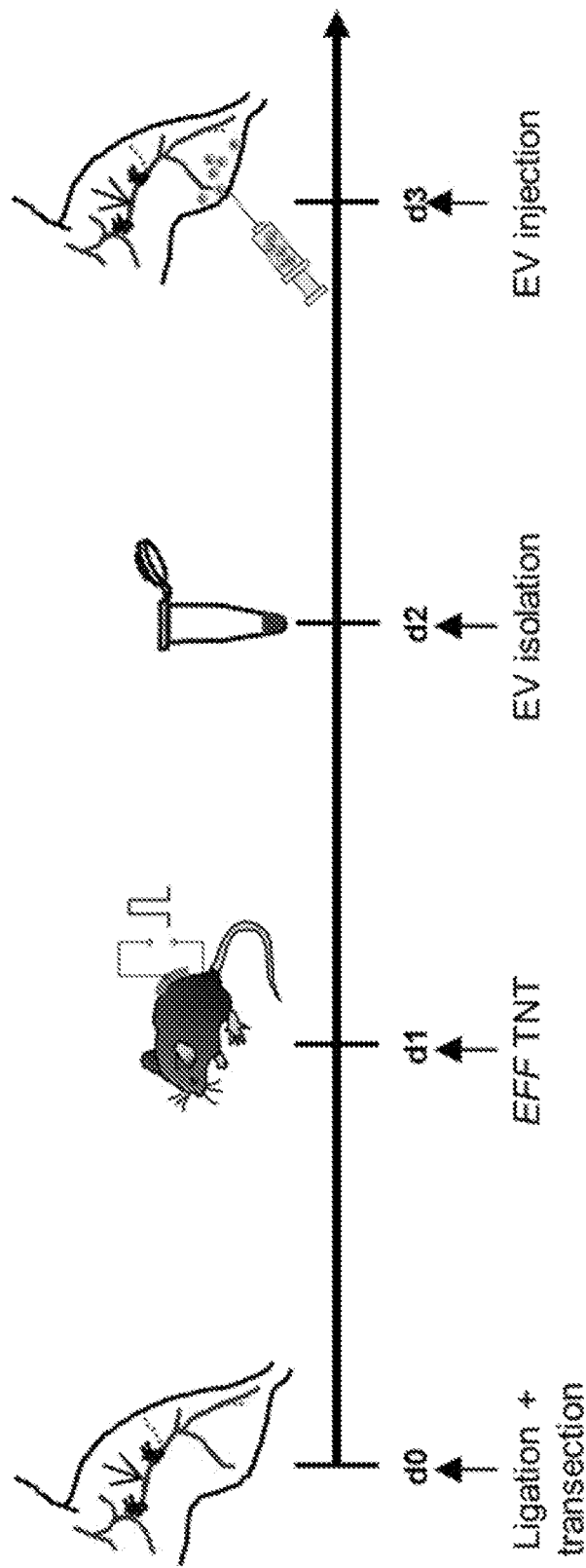
Figure 35B:
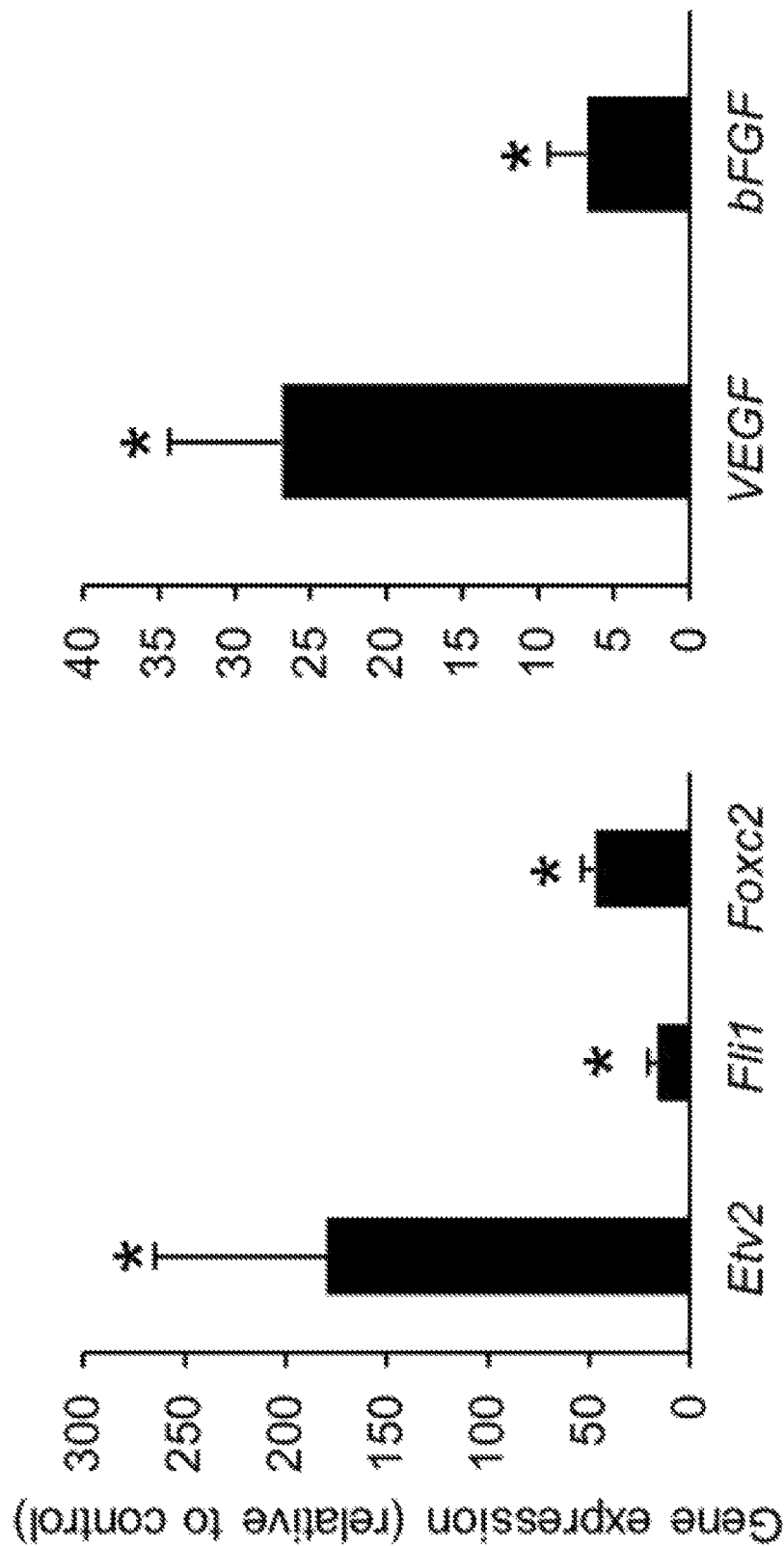
Figure 35C:
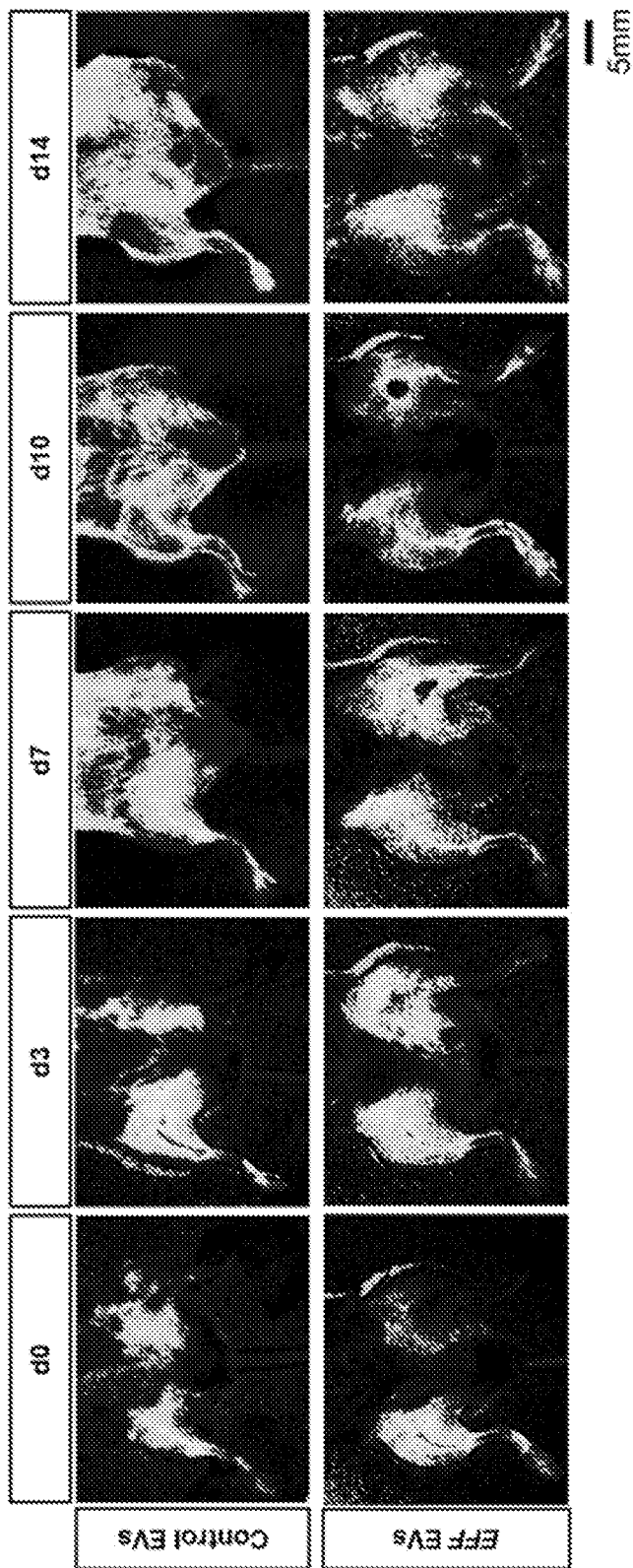
Figure 35D:
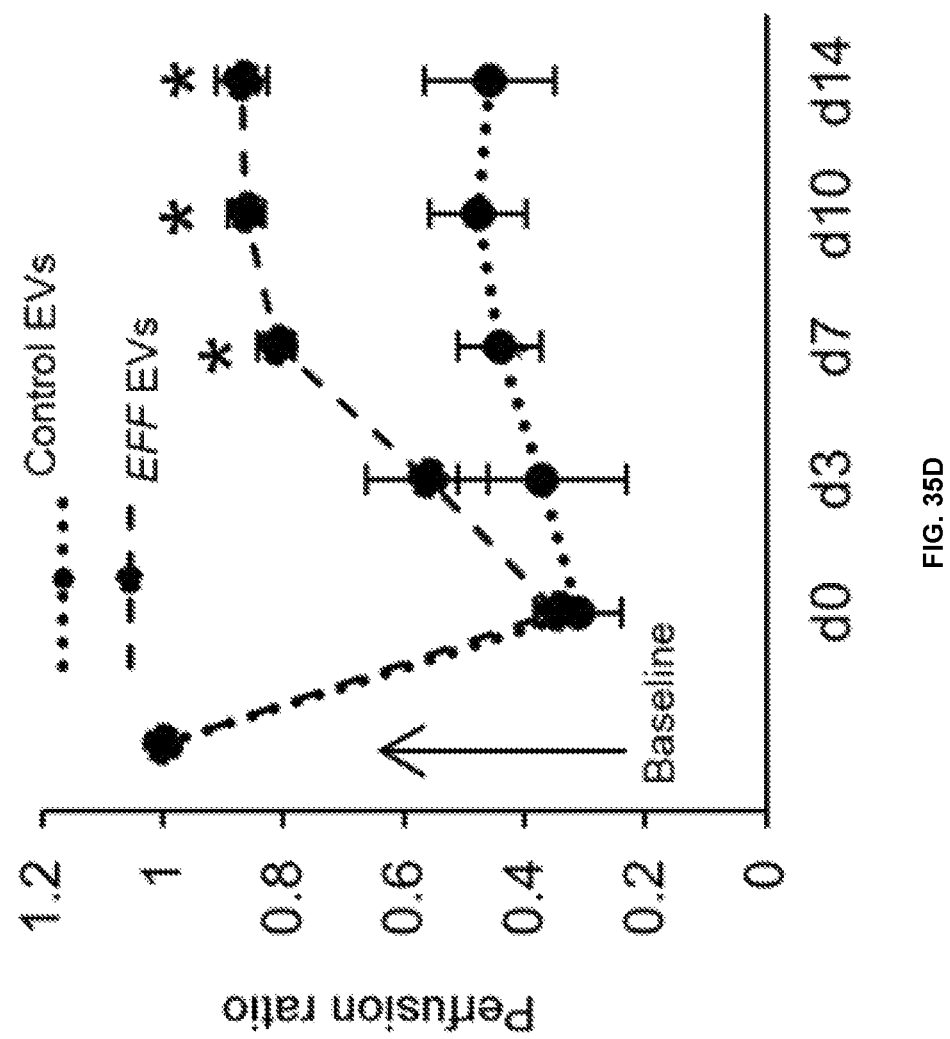
Figure 35E:
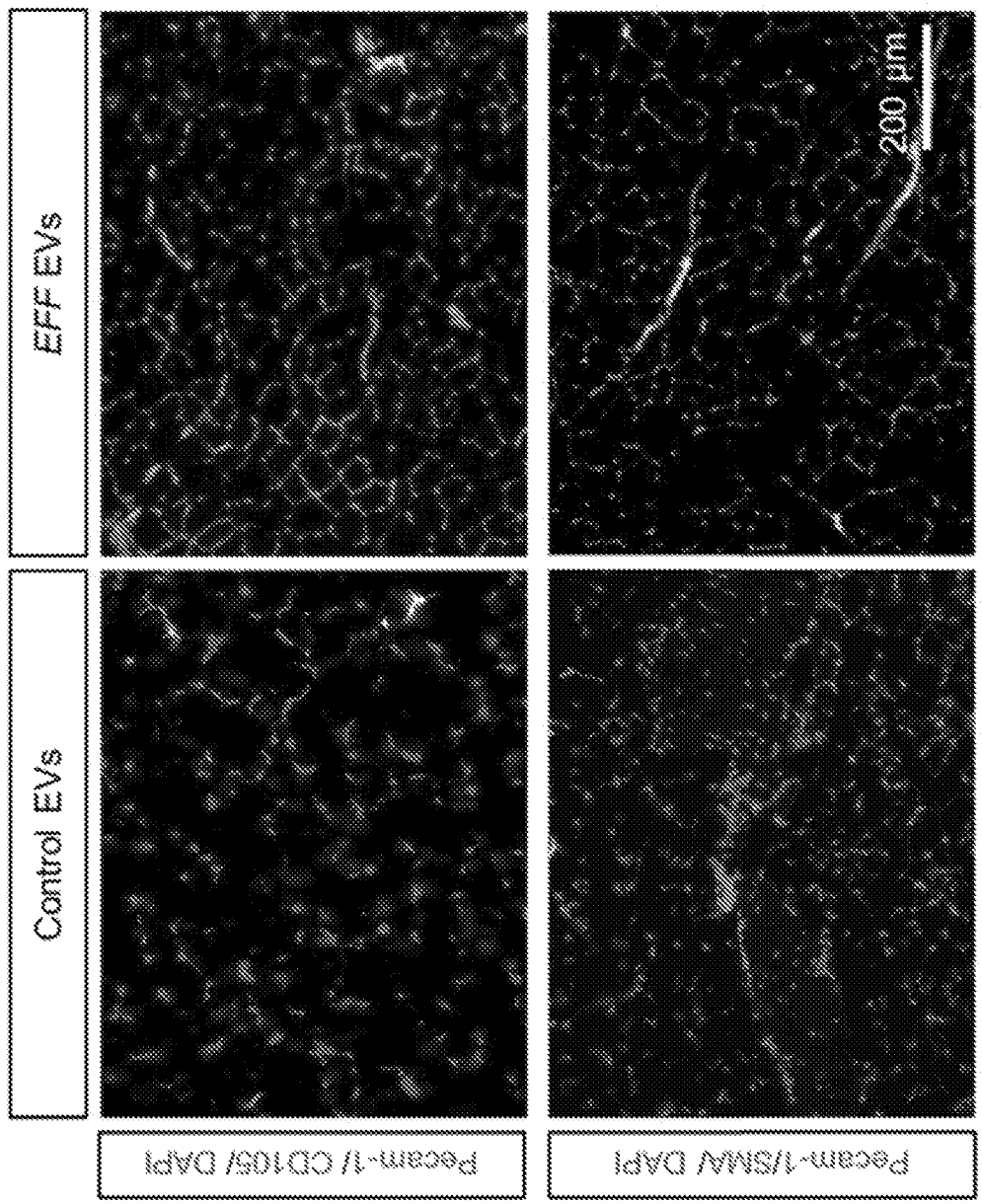
Figure 35F:
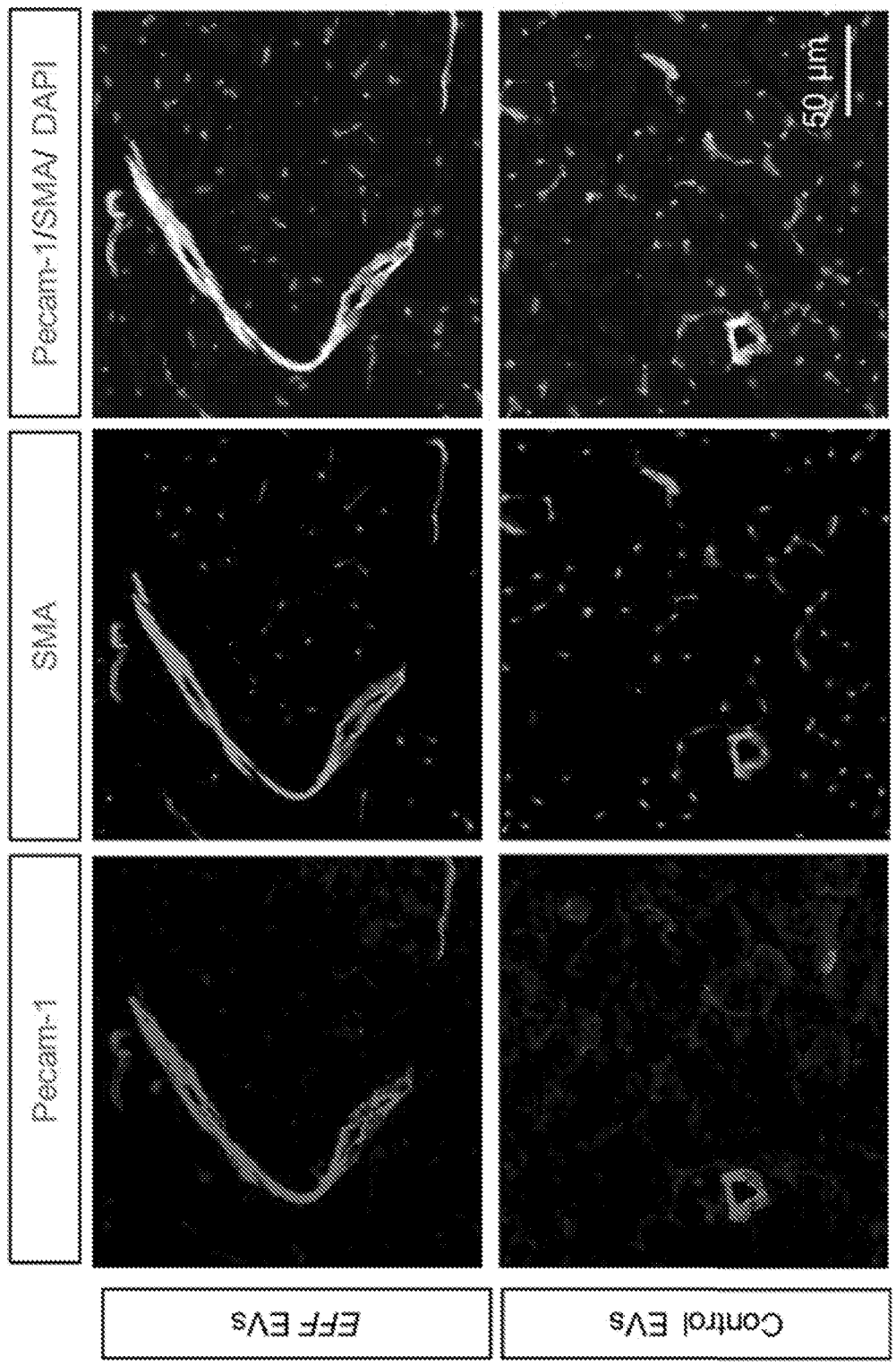
Figure 36B:
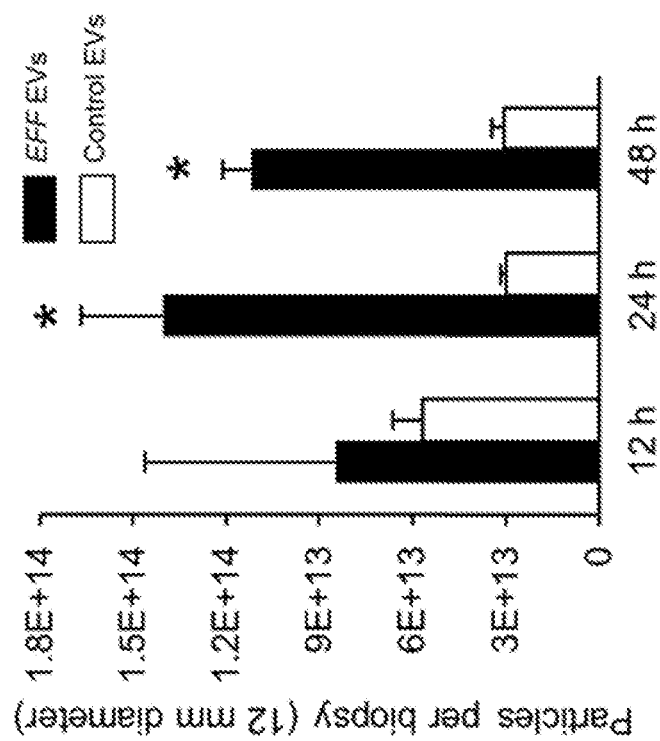
Figure 36A:
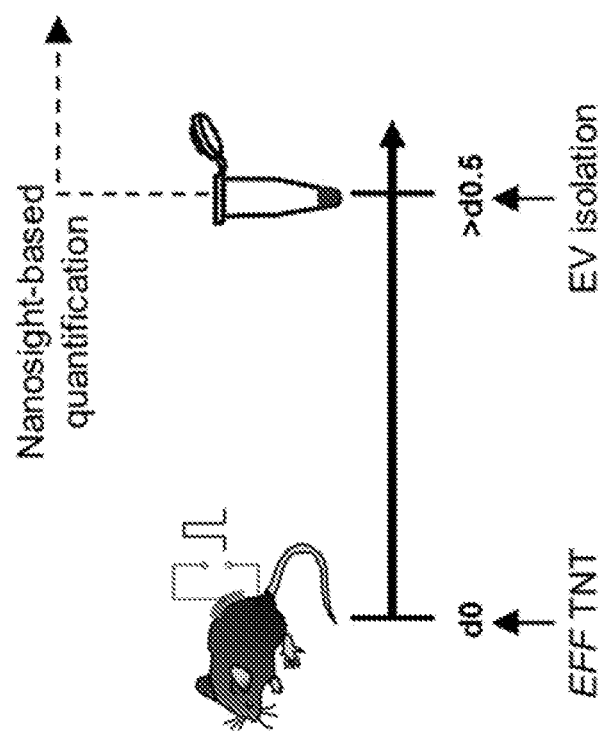
Figure 36C:
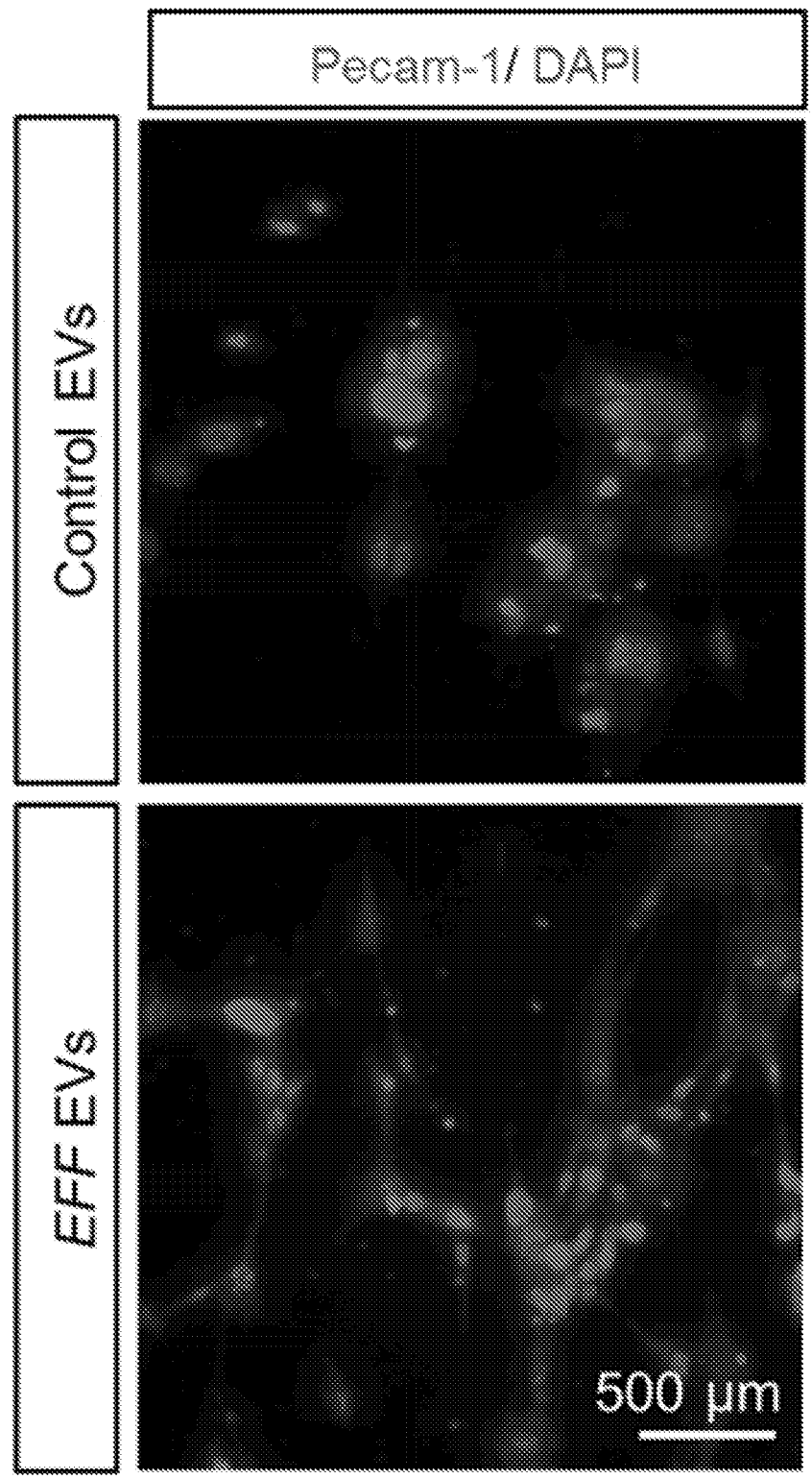
Figure 36D:
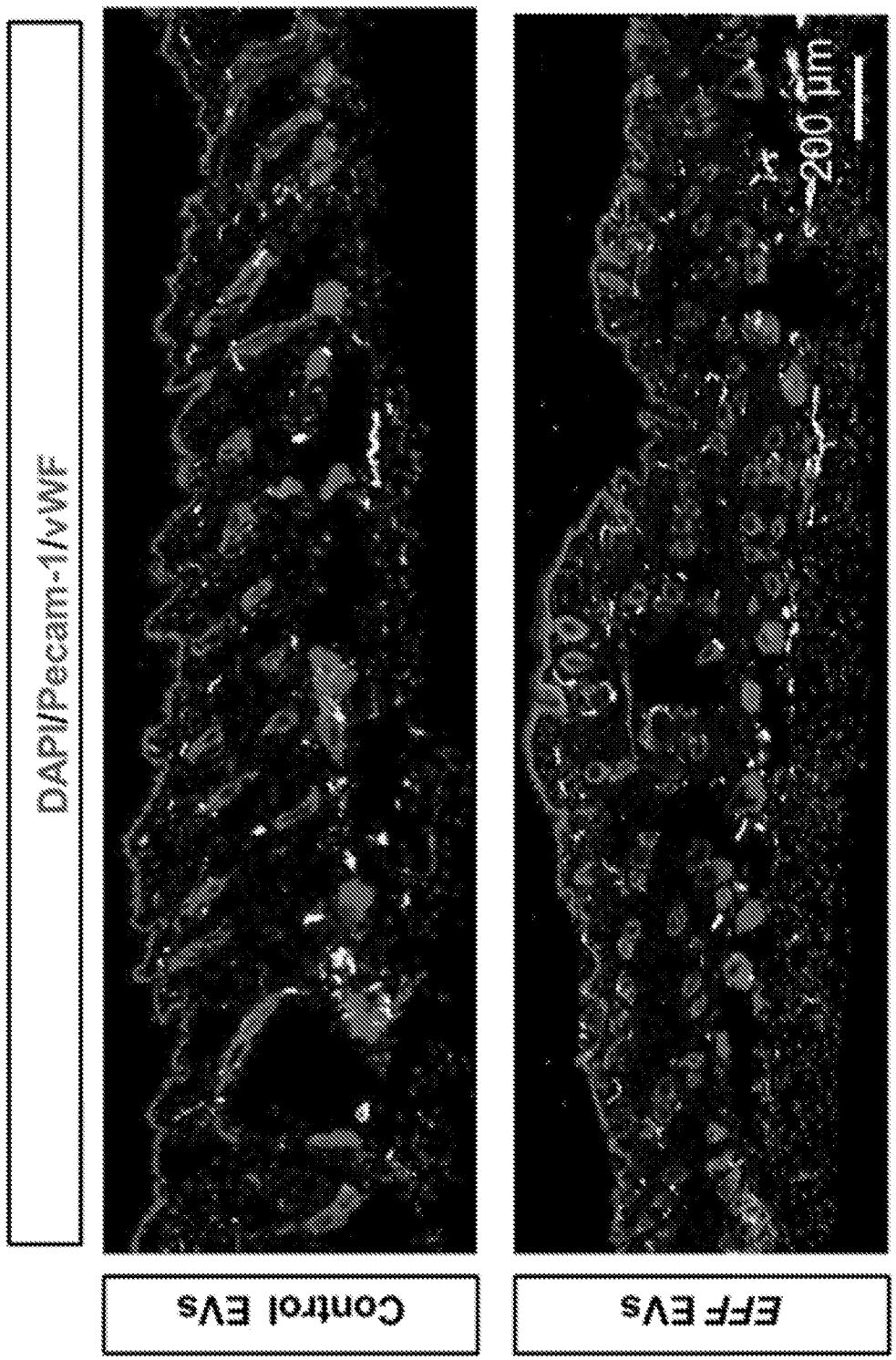
Figure 36E:
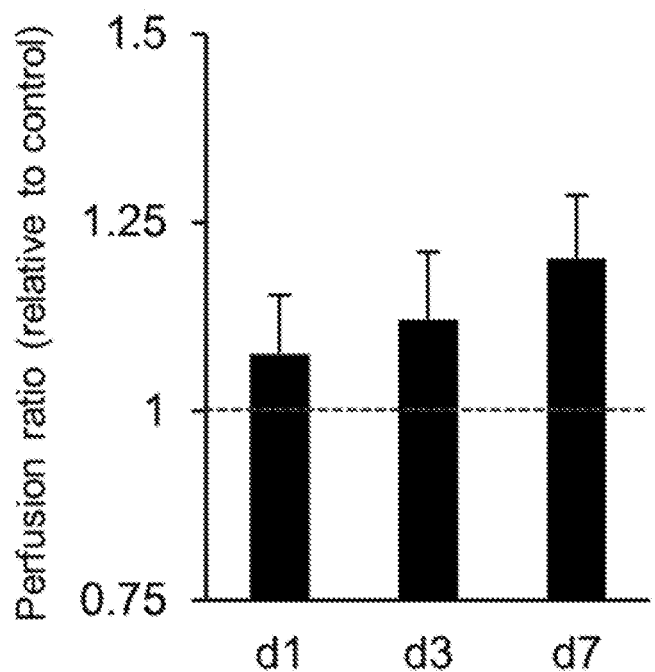

FIG. 34. Hindlimb ischemia experiments conducted using a Fsp1-Cre:R26RtdTomato mouse model show that some of the Pecam-1+ cells in the gastrocnemius muscle also exhibited positive tdTomato reporter signal (colocalization shown in white), thus suggesting a possible fibroblastic origin (e.g., skeletal muscle fibroblasts).

FIG. 35. EVs isolated from EFF TNT-treated dorsal skin help to mediate ischemic limb reperfusion. (a) Schematic diagram of injury/EV-mediated reperfusion. (b) qRTPCR characterization of the EV content. These EVs were isolated from multicellular tissue structures, and thus such fold changes represent averaged values between EVs presumably carrying little to no EFF (and additional factors) cargo, and EVs with relatively large amounts of EFF. Additional experiments (FIG. 25) confirmed that such EVs can reprogram remote naïve cells. (c, d) Laser speckle reperfusion analysis. (e) Immunofluorescence analysis of the gastrocnemius muscle showing increased angiogenesis for the EFF EV-treated limb compared to control (i.e., EVs derived from TNT-treated dorsal skin with a blank/mock solution). (f) High magnification micrographs showing co-expression of vascular markers following EV injection into the gastrocnemius. Such preliminary findings suggest a potentially therapeutic (proangiogenic) effect for in vivo-derived EVs loaded with pro-endothelial factors. n=3. *p<0.05 (Holm-Sidak method).

FIG. 36. EFF-laden EVs derived from EFF-transfected skin can modulate reprogramming in naïve cells. (a) EVs were isolated from TNT-treated (EFF vs. control) dorsal skin at different timepoints and analyzed via Nanosight. (b) EFF transfection led to increased release of EVs (>24 h) (n=3). (c) Exposing MEF cells to EFF-laden EVs resulted in the formation of discrete Pecam-1+ cellular pockets not seen in MEF cultures exposed to control EVs. Reprogramming efficacies, however, appear to be lower compared to direct nanochannel-based injection of EFF plasmids (FIG. 27). This could be potentially due to multiple factors, including differences in the delivery mechanism (e.g., direct electro-injection vs. endocytosis/fusion), and/or differences in local concentration between the in vitro and in vivo microenvironment. Additional experiments showed that (d) injecting EFF-laden EVs into uninjured tissue (i.e., dorsal skin) led to a noticeable increase in cellular components expressing endothelial markers such as Pecam-1 and vWF. (e) Laser speckle analysis, however, showed only a modest (~20%, p>0.05, ANOVA) increase in skin perfusion after day 3 compared to control EVs (red dashed line) (n=4). These findings suggest that the stimulus provided by EFF-laden EVs appears to be less likely to overcome the action of well-known angiostatic mechanisms responsible for modulating vascular homeostasis in healthy/uninjured tissues19. *p<0.05 (Holm-Sidak method).

Figure 37A:
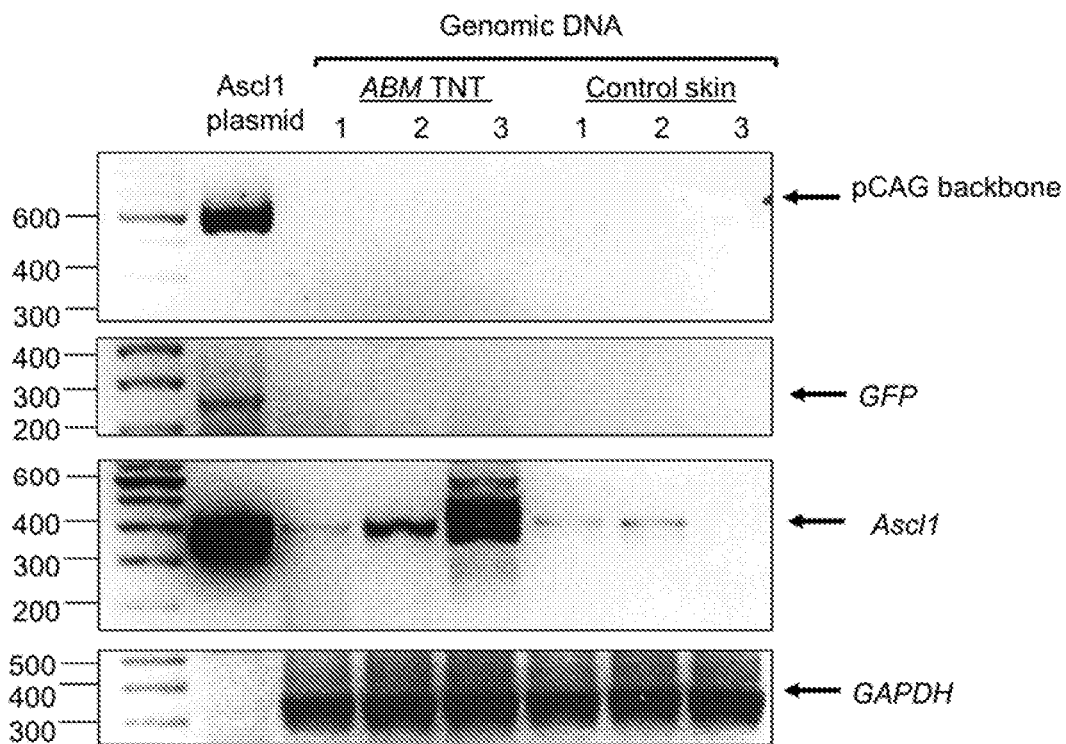
Figure 37B:
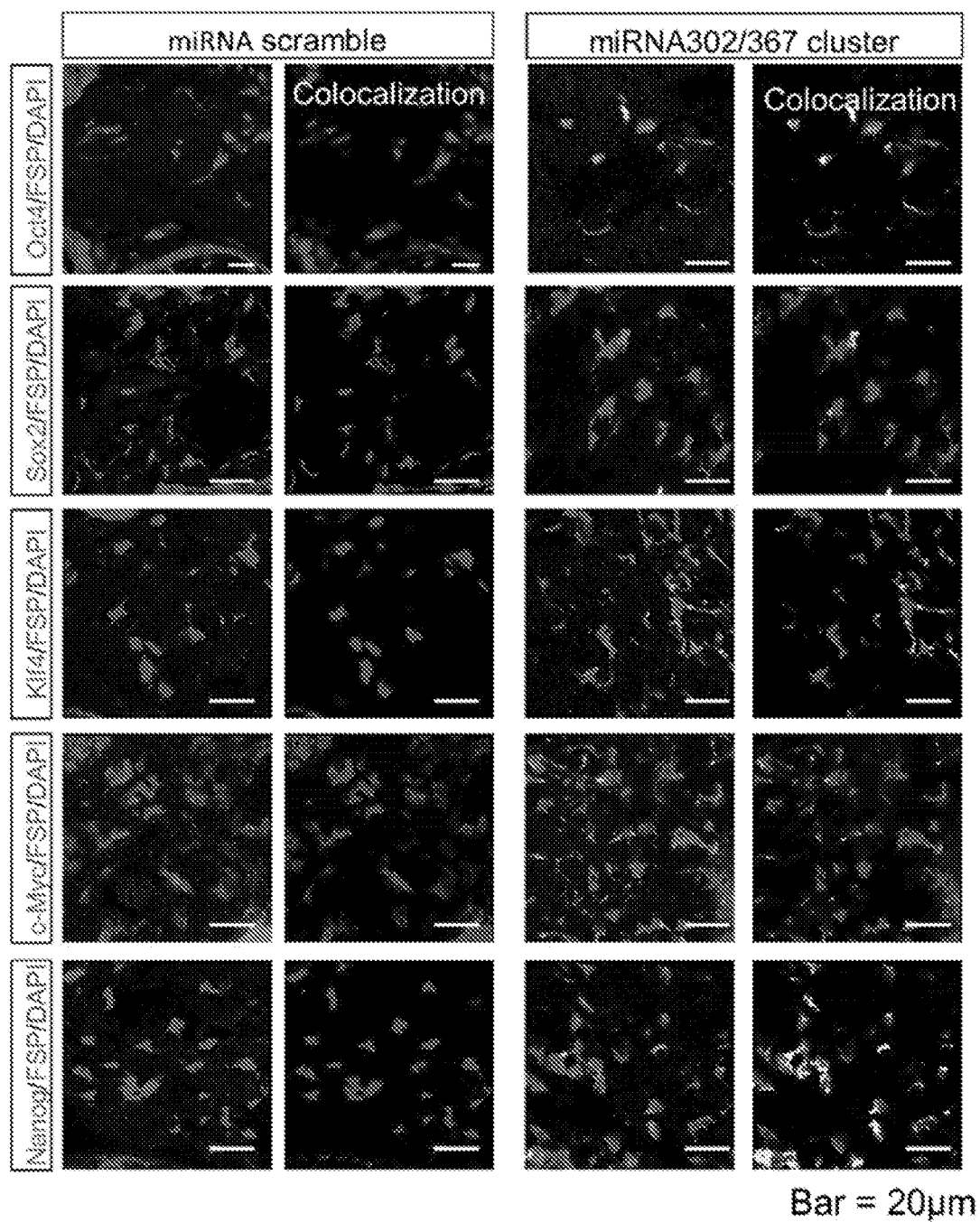
Figure 37C:
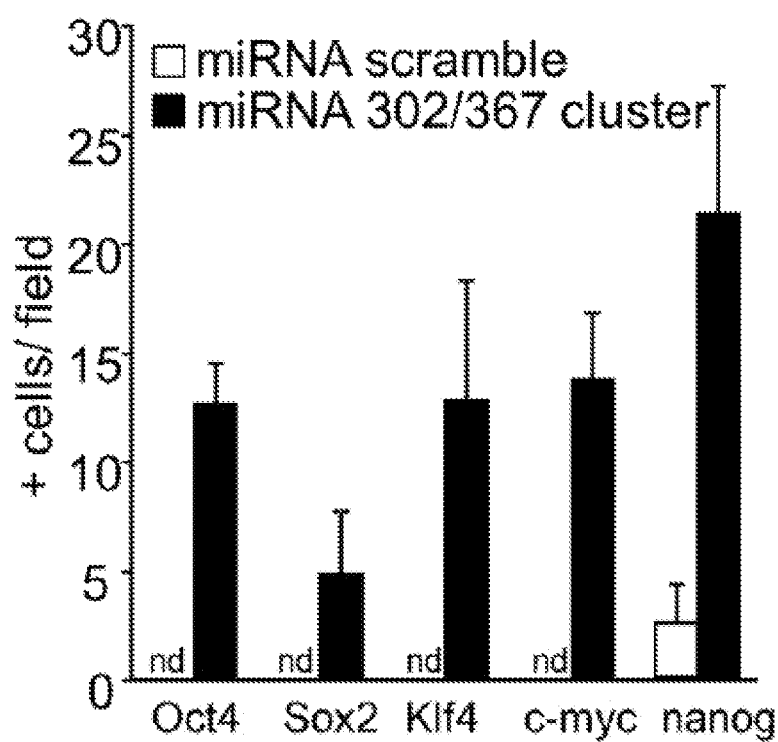

FIG. 37. TNT-based oligo RNA delivery and reprogramming. One of the limitations of plasmidic DNA-based reprogramming is the potential risk of insertional mutagenesis. In order to determine if genomic integration occurred after TNT-mediated delivery of reprogramming gene plasmids, a PCR was conducted from genomic DNA isolated from TNT-treated skin, and screened for sequences matching the plasmid backbone and/or reporter genes. (a) Our results did not show any traces of the plasmid backbone or reporters in genomic DNA, thus suggesting insertion/integration was highly unlikely in this case. However, this does not preclude it from happening in the future, especially if the plasmid configuration is modified (e.g., different backbones, linear vs. circular configurations, etc.). Taking this into consideration experiments were conducted to test whether the TNT platform could be used to reprogram skin tissue via RNA-based transfection. (b, c) TNT experiments with the microRNA302/367 cluster (i.e., miRNA302a/b/c+miRNA367), which has been previously reported to induce pluripotency in somatic cells in vitro20, showed that TNT-based delivery of such cocktail led to a marked induction of pluripotency markers in the skin as early as day 7. Induced pluripotency was not detected in skin tissue that was TNT-treated with scrambled miRNAs.

Figure 38:
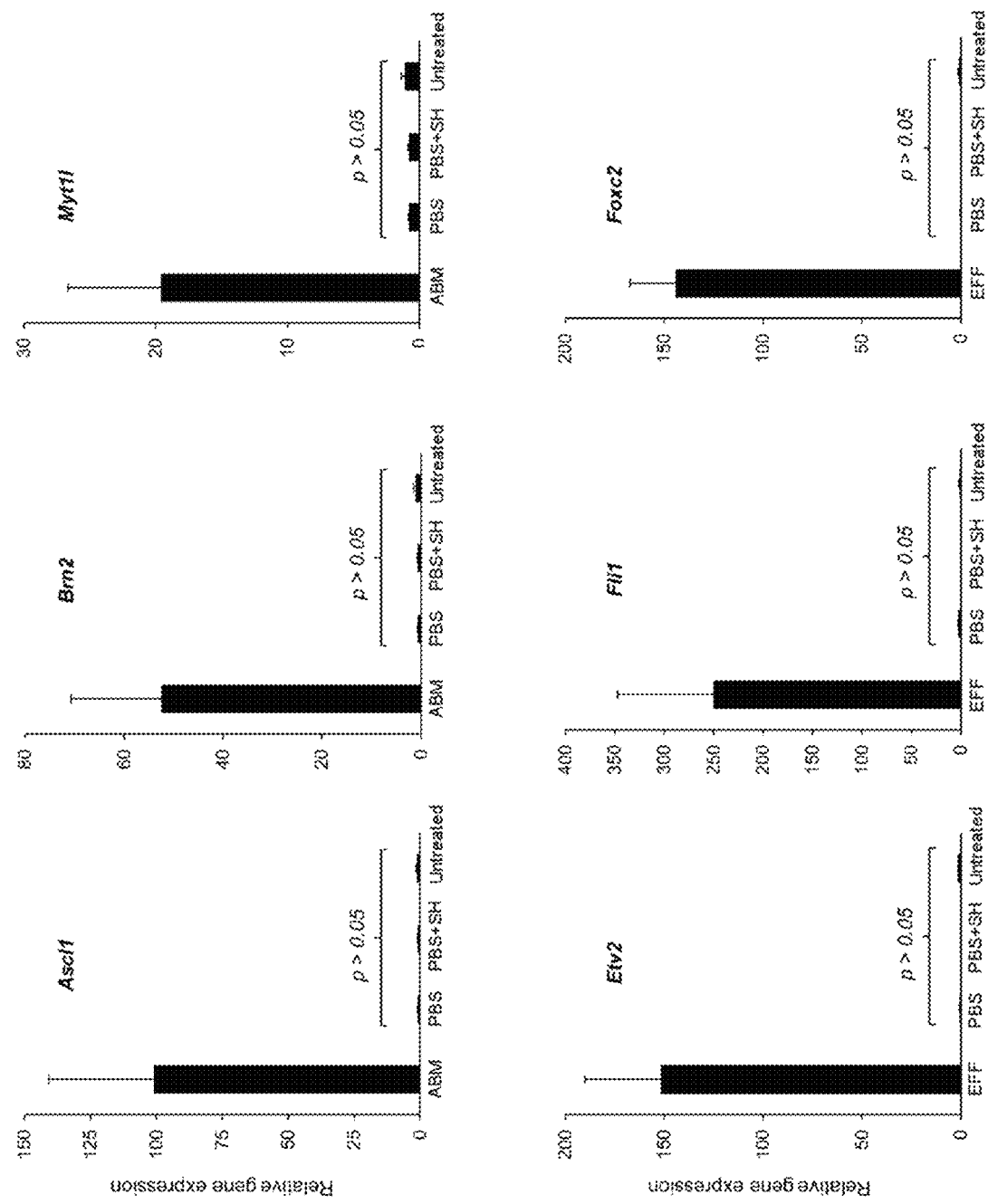

FIG. 38. Comparing different TNT controls. TNT was conducted on dorsal skin of C57BL/6 mice (n=3-5) with ABM/EFF, a blank solution of phosphate buffered saline (PBS), and PBS+sham/empty plasmids (PBS+SH). Untreated skin was used for comparison purposes. Gene expression analysis after 24 h shows no significant differences (ANOVA, Holm-Sidak method) between any of the control groups (PBS, PBS+SH, or untreated skin).

DETAILED DESCRIPTION

Disclosed herein are compositions and methods for reprogramming somatic cells into vasculogenic cells and/or endothelial cells both in vitro and in vivo.

Compositions

Disclosed are polynucleotides comprising two or more nucleic acid sequences encoding proteins selected from the group consisting of ETV2, FOXC2, and FLI1.

The amino acid and nucleic acid sequences encoding ETV2, FOXC2, and FLI1 are known in the art. For example, the gene ID for *Mus musculus* ets variant 2 (Etv2) is 14008. The gene ID for *Mus musculus* forkhead box C2 (Foxc2) is 14234. The gene ID for *Mus musculus* Friend leukemia integration 1 (Fli1) is 14247. While mouse (*Mus musculus*) sequences were used and are disclosed herein, other mammalian forms of these proteins, including human forms, are known in the art and can be used in the disclosed methods.

In some embodiments, the ETV2 comprises the *Mus musculus* amino acid sequence MDLWNWDEASLQEVPPGDKLTGLGAEFGFYFPEVALQEDTPITPMNVEGCWKGFP ELDWNPALPHEDVPFQAEPVAHPLPWSRDWTDLGCNTSDPWSCASQTPGPAPPG TSPSPFVGFEGATGQNPATSAGGVPSWSHPPAAW-STTSWDCSVGPSGATYWDNG LGGEA-HEDYKMSWGGSAGSDYTTTWNTGLQDCSIPFEGHQSPAFTTPSKSNKQS DRATLTRYSKTNHRGPIQLWQFLLELLHDGARSSCIRWTGNSREFQLCDPKEVARL WGERKRKPGM-NYEKLSRGLRYYYRRDIVLKSGGRKYTYRFG-GRVPVLAYQDDMG HLPGAEGQ (SEQ ID NO:2), or an amino acid sequence that has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2.

In some embodiments, the nucleic acid sequence encoding the ETV2 comprises the nucleic acid sequence AGAACCGTCAGAACAAGCATCCATGGACCTGTG-GAACTGGGATGAGGCGTCAC TGCAG-GAAGTGCCTCCTGGGGACAAGCTGACAGGACTGG-GAGCGGAATTTGGT TTCTATTTCCCTGAAGTGGCTCTA-CAAGAGGACACACCGATCACACCAATGAACG TAGAAGGCTGCTG-GAAAGGGTTCCCAGAGCTGGACTG-GAACCCCGCTTTACCT CACGAA-GACGTACCTTTCCAGGCGGAGCCCGTTGCTCACCC CCTTCCGTGGTC GCGAGACTGGACAGACCTGG-GATGCAACACCTCGGACCCGTGGAGCTGTGCTT CACAGACGCCAGGCCCTGCCCCTCCTGGCACGA-GCCCCTCCCCCTTCGTCGG CTTT-GAAGGGGCGACCGGCCAGAATCCTGC-CACCTCGGCAGGAGGGGTCCCC TCGTGGTCGCACCCTCCAGCTGCCTGGAGCAC-TACCAGCTGGGACTGTTCTGT GGGCCCCAGTGGCGCCACC-TACTGGGACAATGGCCTGGGCGGGGAAGCGCAT GAGGACTATAAAATGT-CATGGGGCGGGTCTGCCGGTTCGGACTACACCAC-CACG TGGAATACTGGGCTGCAGGACTGCAG-CATCCCTTTCGAGGGGCACCAGAGTCC AGCATTCACCACGCCCTC-CAAATCGAACAAGCAGTCTGATAGAGCCACAT-TGACT CGCTACTCCAAAACTAACCACCGAGGTCC-CATTCAGCTGTGGCAATTCCTCCTG GAGCTGCTCCACGACGGGGCTCGCAGCAGCTG-CATCCGCTGGACGGGCAATA GCCGCGAGTTCCAGCTGTGCGACCC-CAAAGAGGTGGCCCGGCTGTGGGGCGA GCGCAAGAGGAAGCCGGGAATGAATTAT-GAGAAACTGAGTCGAGGTCTACGTTA TTAT-TACCGCCGCGACATCGTGCT-CAAGAGTGGTGGGCGCAAGTACACATACCG CTTCGGGGGACGTGTGCCTGTCCTCGCCTATCAG-GATGATATGGGGCATCTGCC AGGTGCAGAAGGC-CAATAAAACAAAAAACAAAAACAAAA (SEQ ID NO:3), or a nucleic acid sequence that hybridizes to a nucleic acid sequence consisting of SEQ ID NO:3 under stringent hybridization conditions.

In some embodiments, the FOXC2 comprises the amino acid sequence MQARYSVSDPNALGWPYLSEQNYYRAAGSYGGMASPMGVYSGHPEQYGAGMG RSYAPYHHQPAAPKDLVKPPYSYIALITMAIQNAPEK-KITLNGIYQFIMDRFPFYRENK QGWQNSIRHNLSL-NECFVKVPRDDKKPGKGSYWTLDPDSYNMFENG-SFLRRRRR FKKKDVPKDKEERAHLKEPPSTTAKGAPTGTP-VADGPKEAEKKVVVKSEAASPALP VITKVETL-SPEGALQASPRSASST-PAGSPDGSLPEHHAAAPNGLPGFSVETIMTLRT SPPGGDLSPAAARAGLWPPLALPYAAAPPAAYTQP- CAQGLEAAGSAGYQCSMRA MSLYTGAERPAHVCVPPALDEALSDHPSGPGSPLGALNLAAGQEGALGASGHHHQ HHGHLHPQAPPPAPQPPPAPQPATQATSWYLNHGGDLSHLPGHTFATQQQTFPNV REMFNSHRLGLDNSSLGESQVSNASCQLPYRATPSLYRHAAPYSYDCTKY (SEQ ID NO:4), or an amino acid sequence that has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4.

In some embodiments, the nucleic acid sequence encoding the FOXC2 comprises the nucleic acid sequence GAAACTTTTCCCAATCCTAAAAGGGACT TTGCTTCTTTTTCCGGGCTCGGCCGC GCAGCCTCTCCGGACCCTAGCTCGCTGACGCTGCG GGCTGCAGTTCTCCTGGC GGGGCCCCGAGAGCCGCTGTCTCCTTTTCTAGCAC TCGGAAGGGCTGGTGTCG CTCCACGGTCGCGCGTGGCGTCTGTGCCGCAGCTCAG GGCTGCCACCCGCC AAGCCGAGAGTGCGCGGCCAGCGGGGCCGCCTGCCGTGCACCCTTCAGGATG CCGATCCGCCCGGTCGGCTGAACCCGAGCGCCGGCGTCTTCCGCGCGTGGAC CGCGAGGCTGCCCCGAGTCGGGGCTGCCTGCATCGCTCCGTCCCTTCCTGCTC TCCTGCTCCGGGCCTCGCTCGCCGCGGGCCGCAGTCGGTGCGCGCAGGCGG CGACCGGGCGTCTGGGACGCAGCATGCAGGCGCGTTACTCGGTATCGGACCCC AACGCCCTGGGAGTGGTACCCTATTTGAGTGAGCAAAACTACTACCGGGCGGCC GGCAGCTACGGCGGCATGGCCAGCCCCATGGGCGTCTACTCCGGCCACCCGG AGCAGTACGGCGCCGGCATGGGCCGCTCCTACGCGCCCTACCACCACCAGCCC GCGGCGCCCAAGGACCTGGTGAAGCCGCCCTACAGCTATATAGCGCTCATCACC ATGGCGATCCAGAACGCGCCAGAGAAGAAGATCACTCTGAACGGCATCTACCAG TTCATCATGGACCGTTTCCCCTTCTACCGCGAGAACAAGCAGGGCTGGCAGAAC AGCATCCGCCACAACCTGTCACTCAATGAGTGCTTCGTGAAAGTGCCGCGCGAC GACAAGAAGCCGGGCAAGGGCAGCTACTGGACGCTCGACCCGGACTCCTACAA CATGTTCGAGAATGGCAGCTTCCTGCGGCGGCGGCGGCGCTTCAAGAAGAAGG ATGTGCCCAAGGACAAGGAGGAGCGGGCCCACCTCAAGGAGCCGCCCTCGAC CACGGCCAAGGGCGCTCCGACAGGGACCCCGGTAGCTGACGGGCCCAAGGAG GCCGAGAAGAAAGTCGTGGTTAAGAGCGAGGCGGCGTCCCCGCGCTGCCGG TCATCACCAAGGTGGAGACGCTGAGCCCCGAGGGAGCGCTGCAGGCCAGTCC GCGCAGCGCATCCTCCACGCCCGCAGGTTCCCCAGACGGCTCGCTGCCGGAG CACCACGCCGCGGCGCCTAACGGGCTGCCCG GCTTCAGCGTGGAGACCATCAT GACGCTGCGCACGTCGCCTCCGGCGGCGATCTGAGCCCAGCGGCCGCGCG CGCCGGCCTGGTGGTGCCACCGCTGGCACTGCCATACGCGCAGCGCCACCC GCCGCTTACACGCAGCCGTGCGCGCAGGGCCTGGAGGCTGCGGGCTCCGCG GGCTACCAGTGCAGTATGCGGGCTATGAGTCTGTA CACCGGGGCCGAGCGGCC CGCGCACGTGTGCGTTCCGCCCGCGCTGGACGAG GCTCTGTCGGACCCACCCG AGCGCCCCGGCTCCCCGCTCGGCGCCCT CAACCTCGCAGCGGGTCAGGAGG GCGCGTTGGGGGCCTCGGGTCACCACCACCAGCATCACGGCCACCTCCACCC GCAGGCGCCACCGCCCGCCCCGCAGCCCCCTCCCGCGCCGCAG CCCGCCAC CCAGGCCACCTCCTGGTATCTGAACCACGGCGGGGACCTGAGCCACCTCCCCG GCCACACGTTTGCAACCCAACAGCAAACTTTCCCCAACGTCCGGGAGATGTTCA ACTCGCACCGGCTAGGACTGGACAACTCGTCCCTC GGGGAGTCCCAGGTGAGC AATGCGAGCTGTCAGCTGCCCTATCGAGCTACGCCGTCCCTCTACCGCCACGCA GCCCCCTACTCTTACGACTGCACCAAATACTGAGGCTGTCCAGTCCGCTCCAGC CCCAGGACCGCACCGGCTTCGCCTCCTCCATGGGAACCTTCTTCGACGGAGCC GCAGAAAGCGACGGAAAGCGCCCCTCTCTCAGAACCAGGAGCAGAGAGCTCC GTGCAACTCGCAGGTAACTTATCCGCAGCTCAGTTTGAGATCTCAGCGAGTCCC TCTAAGGGGGATGCAGCCCAGCAAAACGAAATACAGATTTTTTTTTAATTCCTTC CCCTACCCAGATGCTGCGCCTGCTCCCCTTGGGGCTTCATAGATTAGCTTATGGA CCAAACCCCATAGGGACCCCTAATGACTTCTGTGGAGATTCTCCACGGGCGCAA GAGGTCTCTCCGGATAAGGTGCCTTCTGTAAACGAGTGCGGATTTGTAACCAGG CTATTTTGTTCTTGCCCAGAGCCTTTAATATAATATTTAAAGTTGTGTCCACTGGAT AAGGTTTCGTCTTGCCCAACTGTTACTGCCAAATTGAATTCAAGAAACGTGTGTG GGTCTTTTCTCCCACGTCACCATGATAAAATAGGTCCCTCCCAAACTGTAGGT CTTTTACAAAACAAGAAAATAATTTATTTTTTTGTTGTTGTTGGATAACGAAATTAAG TATCGGATACTTTTAATTTAGGAAGTGCATGGCTTTGTACAGTAGATGCCATCTGG GGTATTCCAAAAACACACCAAAAGACTTTAAAATTTCAATCTCACCTGTGTTTGTC TTATGTGATCTCAGTGTTGTATTTACCTTAAAATAAACCCGTGTTGTTTTTCTGCCC AAAAAAAAAAAAAAAA (SEQ ID NO:5), or a nucleic acid sequence that hybridizes to a nucleic acid sequence consisting of SEQ ID NO:5 under stringent hybridization conditions.

In some embodiments, the FLI1 comprises the amino acid sequence MDGTIKEALSWSDDQSLFDSAYGAAAHLPKADMTASGSPDYGQPHKINPLPPQQE WINQPVRVNVKREYDHMNGSRESPVDCSVSKCNKLVGGGEANPMNYNSYMDEKN GPPPPNMTTNERRVIVPADPTLVVTQEHVRQWLEWAIKEYGLMEIDTSFFQNMDGK ELCKMNKEDFLRATSAYNTEVLLSHLSYLRESSLLAYNTTSHTDQSSRLNVKEDPSY DSVRRGAWNNNMNSGLNKSPLLGGSQTMGKNTEQRPQPDPYQILGPTSSRLANP GSGQIQLWQFLLELLSDSANASCITWEGTNGEFKMTDPDEVARRWGERKSKPNMN YDKLSRALRYYYDKNIMTKVHGKRYAYKFDFHGIAQALQPHPTETSMYKYPSDISYM PSYHAHQQKVNFVPSHPSSMPVTSSSFFGAASQYWTSPTAGIYPNPSVPRHPNTH VPSHLGSYY (SEQ ID NO:6), or an amino acid sequence that has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:6.

In some embodiments, the nucleic acid sequence encoding the FLI1 comprises the nucleic acid sequence AAAGTGAAGTCACTTCCCAAAATTAGCTGAAAAAAAGTTTCATCCGGTTAACTGT CTCTTTTTCGATCCGCTACAACAACAAACGTGCACAGGGGAGCGAGGGCAGGG CGCTCGCAGGGGGCACTCAGAGAGGGCCCAGGGCGCCAAAGAGGCCGCGCC GGGCTAATCTGAAGGGGCTACGAGGTCAGGCTGTAACCGGGTCAATGTGTGGA ATATTGGGGGGCTCGGCTGCAGACTTGGCCAAATGGACGGGACTATTAAGGAGG CTCTGTCTGTGGTGAGTGACGATCAGTCCCTTTTTGATTCAGCATACGGAGCGG CAGCCCATCTCCCCAAGGCAGATATGACTGCTTCGGGGAGTCCTGACTACGGGC AGCCCCACAAAATCAACCCCCTGCCACCGCAGCAGGAGTGGATCAACCAGCCA GTGAGAGTCAATGTCAAGCGGGAGTATGACCACATGAATGGATCCAGGGAGTCT CCGGTGGACTGCAGTGTCAGCAAATGTAACAAGCTGGTGGGCGGAGGCGAAGC CAACCCCATGAACTATAATAGCTACATGGATGAGAAGAACGGCCCCCCTCCTCCC AACATGACCACCAACGAACGGAGAGTCATTGTGCCTGCAGACCCCACACTGTG GACACAGGAGCACGTTCGACAGTGGCTGGAGTGGGCTATAAAGGAATACGGATT GATGGAGATTGACACTTCCTTCTTCCAGAACATGGATGGCAAGGAATTGTGTAAA ATGAACAAGGAGGACTTCCTCCGAGCCACCTCCGCCTACAACACAGAAGTGCTG TTGTCGCACCTCAGTTACCTCAGGGAAAGTTCACTGCTGGCCTATAACACAACCT CCCATACAGACCAGTCCTCACGACTGAATGTCAAGGAAGACCCTTCTTATGACTC TGTCAGGAGAGGAGCATGGAACAATAATATGAACTCTGGCCTCAACAAAAGTCCT CTCCTTGGAGGATCACAGACCATGGGCAAGAACACTGAGCAGCGGCCCCAGCC AGATCCTTATCAGATCCTGGGGCCAACCAGCAGCCGCCTAGCAAACCCTGGGAG TGGGCAGATCCAGCTGTGGCAGTTTCTCCTGGAACTACTGTCCGACAGCGCCAA CGCCAGCTGTATCACCTGGGAGGGGACCAACGGGGAGTTCAAAATGACGGACC CTGATGAGGTGGCCAGGCGCTGGGGAGAGCGGAAGAGCAAGCCCAACATGAAT TATGACAAGCTGAGCCGGGCCCTCCGATACTACTATGACAAAAACATTATGACCA AAGTGCATGGCAAAAGGTATGCCTACAAGTTTGACTTCCATGGCATTGCCCAGG CCCTGCAGCCACATCCAACAGAGACATCCATGTACAAGTATCCCTCTGATATCTC CTACATGCCTTCCTACCATGCCCATCAACAGAAGGTGAACTTTGTCCCGTCTCAC CCATCCTCCATGCCTGTCACCTCCTCCAGCTTCTTTTGGAGCAGCATCACAATACT GGACCTCCCCCACTGCTGGGATCTATCCAAACCCCAGTGTCCCCCGCCATCCTA ACACCCACGTGCCTTCACACTTAGGCAGCTACTACTAGAACTAACACCAGTTGGC CTTCTGGCTGAAGTTCCAGCTCTCCTACTGGATACTCTGGACTCTAAAAGGC ACAGTAGCCTTGAAGAGATAAGAAAACTGGATGTTCTTTCTTTTGGATAGAACCTT TGTATTTGTTCTTCTAAAAAAATTATTATTTTTATGTTAAAAACTTTTGTTTCCTCTAC CTGAAAAAAAAAAAAGATCATTCCATGAGCCAGTCCACCAGTTTGGATTCTCAAC CTCCTATCATCGAATGAGTTAAATATTTAGGTTACTGGAACGTTTATACCATGATT CTGAGAAAGGAGTACGCATTTTCTTTACTCTTTTTTTTATGACCAAAGCAGTTTC TTATCAGCACACGGGTCTCATCATTGTAGGATTCCCTACGATCATGAATCATGGAC TTGACCAGGGTTGGTCTGGTTTGAGACTTAGTAAAAGTCAAGGCAGGATGTTTAT AATCTTATCTTCGGAGGACTCAATTCAGTGGATGGCAACTGGAACACTGGCTCTG AGGCCAGTGAAGTTTTTGCCCAACTGGAATTTAAAAGATGTGTGTCTATGTGTG TATTTAAGAAGCCATTATTATTATTACAAAATTCCTCACAATGGGCAGTATGTGTTTGGG TGACTCTTCTCCCCAGAAATAGTCAGAATATGAACAAAGAAAGTTTAACACAAACT CAGACACTCCTGACGGGCAGAGGATTAAATAACATTTTTTTGGAGGGTTTAATAA CATTTTTGGAGGGGTTTTTTTGTTTGTTTTTGTTTTTGGGGGTTTTTTTTGTTTGTT TTTTGTTTTTTGGTTTTTGGTTTTTTTTTGTTTTTTTTTTTTTTGGTTTTGATTTTT AATGACAGTGAGTCCCAGAACTTTGAAAAGTCATGGGGATTCTAAACTCAGATT CGCAAACGCTGTGCGTTTGTCCAGACCAAGGTCAAACAATCAGAATAAG GCAACTAACTGTATAAATTATGCAGAGTTATTTTCCTATATCTCACAGTATTAAAAAA ATAAATAATTAAAAATTAAAGAATAAGTAAACGAGTTGACCTCGGTCACAAATGCA GTTTTACTATCAAATCAATCATTGTTATTTTTTTAAAATATAATTTGTACATCTTTGTC AATCTGTACATTTGGGCTATTTGTACGTTTTTGTAACTGTTTTTTTTTAATAAGCATA ATGTGACTATTGAAAACGAGGAGTTAAAAGTCACTGAGTTTTTAGGAAGAAAAAC CTAAAAATACAGTTATTTAACACGCATGCCCAAACAAGATCTGTTTAGACCTACAA CGCTTTAGAAATGTTTGTAAATAACAGAGTTGCAATAACCTGAAAAGGACAAACAA ACTTTTCTCTGTGCACACGAGGCACTCTCCTGCTCATATATTTTTAG ATGTGCAAATATATATATAATTTTTCAGGTAATCGTGACTTTTTAAACGATATTGTTAA GGTGACAACTCTTAGTCCACTGAAGACTAAGTTGTAAATAATTTGACCTTAATAA ATTGTGCCTTCTTCTTTTTCTTCTTCTCTCAGAAAAAAAAAAA (SEQ ID NO:7), or a nucleic acid sequence that hybridizes to a nucleic acid sequence consisting of SEQ ID NO:7 under stringent hybridization conditions.

In order to express a polypeptide or functional nucleic acid, the nucleotide coding sequence may be inserted into appropriate expression vector. Therefore, also disclosed is a non-viral vector comprising a polynucleotide comprising two or more nucleic acid sequences encoding the proteins selected from the group consisting of ETV2, FOXC2, and FLI1, wherein the two or more nucleic acid sequences are operably linked to an expression control sequence. In some embodiments, the nucleic acid sequences are operably linked to a single expression control sequence. In other embodiments, the nucleic acid sequences are operably linked to two or more separate expression control sequences.

In some embodiments, the non-viral vector comprises a plasmid selected from the group pIRES-hrGFP-21, pAd-IRES-GFP, and pCDNA3.0.

Methods to construct expression vectors containing genetic sequences and appropriate transcriptional and translational control elements are well known in the art. These methods include in vitro recombinant DNA techniques, synthetic techniques, and in vivo genetic recombination. Such techniques are described in Sambrook et al., Molecular Cloning, A Laboratory Manual (Cold Spring Harbor Press, Plainview, N.Y., 1989), and Ausubel et al., Current Protocols in Molecular Biology (John Wiley & Sons, New York, N.Y., 1989).

Expression vectors generally contain regulatory sequences necessary elements for the translation and/or transcription of the inserted coding sequence. For example, the coding sequence is preferably operably linked to a promoter and/or enhancer to help control the expression of the desired gene product.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity.

A "promoter" is generally a sequence or sequences of DNA that function when in a relatively fixed location in regard to the transcription start site. A "promoter" contains core elements required for basic interaction of RNA polymerase and transcription factors and can contain upstream elements and response elements.

"Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers, like promoters, also often contain response elements that mediate the regulation of transcription. Enhancers often determine the regulation of expression.

An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

Promoters used in biotechnology are of different types according to the intended type of control of gene expression. They can be generally divided into constitutive promoters, tissue-specific or development-stage-specific promoters, inducible promoters, and synthetic promoters.

Constitutive promoters direct expression in virtually all tissues and are largely, if not entirely, independent of environmental and developmental factors. As their expression is normally not conditioned by endogenous factors, constitutive promoters are usually active across species and even across kingdoms. Examples of constitutive promoters include CMV, EF1a, SV40, PGK1, Ubc, Human beta actin, and CAG.

Tissue-specific or development-stage-specific promoters direct the expression of a gene in specific tissue(s) or at certain stages of development. For plants, promoter elements that are expressed or affect the expression of genes in the vascular system, photosynthetic tissues, tubers, roots and other vegetative organs, or seeds and other reproductive organs can be found in heterologous systems (e.g. distantly related species or even other kingdoms) but the most specificity is generally achieved with homologous promoters (i.e. from the same species, genus or family). This is probably because the coordinate expression of transcription factors is necessary for regulation of the promoter's activity.

The performance of inducible promoters is not conditioned to endogenous factors but to environmental conditions and external stimuli that can be artificially controlled. Within this group, there are promoters modulated by abiotic factors such as light, oxygen levels, heat, cold and wounding. Since some of these factors are difficult to control outside an experimental setting, promoters that respond to chemical compounds, not found naturally in the organism of interest, are of particular interest. Along those lines, promoters that respond to antibiotics, copper, alcohol, steroids, and herbicides, among other compounds, have been adapted and refined to allow the induction of gene activity at will and independently of other biotic or abiotic factors.

The two most commonly used inducible expression systems for research of eukaryote cell biology are named Tet-Off and Tet-On. The Tet-Off system makes use of the tetracycline transactivator (tTA) protein, which is created by fusing one protein, TetR (tetracycline repressor), found in *Escherichia coli* bacteria, with the activation domain of another protein, VP16, found in the Herpes Simplex Virus. The resulting tTA protein is able to bind to DNA at specific TetO operator sequences. In most Tet-Off systems, several repeats of such TetO sequences are placed upstream of a minimal promoter such as the CMV promoter. The entirety of several TetO sequences with a minimal promoter is called a tetracycline response element (TRE), because it responds to binding of the tetracycline transactivator protein tTA by increased expression of the gene or genes downstream of its promoter. In a Tet-Off system, expression of TRE-controlled genes can be repressed by tetracycline and its derivatives. They bind tTA and render it incapable of binding to TRE sequences, thereby preventing transactivation of TRE-controlled genes. A Tet-On system works similarly, but in the opposite fashion. While in a Tet-Off system, tTA is capable of binding the operator only if not bound to tetracycline or one of its derivatives, such as doxycycline, in a Tet-On system, the rtTA protein is capable of binding the operator only if bound by a tetracycline. Thus the introduction of doxycycline to the system initiates the transcription of the genetic product. The Tet-On system is sometimes preferred over Tet-Off for its faster responsiveness.

In some embodiments, the nucleic acid sequences encoding ETV2, FOXC2, and/or FLI1 are operably linked to the same expression control sequence. Alternatively, internal ribosome entry sites (IRES) elements can be used to create multigene, or polycistronic, messages. IRES elements are able to bypass the ribosome scanning model of 5' methylated Cap dependent translation and begin translation at internal sites. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Disclosed are non-viral vectors containing one or more polynucleotides disclosed herein operably linked to an expression control sequence. Examples of such non-viral vectors include the oligonucleotide alone or in combination with a suitable protein, polysaccharide or lipid formulation.

Non-viral methods present certain advantages over viral methods, with simple large scale production and low host immunogenicity being just two. Previously, low levels of transfection and expression of the gene held non-viral methods at a disadvantage; however, recent advances in vector technology have yielded molecules and techniques with transfection efficiencies similar to those of viruses.

Examples of suitable non-viral vectors include, but are not limited to pIRES-hrGFP-2a, pAd-IRES-GFP, and pCDNA3.0.

Also disclosed are miR-200b inhibitors (antagonists) for use in the disclosed compositions and methods. miRNA antagonists form a duplex with target miRNAs, which prevents the miRNA from binding to its target mRNA. This results in increased translation of the mRNA that is targeted by the miRNA.

The disclosed miRNA antagonists are single-stranded, double stranded, partially double stranded or hairpin structured oligonucleotides that include a nucleotide sequence sufficiently complementary to hybridize to a selected miRNA or pre-miRNA target sequence. As used herein, the term "partially double stranded" refers to double stranded structures that contain less nucleotides than the complementary strand. In general, partially double stranded oligonucleotides will have less than 75% double stranded structure, preferably less than 50%, and more preferably less than 25%, 20% or 15% double stranded structure.

An miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation.

Given the sequence of an miRNA or a pre-miRNA, an miRNA antagonist that is sufficiently complementary to a portion of the miRNA or a pre-miRNA can be designed according to the rules of Watson and Crick base pairing. As used herein, the term "sufficiently complementary" means that two sequences are sufficiently complementary such that a duplex can be formed between them under physiologic conditions. An miRNA antagonist sequence that is sufficiently complementary to an miRNA or pre-miRNA target sequence can be 70%, 80%, 90%, or more identical to the miRNA or pre-miRNA sequence. In one embodiment, the miRNA antagonist contains no more than 1, 2 or 3 nucleotides that are not complementary to the miRNA or pre-miRNA target sequence. In a preferred embodiment, the miRNA antagonist is 100% complementary to an miRNA or pre-miRNA target sequence.

Useful miRNA antagonists include oligonucleotides have at least 6, 7, 8, 9, 10, 11, 12, 13, 14, 15, 16, 17, 18, 19, 20 or more contiguous nucleotides substantially complementary to an endogenous miRNA or pre-miRNA. The disclosed miRNA antagonists preferably include a nucleotide sequence sufficiently complementary to hybridize to an miRNA target sequence of about 12 to 25 nucleotides, preferably about 15 to 23 nucleotides.

In some embodiments, there will be nucleotide mismatches in the region of complementarity. In a preferred embodiment, the region of complementarity will have no more than 1, 2, 3, 4, or 5 mismatches.

In some embodiments, the miRNA antagonist is "exactly complementary" to a human miRNA. Thus, in one embodiment, the miRNA antagonist can anneal to the miRNA to form a hybrid made exclusively of Watson-Crick base pairs in the region of exact complementarity. Thus, in some embodiments, the miRNA antagonist specifically discriminates a single-nucleotide difference. In this case, the miRNA antagonist only inhibits miRNA activity if exact complementarity is found in the region of the single-nucleotide difference.

In one embodiment, the miRNA antagonists are oligomers or polymers of ribonucleic acid (RNA) or deoxyribonucleic acid (DNA) or modifications thereof. miRNA antagonists include oligonucleotides that contain naturally-occurring nucleobases, sugars and covalent internucleoside (backbone) linkages.

The miRNA antagonists can contain modified bases. Adenine, guanine, cytosine and uracil are the most common bases found in RNA. These bases can be modified or replaced to provide RNAs having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine). Alternatively, substituted or modified analogs of any of the above bases can be used. Examples include, but are not limited to, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N4-acetyl cytosine, 2-thiocytosine, N6-methyladenine, N6-isopentyladenine, 2-methylthio-N6-isopentenyladenine, N-methylguanines, or O-alkylated bases.

The disclosed miRNA antagonists can be modified to enhanced resistance to nucleases. Thus, the disclosed miRNA antagonists can be an oligomer that includes nucleotide modification that stabilized it against nucleolytic degradation. The oligomer can be a totalmer, mixmer, gapmer, tailmer, headmer or blockmer. A "totalmer" is a single stranded oligonucleotide that only comprises non-naturally occurring nucleotides. The term "gapmer" refers to an oligonucleotide composed of modified nucleic acid segments flanking at least 5 naturally occurring nucleotides (i.e., unmodified nucleic acids). The term "blockmer" refers to a central modified nucleic acid segment flanked by nucleic acid segments of at least 5 naturally occurring nucleotides. The term "tailmer" refers to an oligonucleotide having at least 5 naturally occurring nucleotides at the 5'-end followed by a modified nucleic acid segment at the 3'-end. The term "headmer" refers to oligonucleotide having a modified nucleic acid segment at the 5'-end followed by at least 5 naturally occurring nucleotides at the 3'-end. The term "mixmer" refers to oligonucleotide which comprise both naturally and non-naturally occurring nucleotides. However, unlike gapmers, tailmers, headmers and blockmers, there is no contiguous sequence of more than 5 naturally occurring nucleotides, such as DNA units.

Modified nucleic acids and nucleotide surrogates can include one or more of: (i) replacement of one or both of the non-linking phosphate oxygens and/or of one or more of the linking phosphate oxygens; (ii) replacement of a constituent of the ribose sugar, e.g., of the 2' hydroxyl on the ribose sugar, or wholesale replacement of the ribose sugar with a structure other than ribose; (iii) wholesale replacement of the phosphate moiety with "dephospho" linkers; (iv) modification or replacement of a naturally occurring base; (v) replacement or modification of the ribose-phosphate backbone; or (vi) modification of the 3' end or 5' end of the RNA, e.g., removal, modification or replacement of a terminal phosphate group or conjugation of a moiety, such as a fluorescently labeled moiety, to either the 3' or 5' end of RNA.

The miRNA antagonists can contain modified sugar groups. For example, the 2' hydroxyl group (OH) can be modified or replaced with a number of different "oxy" or "deoxy" substitutents.

Examples of "oxy"-2' hydroxyl group modifications include alkoxy or aryloxy, "locked" nucleic acids (LNA) in which the 2' hydroxyl is connected, for example, by a methylene bridge or ethylene bridge to the 4' carbon of the same ribose sugar; amino, O-AMINE and aminoalkoxy. Oligonucleotides containing only methoxyethyl groups (MOE) exhibit nuclease stabilities comparable to those modified with the robust phosphorothioate modification.

"Deoxy" modifications include hydrogen, halo, amino, cyano; mercapto, alkyl-thio-alkyl, thioalkoxy, and alkyl, cycloalkyl, aryl, alkenyl and alkynyl, which may be optionally substituted. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Also included are "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The disclosed miRNA antagonists can contain modified phosphate groups. The phosphate group is a negatively charged species. The charge is distributed equally over the two non-linking oxygen atoms. However, the phosphate group can be modified by replacing one of the oxygens with a different substitutent. One result of this modification to RNA phosphate backbones can be increased resistance of the oligoribonucleotide to nucleolytic breakdown.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species.

The phosphate group can be replaced by non-phosphorus containing connectors. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Oligonucleotide-mimicking scaffolds can also be constructed wherein the phosphate linker and ribose sugar are replaced by nuclease resistant nucleoside or nucleotide surrogates. Examples include the mophilino, cyclobutyl, pyrrolidine and peptide nucleic acid (PNA) nucleoside surrogates. A preferred surrogate is a PNA surrogate.

The disclosed miRNA antagonists can also be modified at their 3' and/or 5' ends. Terminal modifications can be added for a number of reasons, including to modulate activity, to modulate resistance to degradation, or to modulate uptake of the miRNA antagonists by cells. Modifications can include modification or replacement of an entire terminal phosphate or of one or more of the atoms of the phosphate group. For example, the 3' and 5' ends of an oligonucleotide can be conjugated to other functional molecular entities such as labeling moieties or protecting groups. The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate. Other examples of terminal modifications include dyes, intercalating agents, cross-linkers, porphyrins, polycyclic aromatic hydrocarbons, artificial endonucleases, lipophilic carriers and peptide conjugates.

In some embodiments, the miRNA antagonists are antagomirs. Antagomirs are a specific class of miRNA antagonists that are described, for example, in US2007/0213292 to Stoffel et al. Antagomirs are RNA-like oligonucleotides that contain various modifications for RNase protection and pharmacologic properties such as enhanced tissue and cellular uptake. Antagomirs differ from normal RNA by having complete 2'-O-methylation of sugar, phosphorothioate backbone and a cholesterol-moiety at 3'-end.

Antagomirs can include a phosphorothioate at least the first, second, or third internucleotide linkage at the 5' or 3' end of the nucleotide sequence. In one embodiment, antagomirs contain six phosphorothioate backbone modifications; two phosphorothioates are located at the 5'-end and four at the 3'-end. Phosphorothioate modifications provide protection against RNase activity and their lipophilicity contributes to enhanced tissue uptake.

Examples of antagomirs and other miRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901, all of which are hereby incorporated by reference.

Custom designed Anti-miR™ molecules are commercially available from Applied Biosystems. Thus, in some embodiments, the antagomir is an Ambion® Anti-miR™ inhibitor. These molecules are chemically modified and optimized single-stranded nucleic acids designed to specifically inhibit naturally occurring mature miRNA molecules in cells.

Custom designed Dharmacon Meridian™ microRNA Hairpin Inhibitors are also commercially available from Thermo Scientific. These inhibitors include chemical modifications and secondary structure motifs. For example, Vermeulen et al. reports in US2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

The compositions disclosed can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Methods

Also disclosed are methods of reprogramming somatic cells into vasculogenic cells and/or endothelial cells that involve delivering intracellularly into the somatic cells a polynucleotide comprising two or more nucleic acid sequences encoding proteins selected form the group consisting of ETV2, FOXC2, and FLI1. In some embodiments, the nucleic acid sequences are present in non-viral vectors. In some embodiments, the nucleic acid sequences are operably linked to an expression control sequence. In other embodiments the nucleic acids are operably linked to two or more expression control sequences.

Also disclosed is a method of reprogramming somatic cells into vasculogenic cells and/or endothelial cells, comprising delivering intracellularly into the somatic cells a polynucleotide comprising one, two, or more nucleic acid sequences encoding proteins selected from the group consisting of ETV2, FOXC2, and FLI1 and a miR-200b inhibitor.

Also disclosed is a method of reprogramming somatic cells into vasculogenic cells and/or endothelial cells, comprising delivering intracellularly into the somatic cells a miR-200b inhibitor.

A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, after transfecting target cells with EFF, the cells can then pack the transfected genes (e.g. cDNA) into EVs, which can then induce endothelium in other somatic cells. Similarly, cells transfected with a miR-200b inhibitor will tend to exocytose part of that inhibitor in EVs, which could subsequently be used to induce endothelium in other/remote somatic cells. Therefore, also disclosed is a method of reprogramming somatic cells into vasculogenic cells and/or endothelial cells that involves exposing the somatic cell with an extracellular vesicle produced from a cell containing or expressing one or more proteins selected from the group consisting of ETV2, FOXC2, and FLI1. Also disclosed is a method of reprogramming somatic cells into vasculogenic cells and/or endothelial cells that involves exposing the somatic cell with an extracellular vesicle produced from a cell containing a miR-200b inhibitor.

Therefore, disclosed are methods of reprogramming somatic cells into vasculogenic cells and/or endothelial cells that involve exposing the somatic cells to extracellular vesicles (EVs) isolated from cells expressing or containing exogenous polynucleotides comprising one or more nucleic acid sequences encoding proteins selected form the group consisting of ETV2, FOXC2, and FLI1. Also disclosed are methods of reprogramming somatic cells into vasculogenic cells and/or endothelial cells that involve exposing the somatic cells to extracellular vesicles (EVs) isolated from cells transfected with a miR-200b inhibitor. For example, in some embodiments, the donor cells are transfected with the one or more disclosed polynucleotides or miR-200b inhibitor and cultured in vitro. EVs secreted by the donor cells can then collected from the culture medium. These EVs can then be administered to the somatic cells to reprogram them into vasculogenic cells and/or endothelial cells. In some embodiments, the donor cells can be any stromal/support cell from connective or epithelial tissues, including (but not limited to) skin fibroblasts, muscle fibroblast, skin epithelium, gut epithelium, and ductal epithelium.

Exosomes and microvesicles are EVs that differ based on their process of biogenesis and biophysical properties, including size and surface protein markers. Exosomes are homogenous small particles ranging from 40 to 150 nm in size and they are normally derived from the endocytic recycling pathway. In endocytosis, endocytic vesicles form at the plasma membrane and fuse to form early endosomes. These mature and become late endosomes where intraluminal vesicles bud off into an intra-vesicular lumen. Instead of fusing with the lysosome, these multivesicular bodies directly fuse with the plasma membrane and release exosomes into the extracellular space. Exosome biogenesis, protein cargo sorting, and release involve the endosomal sorting complex required for transport (ESCRT complex) and other associated proteins such as Alix and Tsg101. In contrast, microvesicles, are produced directly through the outward budding and fission of membrane vesicles from the plasma membrane, and hence, their surface markers are largely dependent on the composition of the membrane of origin. Further, they tend to constitute a larger and more heterogeneous population of extracellular vesicles, ranging from 150 to 1000 nm in diameter. However, both types of vesicles have been shown to deliver functional mRNA, miRNA and proteins to recipient cells.

In some embodiments, the polynucleotides are delivered to the somatic cells, or the donor cells for EVs, intracellularly via a gene gun, a microparticle or nanoparticle suitable for such delivery, transfection by electroporation, three-dimensional nanochannel electroporation, a tissue nanotransfection device, a liposome suitable for such delivery, or a deep-topical tissue nanoelectroinjection device. In some embodiments, a viral vector can be used. However, in other embodiments, the polynucleotides are not delivered virally.

Electroporation is a technique in which an electrical field is applied to cells in order to increase permeability of the cell membrane, allowing cargo (e.g., reprogramming factors) to be introduced into cells. Electroporation is a common technique for introducing foreign DNA into cells.

Tissue nanotransfection allows for direct cytosolic delivery of cargo (e.g., reprogramming factors) into cells by applying a highly intense and focused electric field through arrayed nanochannels, which benignly nanoporates the juxtaposing tissue cell members, and electrophoretically drives cargo into the cells.

In one embodiment, the disclosed compositions are administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of the disclosed compositions administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In some embodiments, the disclosed compositions and methods are used to create a vasculature that can serve as a scaffolding structure. This scaffolding structure can then be used, for example, to aid in the repair of nerve tissue. Applications of this include peripheral nerve injuries, and pathological/injurious insults to the central nervous system such as traumatic brain injury or stroke. In some embodiments, the created vasculature can be used to nourish composite tissue transplants, or any tissue graft.

In some embodiments, the disclosed compositions and methods are used to convert "unwanted" tissue (e.g., fat, scar tissue) into vasculature. Such newly formed vasculature is expected to "resorb" under non-ischemic conditions.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, the term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

A "nucleotide" as used herein is a molecule that contains a base moiety, a sugar moiety, and a phosphate moiety. Nucleotides can be linked together through their phosphate moieties and sugar moieties creating an internucleoside linkage. The term "oligonucleotide" is sometimes used to refer to a molecule that contains two or more nucleotides linked together. The base moiety of a nucleotide can be adenine-9-yl (A), cytosine-1-yl (C), guanine-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide that contains some type of modification to the base, sugar, and/or phosphate moieties. Modifications to nucleotides are well known in the art and would include, for example, 5-methylcytosine (5-me-C), 5 hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but are linked together through a moiety other than a phosphate moiety. Nucleotide substitutes are able to conform to a double helix type structure when interacting with the appropriate target nucleic acid.

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software.

By "specifically hybridizes" is meant that a probe, primer, or oligonucleotide recognizes and physically interacts (that is, base-pairs) with a substantially complementary nucleic acid (for example, a c-met nucleic acid) under high stringency conditions, and does not substantially base pair with other nucleic acids.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

A number of embodiments of the invention have been described. Nevertheless, it will be understood that various modifications may be made without departing from the spirit and scope of the invention. Accordingly, other embodiments are within the scope of the following claims.

EXAMPLES

Example 1: In Vitro Reprogramming of Somatic Cells into Induced Endothelial Cells With reference to FIG. 2, in vitro non-viral transfection and reprogramming experiments showed that the cotransfection of the genes Etv2, Foxc2, and Fli1 (EFF) efficiently reprogramed human and mouse primary fibroblasts into induced endothelial cells in less than one week. In these experiments, HDAF cells were non-virally transfected with EFF. Fluorescence micrographs of transfected cells showed strong expression of the endothelial marker Pecam-1 as well as reduced expression of the fibroblastic marker FSP (t=7 days post transfection). Gene expression analysis of endothelial markers for two different transfection conditions (Etv2 alone vs. cotransfection of EFF). Results showed a marked difference in gene expression, with EFF resulting in significantly stronger endothelial gene expression at day 7 post-transfection compared to Etv2 alone. Results from a tube formation assay showed that EFF-transfection cells were able to form blood vessel-like structures when cultured in Matrigel comparable to endothelial cells (HMEC, positive control). Control HDAF cells, on the other hand, were not able to form tube-like structures when cultured in Matrigel. MEF cells non-virally transfected with EFF also showed endothelial marker expression as early as 7 days post-transfection. tdTomato-MEF cells non-virally transfected with EFF fomented blood vessel formation following flank injection in NSG mice. These data are further summarized in Table 1 below.

TABLE 1

| Gene | Expression level with Etv2 transfection alone | Expression level with EFF cotransfection |
|---|---|---|
| VEGFR2 | <25x control | ~125x control |
| Pecam-1 | ~1.25x control | ~6x control |
| CDH5 | ~2x control | ~5x control |

Example 2: EFF TNT Leads to Increased Vascularization and Rescue of Skin Tissue Under Ischemic Conditions With reference to FIG. 1, once the efficacy of EFF to induce direct endothelial cell reprogramming was established in vitro, methods for in vivo reprogramming were tested. A one-time treatment of dorsal skin of C57BL/6 mice lasting only a few seconds led to increased angiogenesis of skin tissue by day 7, as evidenced by a significant increase in expression of Pecam-1 and vWF relative to control skin. High resolution laser speckle imaging showed enhanced perfusion (blood flow) to the EFF TNT-treated area over time. Ultrasound imaging of EFF TNT-treated skin confirmed the presence of superficial blood vessels with pulsatile behavior only 3 mm away from the surface of the skin, which suggests successful anastomosis with the parent circulatory system.

Monopedicle flap experiments showed increased flap necrosis for control tissue compared to TNT-treated skin. Laser speckle imaging showed increased blood flow to the flapped EFF TNT-treated tissue. These experiments demonstrate that EFF-mediated skin reprogramming led to functional reperfusion of ischemic tissues and that EFF delivery counteracted tissue necrosis under ischemic conditions.

Example 3. EFF TNT Rescues Whole Limbs from Necrotizing Ischemia

With reference to FIG. 3, further experiments verified that EFF delivery led to whole limb rescue in a hindlimb ischemia C57BL/6 mouse model. A one-time treatment of thigh skin lasting only a few seconds led to increased limb reperfusion following transection of the femoral artery. Perfusion was calculated based on the ratio of the ischemic vs. normal/contralateral limb. Control limbs showed more pronounced signs of tissue necrosis compared to EFF TNT-treated limbs at day 14. NMR-based measurements of muscle energetics confirmed increased ATP and PCr levels for EFF TNT-treated limbs compared to controls. Immunofluorescence analysis of the gastrocnemius muscle showed enhanced angiogenesis at day 14.

Figure 4A:
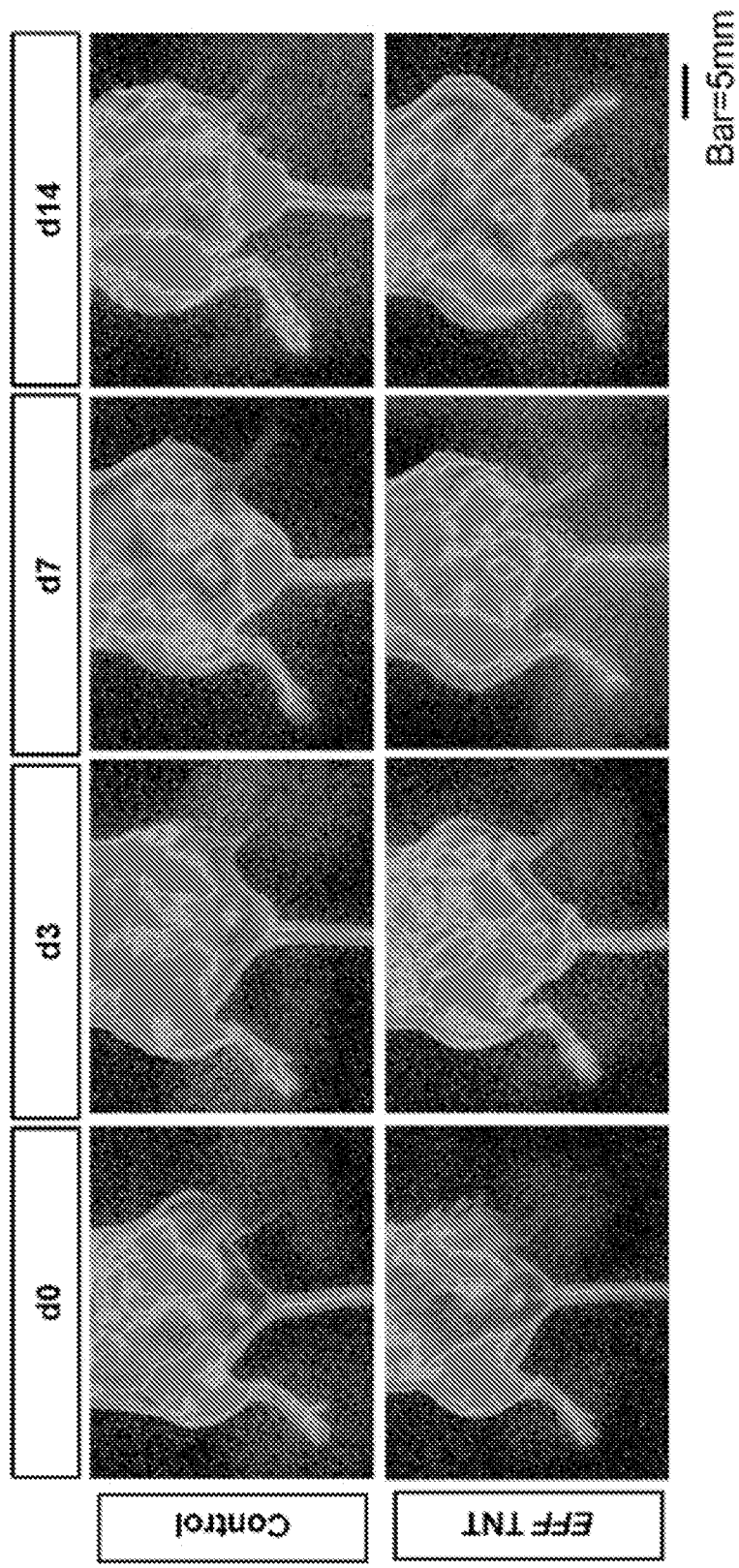
FIGS. 4A and 4B show that EFF-TNT rescues necrotizing limbs in Balb/c hindlimb ischemia models.
Figure 4B:
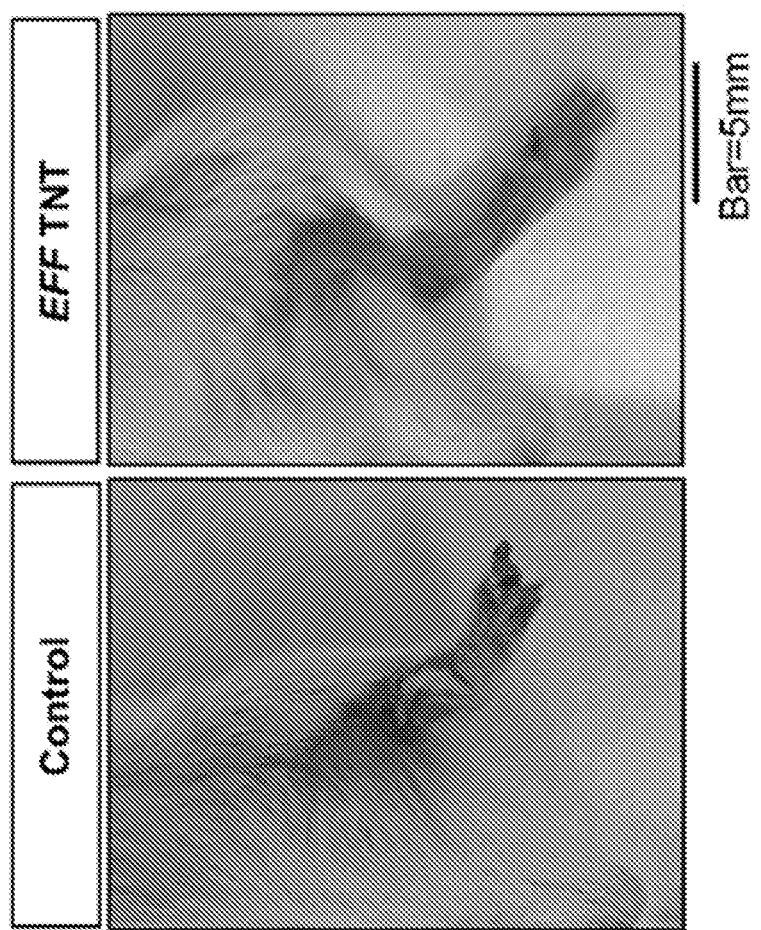
Figure 5A:
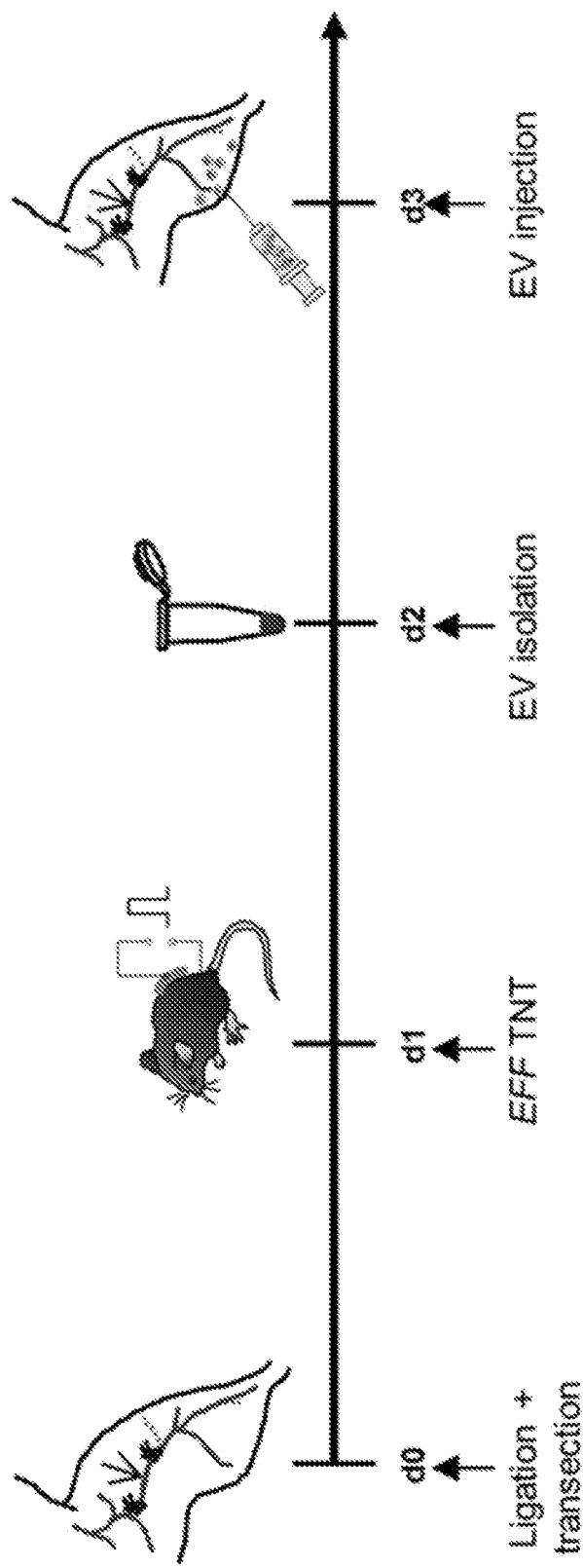
FIGS. 5A to 5E show that extracellular vesicles (EVs) isolated from EFF TNT-treated dorsal skin help to mediate ischemic limb reperfusion and rescue.
Figure 5B:
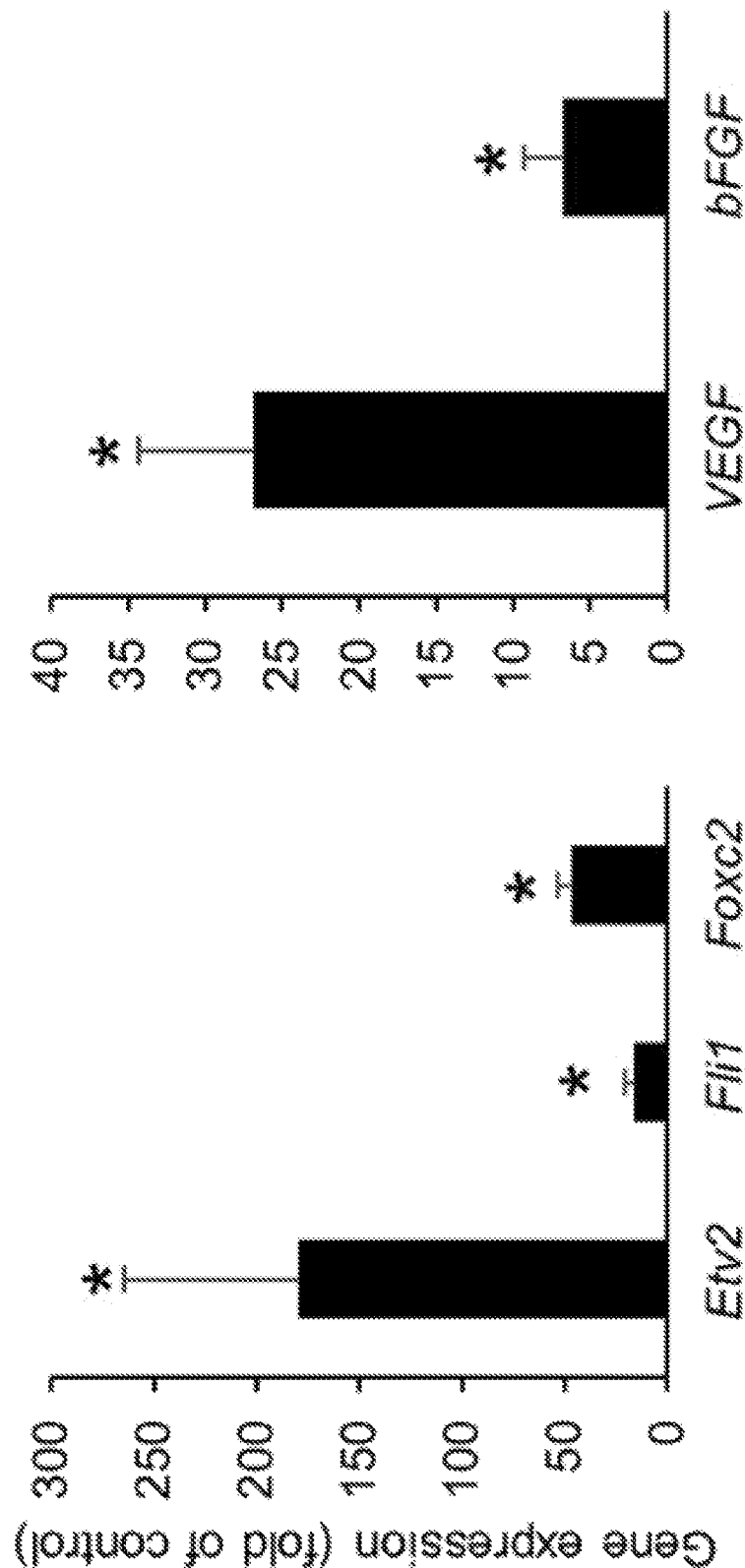
Figure 5C:
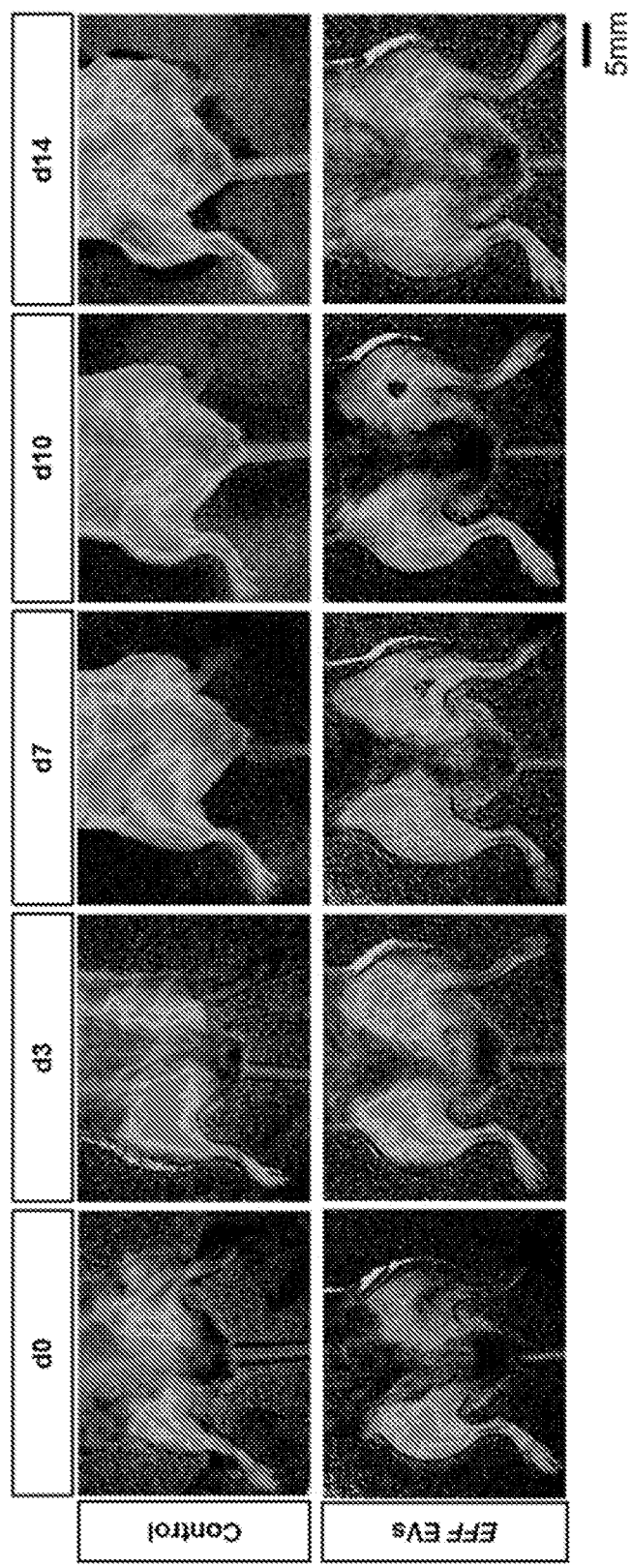
Figure 5D:
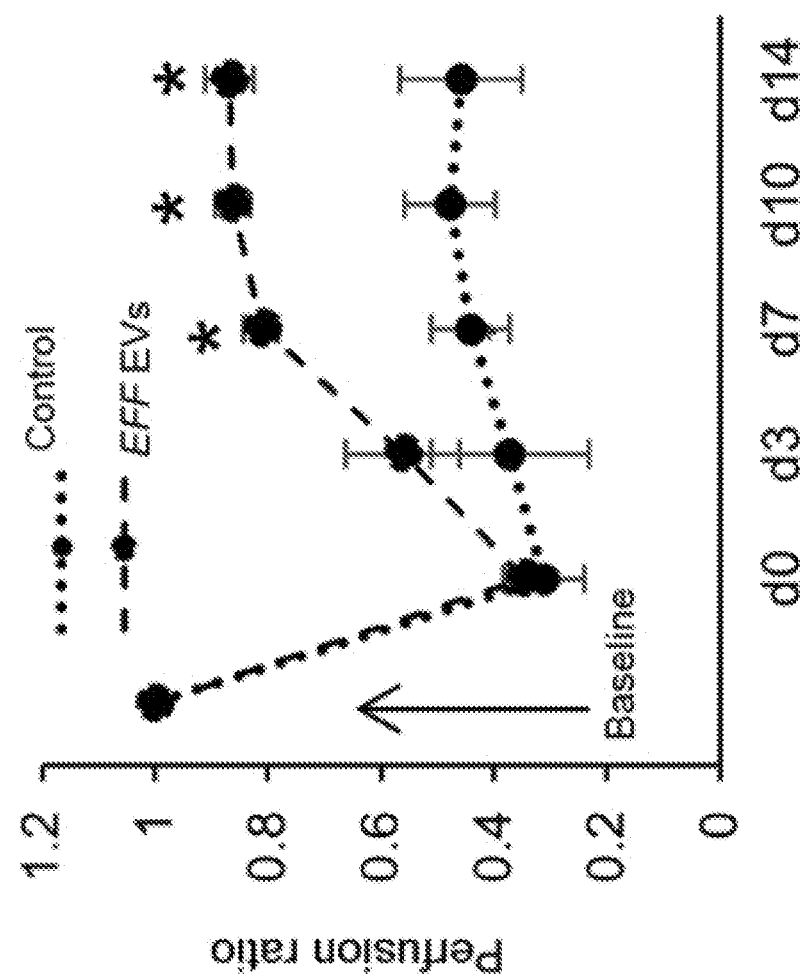
Figure 5E:
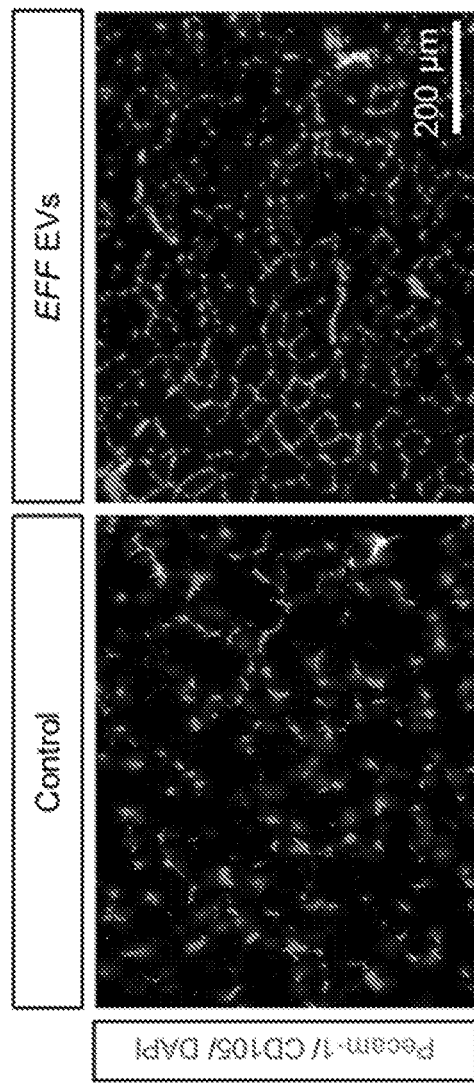

Example 4. EFF-TNT Rescues Necrotizing Limbs in Balb/c Hindlimb Ischemia Models With reference to FIG. 4, additional experiments in Balb/c mice, which have a tendency to experience more deleterious side-effects from injury-induced limb ischemia, showed that EFF treatment led to successful limb perfusion and subsequent rescue from necrosis and auto-amputation. Laser speckle imaging of the limbs showed successful reperfusion after EFF TNT treatment. Panel (b) of FIG. 4. shows macroscopic changes to the ischemic limb with and without TNT treatment.

Example 5. Extracellular Vesicles Isolated from EFF TNT-Treated Dorsal Skin Help to Mediate Ischemic Limb Reperfusion and Rescue With reference to FIG. 5, PCR analysis revealed that in addition to the transfection EFF mRNAs/cDNAs, that extracellular vesicles (EVs) isolated EFF TNT-treated dorsal skin appeared to be preloaded with pro-angiogenic VEGF and bFGF mRNAs. This suggests that EVs derived from EFF TNT-treated skin not only represent a viable mechanism for propagating EFF reprogramming signals throughout the target tissue, but may also play a role in niche preconditioning by spreading pro-angiogenic signals within the first hours after transfection. Panel (a) of FIG. 5 shows a schematic diagram of injury/EV-mediated rescue. qRT-PCR was used to characterize the EV content. Panel (b) of FIG. 5 shows laser speckle reperfusion analysis of EFF-treated skin. Immunofluorescence analysis of the gastrocnemius muscle showing increased angiogenesis for the EV-treated limb.

Example 6. Induced Endothelial Cells in the Skin Originate from Col1A1-Expressing Dermal Sources With reference to FIG. 6, experiments with K14-Cre reporter and Col1A1-eGFP mouse models confirmed that the reprogrammed cell population had for the most part a dermal origin. Fluorescence micrographs of EFF TNT-treated skin sections from the Col1A1-GFP mouse models showing skin cells of Col1A1 origin (green) also expressing the Pecam-1 endothelial marker. Cellular elements that were immunoreactive for both the GFP tracer and Pecam-1 were further analyzed by LCM/qRT-PCR. The results indicate that such double-positive elements had significantly high endothelial marker gene expression. LCM/qRT-PCR measurements of GFP+/CD31+ cellular elements confirmed increased expression of endothelial markers.

Methods

TNT Platform Fabrication.

TNT devices were fabricated from thinned (~200 μm) double-side polished (100) silicon wafers. Briefly, ~1.5 μm thick layers of AZ5214E photoresist were first spin coated on the silicon wafers at ~3000 rpm. Nanoscale openings were subsequently patterned on the photoresist using a GCA 6100C stepper. Up to 16 dies of nanoscale opening arrays were patterned per 100-mm wafer. Such openings were then used as etch masks to drill ~10 μm deep nanochannels on the silicon surface using deep reactive ion etching (DRIE) (Oxford Plasma Lab 100 system). Optimized etching conditions included SF6 gas: 13 s/100 sccm gas flow/700 W ICP power/40 W RF power/30 mT APC pressure; C4F8 gas condition: 7 s/100 sccm gas flow/700 W ICP power/10 W RF power/30 mT APC pressure. Microscale reservoirs were then patterned on the back-side of the wafers via contact photolithography and DRIE. Finally, a ~50 nm thick insulating/protective layer of silicon nitride was deposited on the TNT platform surface.

Animal Husbandry.

Male C57BL/6 mice (8-10 weeks old) were obtained from Harlan Laboratory. B6.129(Cg)-Gt(ROSA)26Sortm4 (ACTB-tdTomato-EGFP)Luo/J mice obtained from Jackson laboratories were bred with K14cre to produce K14cre/Gt (ROSA)26Sortm4(ACTB-tdTomato-EGFP)Luo/J mice. pOBCol3.6GFPtpz mice were gifts from Dr. Traci Wilgus (The Ohio State University). Genotyping PCR for ROSAmT/mG mice was conducted using primers oIMR7318-CTC TGC TGC CTC CTG GCT TCT (SEQ ID NO:8), oIMR7319-CGA GGC GGA TCA CAA GCAATA (SEQ ID NO:9) and oIMR7320-TCAATG GGC GGG GGT CGT T (SEQ ID NO:10), while K-14 Cre transgene was confirmed using primers oIMR1084-GCG GTC TGG CAG TAAAAA CTA TC (SEQ ID NO:11); oIMR1085-GTG AAA CAG CAT TGC TGT CAC TT (SEQ ID NO:12). All animal studies were performed in accordance with protocols approved by the Laboratory Animal Care and Use Committee of The Ohio State University. The animals were tagged and grouped randomly using a computer based algorithm.
Mammalian Cell Culture and In Vitro Reprogramming.

Primary human adult dermal fibroblasts (ATCC PCS-201-012) were expanded in fibroblast basal medium supplemented with fibroblast growth kit-serum-free (ATCC PCS 201-040) and penicillin/streptomycin. E12.5-E14 mouse embryonic fibroblasts (MEFs) were cultured in DMEM/F12 supplemented with 10% fetal bovine serum. Non-viral cell transfection and reprogramming experiments were conducted via 3D Nanochannel Electroporation (NEP) as described previously. Briefly, the cells were first grown to full confluency overnight on the 3D NEP device. Subsequently, a pulsed electric field was used to deliver cocktail of plasmids (0.05 µg/µl) into the cells consisting of a 1:1:1 mixture of Fli1:Etv2:Foxc2. The cells were then harvested 24 h after plasmid delivery, placed in EBM-2 basal medium (CC-3156, Lonza) supplemented with EGM-2 MV Single-Quot kit (CC-4147, Lonza), and further processed for additional experiments/measurements. Etv2 and Fli1 plasmids were kindly donated by Dr. Anwarul Ferdous (Department of Internal Medicine, UT Southwestern Medical Center, Texas). Foxc2 plasmids were kindly donated by Dr. Tsutomu Kume (Department of Medicine-Cardiology and Pharmacology, Northwestern University-FCVRI, Chicago).
In Vivo Reprogramming.

The areas to be treated were first naired 24-48 h prior to TNT. The skin was then exfoliated to eliminate the dead/keratin cell layer and expose nucleated cells in the epidermis. The TNT devices were placed directly over the exfoliated skin surface. EFF plasmid cocktails were loaded in the reservoir at a concentration of 0.05-0.1 µg/µl. A gold-coated electrode (i.e., cathode) was immersed in the plasmid solution, while a 24 G needle counter-electrode (i.e., anode) was inserted intradermally, juxtaposed to the TNT platform surface. A pulsed electrical stimulation (i.e., 10 pulses of 250 V in amplitude and a duration of 10 ms per pulse) was then applied across the electrodes to nanoporate the exposed cell membranes and drive the plasmid cargo into the cells through the nanochannels.
Hindlimb Ischemia Surgery.

Unilateral hind-limb ischemia was induced via occlusion and subsequent transection of the femoral artery. Briefly, 8-10 week mice were anesthetized with 1-3% isoflurane, placed supine under a stereomicroscope (Zeiss OPMI) on a heated pad. The femoral artery was exposed and separated from the femoral vein through a ~1 cm incision. Proximal and distal end occlusion were induced with 7-0 silk suture, which was then followed by complete transfection of the artery. Finally, a single dose of buprenorphine was administered subcutaneously to control pain. Laser speckle imaging (MoorLDI-Mark 2) was conducted 2 h post-surgery to confirm successful blood flow occlusion.
Isolation of Extracellular Vesicles (EVs).

EVs were isolated from 12 mm diameter skin biopsies that were collected in OCT blocks and stored frozen for later use. Briefly, the blocks were thawed and washed with phosphate buffer saline (PBS) to eliminate the OCT. Following removal of the fat tissue with a scalpel, the skin tissue was minced into ~1 mm pieces and homogenized with a micro-grinder in PBS. After centrifugation at 3000 g, an Exoquick kit (System Biosciences) was used at a 1:5 ratio (Exoquick:supernatant) to isolate EVs from the supernatant for 12 h at 4° C. EVs were precipitated via centrifugation at 1500 g for 30 min. Total RNA was then extracted from pellet using the mirVana kit (Life technologies) following the recommendations provided by the manufacturer.
DNA Plasmid Preparation.

EFF plasmids were prepared using plasmid DNA purification kit (Qiagen Maxi-prep, catalogue number 12161, and Clontech Nucleobond catalogue number 740410). DNA concentrations were obtained from a Nanodrop 2000c Spectrophotemeter (Thermoscientific). For a list of plasmid DNA constructs and their original sources, please see Table 2.

TABLE 2

Plasmid cDNA

| Construct Name | Gene insert | Plasmid Backbone |
|---|---|---|
| pIRES-ER71(HA)$_3$ | Etsvp71 (ER71) | pIRES-hrGFP-2a |
| pAd -HA-Fli1-IRES-hrGFP | HA-Fli1 | pAd-IRES-GFP |
| mFoxc2 | mFoxc2 | pCDNA3.0 |

Laser Capture Microdissection (LCM) and Quantitative Real-Time PCR.

LCM was performed using a laser microdissection system from PALM Technologies (Bernreid, Germany). Specific regions of tissue sections, identified based on morphology and/or immunostaining, were cut and captured under a 20× ocular lens. The samples were catapulted into 25 µl of cell direct lysis extraction buffer (Invitrogen). Approximately 1,000,000 µm$^2$ of tissue area was captured into each cap and the lysate was then stored at −80° C. for further processing. qRT-PCR of the LCM samples were performed from cell direct lysis buffer following manufacture's instruction. A list of primers is provided in Table 3.

TABLE 3

List of primers

| Primer/probe Name | Primer Sequence |
|---|---|
| AscI1_q_F | CGACGAGGGATCCTACGAC (SEQ ID NO: 13) |
| AscI1_q_R | CTTCCTCTGCCCTCGAAC (SEQ ID NO: 14) |
| Brn2_q_F | GGTGGAGTTCAAGTCCATCTAC (SEQ ID NO: 15) |
| Brn2_q_R | TGGCGTCCACGTAGTAGTAG (SEQ ID NO: 16) |
| Etv2_F | CGCGAGTTCCAGCTGTGCGA (SEQ ID NO: 17) |
| Etv2_R | GGCGAGGACAGGCACACGTC (SEQ ID NO: 18) |
| Fli1_F | GGGCTGGGCTGCAGACTTGG (SEQ ID NO: 19) |
| Fli1_R | GGGGCTGCCCGTAGTCAGGA (SEQ ID NO: 20) |
| Foxc2_F | TACGCGCCCTACCACCACCA (SEQ ID NO: 21) |
| Foxc2_R | GCCCTGCTTGTTCTCGCGGT (SEQ ID NO: 22) |
| PECAM1_F | GGACCAGTCCCCGAAGCAGC (SEQ ID NO: 23) |
| PECAM1_R | AGTGGAGCAGCTGGCCTGGA (SEQ ID NO: 24) |
| VEGFR2_F | AGCGCTGTGAACGCTTGCCT (SEQ ID NO: 25) |
| VEGFR2_R | CATGAGAGGCCCTCCCGGCT (SEQ ID NO: 26) |
| EGFP-N | CCGTCCAGCTCGACCAG (SEQ ID NO: 27) |
| EGFP-C | GATCACATGGTCCTGCTG (SEQ ID NO: 28) |
| Cdh5_F | GTGCAACGAGCAGGGCGAGT (SEQ ID NO: 29) |

TABLE 3-continued

List of primers

| Primer/probe Name | Primer Sequence |
|---|---|
| Cdh5_R | GGAGCCACCGCGCACAGAAT (SEQ ID NO: 30) |
| m-K14_F | GCTGGTGCAGAGCGGCAAGA (SEQ ID NO: 31) |
| m-K14_R | AGACGGCGGTAGGTGGCGAT (SEQ ID NO: 32) |
| m-Col1A1_F | GTGTGATGGGATTCCCTGGACCTA (SEQ ID NO: 33) |
| m-Col1A1_R | CCTGAGCTCCAGCTTCTCCATCTT (SEQ ID NO: 34) |
| m-GAPDH_F | GTGCAGTGCCAGCCTCGTCC (SEQ ID NO: 35) |
| m-GAPDH_R | GCACCGGCCTCACCCCATTT (SEQ ID NO: 36) |

Immunohistochemistry and Confocal Microscopy.

Tissue immunostaining was carried out using specific antibodies and standard procedures. Briefly, OCT-embedded tissue was cryosectioned at 10 μm thick, fixed with cold acetone, blocked with 10% normal goat serum and incubated with specific antibodies (Table 4). Signal was visualized by subsequent incubation with fluorescence-tagged appropriate secondary antibodies (Alexa 488-tagged α-guinea pig, 1:200, Alexa 488-tagged α-rabbit, 1:200; Alexa 568-tagged α-rabbit, 1:200) and counter stained with DAPI. Images were captured by laser scanning confocal microscope (Olympus FV 1000 filter/spectral).

IVIS Imaging.

TABLE 4

Primary antibodies

| Antibody Name | Company (catalogue #) | Dilution |
|---|---|---|
| Purified Rat Anti Mouse CD31 | BD Pharmingen # 550274 | 1:400 |
| Anti-S100A4 antibody | Abcam (ab27957) | 1:200 |
| Anti-Von Willebrand Factor antibody | Abcam (ab6994) | 1:200 |
| Anti-CD105 antibody | Abcam (ab107595) | 1:400 |
| Anti-Keratin 14 | Covance (PRB-155P-100) | 1:400 |
| Anti-GFP | Abcam (ab32146) | 1:500 |

The animals were imaged with anesthesia 24 h after FAM-DNA transfection using IVIS Lumina II optical imaging system. Overlay images with luminescence images were made using Living Image software.

Magnetic Resonance Imaging (MRI) of Stroked Brains.

Magnetic resonance angiography was used to validate our MCAO model in mice and to optimize the occluder size and the internal carotid artery insertion distance for effective MCAO. T2-weighted MRI was performed on anesthetized mice 48 h after MCA-reperfusion using 9.4 T MRI (Bruker Corporation, Bruker BioSpin Corporation, Billerica, Mass., USA). MR images were acquired using a Rapid Acquisition with Relaxation Enhancement (RARE) sequence using the following parameters: field of view (FOV) 30×30 mm, acquisition matrix 256×256, TR 3,500 ms, TE 46.92 ms, slice gap 1.0 mm, rare factor 8, number of averages 3. Resolution of 8.5 pixels per mm. Raw MR images were converted to the standard DICOM format and processed. After appropriate software contrast enhancement of images using Osirix v3.4, digital planimetry was performed by a masked observer to delineate the infarct area in each coronal brain slice. Infarct areas from brain slices were summed, multiplied by slice thickness, and corrected for edema-induced swelling as previously described to determine infarct volume (Khanna S, et al. J Cereb Blood Flow Metab 2013, 33(8):1197-1206).

Analysis of Muscle Energetics.

Muscle energetics was evaluated NMR spectroscopy measurements on a 9.4 Tesla scanner (Bruker BioSpec) using a volume coil for RF transmission and a 31P coil for reception. In vivo imaging was conducted in a custom-made 1H/31P transceiver coil array. Data were acquired using single pulse sequence. The raw data were windowed for noise reduction and Fourier transformed to spectral domain.

Ultrasound-Based Imaging and Characterization of Blood Vessels.

Blood vessel formation was parallelly monitored via ultrasound imaging. Briefly, a Vevo 2100 system (Visual Sonics, Toronto, ON, Canada) was used to obtain ultrasound images on B-mode with a MS 250 linear array probe. Doppler color flow imaging was implemented to monitor and quantify blood flow characteristics under systole and diastole.

Statistical Analysis.

Samples were coded and data analysis was performed in a blinded fashion. For animal studies, data are reported as mean±SD of at least 3 animals. In vitro data are reported as mean±SD of 3-6 experiments. All statistics were performed in SigmaPlot version 13.0.

Example 7. Direct In Vivo Reprogramming of Dermal Fibroblasts into Functional Endothelial Cells by Targeting a Single miRNA Results Inhibition of miR-200b Alone Converted Cultured Fibroblasts to Induce Endothelial Cells (iECs)

Figure 7A:
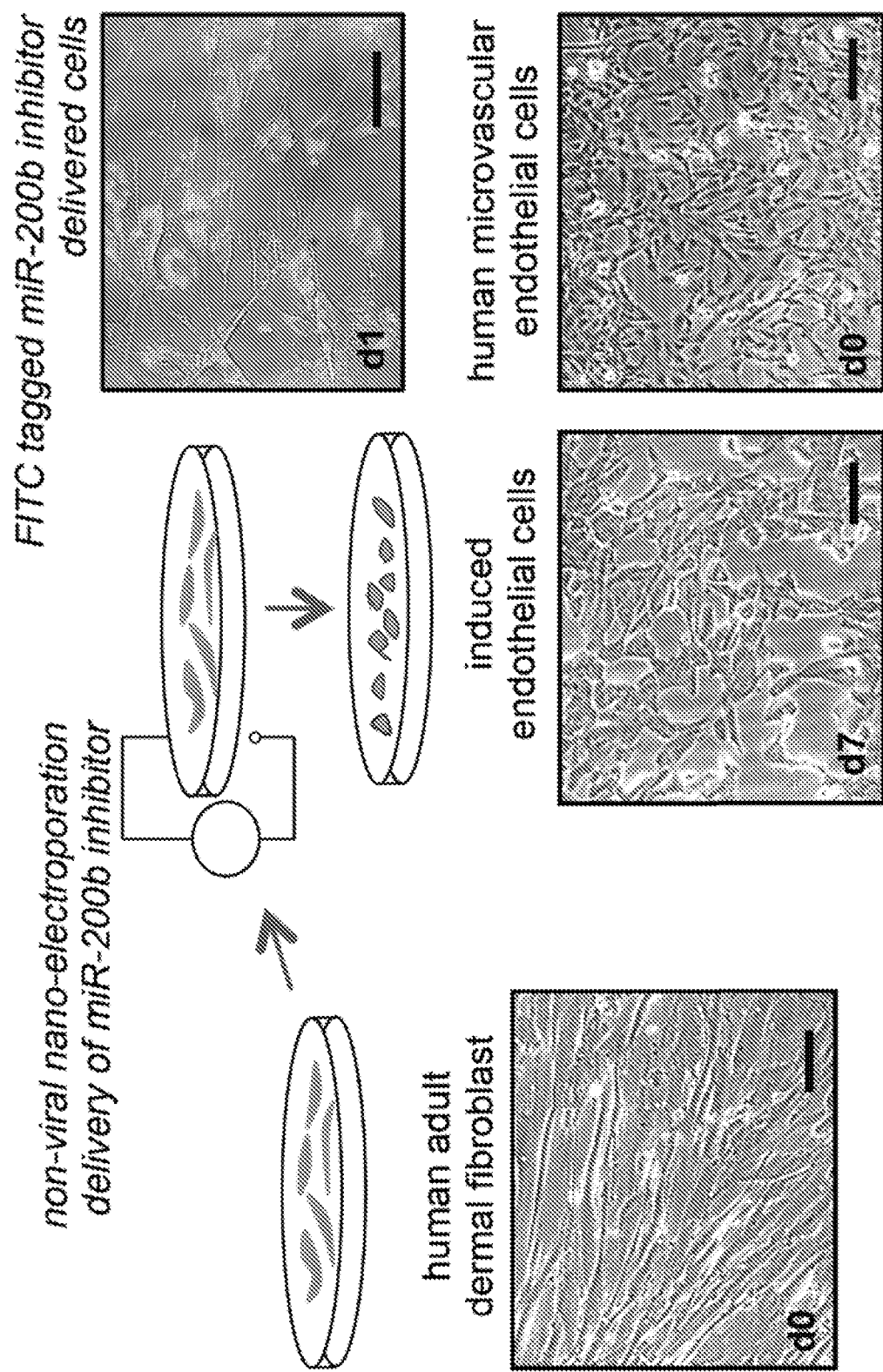
FIG. 7. Inhibition of miR-200b in dermal fibroblasts induces direct conversion to iECs. (A) Schematic diagram of nano-electroporation delivery of FITC tagged miR-200b inhibitor in human adult dermal fibroblasts (HADF) and representative image showing induced cobblestone endothelial cells (iECs) formation. Human microvascular endothelial cells (HMEC) used as positive control. (B) Flow cytometric analysis of CD90 and CD31 expression in control or miR200b inhibitor transfected iECs. Number in each plot (yellow box) denotes percentage of CD31$^+$CD90$^+$ transition cells. (C) Quantification of dual positive cells for CD31$^+$ CD90$^+$ (left) or VEGFR2$^+$ fibroblast$^+$ (right) were plotted (n=3). Values represent mean±s.d.*P<0.001; versus day 1. (D) Gene expression profile analysis of control or miR-200b inhibitor transfected iECs by cDNA microarray (n=3). Data represented by 'heat map' image illustrating differentially expressed genes in miR-200b inhibitor transfected iECs compared to control inhibitor treated HADF on day 7. Red color indicates that the gene is expressed at a higher level than average, and green denote the gene is expressed at a lower level. (E) Quantification of Col1A1 and Fsp-1 (fibroblast markers), Cd31 and Vegfr2 (endothelial marker), Tie2 (arterial marker), Coup-TFII (venous marker) and Prox1 (lymphatic marker) expression level in anti-miR200b transfected iECs (n=3). Gene expressions were normalized to corresponding 18s values and are shown as fold change relative to the value of the control sample (as day 0). Data represent mean±s.d. **P<0.01; #P<0.05 versus control (F) Representative image of acetylated LDL (AcLDL) uptake (top) and quantification of mean AcLDL intake (bottom) by iECs (n=3). Scale bar, 50 μm. (G) Representative image displaying capillary-like structures (top) and quantification of tube length (bottom) by iECs in vitro matrigel plug assay (n=3). Scale bar, 200 μm. Human microvascular endothelial cells (HMEC) were used as positive control. Data represent mean±s.d. *P<0.001 versus control inh.
Figure 7B:
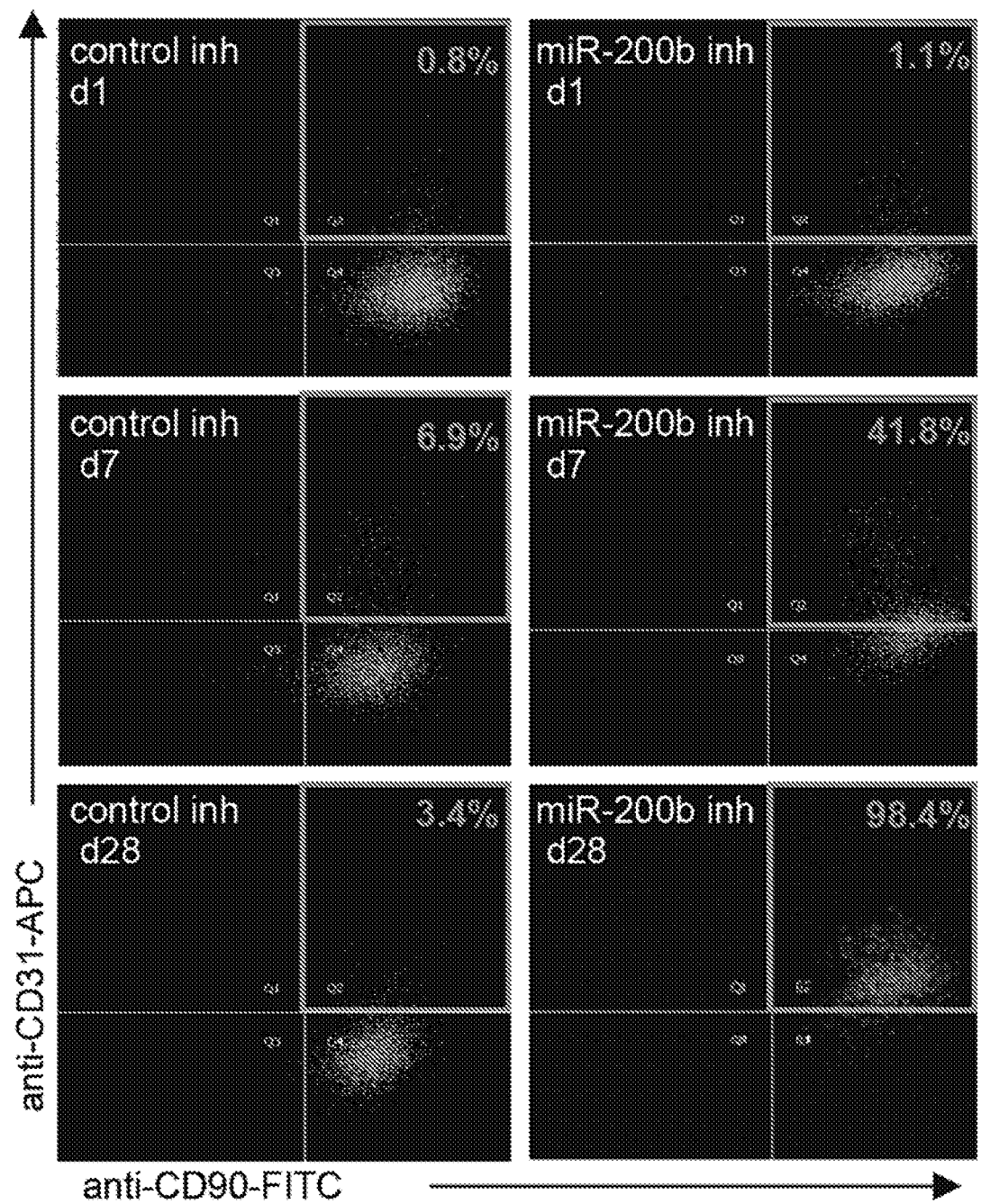
Figure 7C:
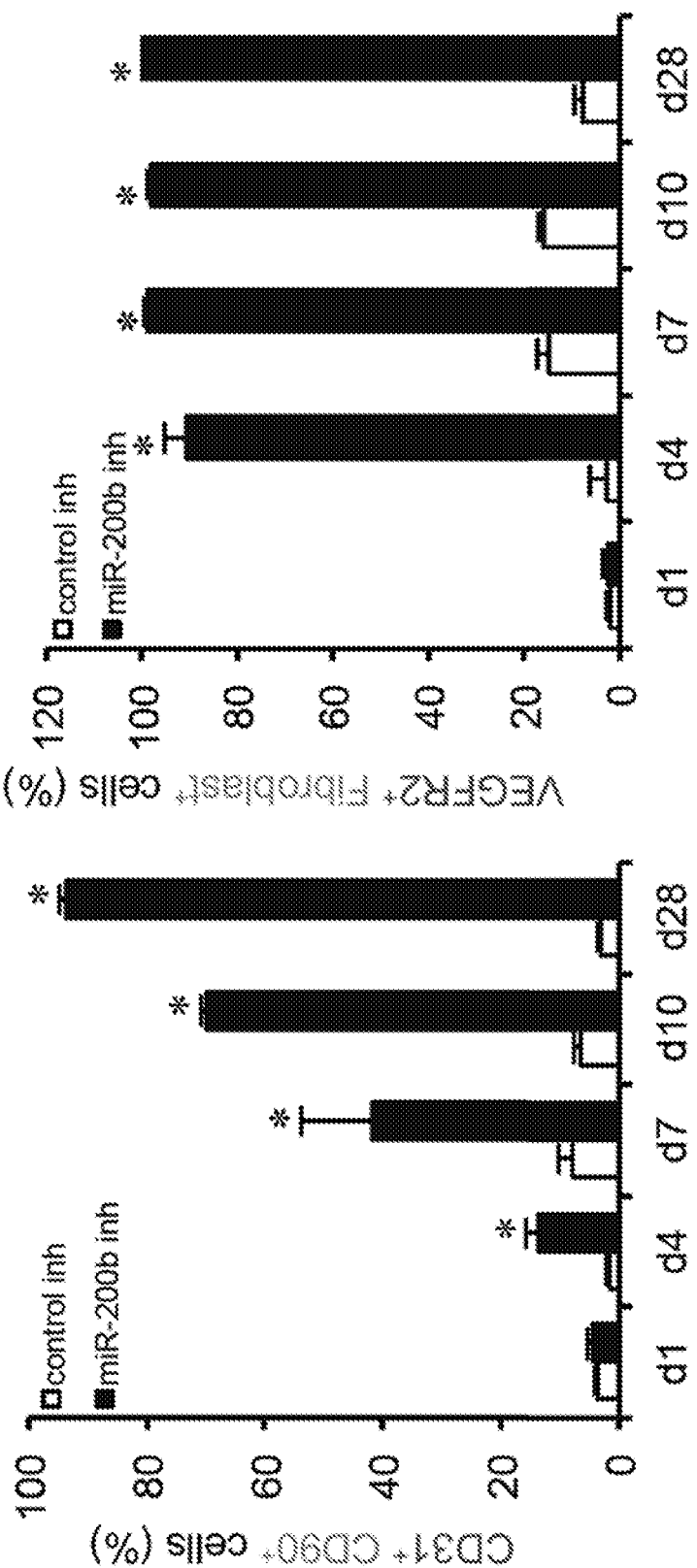
Figure 7D:
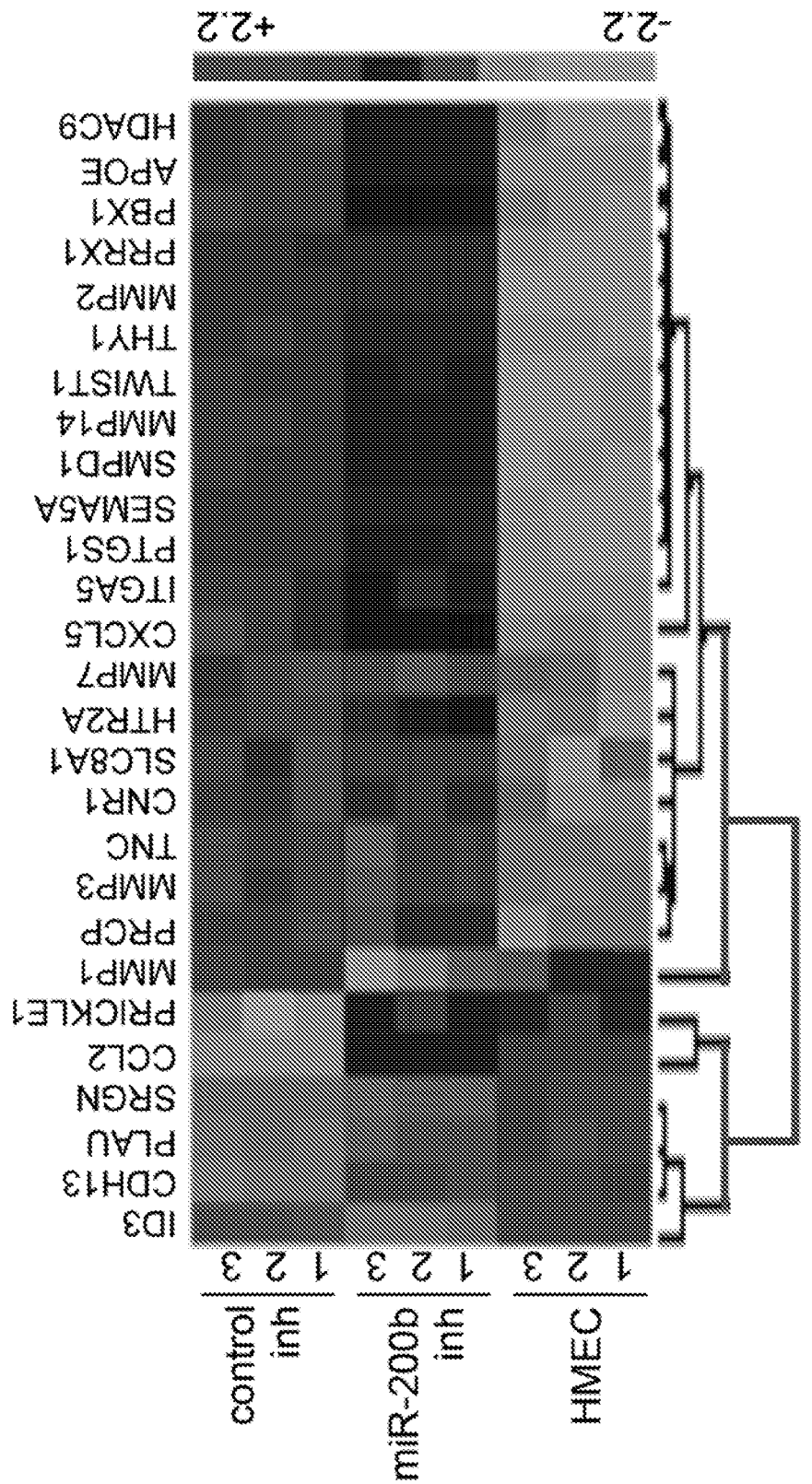
Figure 7E:
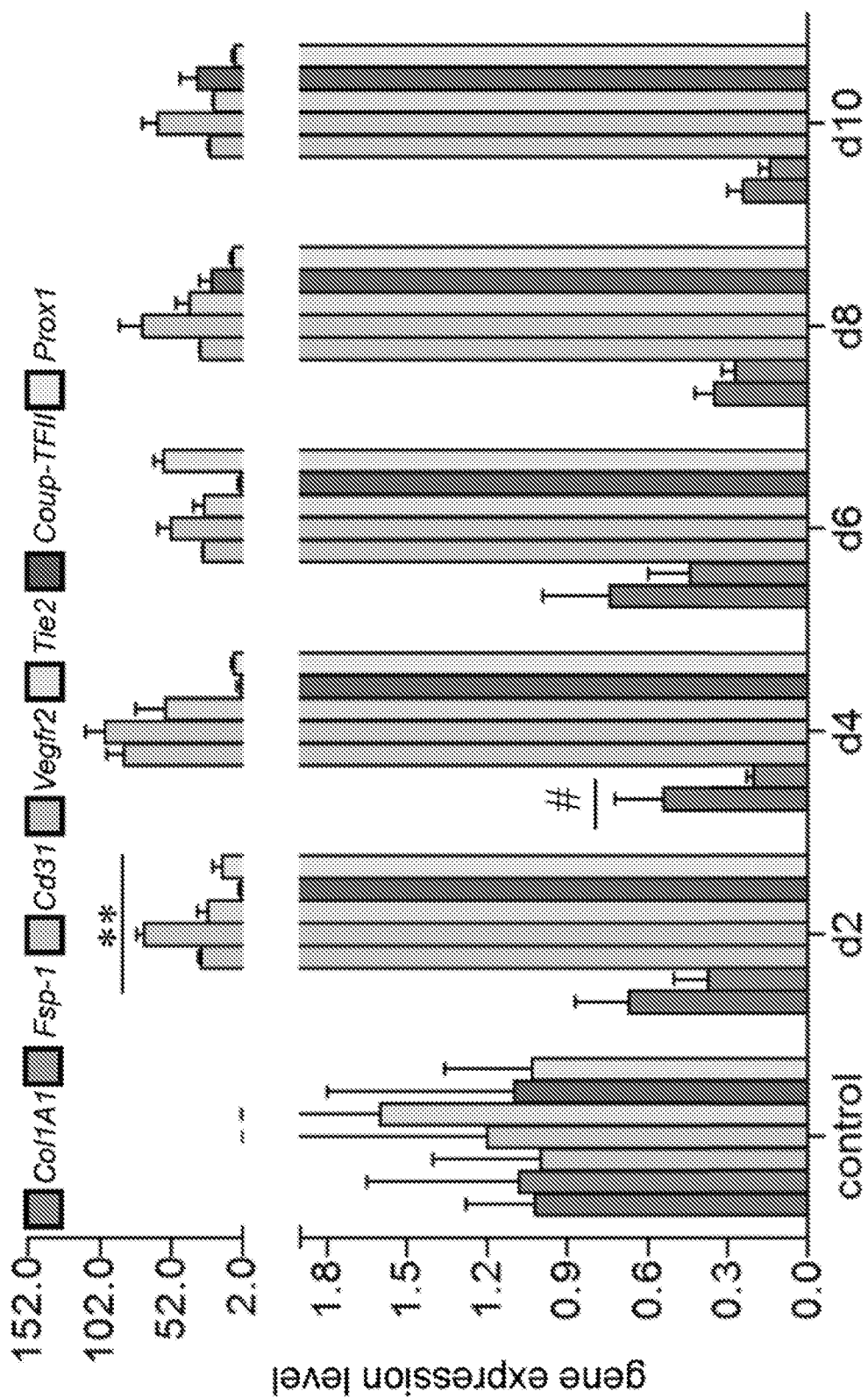
Figures 7F, 7G:
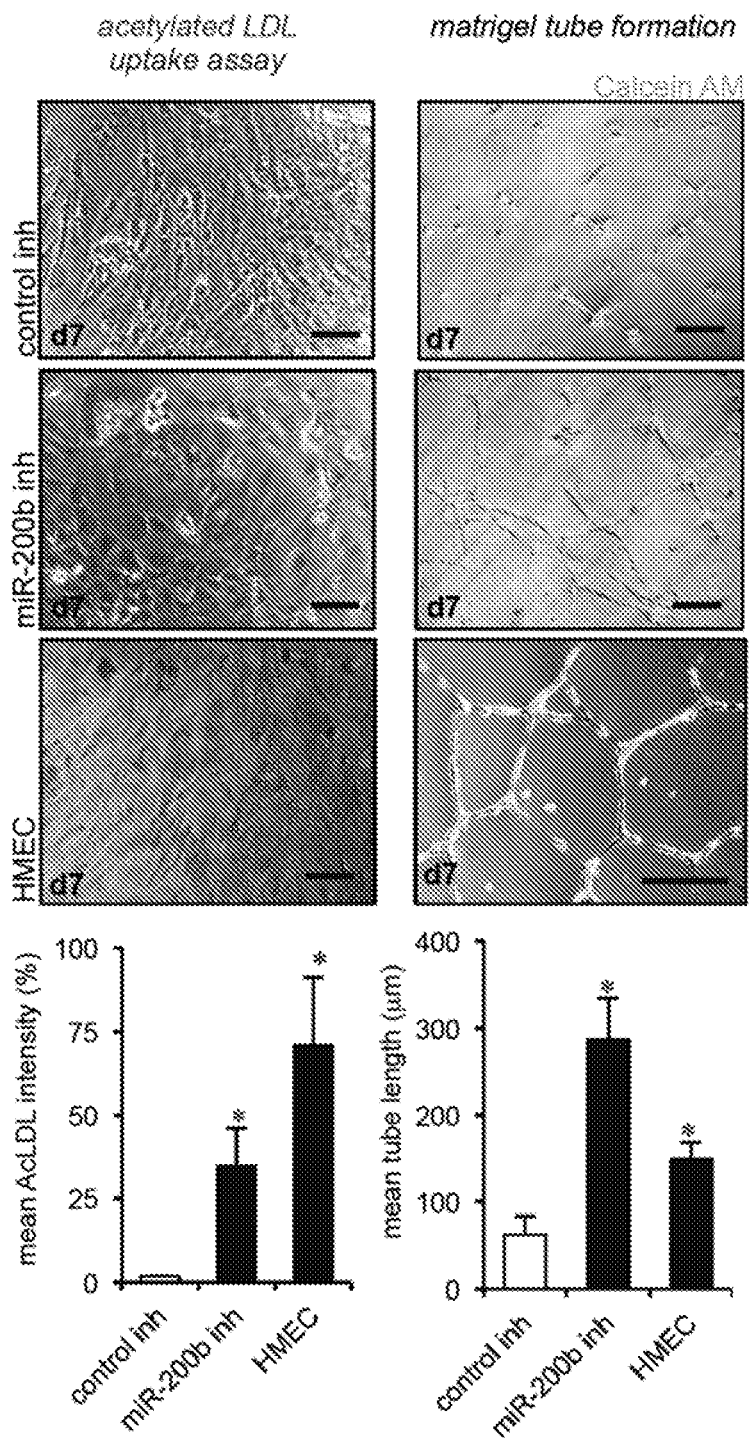
Figures 12A, 12B:
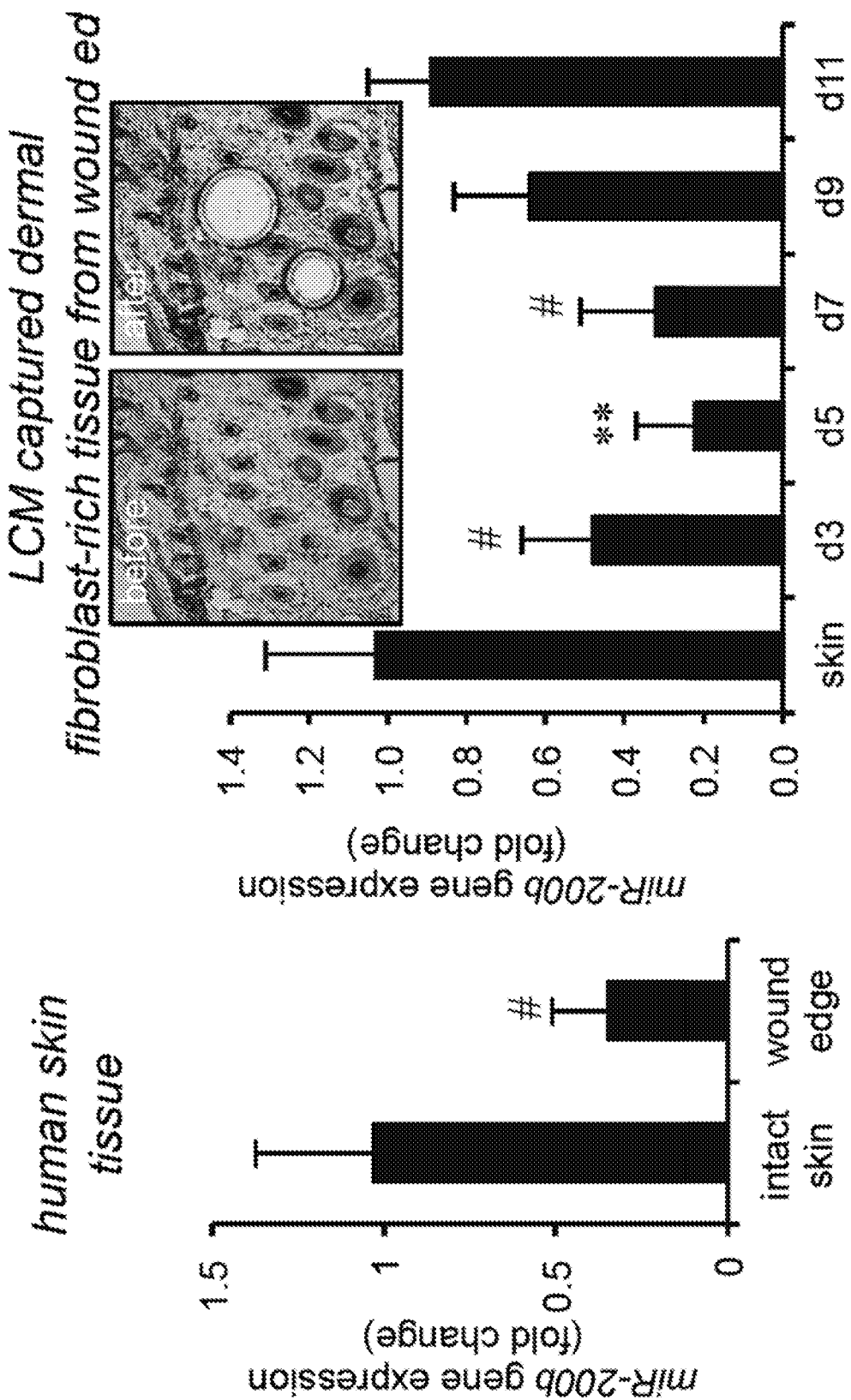
FIG. 12. Direct reprogramming of dermal fibroblasts to endothelial cells by anti-miR200b. (A) miR-200b expression level in human skin and the wound edge skin tissue (n=3). Values represent mean±s.d., #P<0.05 versus skin (B) Differential miR-200b expression was analyzed by RT-qPCR in Laser Captured Microdissection (LCM) of dermal fibroblast-rich wound edge tissue of C57BL/6 mice indicated days post wounding (n=3). Values represent mean±s.d., #P<0.05; P<0.01 versus skin (C) HADF cells were subjected to flow cytometry analysis on day 1, 4, 7, 10 and 28 after nanoelectrotransfection of control or miR-200b inhibitor. Representative images of flow cytometry gating (top) and analysis (bottom) of dual positive cell population with VEGFR2+Fibroblast+ expression. Number embedded in each plot (yellow box) indicates the percentage of VEGFR2+Fibroblast+ cells (n=3). (D) Immunofluorescence cytostaining of FSP-1 (green) and CD31 (red) in control or miR-200b inhibitor transfected HADF on day 7. DAPI was used for nuclear counterstaining (n=3). Scale bar, 100 μm. (E) Hierarchical clustering of microarray data of control or anti-miR200b transfected HADF generated by Ingenuity® Pathway Analysis (IPA®) showing upregulation (red) and downregulation (green) of several genes which are involved in angiogenesis, vasculogenesis and growth of vessels. (F) miR-200b induced endothelial cells showed less expression of Col1A1, Fsp-1 (fibroblast) and high expression of Ccl2 (endothelial) markers (n=3). Data represent mean±s.d., #P<0.05, versus control inh (G) Gene expression analysis of pluripotency factors (Oct4, Sox2, Klf4 and Nanog) of antimiR200b post-transfected HADF cells. Data represent mean±s.d., #P<0.05; P<0.01; ns=non significant, versus control (as day 0).
Figure 12C:
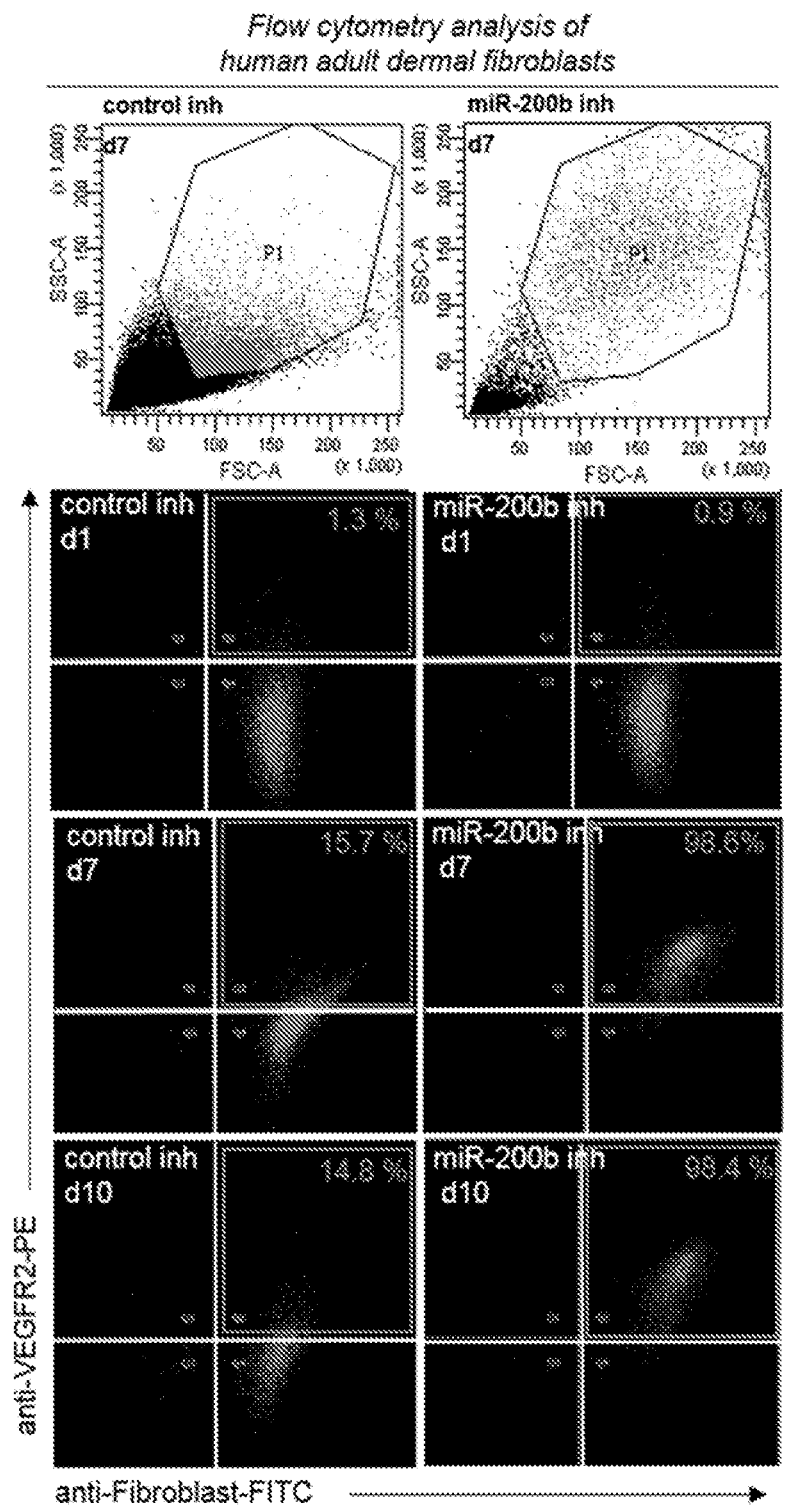
Figure 12D:
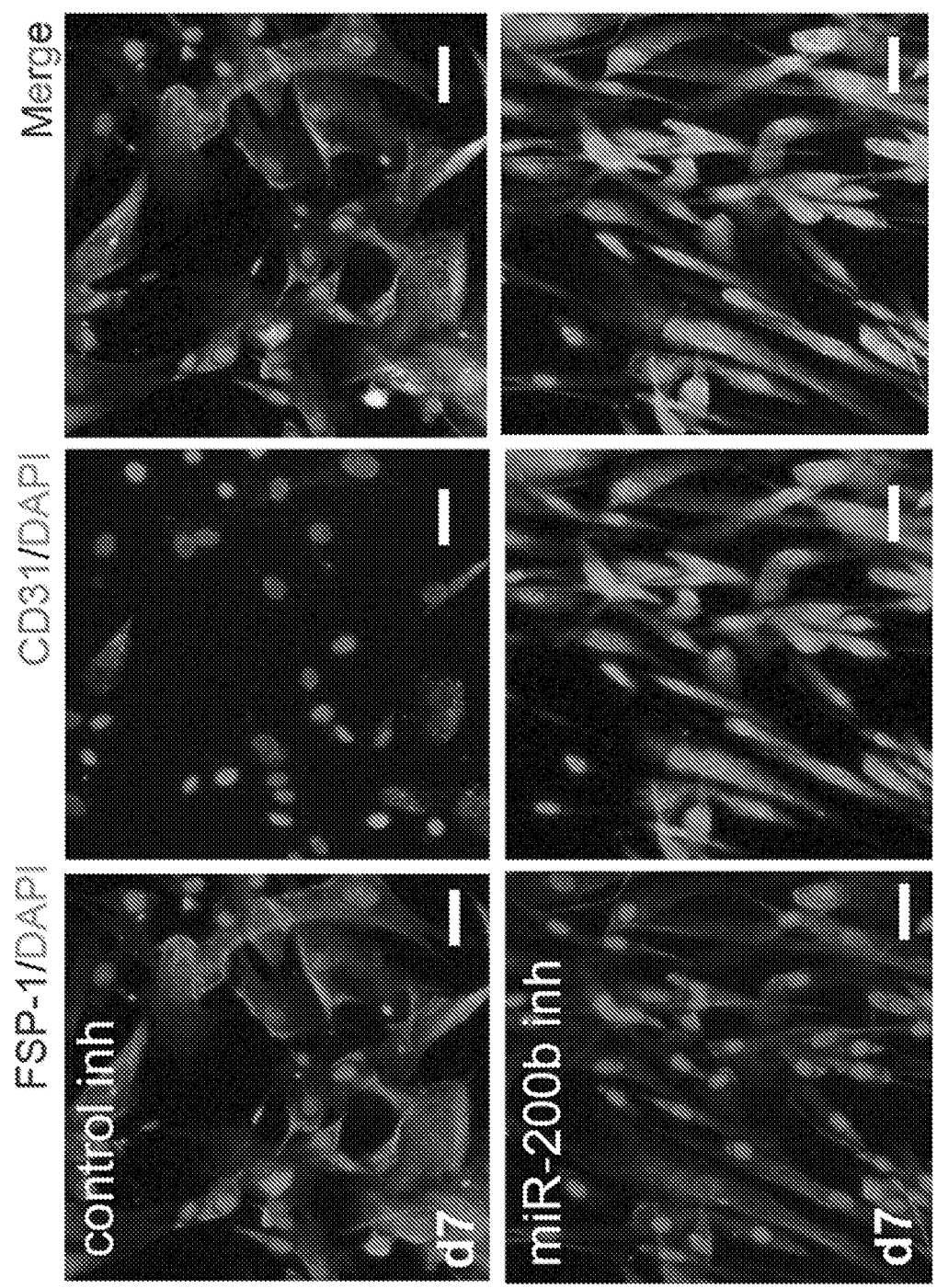
Figure 12E:
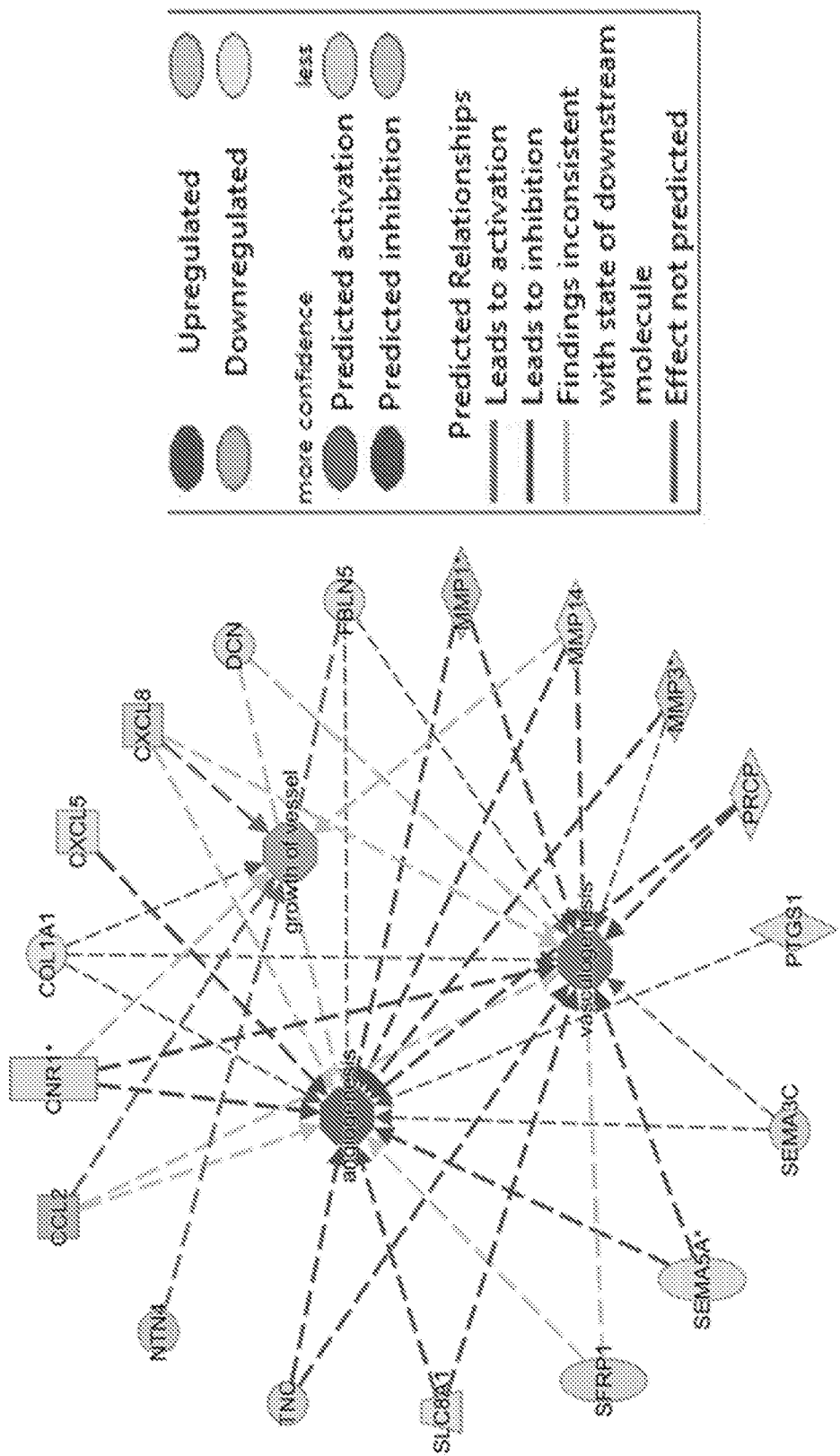
Figure 12F:
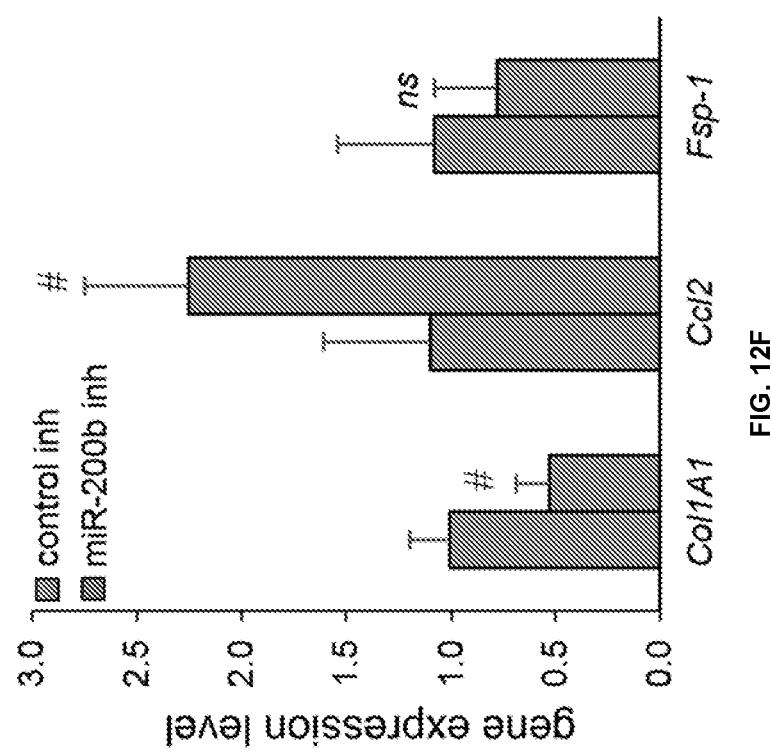
Figure 12G:
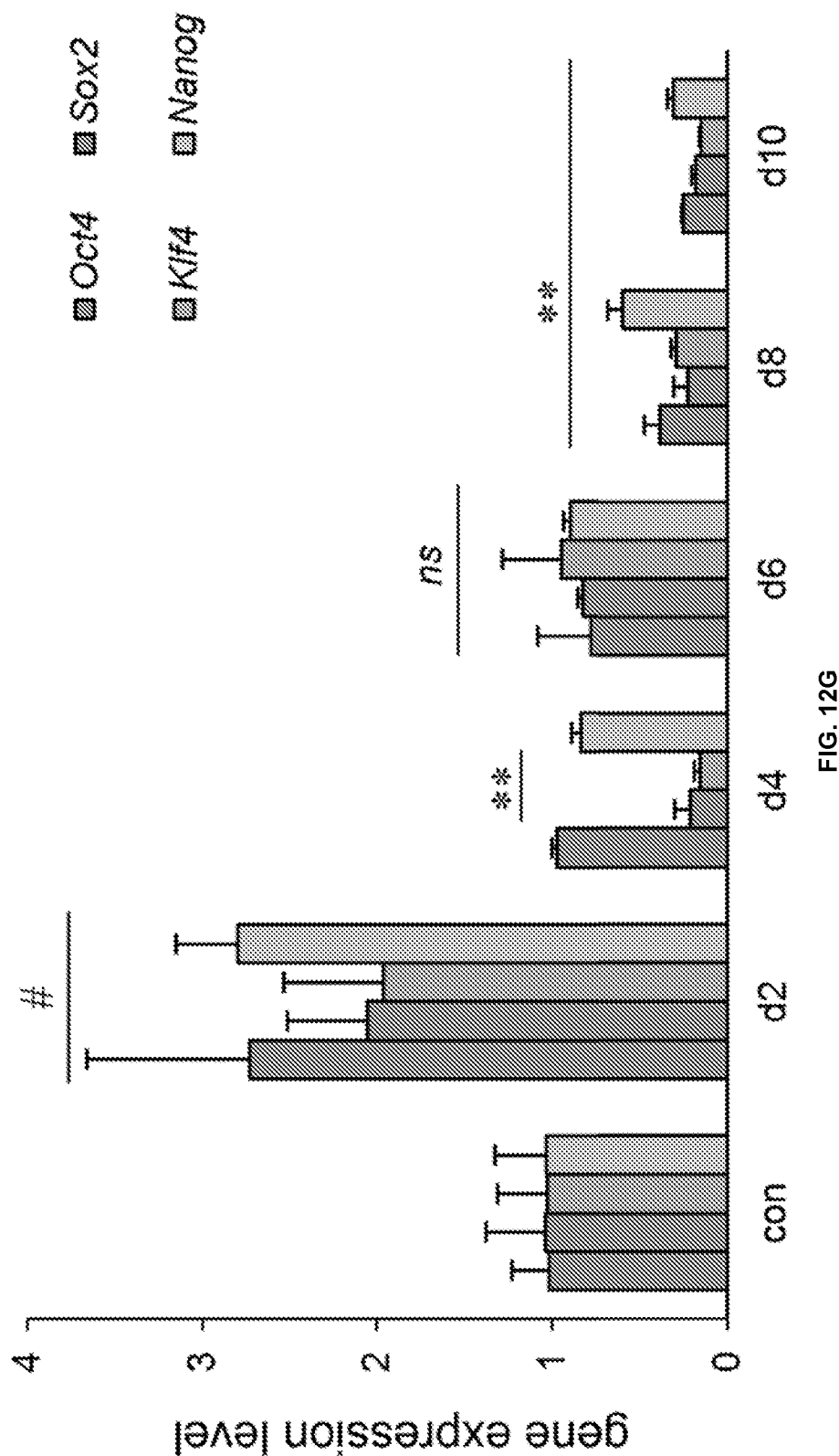

This line of investigation was inspired by the observation that at the wound-edge of chronic wound patients miR-200b levels are sharply lower than that in skin (FIG. 12A). In mice, wounding induced transient inhibition of miR-200b which rebounded to their pre-wounding values following wound closure (FIG. 12B). To understand the significance of such wound-induced inhibition of miR-200b, anti-miR-200b inhibitor molecule was delivered to human adult dermal fibroblasts via nanochannel-based electroporation (Boukany et al., 2011; Gallego-Perez et al., 2016). A robust phenotypic switch of cellular architecture towards cobblestone morphology was noted preliminarily suggesting conversion of fibroblast to endothelial cell (FIG. 7A). miR-200b inhibition in fibroblast cells notably induced endothelial marker CD31 over fibroblast-specific CD90 from day 4 onwards. Such transition was progressive with a maximum at day 28 (98.4%) demonstrating rapid appearance and sustenance of endothelial characteristics in fibroblast cells (FIGS. 7B and 7C). This observation was consistent with the progressive appearance of another angiogenic factor VEGFR2+ over fibroblast FSP1+ cells (FIGS. 7C and 12C). Gain of endothelial marker CD31 coupled with concomitant loss of fibroblast FSP-1 was evident in miR-200b suppressed cells (FIG. 12D). Transcriptome array of anti-miR200b transfected fibroblasts demonstrated a shift of expression profile from fibroblast-specific genes such as Col1A, MMPs, CXCL5 towards endothelial gene clusters represented by angiogenic CCL2 (Stamatovic et al., 2006) and CXCL8 (Heidemann et al., 2003) (FIGS. 7D and 12E-12F). Characterization of iECs revealed co-existence of arterial (PE-CAM1, VEGFR2 and TIE2), venous (COUP-TFII), lymphatic (PROX1) features with trace remnants of fibroblast (COL1A1 and FSP1) markers (FIG. 7E). Akin to human microvascular endothelial cells, Ac-LDL uptake (FIG. 7F) and Matrigel tube formation were high (FIG. 7G) in miR-200b suppressed fibroblasts. Thus, fibroblasts had attained the functional characteristics of endothelial cells in response to miR-200b inhibition. Pluripotency genes such as Oct4, Sox2, Klf4 and Nanog remained at a very low level from day 4 onwards of anti-miR-200b transfection (FIG. 12G) indicating that fibroblast to iECs conversion was direct.

miR-200b Inhibition De-Silenced Fli-1

Figure 8A:
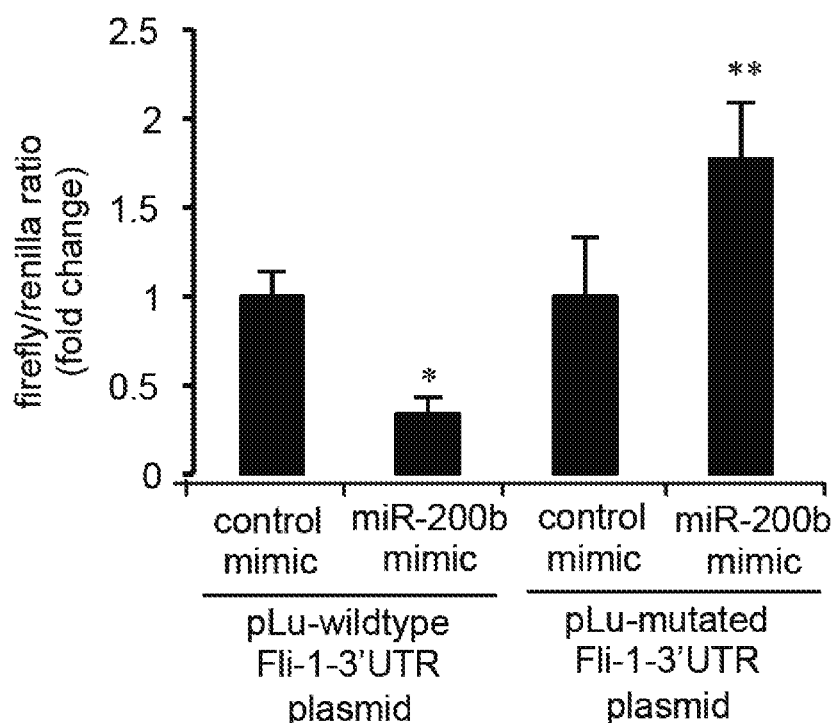
FIG. 8. miR-200b inhibition desilences Fli-1 to promote Etv2 expression that activates the angiogenesis switch. (A) miR target reporter luciferase assay was studied either by transfecting wild type Fli-1 3'UTR plasmid or mutated Fli-1 3'UTR plasmids in control or miR-200b mimic transfected iECs. Results were normalized with renilla luciferase activity (n=6). Data represent mean±s.d., *P<0.001 versus wild-type control mimic; **P<0.01 versus mutated control mimic. (B) Western blot analysis (left) and quantification (right) of FLI-1 protein level of miR-200b mimic or inhibitor (inh) delivered iECs. β-actin serves as loading control (n=3). Data represent mean±s.d., *P<0.001 versus control control inh.*P<0.05 versus respective control. (C) Western blot analysis (top) and quantification (bottom) showing FLI-1 protein level in HADF cells transfected with miR-200b inh or Fli-1 siRNA or both. β-actin serves as loading control (n=3). Data expressed as mean±s.d., *P<0.001 (versus respective control or versus miR-200b inh). (D) Representative images of Matrigel plug assay showing tube like capillary structures (left) and quantified the tube length on day 7 (right) of miR-200b inh transfected iECs in absence or presence of con or Fli-1 siRNA (n=3). Scale bar, 100 μm. Data represent mean±s.d., *P<0.001 versus respective control (E) ChIP assay showing FLI-1 binding to Etv2 promoter in Fli-1 silenced or overexpressed HADF cells. IgG used as negative control (n=3). (F) Etv2 promoter luciferase activity was measured by calculating GLUC/SEAP ratio in Fli1 silenced or overexpressed HADF cells co-transfected with miR200b mimic or inhibitor (n=4). Data represent mean±s.d., #P<0.05; P<0.01. (G) Quantification of Etv2 gene expression in HADF cells transfected with miR-200b inhibitor or Fli-1 siRNA or both (n=3). Data expressed as mean±s.d., #P<0.05; P<0.01.
Figure 8B:
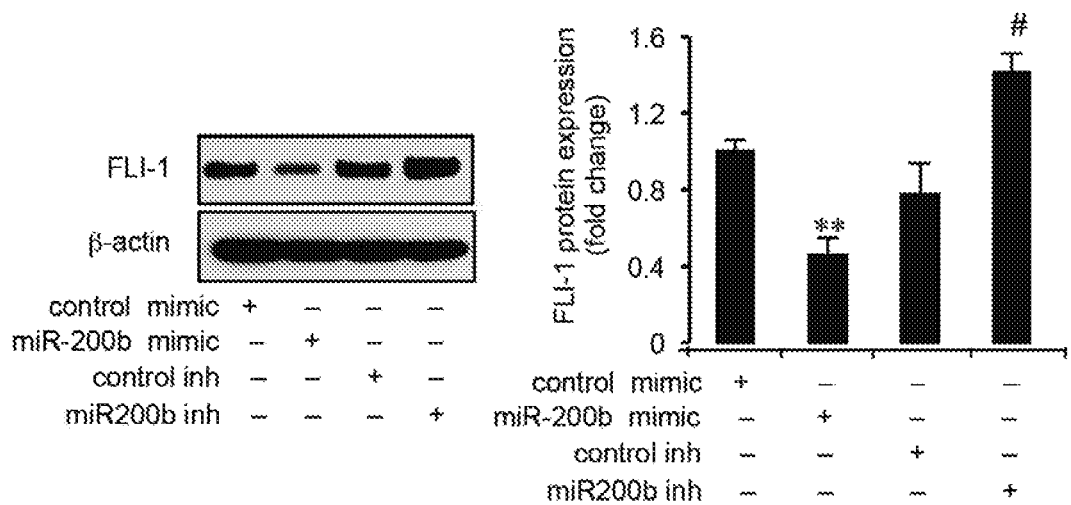
Figure 8C:
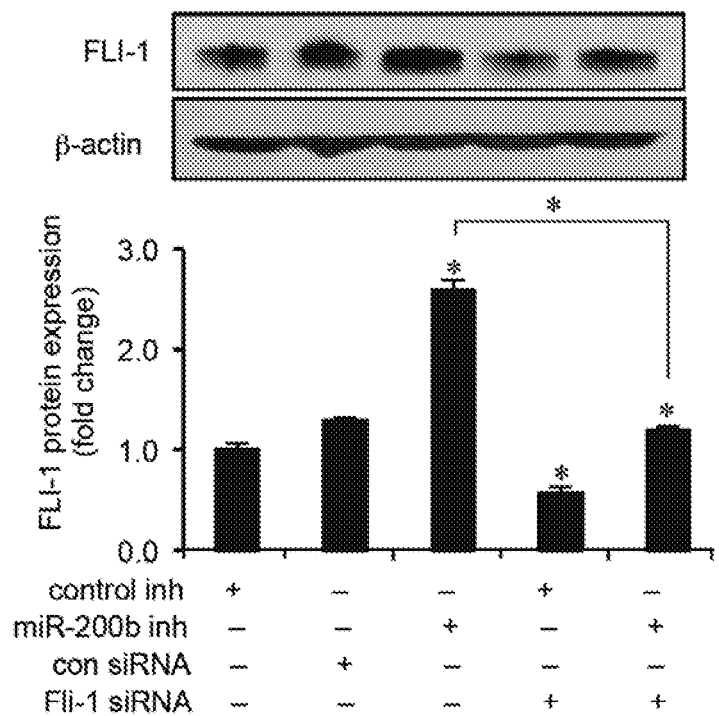
Figure 8D:
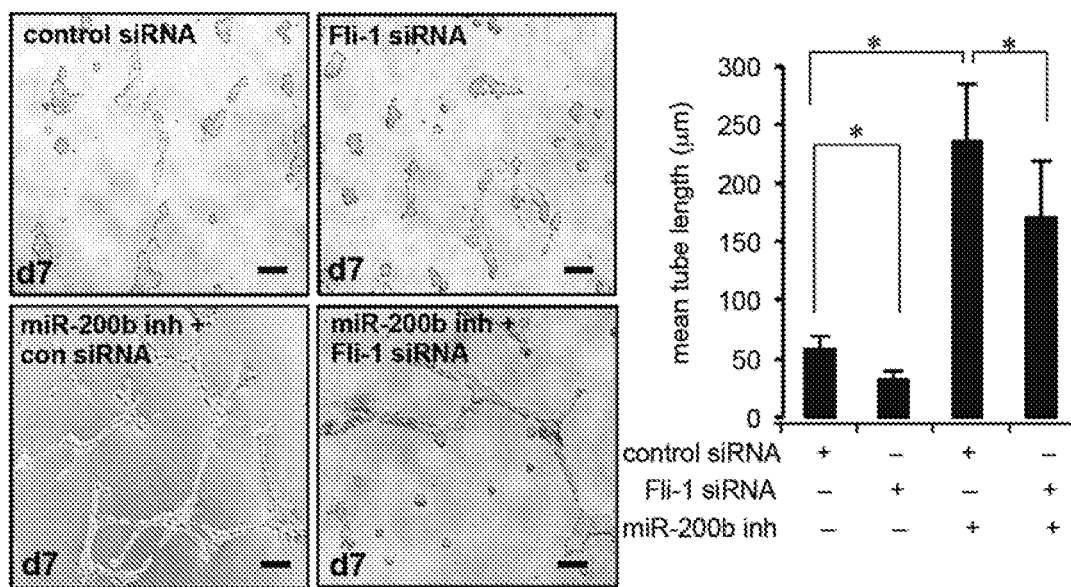
Figure 13B:
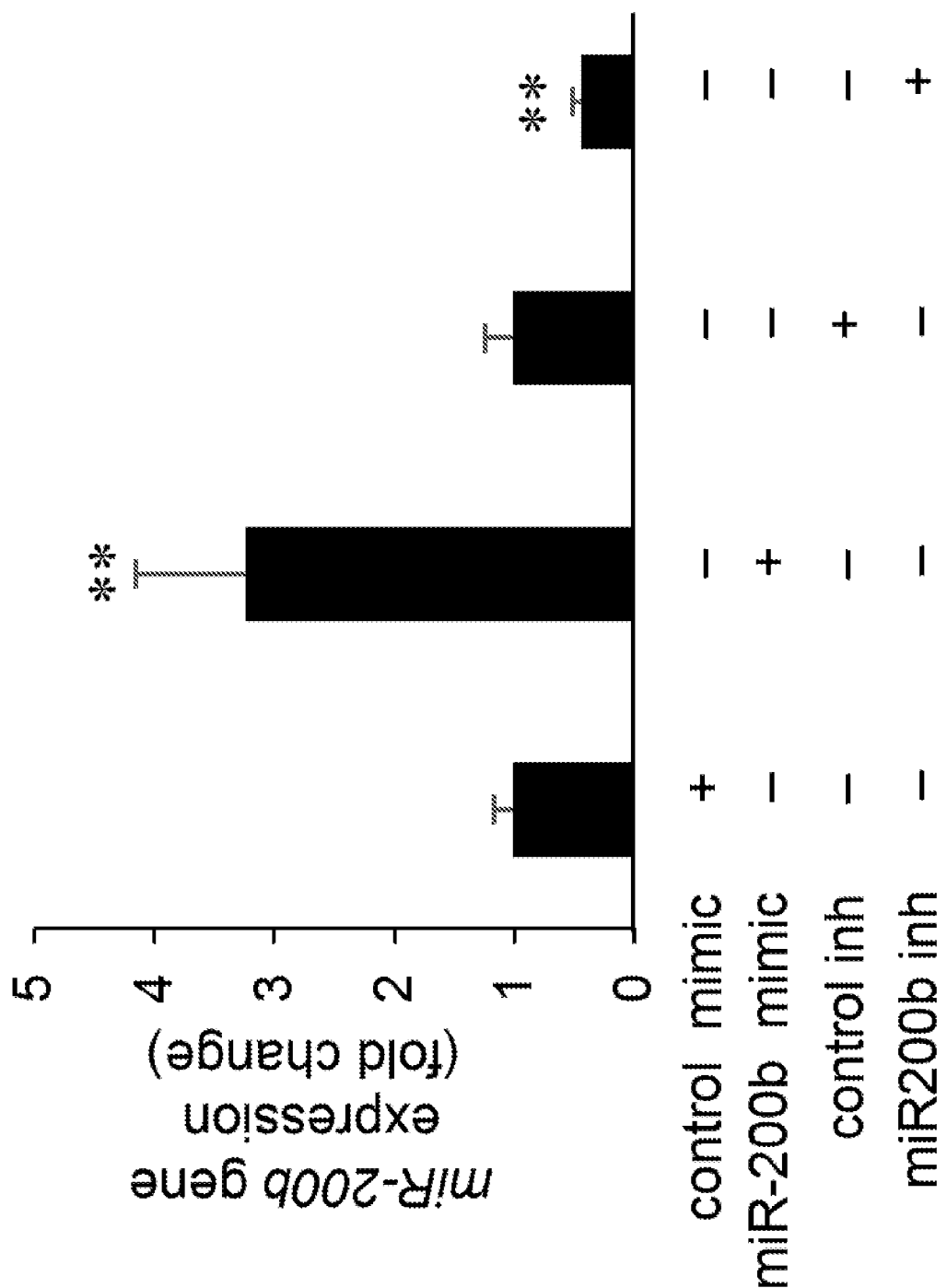
FIG. 13. In-silico analysis of Fli-1 and its downstream target regulation. (A) In silico study showing putative binding site in human and mouse Fli-1 3'UTR for human and mouse miR-200b, respectively, as predicted by TargetScan, miRDB, miRanda, PicTar and Diana-microT database. (B) RT-qPCR analysis showing miR-200b gene expression in control or miR-200b mimic or inhibitor delivered HADF cells (n=3). Data represent mean±s.d. **p<0.01 versus respective control. (C) Etv2 promoter analysis by MatInspector database revealing possible binding sites for Fli-1. The human Etv2 promoter region GXP_2054052 spanning −1357/−642 fragment contains six Fli-1 (ETS family transcription factor) binding sites and region GXP_6038330 spanning −183/−40 contain two putative binding sites for Fli-1 which are responsible for Etv2 transactivation. In mouse, Etv2 promoter region of GXP_3623379 spanning −560/−151 contains five binding sites for Fli-1 responsible to transactivation of Etv2. (D) Table showing detailed description of individual Fli-1 (ETS) binding sites with start and end position on human and mouse Etv2 promoter regions along with binding sequences. (E) Gene expression analysis of early angiogenesis marker (Tie2, Tall, Cd31 and Vegfr2) in Etv2 silenced and Fli-1 overexpressed cells. Data represent mean±s.d., *P<0.001; **P<0.01 versus control cells.

In silico studies using TargetScan, miRanda, and Diana-MicroT algorithms predicted targets of miR-200b that could regulate angiogenic outcomes. The 3'-untranslated regions (3'UTRs) of Friend Leukemia Integration 1 (Fli-1) transcription factor contain binding sites for miR-200b (FIG. 13A). Delivery of miR-200b mimic significantly suppressed Fli-1-3'UTR reporter luciferase activity (FIG. 8A). Such effect was abrogated in cells with mutated Fli-1 3'UTR (FIG. 8A) recognizing the significance of specificity of miR-200b binding in the regulation of Fli-1 expression. Thus, Fli-1, a member of the ETS family of transcription factors which are central regulators involved in vascular development and angiogenesis (Meadows et al., 2011; De Val et al., 2009), is subject to post-transcriptional gene silencing by miR-200b. Direct support to the notion that miR-200b targets Fli-1 in primary human dermal fibroblasts was obtained in studies using miR-200b mimic or inhibitor (FIG. 13B). miR-200b mimic lowered Fli-1 protein level, in contrast, Fli-1 protein was induced in fibroblasts transfected with miR-200b inhibitor (FIG. 8B). To determine the significance of Fli-1 in the angiogenic outcome caused by miR-200b inhibition fibroblasts, were transfected with either anti-miR-200b or Fli-1 siRNA alone or in combination. While inhibition of miR-200b alone was potent in de-silencing Fli-1 protein, such effect was blunted in cells subjected to Fli-1 knock-down (FIG. 8C). Consistent with these findings, it was observed that the angiogenic effect of miR-200b inhibition on endothelial tube length in Matrigel assay was Fli-1 dependent (FIG. 8D).

Fli-1 Dependent Transactivation of Etv2 Triggered an Angiogenic Switch

Figure 8E:
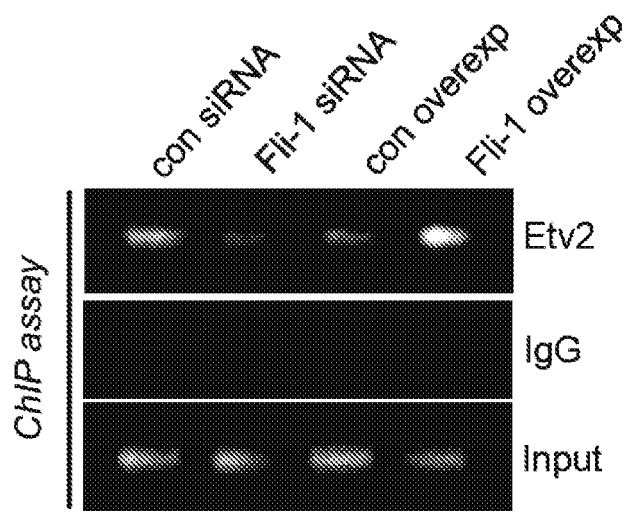
Figure 8F:
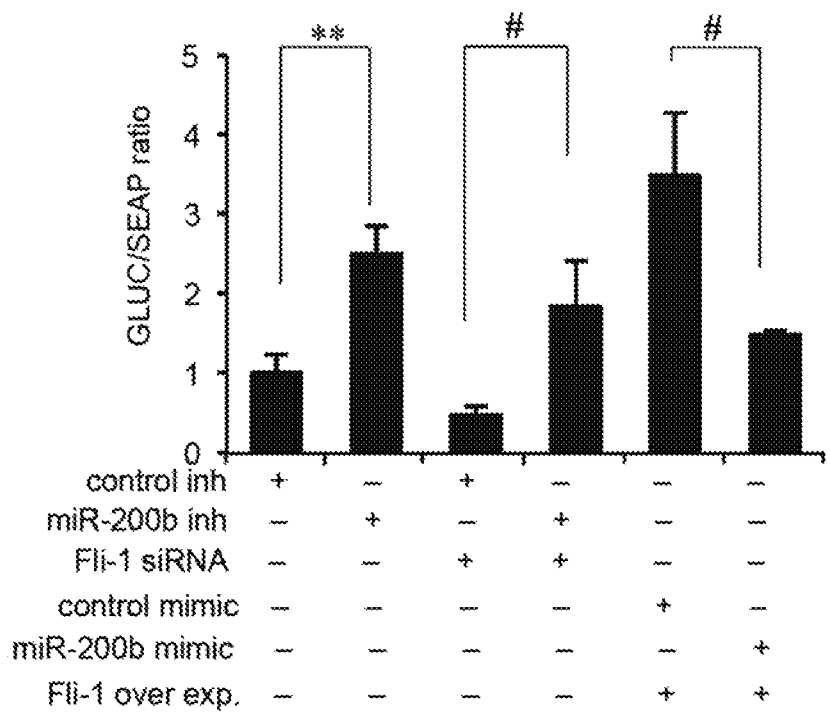
Figure 8G:
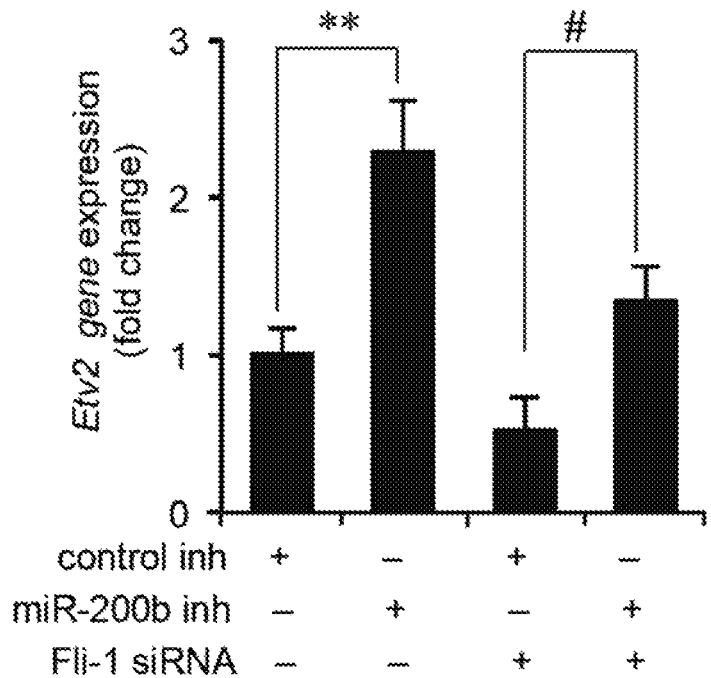
Figure 13C:
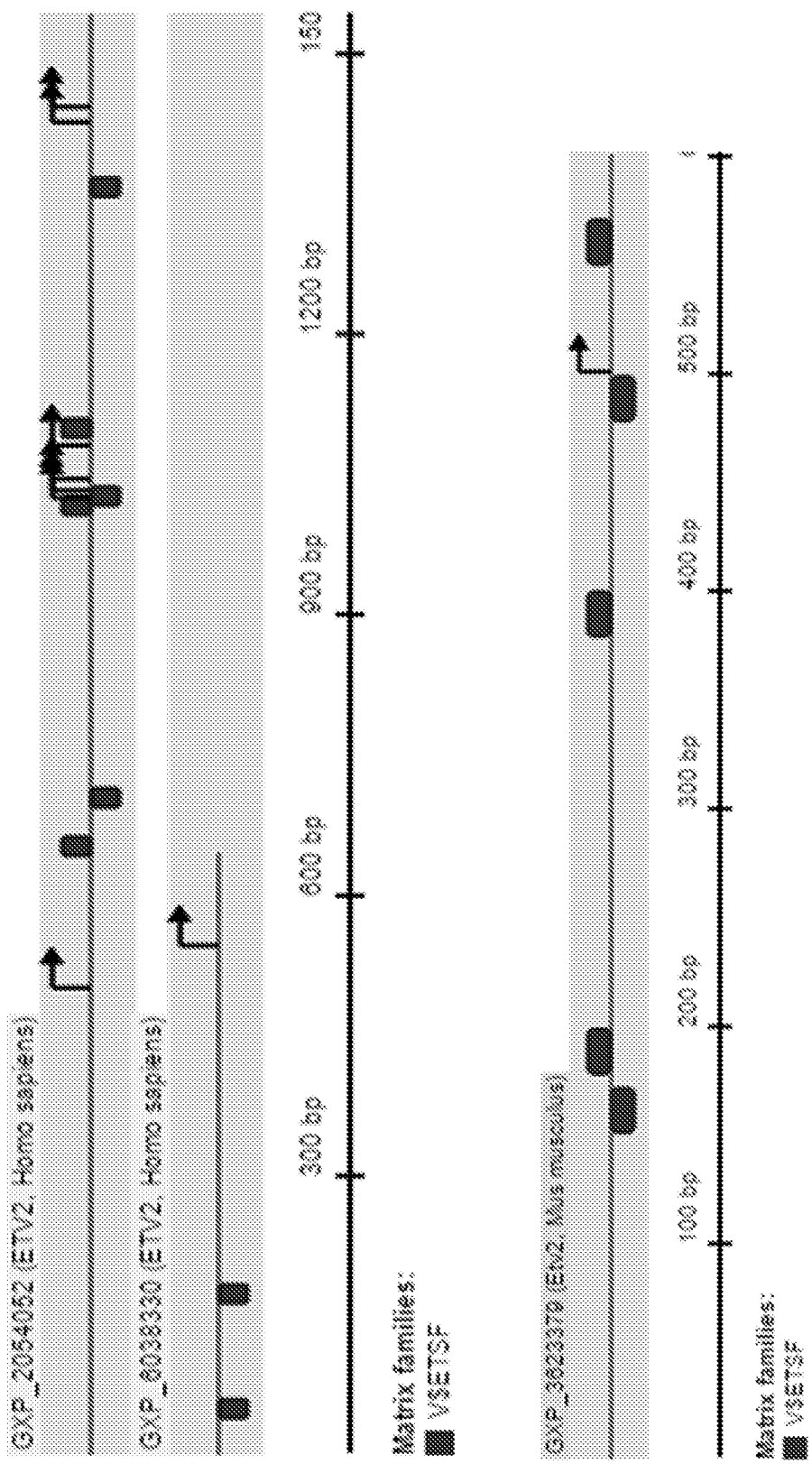
Figure 13E:
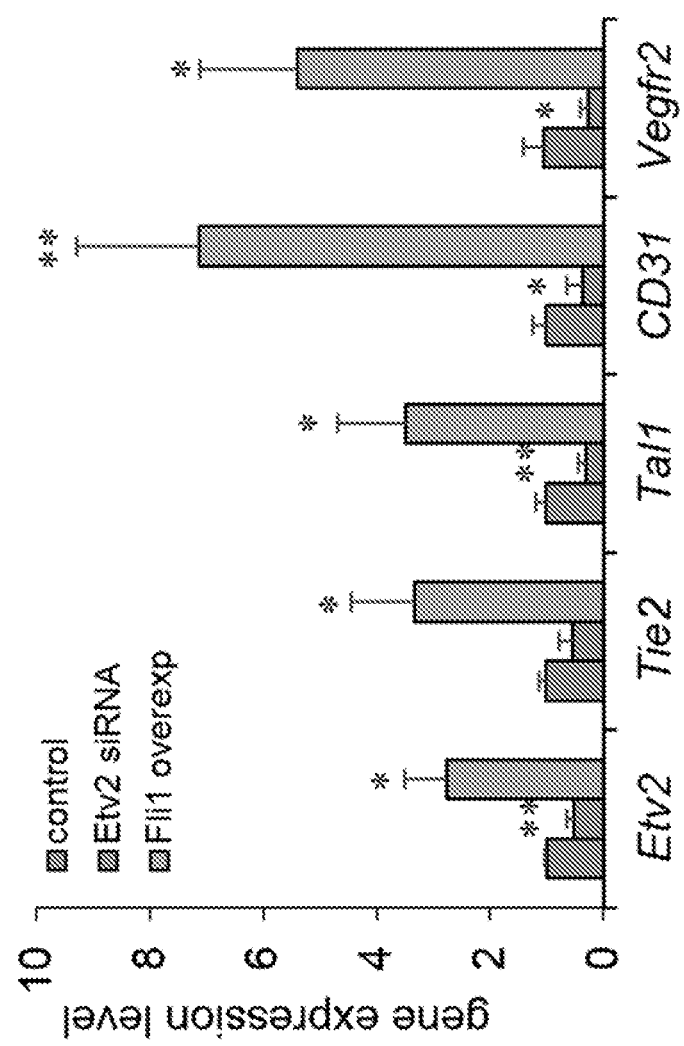
Figure 13D:
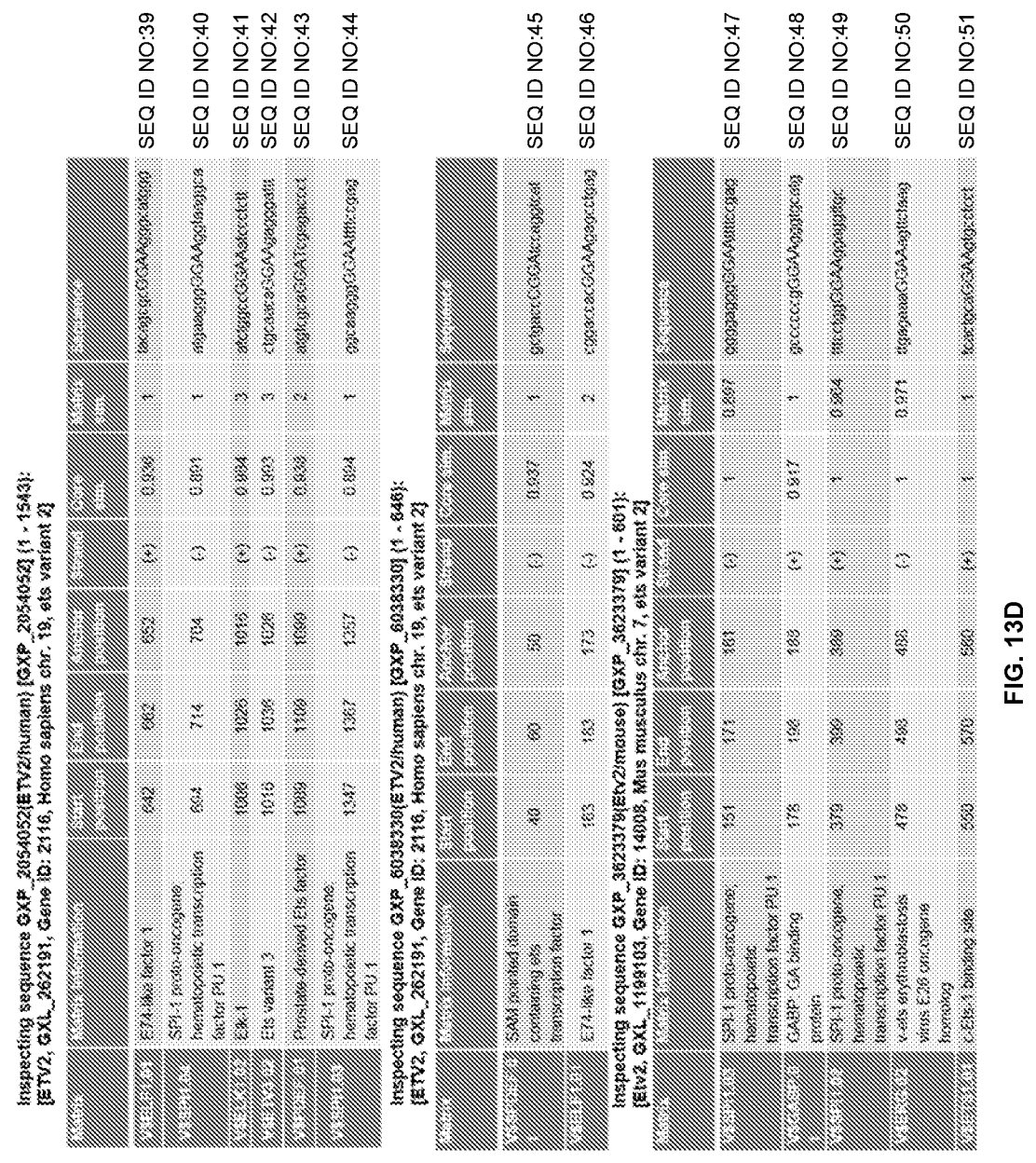

In the pathway of angiogenesis caused by miR-200b inhibition, components downstream of Fli-1 action were characterized using the MatInspector software for promoter analyses. The Etv2 promoter region contains eight known ETS binding sites which are necessary for the activation of Etv2 (FIGS. 13C and 13D). Chromatin immunoprecipitation (ChIP) assay demonstrated that enhanced binding of Fli-1 to Etv2 promoter was inhibited in Fli-1 silenced dermal fibroblasts whereas forced expression of Fli-1 improved Etv2 promoter occupation by Fli-1 (FIG. 8E). These results were corroborated using Etv2 promoter-reporter assay in Fli-1 silenced or overexpressed cells treated with either miR-200b inhibitor or mimic, respectively. Increased reporter activity was detected in cells transfected with miR-200b inhibitor. Blunting of such activity in response to Fli1 knockdown underscored the significance of Fli-1 in Etv2 transactivation. Consistently, increased Etv2 promoter activity in Fli-1 overexpressed cells was completely abolished when the cells were co-transfected with miR-200b mimic and Fli-1 forced expression vector (FIG. 8F). Silencing or de-silencing of Fli-1 in iECs downregulated or upregulated Etv2 mRNA expression, respectively (FIG. 8G). Thus, miR-200b inhibition de-silences Fli-1 which in turn upregulates Etv2 to activate the angiogenic switch (FIG. 13E).

Figure 9A:
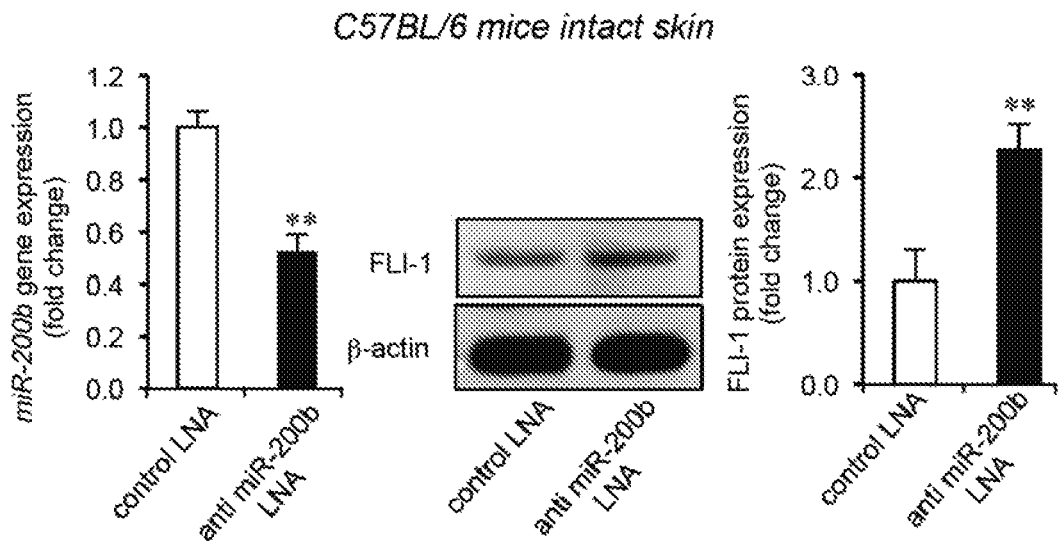
FIG. 9. In vivo reprogramming of dermal fibroblasts into iECs by wound induced suppression of miR200b. (A) RT-qPCR analysis of miR-200b expression (left) and western blot analysis of FLI-1 protein expression (middle) and quantification (right) after the delivery of control-LNA or anti-miR-200b-LNA in C57BL/6 mice skin. 18s used for mRNA normalization and β-actin serves as loading controls for protein (n=3). Results are mean±s.d., P<0.01 versus control-LNA. (B) Western blot showing FLI-1 expression (top) and quantification (bottom) of post-wounding days in wound edge skin tissue of C57BL/6 mice. β-actin serves as a loading control (n=3). Results are mean±s.d., P<0.01 versus skin. (C) Representative immunofluorescence image of wound-edge tissue of lineage tracing Fsp1-Cre:R26R$^{tdTomato}$ mice showing td-tomato expressing (red endogenous fluorescence) fibroblasts coincided with green fluorescence when stained with anti-CD31-FITC antibody. Co-localization of td-tomato and CD31 in wound-edge dermal fibroblasts was quantified by calculating Pearson's correlation coefficient (n=3). Scale bar, 50 μm. *P<0.001 (D) RT-qPCR analysis of LCM captured tdTomato$^+$ fibroblast cells from intact skin and wound-edge skin tissue showed Fsp-1 (left) and Cd31 (right) gene expression of day 5 (n=4). Results are mean±s.d., n.s.=non-significant; *P<0.001 versus skin. (E) Representative immunofluorescence image of wound-edge tissue of STZ induced diabetic mice in the background of Fsp1-Cre:R26R$^{tdTomato}$ showing td-tomato expressing fibroblasts are less coincided with green fluorescence when stained with anti-CD31-FITC antibody. Co-localization of td-tomato and CD31 in diabetic dermal fibroblasts was quantified by calculating Pearson's correlation coefficient (n=3). Scale bar, 50 μm. *P<0.001
Figure 9B:
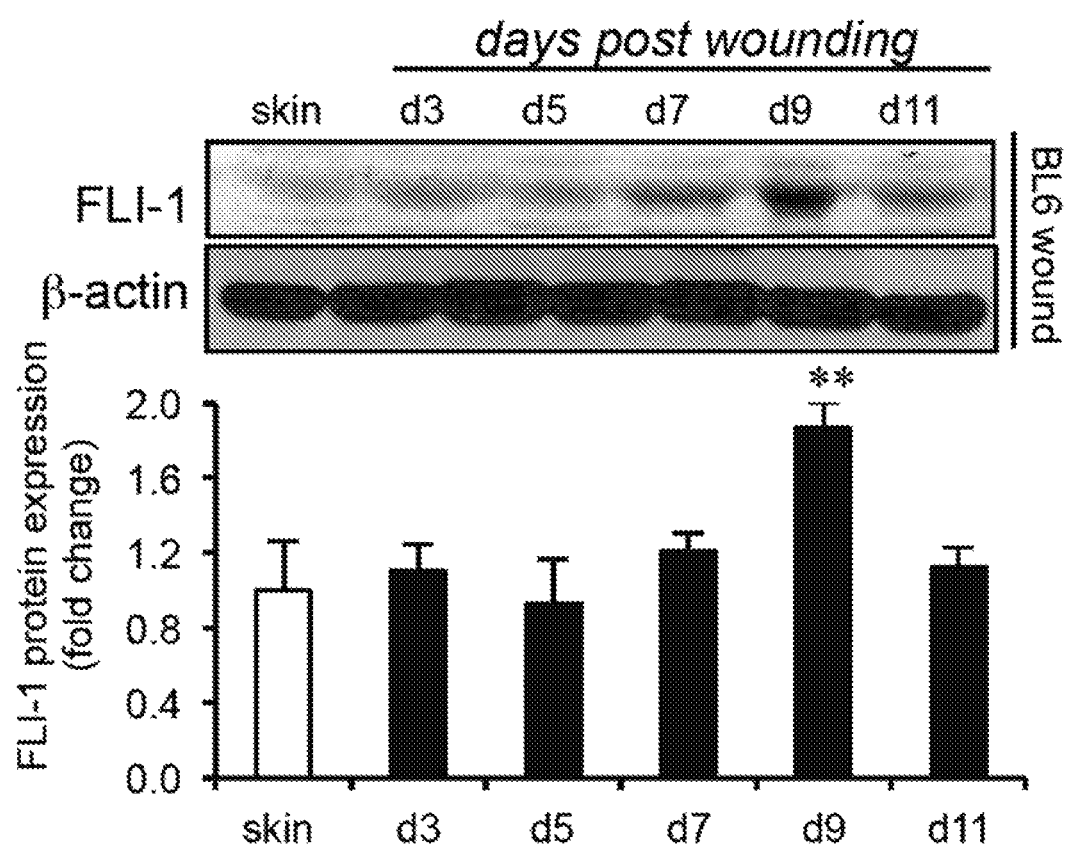
Figure 9C:
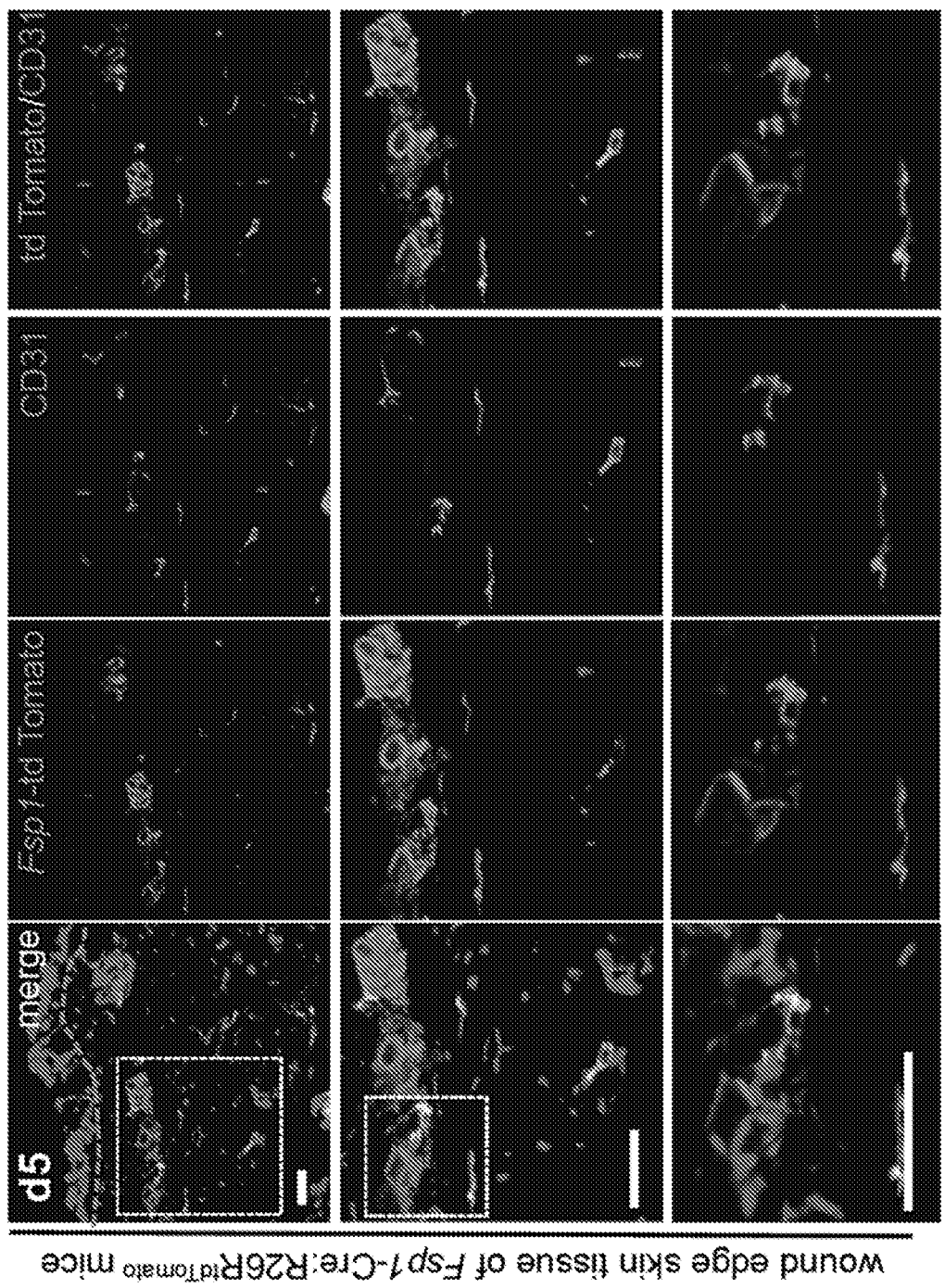
Figure 9D:
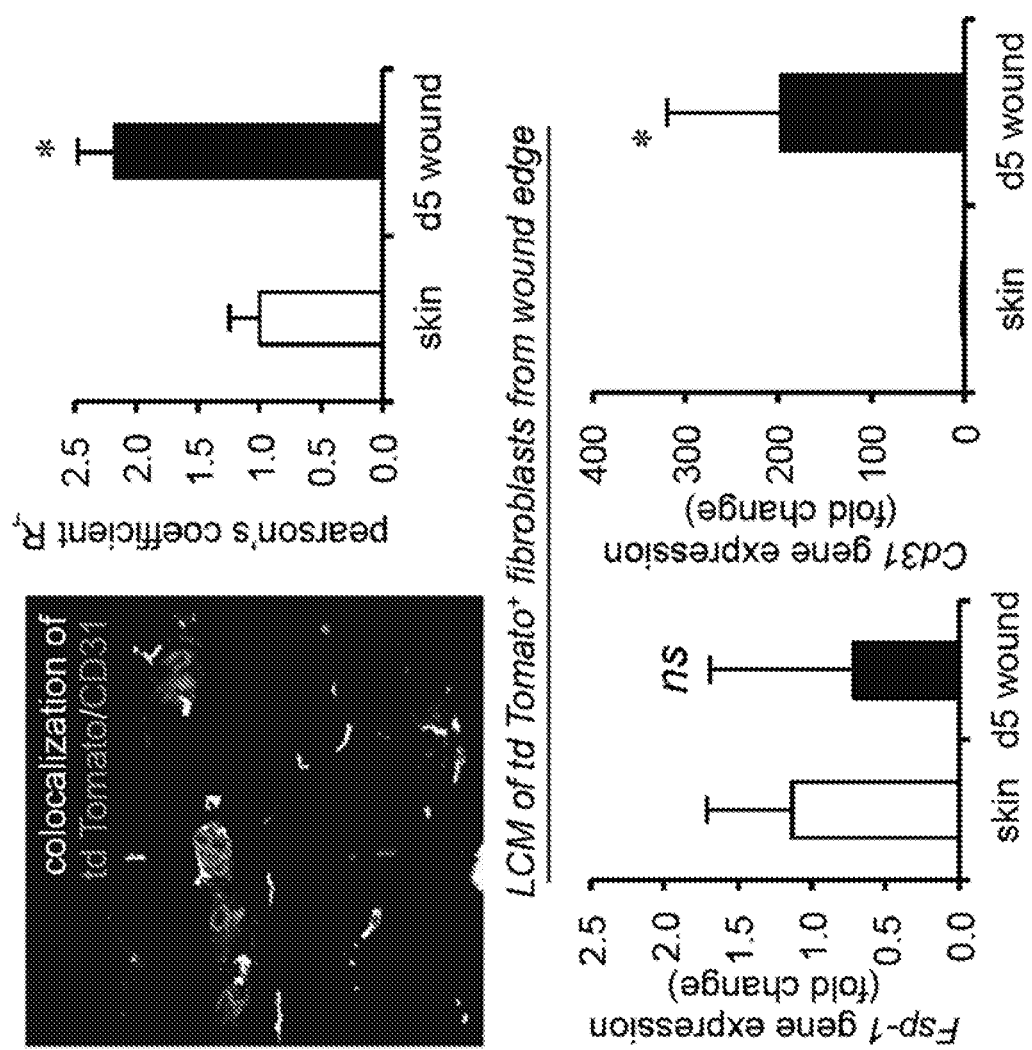
Figure 9E:
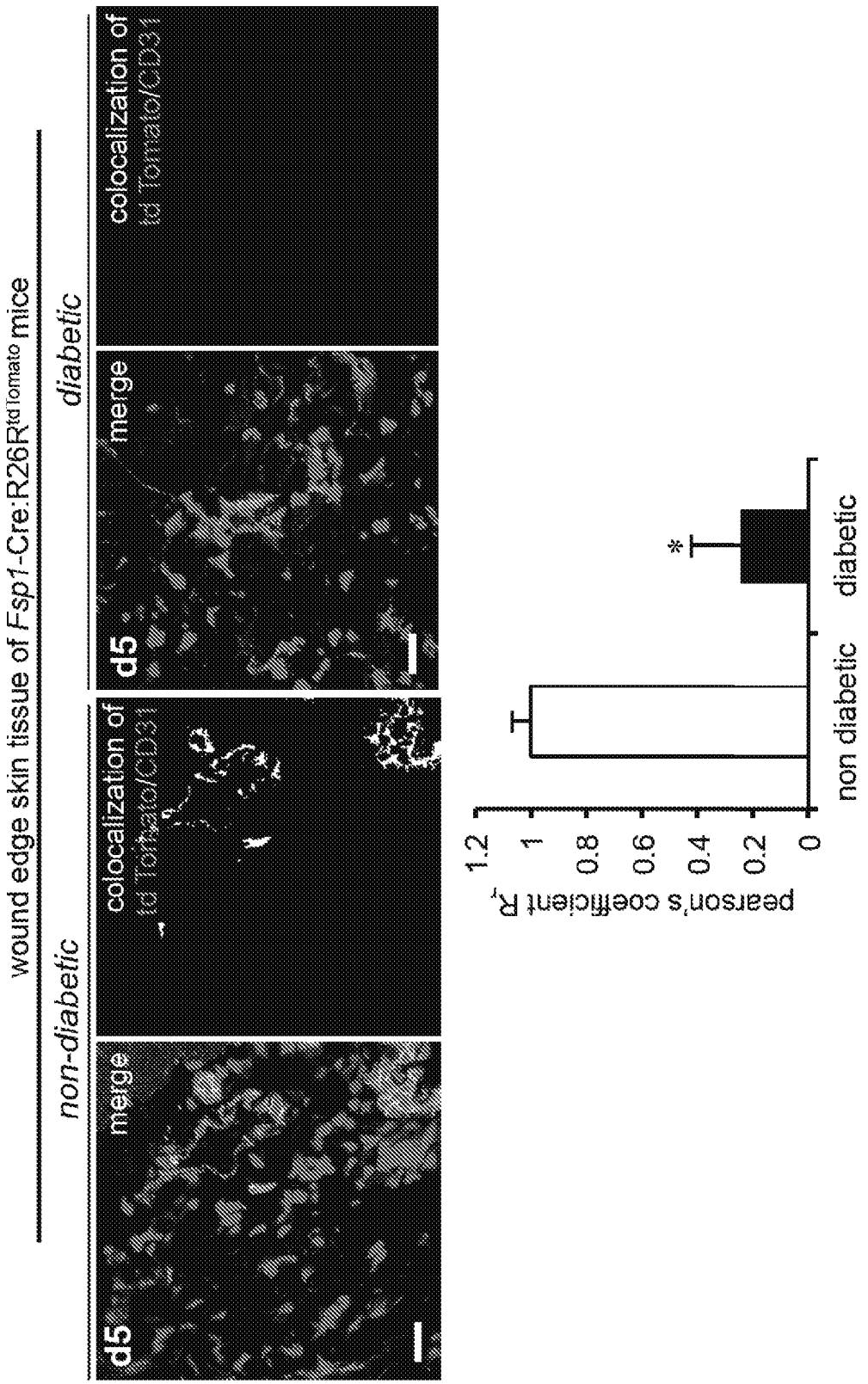
Figure 14A:
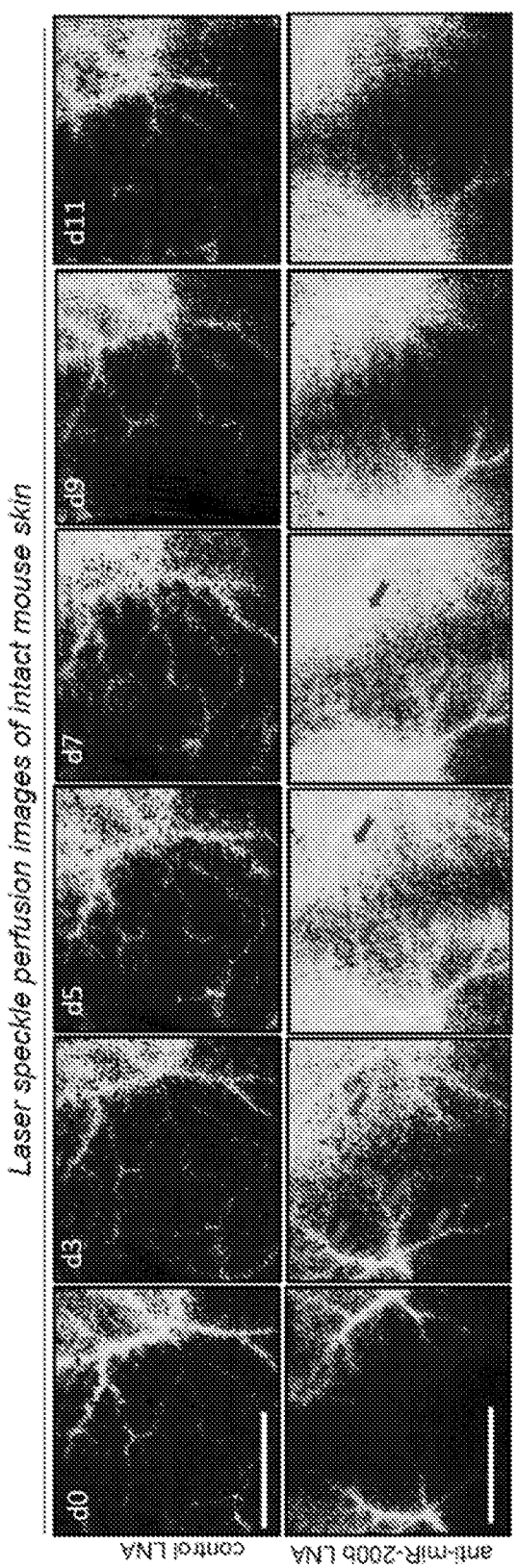
FIG. 14. Increased wound angiogenesis following anti-miR200b-LNA delivery. (A) Representative images of skin blood perfusion measured by laser speckle at the indicated days post transfection with control-LNA or anti-miR200b-LNA in the skin of C57BL/6 mice (n=3). Scale bar, 10 mm. (B) Image showing before and after capture of FSPcre tdTomato+ fibroblasts by LCM.
Figure 14B:
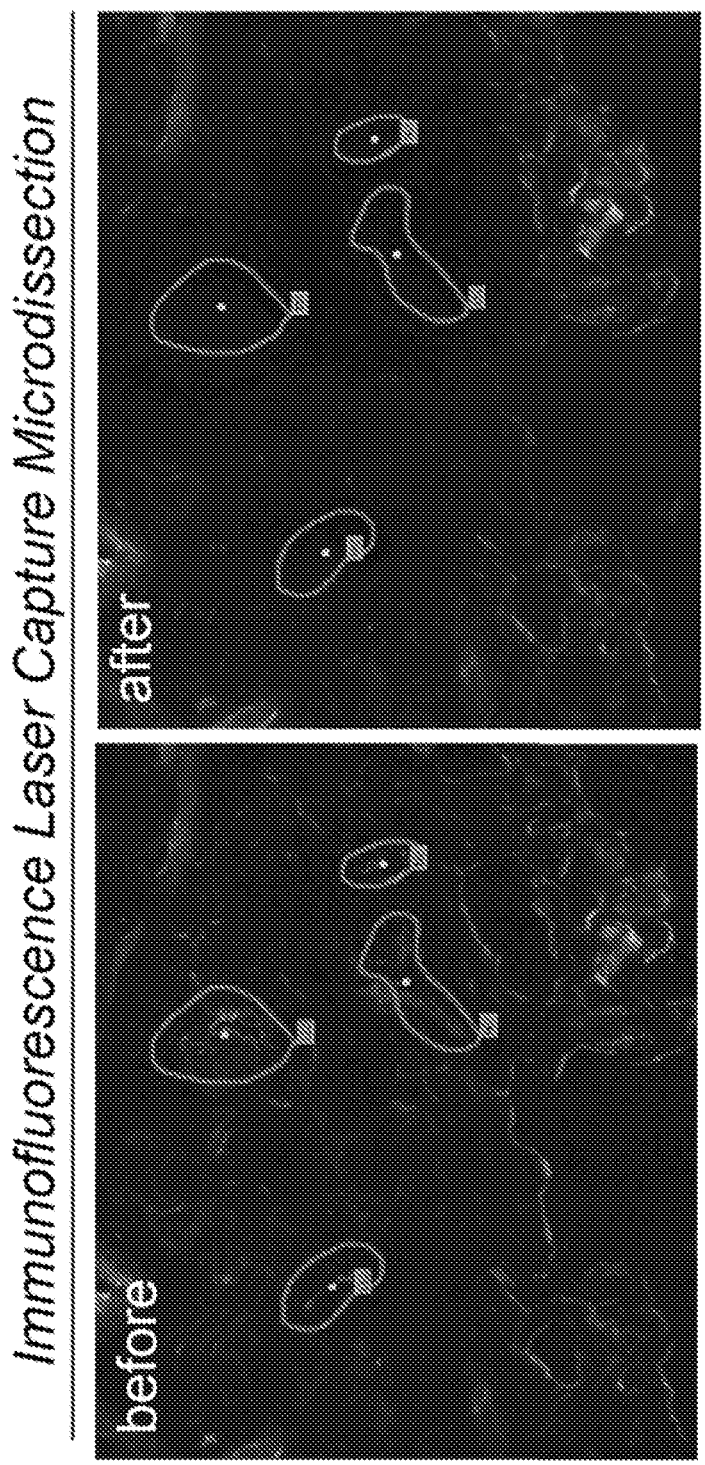

Lineage Tracing Evidence for Direct In Vivo Reprogramming of Dermal Fibroblasts into Vasculogenic iECs Direct conversion of dermal fibroblasts to iECs in vivo was achieved by inhibition of miR-200b in the intact skin of immune-sufficient C57BL/6 mice. Topical nanoelectroporation-based delivery of anti-miR200b-LNA to the skin de-silenced Fli-1 (FIG. 9A). At the same time, improved blood flow in the dorsal skin was observed. Such improvement was transient, peaking at day 7 of miR-200b inhibition followed by lowering of induced perfusion during the subsequent 4 days (FIG. 14A). This line of evidence pointing towards a timely regression of induced vasculature in the intact skin weighs against the possibility of teratoma formation by resulting iECs in vivo. Unlike the intact healthy skin which is adequately perfused, the significance of induced perfusion is different in a wound where angiogenesis is necessary (Tonnesen et al., 2000). Consistent with the notion of an integral role of direct cell conversion in the physiology of tissue repair, injury itself triggered miR-200b inhibition at the wound-edge tissue (FIG. 12A). Such inhibition was associated with concomitant increase of Fli-1 expression in the wound-edge tissue on post-wound days 7 and 9 (FIG. 9B). The search for direct proof of cell conversion in vivo necessitated lineage tracing studies using Fsp1-Cre: R26RtdTomato mice (Ubil et al., 2014). Day 5 post-injury was marked by the abundant presence of transition cells of fibroblast lineage that were also CD31+(FIG. 9C). Wound-edge fibroblasts isolated by laser capture microdissection (LCM) (FIG. 14B) showed transition features such as attenuated FSP1 expression along with gain of endothelial marker CD31 (FIG. 9D). This constitutes direct proof that fibroblasts are converted to iECs at the injury-site where miR-200b is inhibited. However, such injury-induced miR-200b-dependent physiological conversion of fibroblast to endothelial cells was impaired in diabetic mice (FIG. 9E) recognizing diabetic conditions as a barrier to such vasculogenic cell conversion.

Figure 10A:
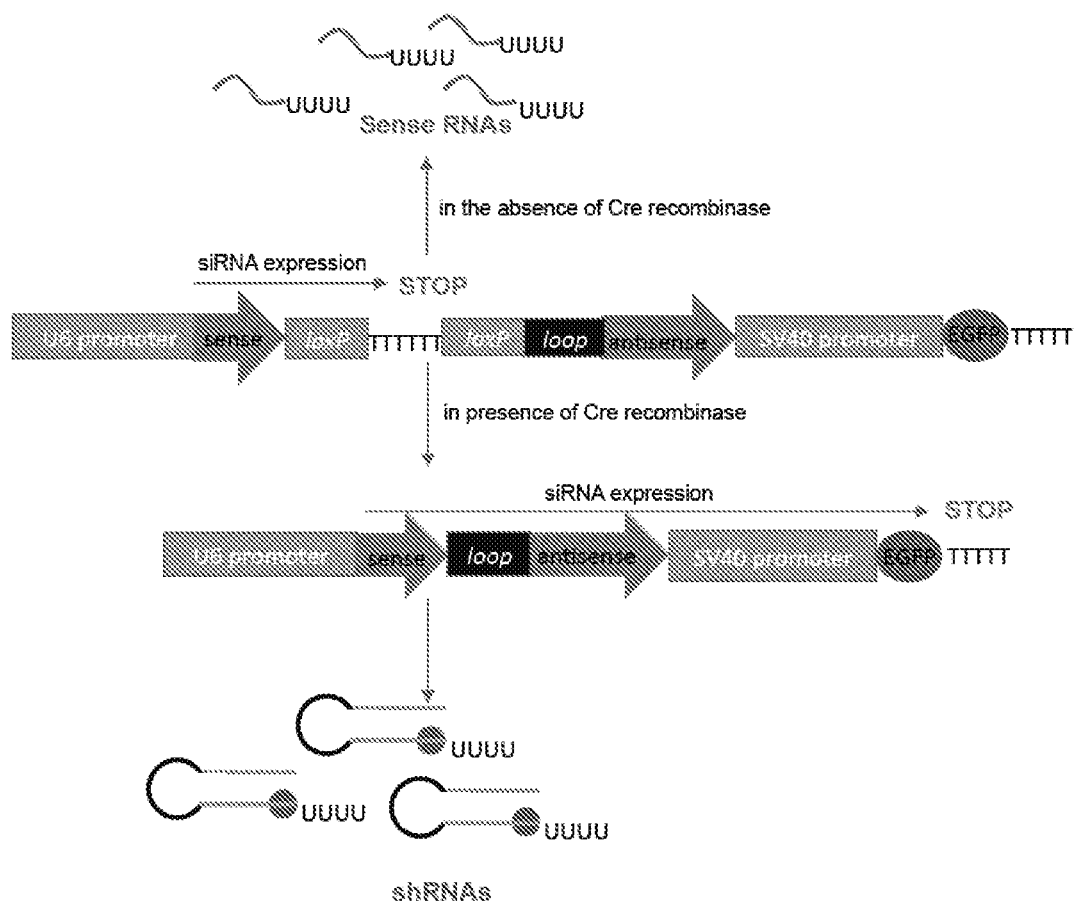
FIG. 10. Inhibition of miR-200b improves diabetic wound healing by desilencing Fli-1 expression. (A) Schematic diagram showing Cre/loxP regulated fibroblast specific Fli-1 shRNA expression. (B) Diagrammatic view of study design for targeted knocking down of Fli-1 at wound edge fibroblast (C) Representative immunofluorescence images of FSP-Cre mice where control-LNA or anti-mir-200b-LNA was delivered at the wound-edge along with lentiviral (LV) injection of LoxP flanked control scrambled or Fli1 shRNA-EGFP cassettes. Due to Cre/loxP regulated RNA interference, wound-edge fibroblasts expressed green fluorescence (left). (D) Graph showing co-localization analysis of confocal images where dermal fibroblasts (green) also expressed CD31 (red) endothelial marker (right) (n=6). Scale bar, 50 μm. Data represent mean±s.d. **P<0.01 versus con LNA+con shRNA LV; *P<0.001 versus anti-miR-200b LNA+con shRNA LV.
Figure 10B:
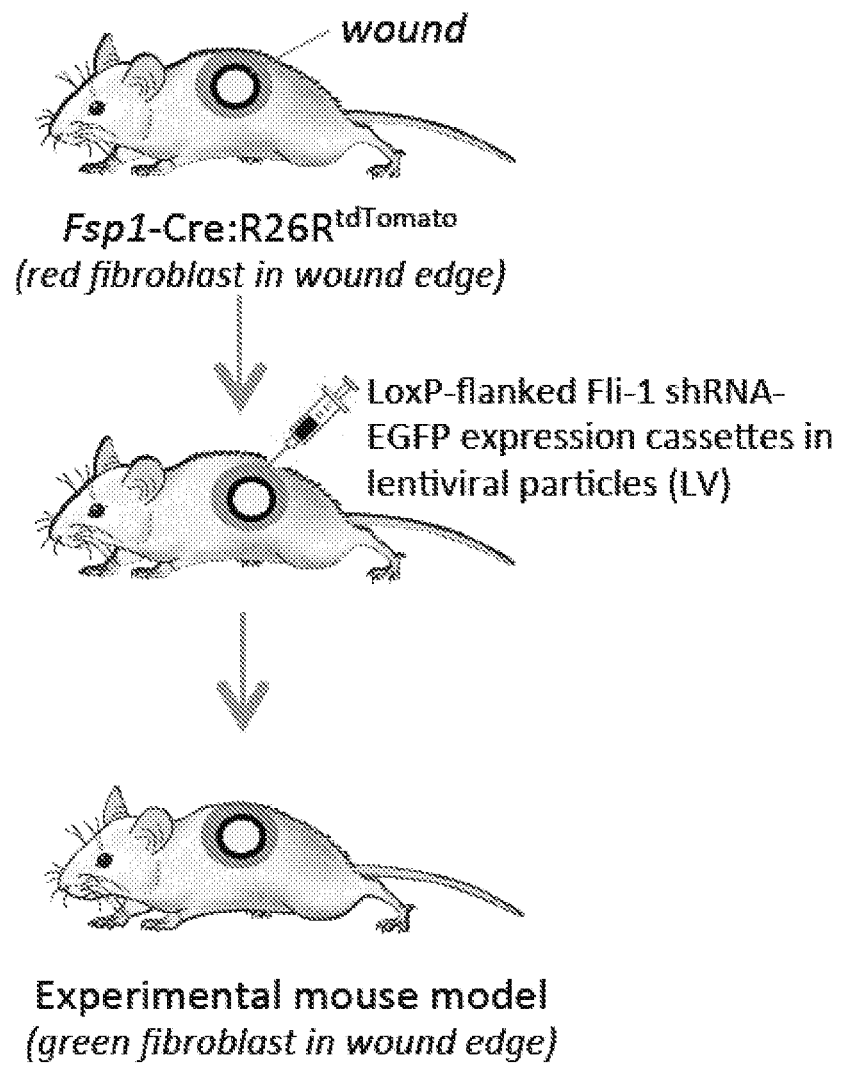
Figure 10C:
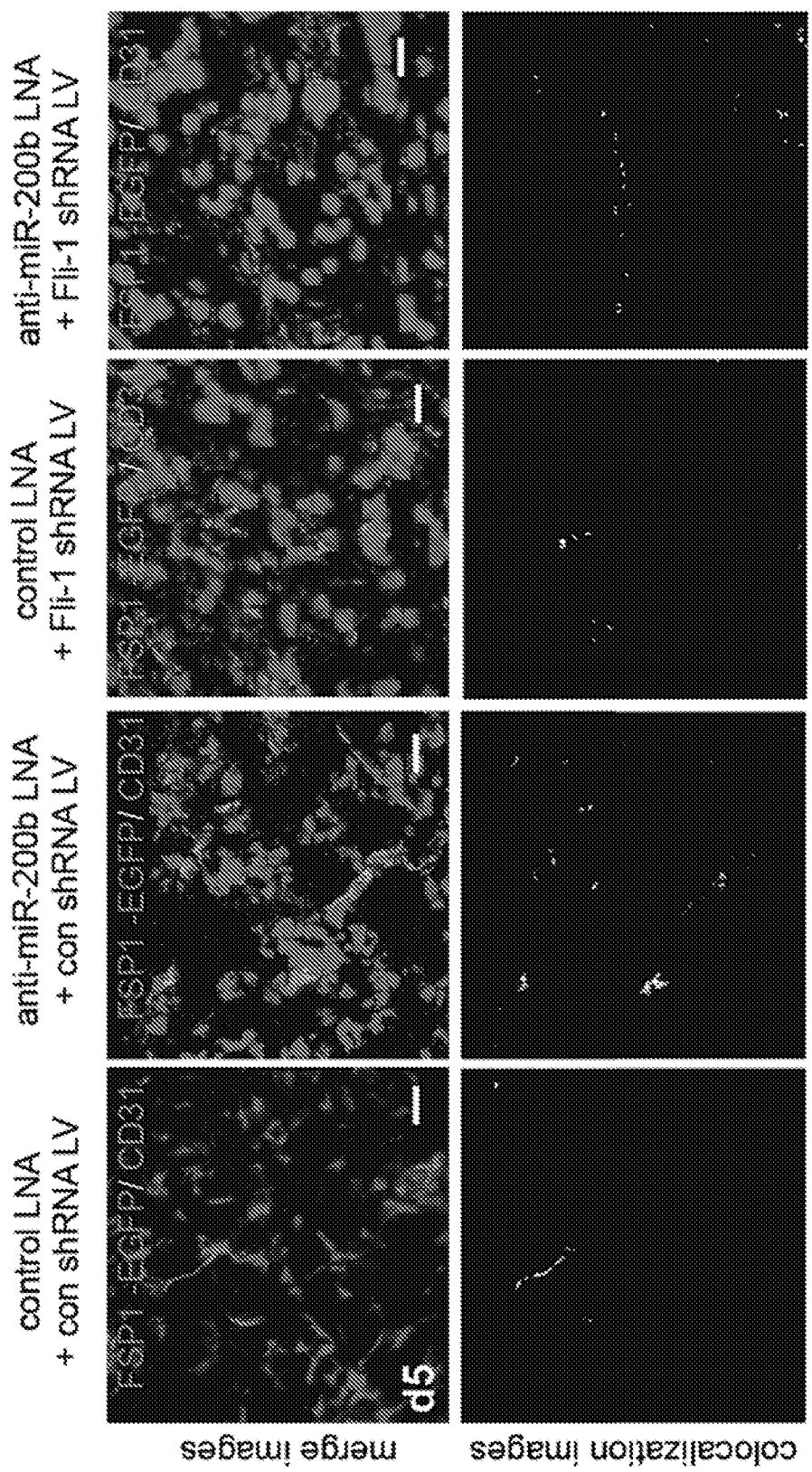
Figure 10D:
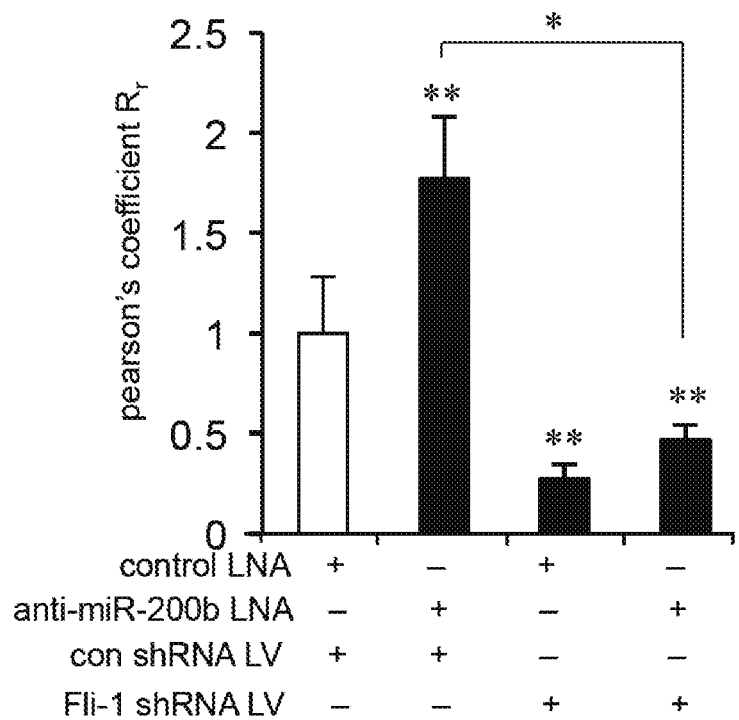
Figure 15A:
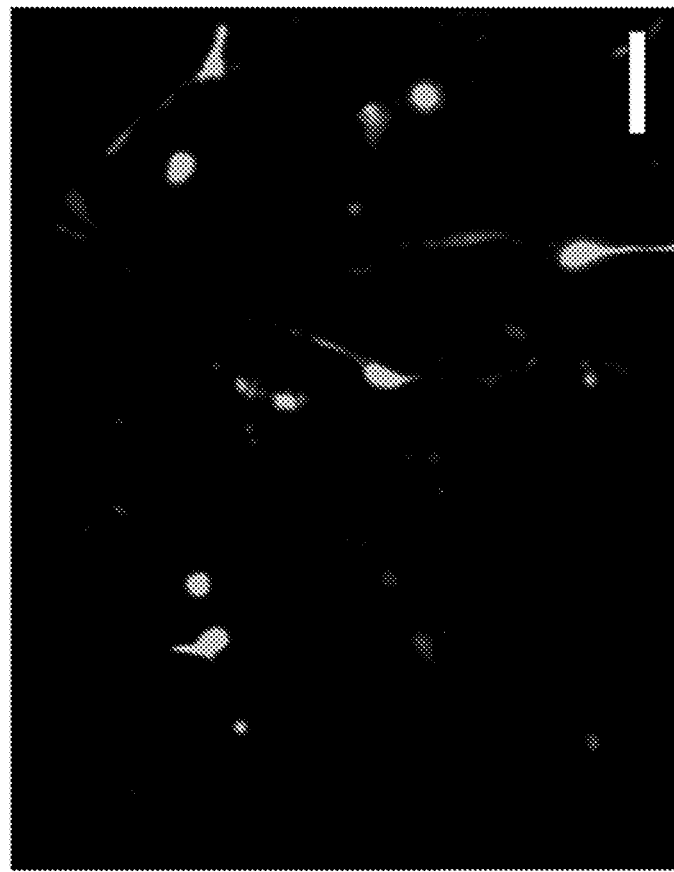
FIG. 15. Increased wound angiogenesis following anti-miR200b-LNA delivery was abrogated by fibroblast specific silencing of Fli-1. (a) Representative image showing EGFP fluorescence in HADF-Cre cells transfected with LoxP flanked Fli-1 shRNA expression cassettes. Scale bar, 100 μm. (b) Four different Fli-1 shRNA vectors were validated in dermal fibroblasts upon Cre mediated deletion of the STOP cassette. Western blot showing FLI-1 protein expression in cells co-transfected with cre recombinase vector (pCSCre2, a gift from G. Ryffel, Addgene plasmid #31308) and each of four different Fli-1 shRNA expression cassettes. CC, control shRNA construct and VC, lentiviral Fli-1 shRNA constructs (c) Fibroblast-specific Fli-1 knockdown was also confirmed at wound-edge tissue by immunostaining of Fli-1. Representative image of Fli-1 positive staining of cutaneous wound-edge tissue on day 5 post-wounding. (d) Representative image of blood perfusion at wound site on day 9 post-wounding in mice treated with control LNA or anti-miR-200b-LNA in absence or presence of control or Fli-1 shRNA lentiviral particles. Scale bar, 5 mm. (e) Wound perfusion was measured in above-mentioned mice (n=4). Data represent mean±s.d., #P<0.05; P<0.01 versus respective control. (f) Representative image of wound closure on day 9 post-wounding in mice treated with control-LNA or antimiR-200bLNA in absence or presence of control or Fli-1 shRNA lentiviral particles. Scale bar, 5 mm. (g) Wound closure monitored in above-mentioned mice by calculating percentage of wound area (n=4). Data represent mean±s.d., P<0.01 versus respective control. (h) Representative image of immunofluorescence staining of K14 showing wound epithelialization. Scale bar, 500 μm.
Figure 15B:
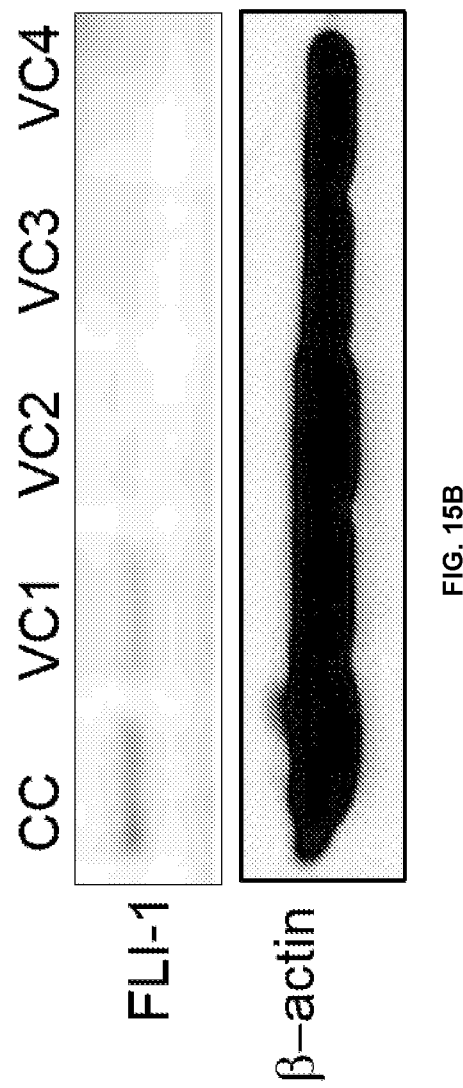
Figure 15C:
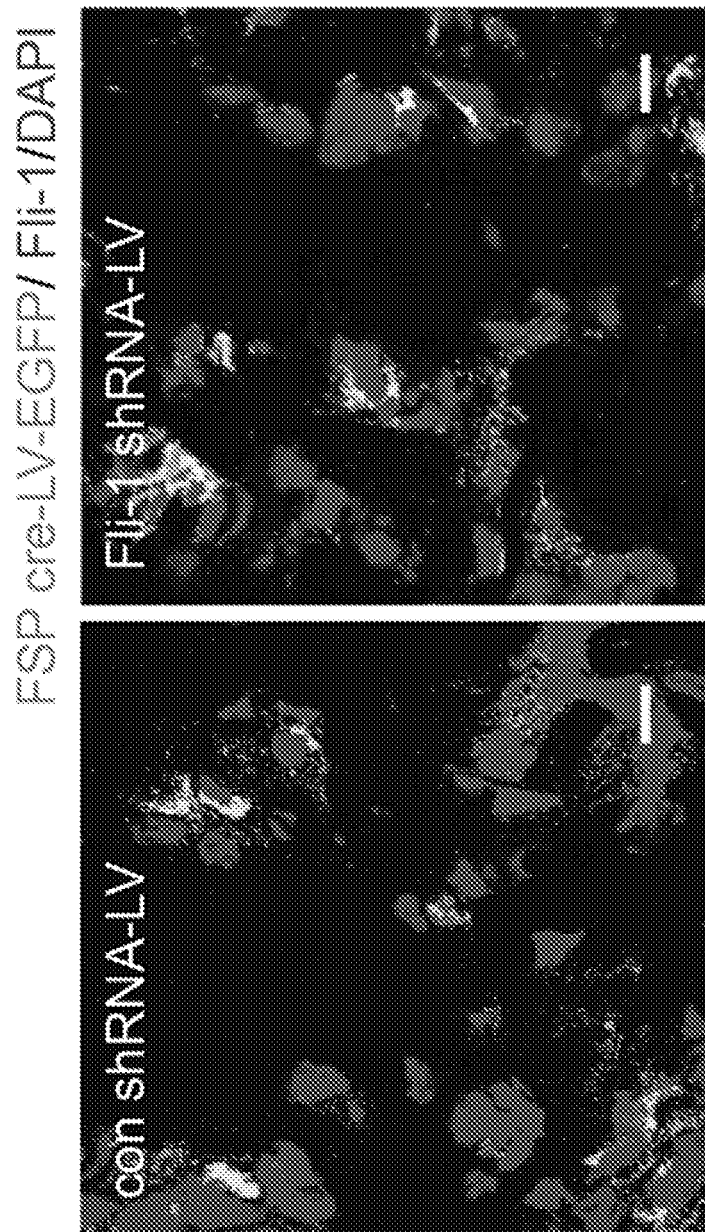
Figure 15D:
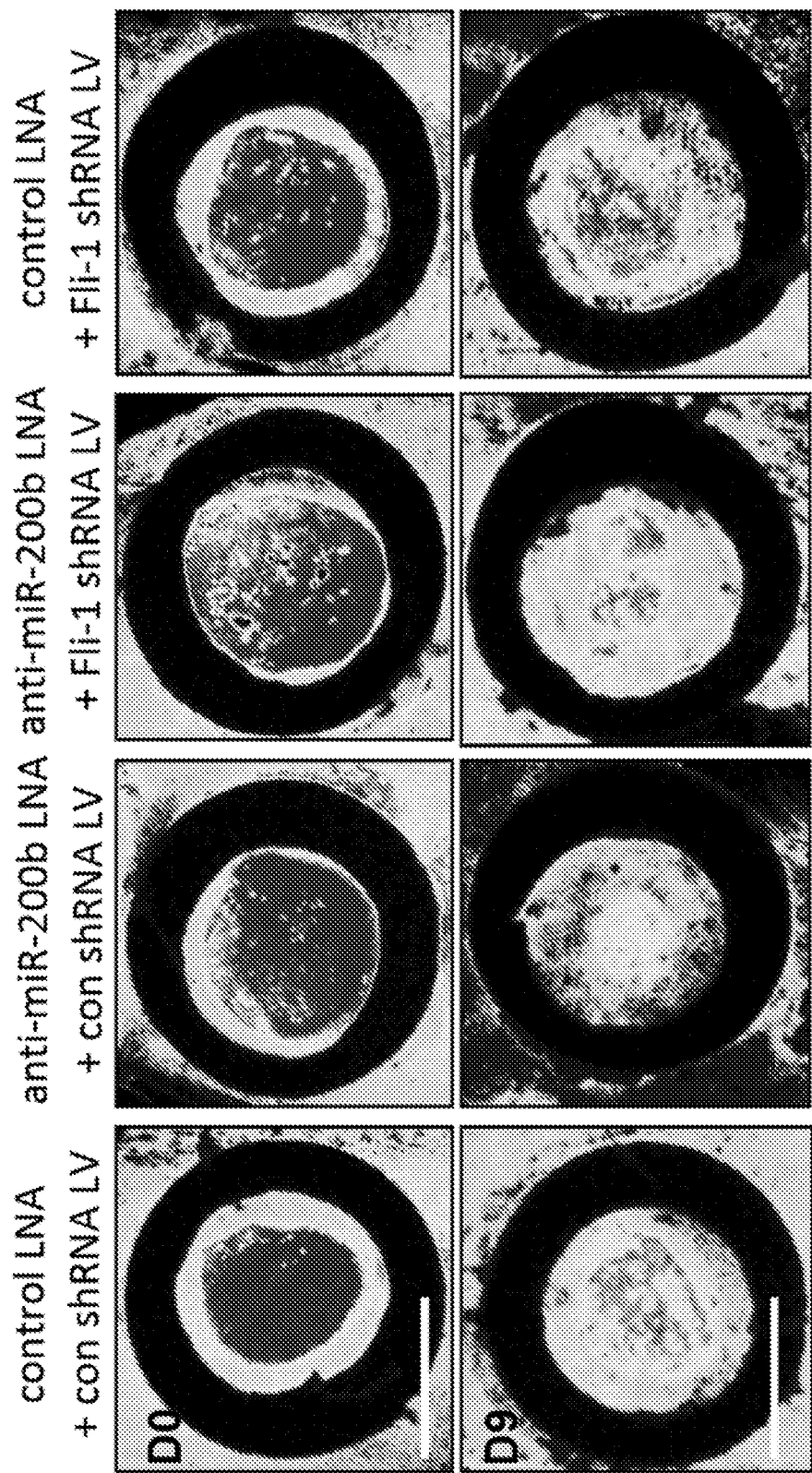
Figure 15E:
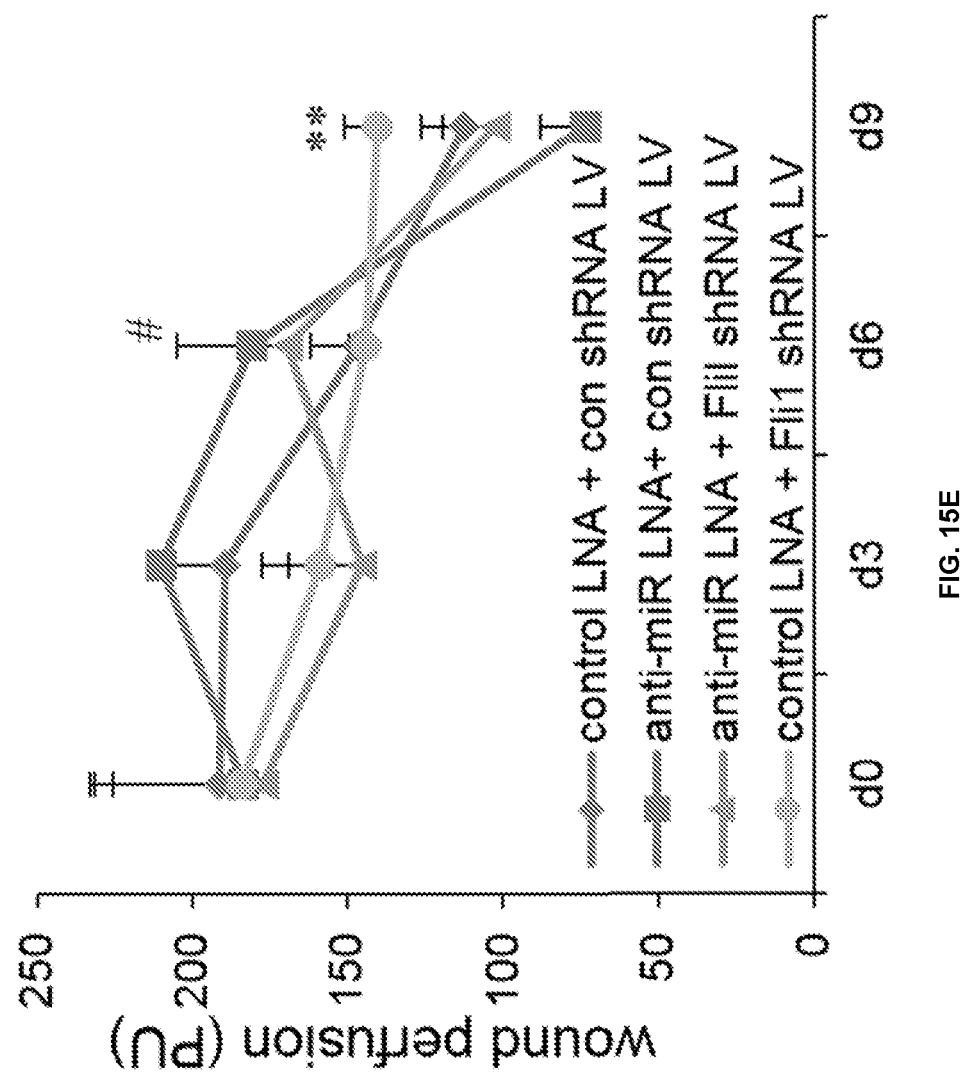
Figure 15F:
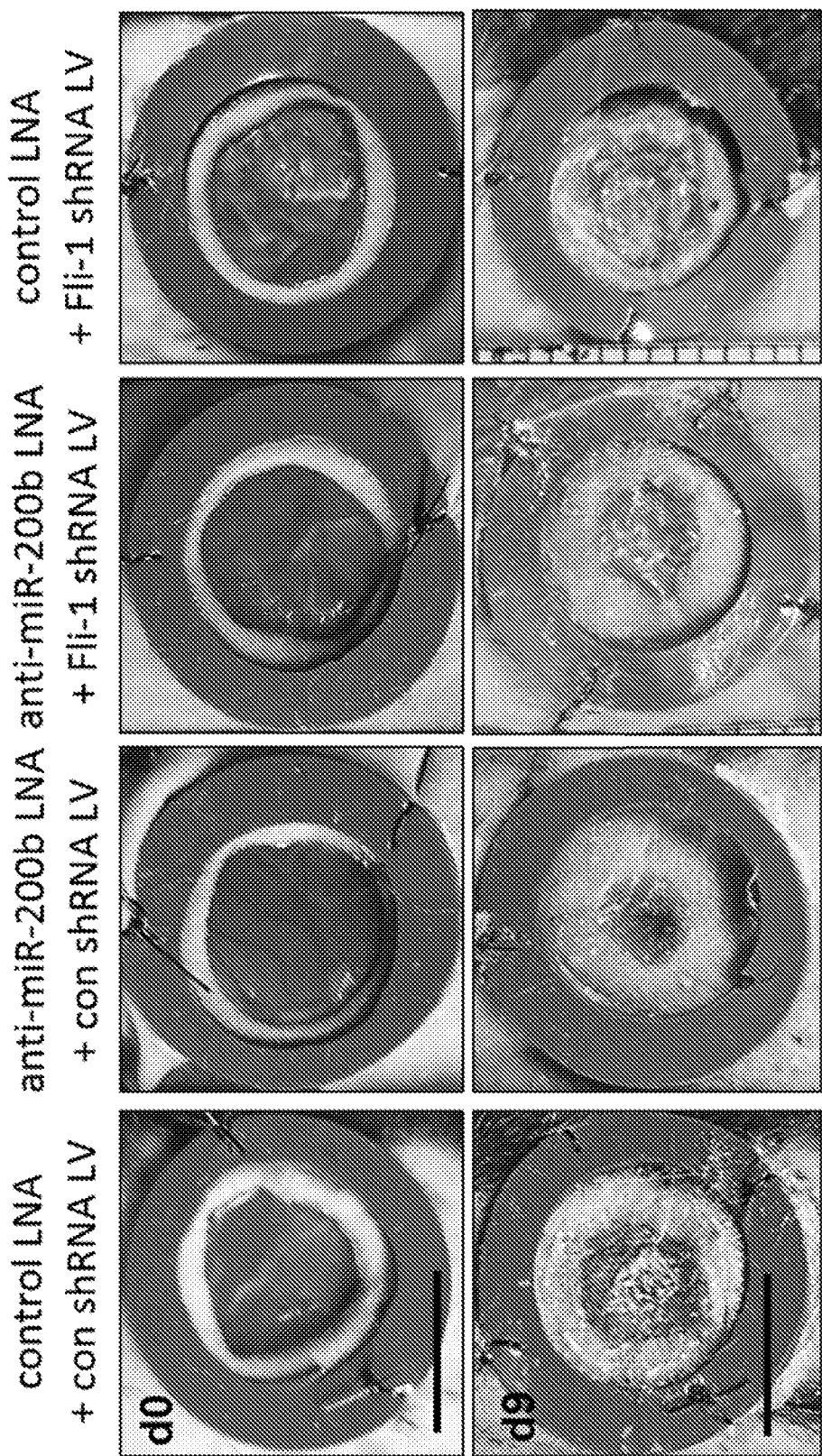
Figure 15G:
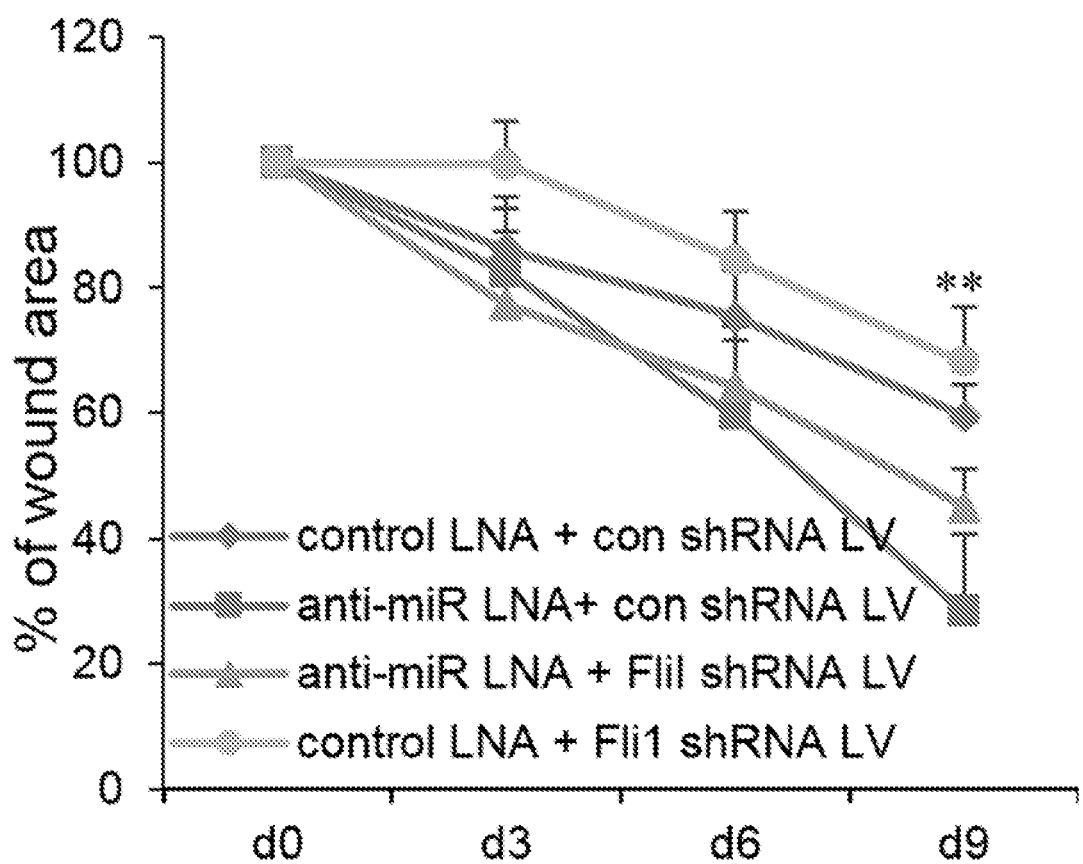
Figure 15H:
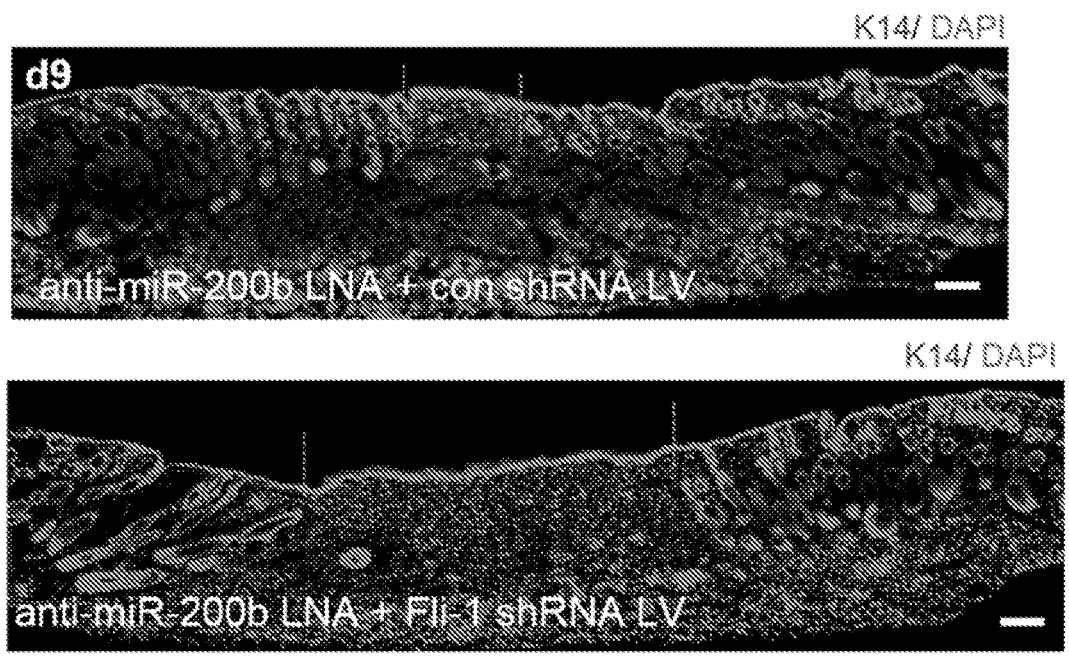

Conditional In Vivo Knockdown of Fli-1 in Dermal Fibroblasts Impaired Physiological Reprogramming to iECs To test the significance of Fli-1 in the conversion of fibroblasts to iECs conversion at the injury-site, Cre/loxP regulated RNA interference was utilized to obtain conditional fibroblast-specific gene knockdown in mice (Hitz et al., 2007; Kasim et al., 2004). Fibroblast-specific Fli-1 was knocked down in vivo by LoxP-flanked Fli-1 shRNA expression cassettes (FIG. 10A). Four LoxP flanked Fli-1 shRNA expression cassettes were designed, and based on their efficiency for downregulating Fli-1 protein expression in vitro (FIGS. 15A and 15B), three cassettes were pooled and used for lentiviral transfection at the wound edge of Fsp1-Cre mice. Validation of the Fli-1 shRNA vector is reported in FIGS. 15B and 15C. Delivery of anti-miR200b-LNA at the wound-edge tissue (FIG. 10B) showed increased co-localization of FSP1 and CD31 in support of the role of miR-200b in the conversion of fibroblast to iEC (FIGS. 10C and 10D). Such co-localization was markedly blunted by fibroblast-targeted knockdown of Fli-1 implicating Fli-1 as a critical mediator of miR-200b function (FIGS. 10C and 10D). Indeed, under the same experimental conditions, Fli-1 knockdown in dermal fibroblasts significantly attenuated wound perfusion (FIGS. 15D and 15E) and impaired wound closure (FIG. 15F-15H). These results demonstrate that fibroblast-originated mature iECs at injury site caused by miR-200b inhibition is Fli-1 dependent that helps in tissue vascularization.

Figure 11A:
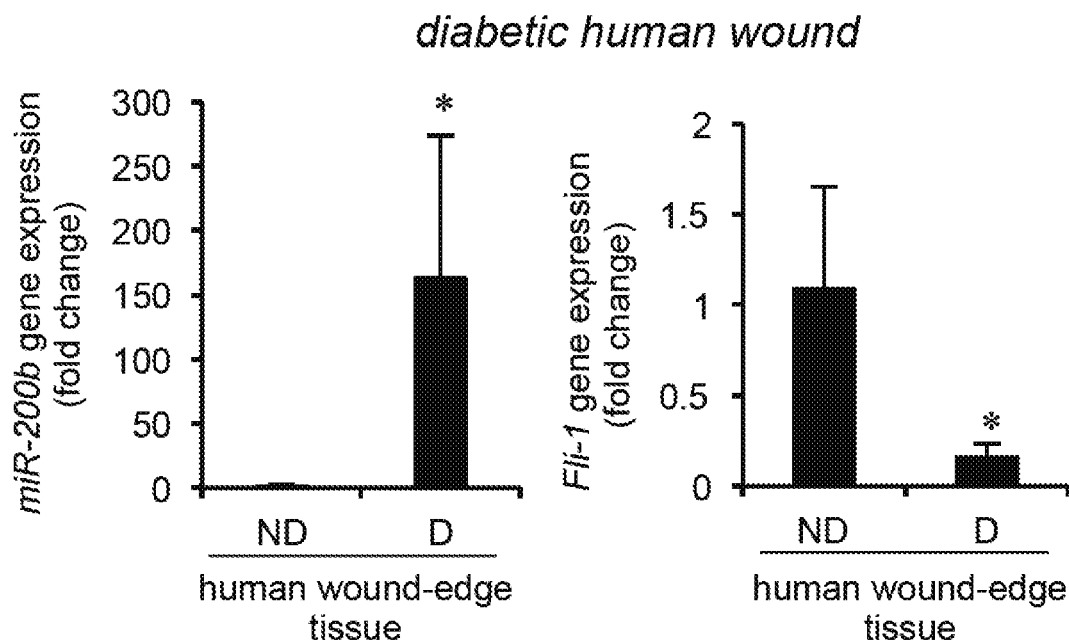
FIG. 11. Inhibition of miR-200b improves diabetic wound healing by desilencing Fli-1 expression. (A) RT-qPCR analysis of miR-200b and Fli-1 gene expression in wound edge tissue of non-diabetic (n=3) and diabetic human subjects (n=3). Data represent mean±s.d., *P<0.001 versus non-diabetic subjects. (B) Immunohistochemistry of FLI-1 protein represented in lower (top) and higher (bottom) magnification views in wound-edge tissue of non-diabetic and diabetic subjects. Scale bar, 200 μm. (C) RT-qPCR analysis of miR-200b expression of post wound-edge tissue of diabetic db/db mice treated with control-LNA or anti-miR-200b-LNA (n=3). Data represent mean±s.d., *P<0.001; P<0.01 versus control-LNA. (D) Western blot analysis of FLI-1 protein expression (top) and quantification (bottom) of same wound-edge tissue of db/db mice. β-actin serves as a loading control (n=3). Data represent mean±s.d., P<0.01 versus control-LNA. (E) Representative immunofluorescence image showing CD31 (red) and FSP1 (green) (left panel) and its colocalization analysis (right) in control-LNA or anti-miR-200b-LNA delivered wound edge tissue of db/db mice. Scale bar, 200 μm. **P<0.01 versus control-LNA (F) Representative image showing blood perfusion in wound bed of control-LNA or anti-miR-200b-LNA treated db/db mice (n=4). (G,H) Representative image showing wound vasculature (g) and wound closure (h) at day 10 of the above-mentioned mice. (I) Wound closure was measured by calculating percentage of wound area in above-mentioned mice. Data represent mean±s.d., *P<0.001; #P<0.05 versus control-LNA. (J) Representative immunofluorescence image showing abundance of CD31 (red) and CD105 (green) level in control-LNA or anti-miR-200b-LNA delivered wound edge tissue of db/db mice. Scale bar, 500 μm.
Figure 11B:
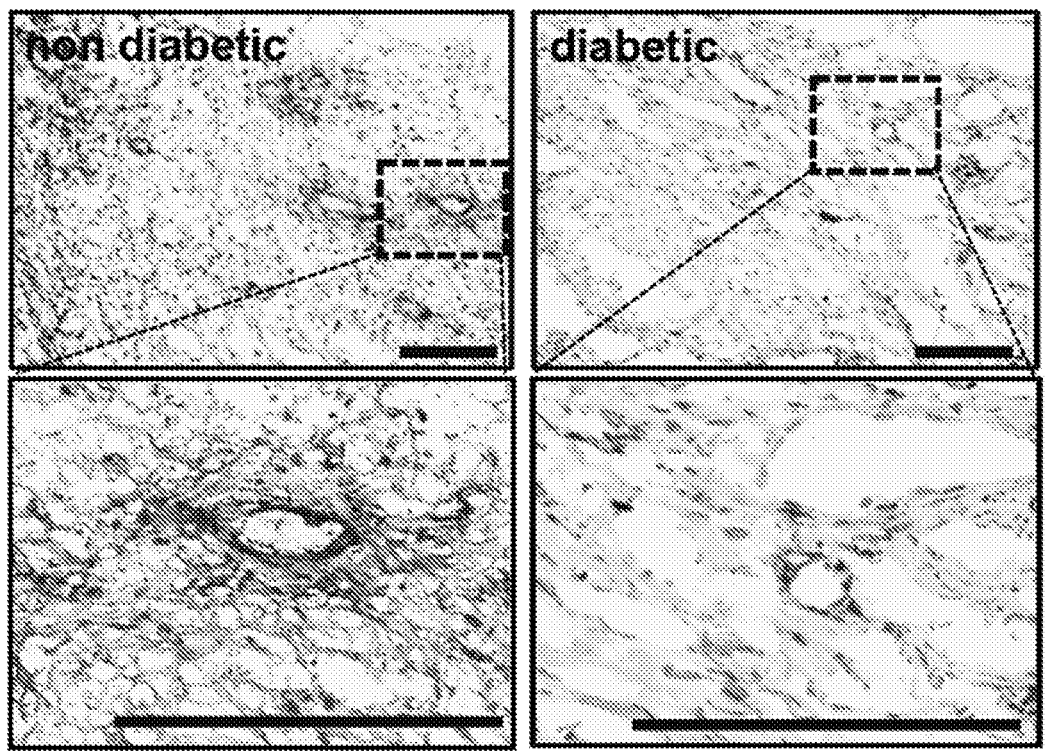
Figure 11C:
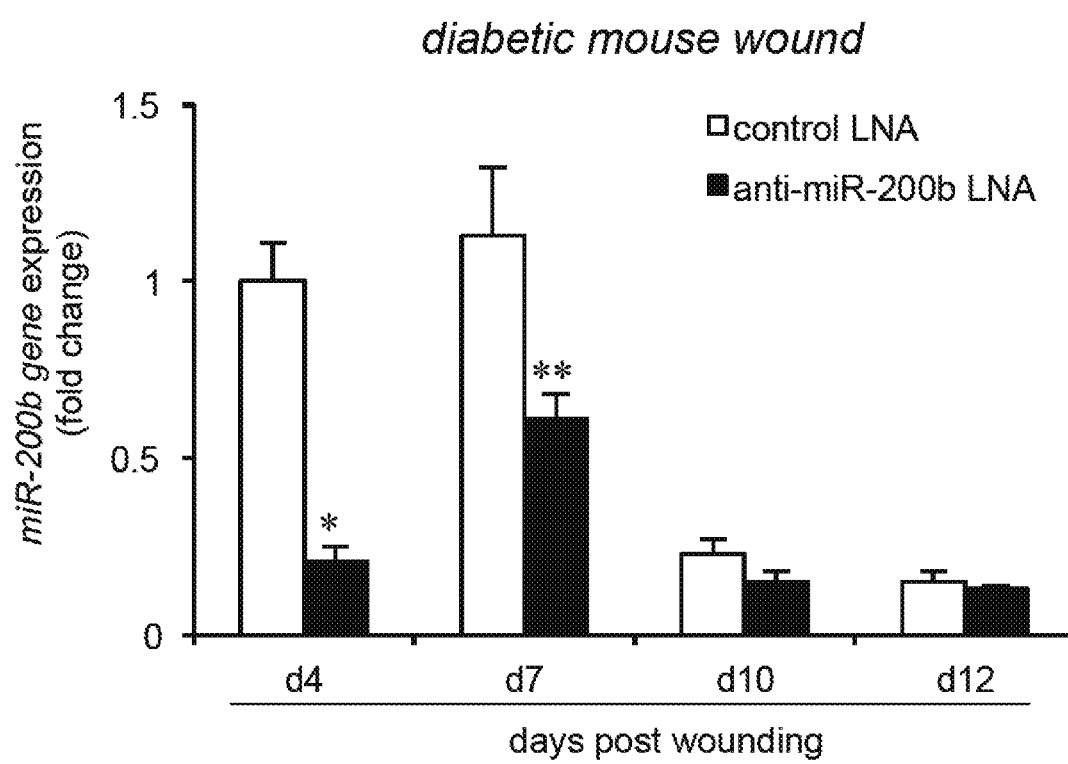
Figure 11D:
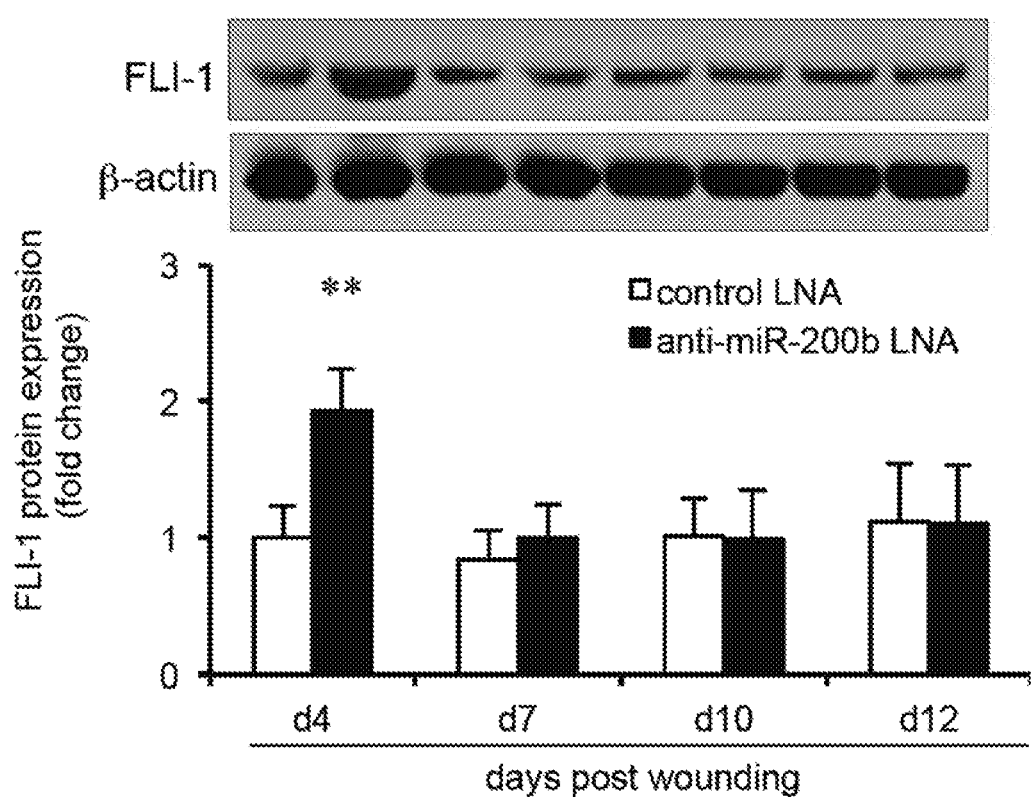
Figure 11E:
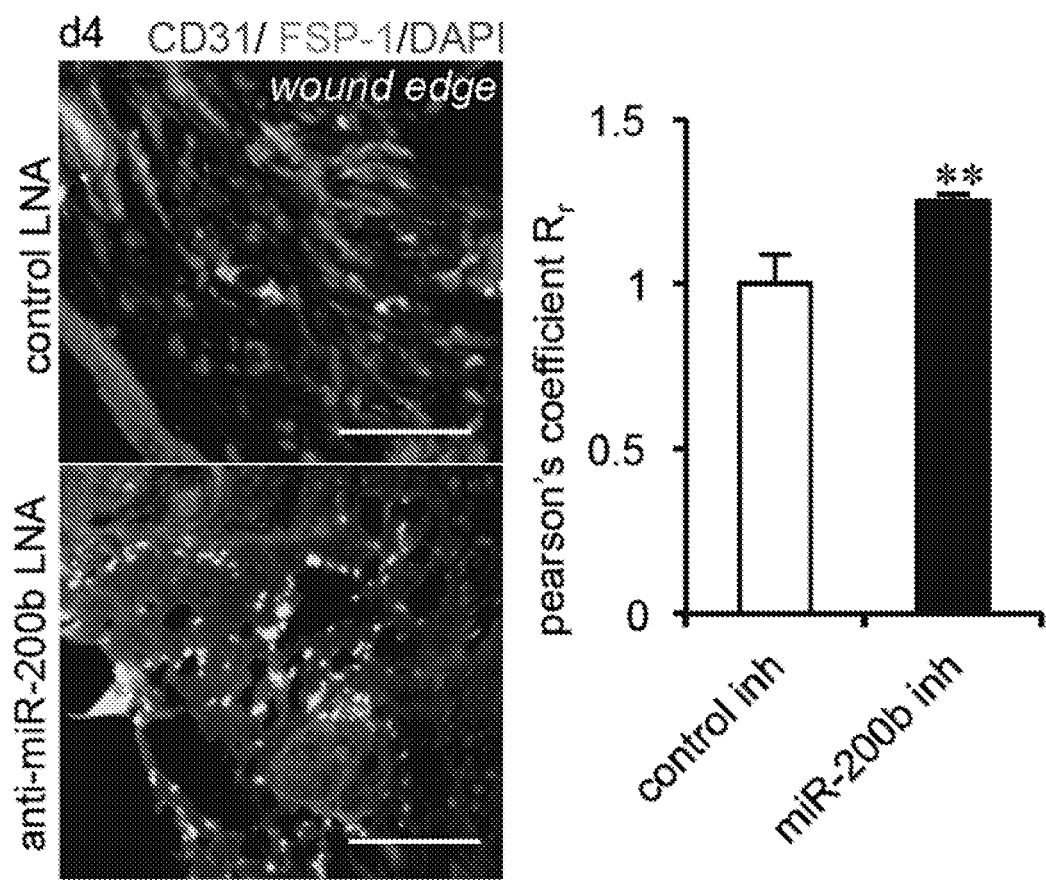
Figure 11F:
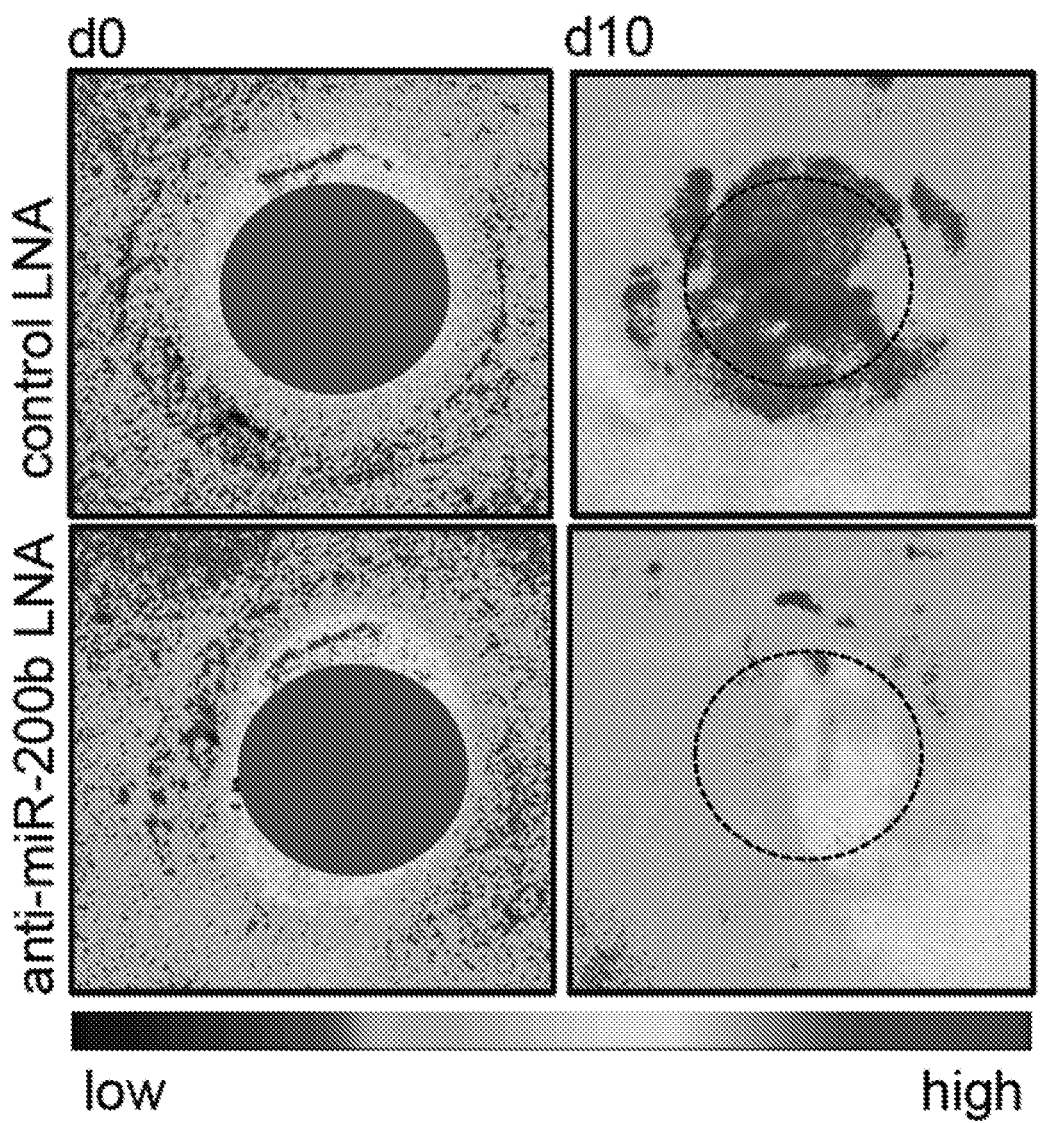
Figure 11G:
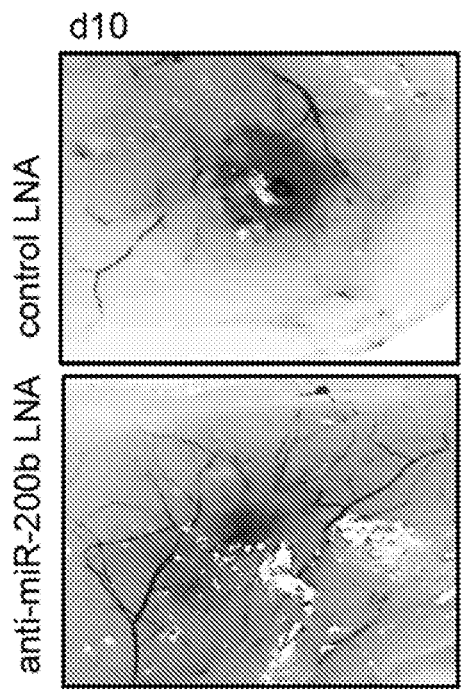
Figure 11H:
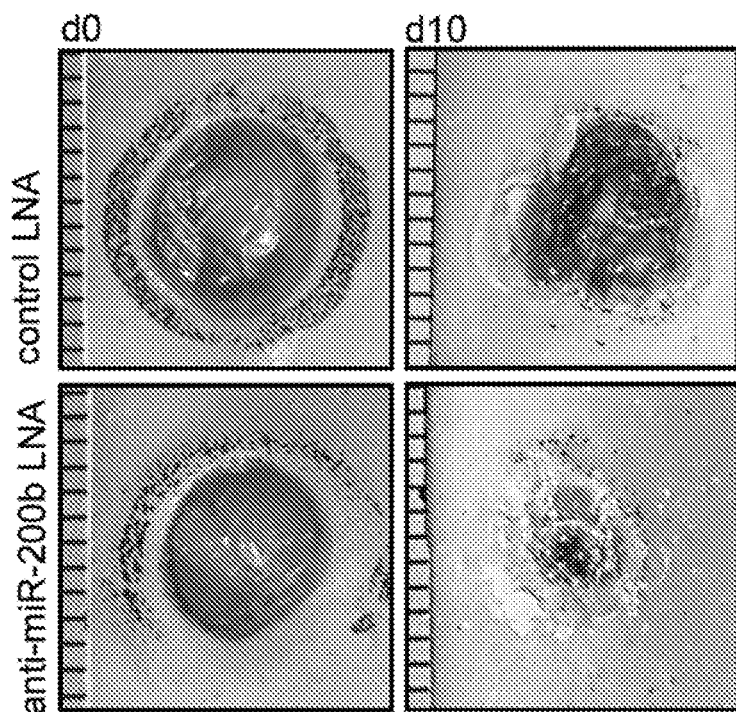
Figure 11I:
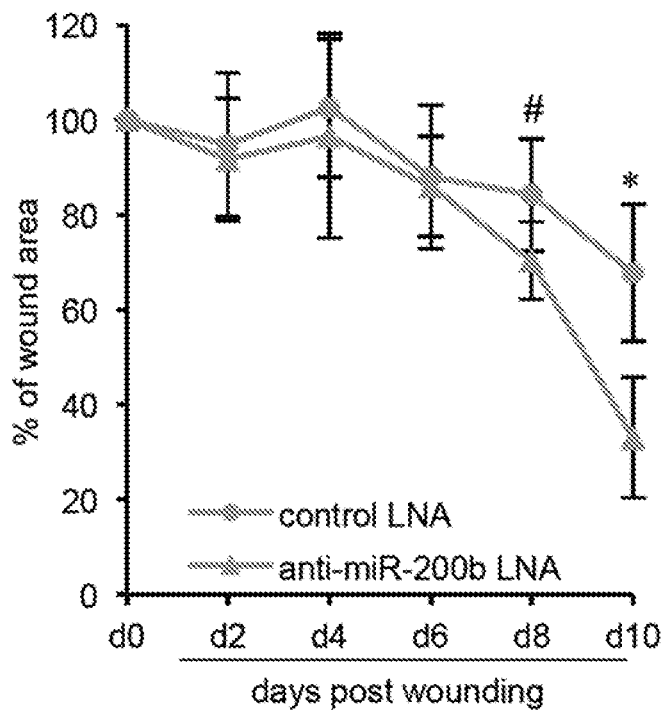
Figure 11J:
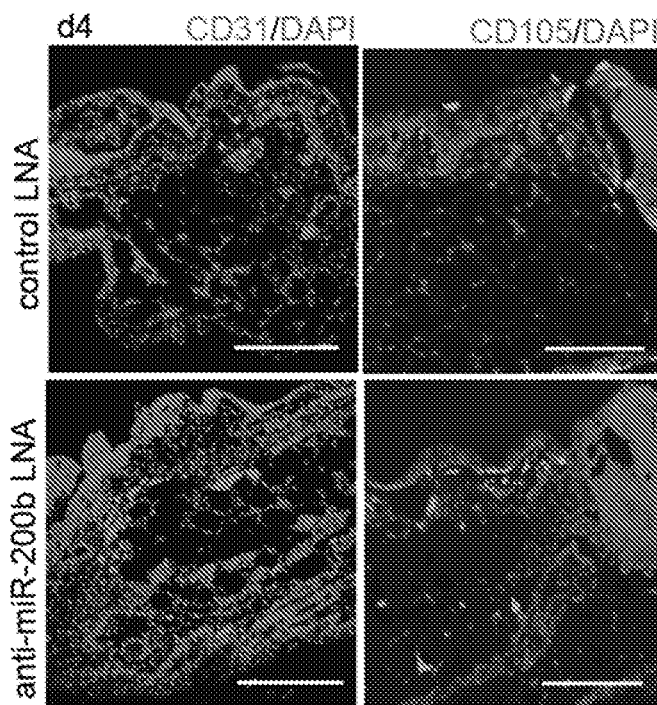
Figure 16A:
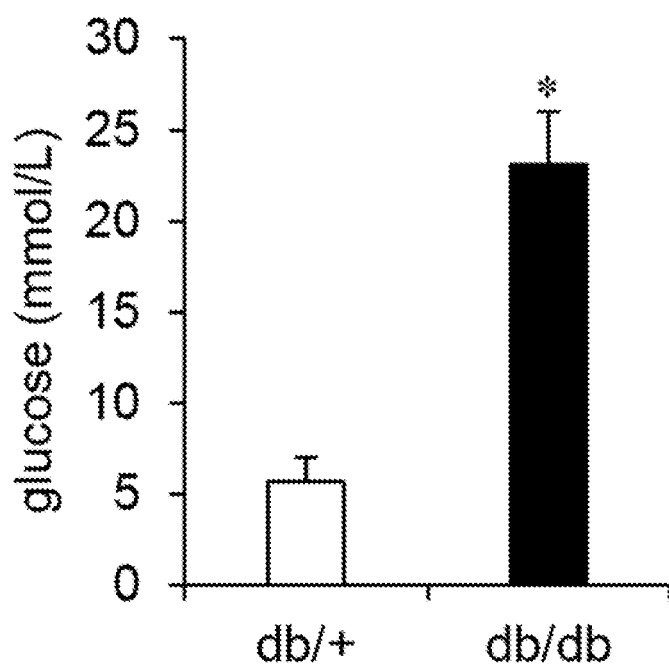
FIG. 16. Administration of anti-miR-200b-LNA attenuates impairment of wound healing in db/db mice. (a) Blood glucose level in non-diabetic (db/+) and diabetic (db/db) mice (n=3). Data represent mean±s.d., *P<0.001 versus db/+. (b) RT-qPCR analyses of miR-200b gene expression in intact and wound skin of db/+ and db/db mice (n=3). Data represent mean±s.d., #P<0.05 versus intact skin. (c) Western blot showing abundance of ETV2 protein level in db/db wound treated with control-LNA or anti-miR-200b-LNA of day 4 (n=3). b-actin serves as a loading control. (d) Wound perfusion was measured in above-mentioned mice (n=4). Data represent mean±s.d., *P<0.001; **P<0.01 versus respective control LNA. (e) Eschar shedding curve showing early shed of eschar (day 10) in anti-miR-200b LNA delivered wound of db/db mice as compared to control-LNA wound. Green line indicates anti-miR-200b-LNA treated wound, whereas red line indicates control LNA treated wound. (f,g) Immunofluorescence image of CD31 (red) and CD105 staining in control-LNA and anti-miR-200b-LNA delivered wound tissue of db/db mice. Scale bar, 500 mm (f) and 1000 mm (g), respectively.
Figure 16B:
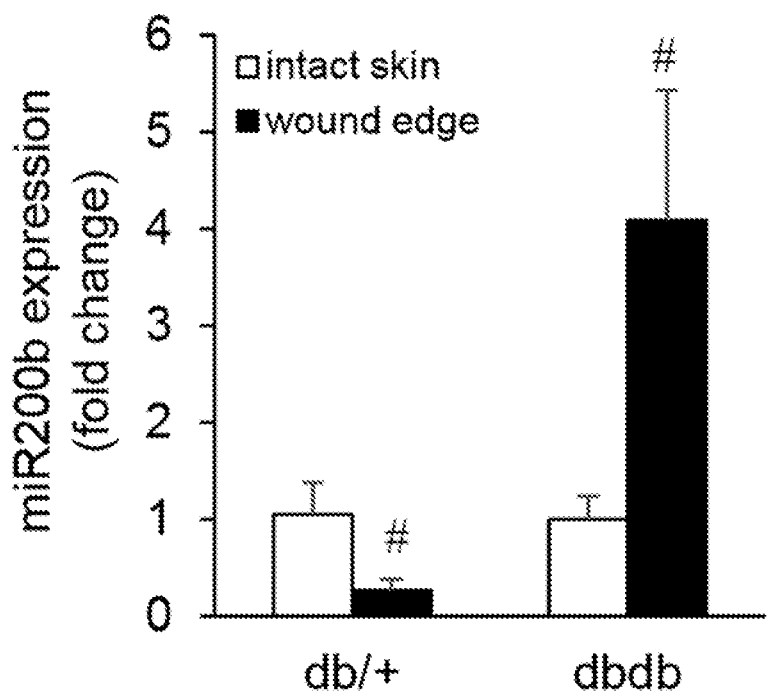
Figure 16C:
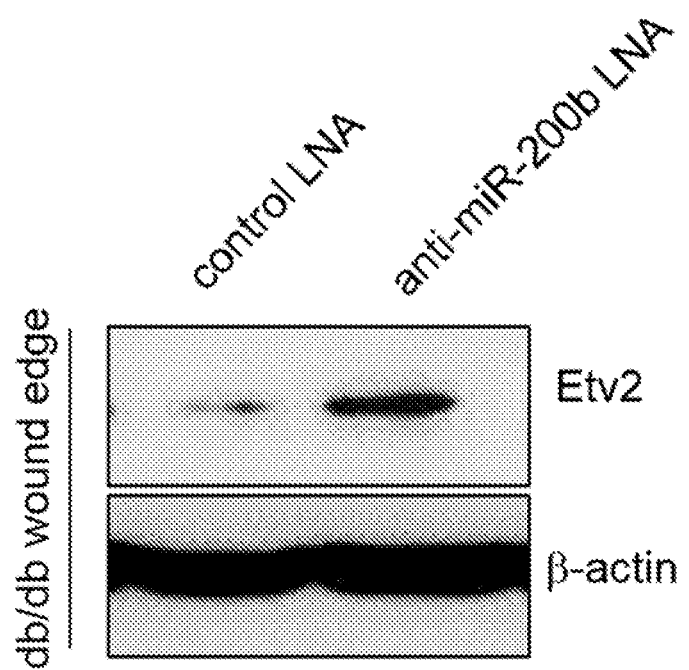
Figure 16D:
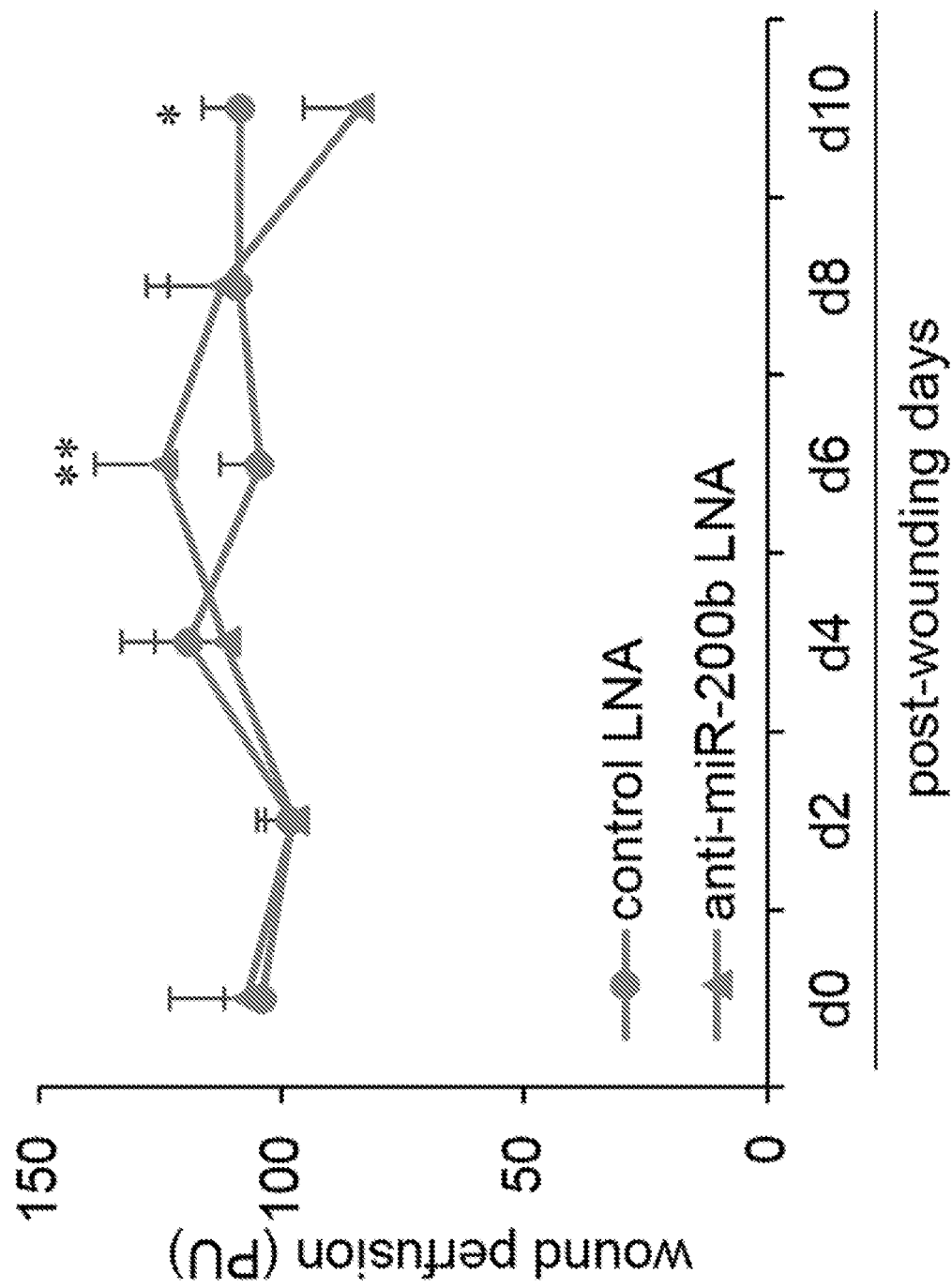
Figure 16E:
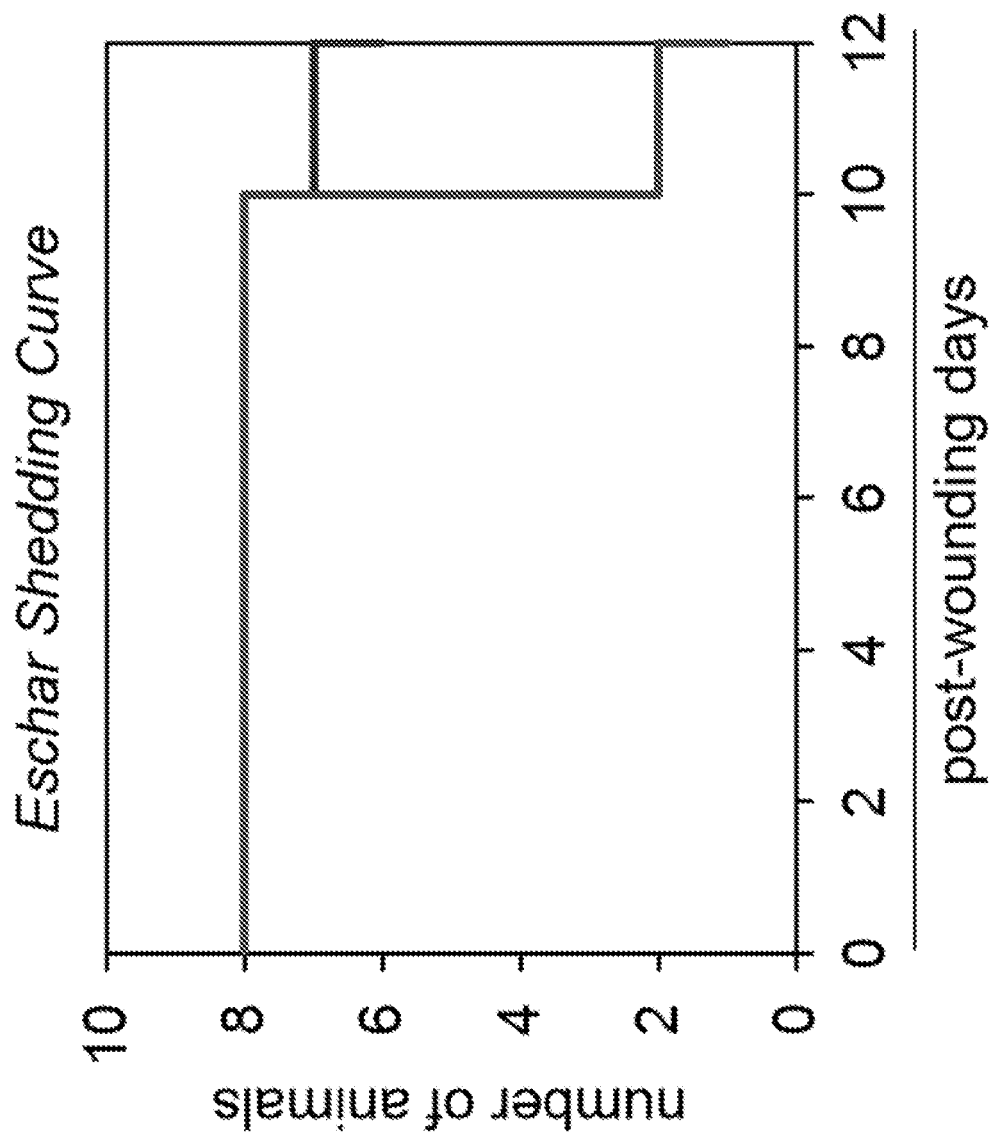
Figure 16F:
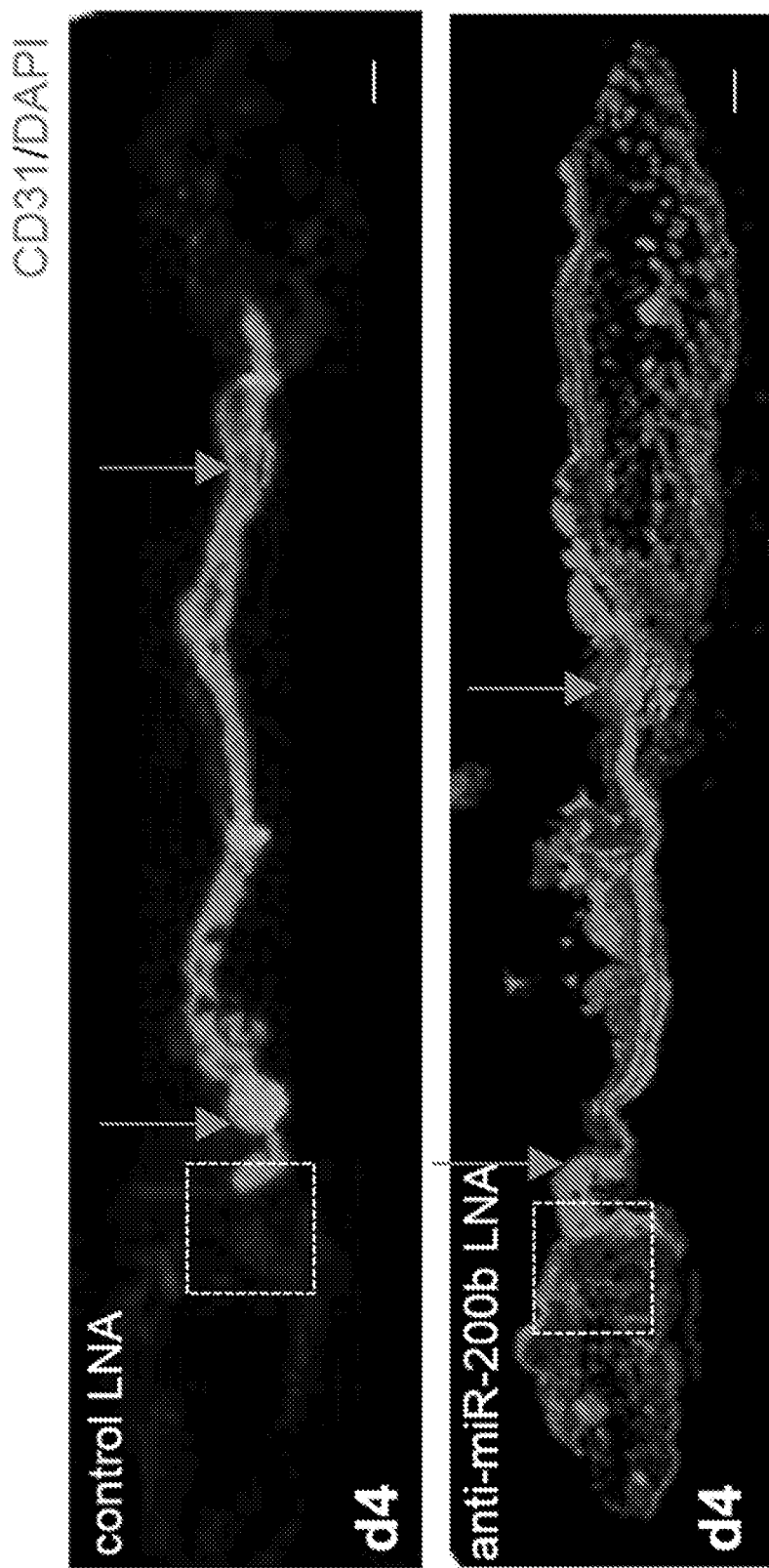
Figure 16G:
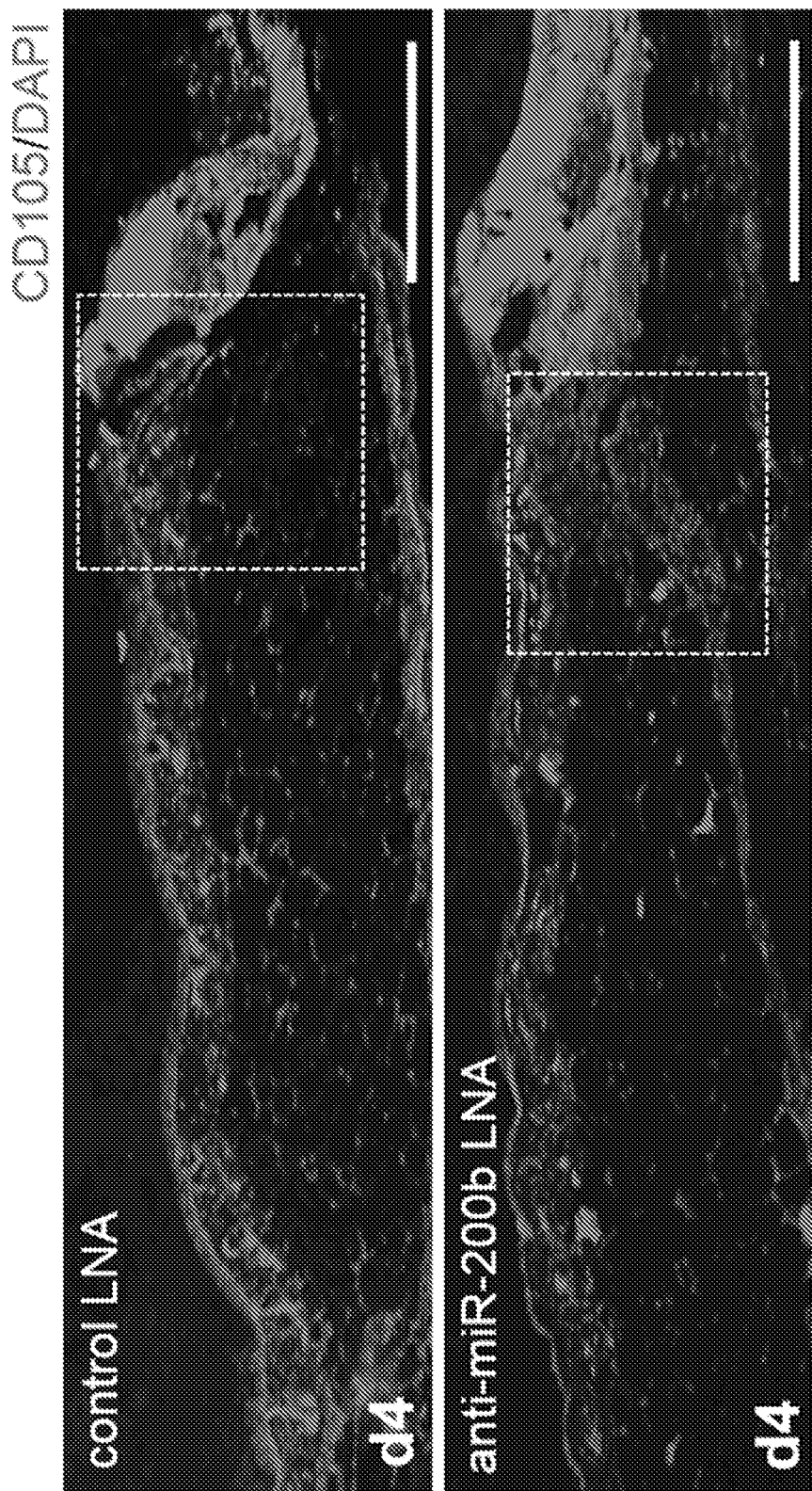

Topical Anti-miR-200b-LNA Rescue Diabetic Wound Angiogenesis by In Vivo Conversion of Dermal Fibroblast to iECs Impaired wound healing is a common diabetic complication (Brem and Tomic-Canic, 2007). Compared to non-diabetic subjects, the wound-edge of diabetic patients showed remarkably elevated miR-200b abundance while Fli-1 mRNA levels were low (FIG. 11A). Immunohistochemical study revealed poor abundance of Fli-1 protein in the wound edge tissue of diabetic patients in comparison to non-diabetic human subjects (FIG. 11B). In db/db mice, an established model of type II diabetes, wounding failed to suppress miR-200b expression (FIGS. 16A and 16B). Forced miR-200b inhibition by delivering a single anti-miR200b-LNA molecule at wound-edge of db/db mice (FIG. 11C) led to significant enhancement of Fli-1 (FIG. 11D) and its downstream Etv2 protein expression (FIG. 16C) followed by emerging abundance of iECs at the wound edge tissue of diabetic mice (FIG. 11E). Such response culminated in improved wound perfusion and healing (FIGS. 11F-11I and 16D-16E). Improved vascularisation was also evident by higher abundance of CD31+ and CD105+ endothelial cells in anti-miR200b treated wound-edge tissue of db/db mice (FIGS. 11J and 16F-16G). In summary, this work introduces a new paradigm recognizing miR-200b of dermal fibroblast as a critical switch which when transiently turned off during injury induces the Fli-1-Etv2 axis for direct cellular conversion to iECs.

Materials and Methods

Reagents and Antibodies.

All tissue culture materials were either obtained from Gibco-BRL/Life Technologies, Gaithersburg, Mass. or Lonza, Allendale, N.J. miRIDIAN microRNA Hairpin inhibitor negative control (cat. no. IN-001005-01-05), miRIDIAN microRNA hsa-miR-200b-3p hairpin inhibitor (cat. no. IH-300582-08-0005), miRIDIAN microRNA Mimic Negative control (cat. No. CN-001000-01-05), miRIDIAN microRNA Human hsa-miR-200b-3p mimic (cat. no. C-300582-07-0010) and ON-TARGETplus FLI1 siRNA (cat. no. L-003892-00-0005) were purchased from GE Dharmacon, Lafayette, Colo. Human Fli1-3'UTR (cat. no. HmiT056673-MT05), control vector (CS-MmiT027104-MT06-01) and Promoter reporter clone for Etv2 (NM_014209) (cat. no. HPRM12894-PG04) were procured from GeneCopoeia, Rockville, Md. Antibodies were purchased against FLI-1 (cat. no. ab15289), Etv2 (cat. no. ab181847), S100A4 (also known as FSP-1) (cat. no. ab27957), CD105 (cat. no. ab107595), Goat Anti-Rat IgG H&L (Cy5®) preadsorbed (cat. no. ab6565) from Abcam, Cambridge, Mass. Purified Rat Anti-Mouse CD31 (also known as PECAM-1) (cat. no. 550274) obtained from BD Pharmingen™, San Jose, Calif. Allophycocyanin (APC) conjugated anti-human CD31 antibody (Clone: WM59, cat. no. 303115), Fluorescein-isothiocyanate (FITC) conjugated anti-human CD90 (Thy1) antibody (Clone: 5E10, cat. no. 328107) and Phycoerythrin (PE) tagged anti-human CD309 (VEGFR2) antibody (Clone: 7D4-6, cat. no. 359903) were procured from BioLegend, San Diego, Calif. Anti-Fibroblast antibody, human (clone: REA165, cat. no. 130-100-135) was obtained from Miltenyi Biotec Inc, San Diego, Calif. Anti-mouse 1-actin (cat. no. A5441), streptozotocin (cat. no. S0130) purchased from Sigma, St. Louis, Mo. Horseradish peroxidase conjugated anti-rabbit-IgG (cat. no. NA934V, anti-mouse-IgG (cat. no. NA931V) and Amersham ECL Prime Western Blotting Detection Reagent were procured from GE Healthcare Bio-Sciences, Pittsburgh, Pa. Low Density Lipoprotein from Human Plasma, Acetylated, Alexa Fluor® 594 Conjugate (Alexa Fluor® 594 AcLDL) (cat. no. L35353) and Calcein AM (cat. no. C3099) were purchased from Molecular Probes™, Thermo Fisher Scientific, Waltham, Mass. Cultrex PathClear Reduced Growth Factor BME was procured (cat. no. 3433-005-01) from R&D Systems, Minneapolis, Minn., Secrete-Pair Dual luminescence assay kit (cat. no. SPDA-D010) from GeneCopoeia, and SimpleChIP® Plus Enzymatic Chromatin IP Kit (Agarose Beads) (cat. no. 9004) from Cell Signaling Technology, Danvers, Mass. U6 snRNA primer (cat. no. 4427975; ID: 001973) and hsa-miR-200b primer (cat. no. 4427975; ID: 002251) were obtained from Applied Biosystem, Foster City, Calif. All other chemicals were procured from Sigma-Aldrich.

Non-Viral Nano-Electroporation Device Fabrication.

Tissue nanotransfection devices were fabricated from thinned (~200 μm) double-side polished (100) silicon wafers using standard cleanroom fabrication technologies. Briefly, a ~1.5 μm thick layer of AZ5214E was spin coated on the wafer surface. Nanopores were subsequently patterned on the photoresist via projection lithography. Such pores were then used as etch masks to drill ~10 μm deep nanochannels on the silicon surface by deep reactive ion etching (DRIE) using a combination of SF6/C4F8 gases. Microscale reservoirs were then etched on the back-side of the wafers via contact photolithography and DRIE in order to gain fluidic access to the nanochannels. Finally, a ~50 nm thick insulating layer of silicon nitride was deposited on the wafer surface.

Cell Culture and In Vitro Non-Viral Transfection.

Primary human adult dermal fibroblasts (ATCC, Manassas, Va., cat. no. PCS-201-012) were expanded in fibroblast basal medium (ATCC cat. no. PCS-201-030) supplemented with fibroblast growth kit-serum-free (ATCC, cat. no. PCS-201-040) containing Penicillin-Streptomycin (10,000 U/mL) solution (Gibco™/Life Technologies, Waltham, Mass., cat. no. 15140122) at 37° C. in humidified atmosphere consisting of 95% air and 5% CO2. Human dermal microvascular endothelial cells (HMECs) were cultured in MCDB-131 medium (Gibco™/Life Technologies, cat. no. 10372-019).

Non-viral cell transfection was conducted via 3D Nanochannel Electroporation (NEP) as described previously (Gallego-Perez et al., 2016 Nanomedicine 12, 399-409). Briefly, the cells were first grown to full confluency overnight on the 3D NEP device. Subsequently, a pulsed electric field was used to deliver control or miR200b inhibitor (50 nM) into the cells. The cells were then harvested 24 h after miRNA delivery, placed in EBM-2 basal medium (Lonza, cat. no. CC-3156) supplemented with EGM-2 MV Single-Quot kit components (Lonza, cat. no. CC-4147) and processed further for additional experiments.

miR Inhibitors/Mimic and siRNA Transfection.

Cells were seeded in 12-well plate at density $0.1 \times 10^6$ cells/well in antibiotic free medium for 24 h prior to transfection. Confluence will reach approximately 70% at the time of transfection. Transfection was achieved by liposome-mediated delivery of miR-200b inhibitor (100 nM) or miR-200b mimic (50 nM), or siRNA smart pool for human FLI-1 (100 nM) using DharmaFECT™ 1 transfection reagent (GE Dharmacon) and OptiMEM serum-free medium (Invitrogen, Thermo Fisher Scientific, Waltham, Mass.). Samples were collected after 72 h of control and miR200b inhibitor/mimic or control and Fli-1 siRNA transfection for quantification of miRNA, mRNA, or protein expression.

Animal Studies and In Vivo Reprogramming and Lentiviral Delivery.

Male C57BL/6 mice (8-10 weeks old) were obtained from Harlan Laboratory, Indianapolis, Ind. Mice homozygous (BKS.Cg-m+/+Leprdb/J, or db/db; stock no 000642) for spontaneous mutation of the leptin receptor (Leprdb) or their respective non-diabetic lean control littermates m+/db (aged 8-10 weeks) were obtained from Jackson Laboratory, Bar Harbor, Me. FSP1-Cre mouse was a obtained (University of California, Los Angeles, Calif. 90095, USA). FSP1-Cre mice were crossed with the R26RtdTomato mice (JAX) carrying floxed tdTomato allele. Since FSP1 is specifically expressed in fibroblasts, the progeny of these mice (FSP1-Cre:R26RtdTomato) would have the red fluorescent protein tdTomato expressed specifically in the fibroblasts (Ubil et al., 2014). C57BL/6 mice were made diabetic by intraperitoneal injection of streptozotocin (STZ; 50 mg/kg body weight for 5 days) or the vehicle, citrate buffer (0.05 M sodium citrate, pH 4.5) and blood glucose levels were assessed regularly using Accu-Chek glucometer (Roche, Basel, Switzerland). Food intake and body weight were also recorded every day. Mice with blood glucose levels higher than >20 mmol/L were defined diabetic and chosen for experiments. All animal studies were performed in accordance with protocols approved by the Laboratory Animal Care and Use Committee of The Ohio State University. The animals were tagged and grouped randomly.

Animal fur on the area of interest was trimmed prior to the transfection. Solutions containing miRCURY LNA™ microRNA Power Inhibitors of miR-200b (cat. no. 4104042-101) or negative control (cat. no. 199006-101) purchased from Exiqon, Inc, Woburn, Mass. were loaded (at a concentration of 100 nM) in the reservoir of the non-viral transfection device and the device was subsequently place in contact with the skin. A gold-coated electrode (i.e., cathode) was immersed in the cargo solution, while a 24 G needle counter-electrode (i.e., anode) was inserted intradermally juxtaposed to the transfection platform. A pulsed electrical stimulation (i.e., 10 pulses of 250 V in amplitude and duration of 10 ms per pulse) was then applied across the electrodes to nanoporate the skin cells and drive the inhibitor or control cargo into the cells through the nanochannels.

Delivery of shRNA lentivirus particles (LV) was achieved by intradermal injection. The shRNA clone set (4 constructs) for mouse Fli1 in lentiviral vector with loxp-STOP-loxp-sense-loop-antisense structure and shRNA scrambled control were customized from GeneCopoeia. Briefly, LV particles (Fli-1 shRNA clone set of 3) was intradermally injected into the skin at titer $1 \times 10^7$ cfu/mL (50 µL per wound), 1 mm away from the wound edge 2 days before wound. The injection procedure was repeated on the day of wounding and at day 3 post wounding.

Wound Models.

Two 6 mm biopsy punch excisional wounds were created on the dorsal skin, equidistant from the midline and adjacent to the 4 limbs and splinted with a silicon sheet to prevent contraction thereby allowing wounds to heal through granulation and re-epithelialization. During the wounding procedure, mice were anesthetized by low-dose isoflurane inhalation as per standard recommendation. Each wound was digitally photographed and perfusion was checked by laser speckle at different time point mentioned. Wound area was analysed by the ImageJ software. Skin from age-matched unwounded animals was served as controls. All animal studies were approved by the OSU Institutional Animal Care and Use Committee (IACUC). The animals were euthanized at the indicated time and wound edges were collected for analyses. For wound-edge harvest, 1-1.5 mm of the tissue from the leading edge of the wounded skin was excised around the entire wound. The tissues were snap frozen and collected either in 4% paraformaldehyde or in optimal cutting temperature (OCT) compound.

Laser Capture Microdissection (LCM) of Dermal Fibroblasts.

Laser capture microdissection was performed using the laser microdissection system from PALM Technologies (Bernreid, Germany) as described previously by our group. For dermal-fibroblast rich region captures, sections were stained with hematoxylin for 30 s, subsequently washed with DEPC-H2O and dehydrated in ethanol. Dermal fraction was identified based on the histology. For capturing of fibroblast from FSP1-Cre:R26RtdTomato mice, sections were subsequently washed with DEPC-H2O and dehydrated in ethanol. Fibroblasts were identified based on the red fluorescence. Tissue sections were typically cut and captured under a 20× ocular lens. The samples were catapulted into 25 µl of cell direct lysis extraction buffer (Invitrogen). Approximately 10,00,000 µm$^2$ of tissue area was captured into each cap and the lysate was then stored at −80° C. for further processing.

Human Samples.

Human skin and wound biopsy samples were obtained from healthy adult human subjects or chronic wound patients, respectively, at OSU Comprehensive Wound Center (CWC). All human studies were approved by The Ohio State University's (OSU) Institutional Review Board (IRB). Declaration of Helsinki protocols was followed and patients gave their written informed consent.

Immunohistochemistry (IHC), Immunocytochemistry (ICC) and Confocal Microscopy.

Immunostaining was performed on cryosections of wound sample using specific antibodies. Briefly, OCT embedded tissue were cryosectioned at 10 µm thick, fixed with cold acetone, blocked with 10% normal goat serum and incubated with specific antibodies against CD31 (1:400 dilution), CD105 (1:400 dilution), Keratin14 (1:1000 dilution). For immunocytochemistry, cells ($0.1 \times 10^6$ cells/well) were seeded on a coverslip, fixed with ICC fixation buffer (BD Biosciences, San Jose, Calif.; cat. no. 550010), blocked with 10% normal goat serum and incubated overnight with primary antibody against CD31 and FSP1. Signal was visualized by subsequent incubation with fluorescence-tagged appropriate secondary antibodies (Alexa 568-tagged α-rat, 1:200 dilution; Alexa 488-tagged α-rabbit, 1:200 dilution) and counter stained with DAPI. Images were captured by microscope and analysis was performed using Axiovision Rel 4.8 software, (Axiovert 200M; Carl Zeiss Microscopy GmbH, Germany)

Western Blots.

Protein concentration of tissue extract or cell lysates was determined by BCA method and protein samples were resolved on SDS-PAGE and transferred it to PVDF membranes (GE Healthcare Bio-Sciences, Pittsburgh, Pa., cat no. IPVH00010). The membranes were first blocked in 10% skim milk and incubated with primary antibody at 1:1000 dilutions overnight at 40 C, followed by specific secondary antibody conjugated with horseradish peroxidase at 1:3000 dilutions. Signal was visualized using Amersham ECL Prime Western Blotting Detection Reagent. Pixel densitometry analysis was performed for individual band using image J software. Anti-mouse ß-actin (1:10000 dilution) serves as loading control.

RNA Extraction and Real-Time Quantitative PCR.

RNA from cells or wound edge tissue sample was extracted by using miRVana miRNA isolation kit (Ambion™, Thermo Fisher Scientific, cat. no. AM 1560) according to the manufacturer's instructions. The RNA quantity was measured using a NanoDrop ND-1000 spectrophotometer (NanoDrop Technologies, Wilmington, Del.), and RNA quality was checked using RNA6000 NanoAssay on Agilent BioAnalyzer 2100 (AgilentTechnologies, Santa Clara, Calif.). RNA was reverse transcribed using SuperScript® III First-Strand Synthesis System (Invitrogen™, ThermoFisher Scientific, cat. no. 18080051). SYBR green-based real-time quantitative PCR reactions (Applied Biosystems) by using gene-specific primers were used. After the final extension, a melting curve analysis was performed to ensure the specificity of the products. 18 s was simultaneously amplified in separate reactions and used for correcting the Ct value. For determination of miRNA expression, specific TaqMan assays for miRNAs and the TaqMan miRNA reverse transcription kit (Applied Biosystems™, ThermoFisher Scientific, Foster City, Calif., cat. no. 4366596) were used, followed by real time PCR using the Universal PCR Master Mix (Applied Biosystems™, cat. no. 4304437).

miR Target Luciferase Reporter Assay.

HADF cells were transfected with 100 ng of human Fli1-3'UTR or a mutant vector for 48 h using Lipofectamine LTX/Plus reagent. The reporter constructs 3'UTR of Friend leukemia virus integration 1 (pLuc-Fli1-3'UTR Human plasmid) (cat. no. HmiT054456-MT06) was obtained from GeneCopoeia. For mutated construct, the seed sequence regions were replaced to non-sense sequence (for details, please see FIG. 16). Firefly luciferase was cloned under the control of CMV promoter. Cells were lysed, and luciferase activity was determined using dual-luciferase reporter assay system (Promega, Madison, Wis.) according to manufacturer's protocol. Data normalization was achieved by co-transfecting cell with Renilla plasmid (10 ng). Data are presented as ratio of firefly to Renilla luciferase activity (FL/RL).

Promoter Luciferase Assay.

For analysing Fli-1 involvement in Etv2 promoter activation, Etv2 promoter reporter clone was cotransfected with either control or miR200b inhibitor or mimic or Fli-1 siRNA in HADF cells. After 72 h of transfection, Secrete-Pair dual luminescence assay kit was used to analyse the activities of Gaussia Luciferase (GLuc) and secreted alkaline phosphatase (SEAP) in cell culture medium according to manufacturer's instructions. Etv2 controls GLuc reporter gene expression, while SEAP is controlled by a cytomegalovirus (CMV) promoter. SEAP expression was used as a normalization factor (internal standard control). Briefly, 10 µl of culture medium samples were either mixed with 100 µl of GLuc assay working solution or SEAP assay working solution and incubated at room temperature for 1 min (GLuc) or 5 min (SEAP) and luminescence was subsequently measured in luminometer. The ratio of luminescence intensities (RLU, relative light unit) of GLuc over SEAP was calculated for each sample.

Flow Cytometry Analysis.

The expression of CD31 and CD90 or VEGFR2 and Fibroblast protein on control or miR200b inhibitor transfected HADF cells were assessed through flow cytometry (BD™ LSR II flow cytometer). Briefly, HADF cells ($1 \times 10^6$) were harvested on day 1, 4, 7, 10, and 28 after transfection, resuspended in PBS-containing 2% FBS and 2 mM EDTA, and then stained with fluorochrome-labeled antibodies (5 µl per test) against CD90 and CD31 or VEGFR2 and Fibroblast protein for 30 min at RT. Data were analyzed with BD CellQuest Pro software (version 5.2.1).

LDL Uptake Assays.

HDAF cells were transfected with either control or miR200b inhibitor and on day 7, cells were incubated with AlexaFluor 594-labeled Ac-LDL (10 µg/ml) in DMEM at 37° C. for 4 h. HDMEC used as positive control cells. On termination of incubations, cells were washed in phosphate buffered saline (PBS) and fixed with 4% paraformaldehyde for 30 min. The uptake of Ac-LDL was analysed by fluorescence microscopy using the AxioVision Rel 4.8 software (Zeiss).

In-Vitro Angiogenesis Assay.

In vitro angiogenesis was assessed by the tube formation ability on Matrigel as described previously (Chan et al., 2012). Briefly, HADF cells were transfected with control or miR200b inhibitor and after day 7 post transfection, the cells were seeded on a Matrigel pre-coated 4-well plates at $5 \times 10^4$ cells/well. HMEC used as positive control cells. The angiogenic property was assessed by measuring the tube length after 8 h of cell seeding using the AxioVision Rel 4.8 software (Zeiss).

Chromatin Immunoprecipitation (ChIP) Assay.

Chromatin immunoprecipitation (ChIP) assay was performed according to the manufacturer's instructions to evaluate Fli-1 binding to Etv2 promoter in different treatment conditions. Briefly, control or Fli-1 siRNA and control or Fli-1 forced expression vector transfected HADF cells were fixed with 1% formaldehyde for 10 min at room temperature and then quenched by addition of glycine. The cells were processed for nuclei preparation and pelleted nuclei incubated with Micrococcal Nuclease to generate chromatin samples with average fragment sizes of 150-900 bp. Enzymatic digestion was stopped by addition of 0.5 M EDTA, samples were then sonicated on ice and centrifuged at 10,000 rpm for 10 min at 4° C. Samples were incubated with Fli-1 antibody or control normal rabbit IgG at 4° C. overnight on rotator. Antibody-chromatin complexes were pelleted with Protein G-agarose beads and immunoprecipitated DNA was eluted and purified. RT-PCR was then performed using primers targeting the promoter region of Etv2 gene. Primers used for amplification of the human Etv2 promoter sequence were 5'-TGATCTTGGCT-CACTGCAAC-3' (forward) and 5'-TAATCCCAGCACTTTGGGAG-3' (reverse) of product length 214 bp PCR products were run on ethidium bromide-stained 1.5% agarose gel, and the image was captured by the Bio-Rad gel documentation system using Image Lab software.

Statistical Analysis.

Samples were coded and data analysis was performed in a blinded fashion. Student's t test (two-tailed) was used to determine significant differences. Comparisons among multiple groups were tested using analysis of variance (ANOVA). $p<0.05$ was considered statistically significant.

Example 8. Topical Tissue Nano-Transfection Mediates Non-Viral Stroma Reprogramming and Rescue Although cellular therapies represent a promising strategy for a number of conditions, current approaches face major translational hurdles, including limited cell sources and the need for cumbersome pre-processing steps (e.g., isolation, induced pluripotency) (Rosova I, et al. Stem Cells 2008, 26(8): 2173-2182; Kinoshita M, et al. Atherosclerosis 2012, 224(2): 440-445; Losordo D W, et al. Circulation 2004, 109(22): 2692-2697; Lee A S, et al. Nat Med 2013, 19(8): 998-1004; Cunningham J J, et al. Nat Biotechnol 2012, 30(9): 849-857; Leduc P R, et al. Nat Nanotechnol 2007, 2(1): 3-7). In vivo cell reprogramming has the potential to enable more effective cell-based therapies by utilizing readily-available cell sources (e.g. fibroblasts), and circumventing the need for ex vivo pre-processing (Heinrich C, et al. Nat Cell Biol 2015, 17(3): 204-211; Karagiannis P, et al. Nat Methods 2014, 11(10): 1006-1008). Existing reprogramming methodologies, however, are fraught with caveats, including heavy reliance on viral transfection (Grande A, et al. Nat Commun 2013, 4: 2373; Morita R, et al. Proc Natl Acad Sci USA 2015, 112(1): 160-165). Moreover, capsid size constraints and/or the stochastic nature of status quo approaches (viral and non-viral) pose additional limitations, thus highlighting the need for safer and more deterministic in vivo reprogramming methods (Gallego-Perez D, et al. Nanomedicine 2016, 12(2): 399-409; Marx V. Nat Meth 2016, 13(1): 37-40). Disclosed is a novel yet simple-to-implement non-viral approach to topically reprogram tissues through a nanochanneled device validated with well-established and newly developed reprogramming models of induced neurons and endothelium, respectively. The simplicity and utility of this approach is demonstrated by rescuing necrotizing tissues and whole limbs using two murine models of injury-induced ischemia.

Materials and Methods

TNT Platform Fabrication.

TNT devices were fabricated from thinned (~200 μm) double-side polished (100) silicon wafers (FIG. 20). Briefly, ~1.5 μm thick layers of AZ5214E photoresist were first spin coated on the silicon wafers at ~3000 rpm. Nanoscale openings were subsequently patterned on the photoresist using a GCA 6100C stepper. Up to 16 dies of nanoscale opening arrays were patterned per 100-mm wafer. Such openings were then used as etch masks to drill ~10 μm deep nanochannels on the silicon surface using deep reactive ion etching (DRIE) (Oxford Plasma Lab 100 system). Optimized etching conditions included $SF_6$ gas: 13 s/100 sccm gas flow/700 W ICP power/40 W RF power/30 mT APC pressure; $C_4F_8$ gas condition: 7 s/100 sccm gas flow/700 W ICP power/10 W RF power/30 mT APC pressure. Microscale reservoirs were then patterned on the back-side of the wafers via contact photolithography and DRIE. Finally, a ~50 nm thick insulating/protective layer of silicon nitride was deposited on the TNT platform surface.

Animal Husbandry.

C57BL/6 mice were obtained from Harlan Laboratory. B6.129(Cg)-Gt(ROSA)26Sortm4(ACTB-tdTomato-EGFP) Luo/J mice obtained from Jackson laboratories were bred with K14cre to produce K14cre/Gt(ROSA)26Sortm4 (ACTB-tdTomato-EGFP)Luo/J mice. pOBCol3.6GFPtpz mice were gifts from Dr. Traci Wilgus (The Ohio State University). repTOP™ mitoIRE mice were obtained from Charles River Laboratories. Fsp1-Cre mice were obtained (University of California, Los Angeles). Fsp1-Cre mice were crossed with the B6. Cg-Gt(ROSA) 26Sor$^{tm9(CAG-tdTomato)Hze}$/J mice (Jackson laboratories) to generate mice with tdTomato expression specific to fibroblasts. All mice were male and 8-12 weeks old at the time of the study. Genotyping PCR for ROSAmT/mG mice was conducted using primers oIMR7318-CTC TGC TGC CTC CTG GCT TCT, oIMR7319-CGA GGC GGA TCA CAA GCA ATA and oIMR7320-TCA ATG GGC GGG GGT CGT T, while K-14 Cre transgene was confirmed using primers oIMR1084-GCG GTC TGG CAG TAA AAA CTA TC; oIMR1085-GTG AAA CAG CAT TGC TGT CAC TT.

Genotyping PCR for Fsp1-Cre mice was conducted using primers Forward-CTAGGCCACAGAATTGAAAGATCT, Reverse-GTAGGTGGAAATTCTAGCATCATCC (for wild type, product length=324 bp) and Forward-GCGGTCTGGCAGTAAAAACTATC, Reverse-GTGAAACAGCATTGCATTGCTGTCACTT (for Cre transgene, product length=100 bp), while td tomato was confirmed using primers Forward-AAGGGAGCTGCAGTGGAGTA, Reverse-CCGAAAATCTGTGGGAAGTC (for wild type, product length=196 bp) and Forward-GGCATTAAAGCAGCGTATCC, Reverse-CTGTTCCTGTACGGCATGG (mutant type, product length=297 bp). All animal studies were performed in accordance with protocols approved by the Laboratory Animal Care and Use Committee of The Ohio State University. No statistical method was used to predetermine the sample size. Power analysis was not necessary for this study. The animals were tagged and grouped randomly using a computer based algorithm (www-.random.org).

Mammalian Cell Culture and In Vitro Reprogramming.

Primary human adult dermal fibroblasts (ATCC PCS-201-012) were purchased, *mycoplasma*-free and certified, directly from ATCC. No further cell line authentication/testing was conducted. These cells were expanded in fibroblast basal medium supplemented with fibroblast growth kit-serum-free (ATCC PCS 201-040) and penicillin/streptomycin. E12.5-E14 mouse embryonic fibroblasts (MEFs) were cultured in DMEM/F12 supplemented with 10% fetal bovine serum. Non-viral cell transfection and reprogramming experiments were conducted via 3D Nanochannel Electroporation (NEP) as described previously11. Briefly, the cells were first grown to full confluency overnight on the 3D NEP device. Subsequently, a pulsed electric field was used to deliver cocktail of plasmids (0.05 μg/μl) into the cells consisting of a 1:1:1 mixture of Fli1:Etv2:Foxc2. The cells were then harvested 24 h after plasmid delivery, placed in EBM-2 basal medium (CC-3156, Lonza) supplemented with EGM-2 MV SingleQuot kit (CC-4147, Lonza), and further processed for additional experiments/measurements. Etv2 and Fli1 plasmids were obtained (Department of Internal Medicine, UT Southwestern Medical Center, Texas). Foxc2 plasmids were kindly donated by Dr. Tsutomu Kume (Department of Medicine-Cardiology and Pharmacology, Northwestern University-FCVRI, Chicago).

In Vivo Reprogramming.

The areas to be treated were first naired 24-48 h prior to TNT. The skin was then exfoliated to eliminate the dead/keratin cell layer and expose nucleated cells in the epidermis. The TNT devices were placed directly over the exfoliated skin surface. ABM or EFF plasmid cocktails were loaded in the reservoir at a concentration of 0.05-0.1 μg/μl. A gold-coated electrode (i.e., cathode) was immersed in the plasmid solution, while a 24 G needle counter-electrode (i.e., anode) was inserted intradermally, juxtaposed to the TNT platform surface. A pulsed electrical stimulation (i.e., 10 pulses of 250 V in amplitude and a duration of 10 ms per pulse) was then applied across the electrodes to nanoporate the exposed cell membranes and drive the plasmid cargo into the cells through the nanochannels. ABM plasmids were mixed at a 2:1:1 molar ratio as described previously11. Unless otherwise specified, control specimens involved TNT treatments with a blank, phosphate buffer saline (PBS)/mock plasmid solution (FIG. 38).

Electrophysiological Activity Measurements.

The general principle of extracellular recordings was used to detect electrophysiological activity in the skin. Chronoamperometric measurements were conducted using PPy-based probes to detect neuronal excitability through two small incisions on the skin of sedated mice.

MCAO Stroke Surgery and Analysis.

Transient focal cerebral ischemia was induced in mice by middle cerebral artery occlusion (MCAO) was achieved by using the intraluminal filament insertion technique previously described (Khanna S, et al. J Cereb Blood Flow Metab 2013, 33(8): 1197-1206). MRI images were used to determine infarct size as a percentage of the contralateral hemisphere after correcting for edema.

Ischemic Skin Flaps.

Monopedicle (i.e., random-pattern) ischemic flaps measuring 20 mm by 10 mm were created on dorsal skin of C57BL/6 mice. Briefly, 8-10 week mice were anesthetized with 1-3% isoflurane. The dorsum were naired, cleaned, and sterilized with betadine. A monopedicle flap was created on the dorsal skin of the mice by making 20 mm long full-thickness parallel incisions 10 mm apart. The bottom part of the skin was cut to make a free hanging flap. Flap edges were cauterized. A 0.5 mm silicon sheet was placed under the flap and then sutured to the adjacent skin with 5-0 ethicon silk suture. Finally, a single dose of buprenorphine was administered subcutaneously to control pain. Laser speckle imaging (Perimed) was conducted 2 h post-surgery to confirm successful blood flow occlusion. TNT-based transfections were conducted 24 h prior to skin flapping.

Hindlimb Ischemia Surgery.

Unilateral hind-limb ischemia was induced via occlusion and subsequent transection of the femoral artery followed by transection (Limbourg A, et al. Nat Protoc 2009, 4(12): 1737-1746). Briefly, 8-10 week mice were anesthetized with 1-3% isoflurane, placed supine under a stereomicroscope (Zeiss OPMI) on a heated pad. The femoral artery was exposed and separated from the femoral vein through a ~1 cm incision. Proximal and distal end occlusion were induced with 7-0 silk suture, which was then followed by complete transaction of the artery. Finally, a single dose of buprenorphine was administered subcutaneously to control pain. Laser speckle imaging (MoorLDI-Mark 2) was conducted 2 h post-surgery to confirm successful blood flow occlusion.

Isolation of Extracellular Vesicles (EVs).

EVs were isolated from 12 mm diameter skin biopsies that were collected in OCT blocks and stored frozen for later use. Briefly, the blocks were thawed and washed with PBS to eliminate the OCT. Following removal of the fat tissue with a scalpel, the skin tissue was minced into ~1 mm pieces and homogenized with a micro-grinder in PBS. After centrifugation at 3000 g, an Exoquick kit (System Biosciences) was used at a 1:5 ratio (Exoquick:supernatant) to isolate EVs from the supernatant for 12 h at 4° C. EVs were precipitated via centrifugation at 1500 g for 30 min. Total RNA was then extracted from pellet using the mirvana kit (Life technologies) following the recommendations provided by the manufacturer.

DNA Plasmid Preparation.

Plasmids were prepared using plasmid DNA purification kit (Qiagen Maxi-prep, catalogue number 12161, and Clontech Nucleobond catalogue number 740410). DNA concentrations were obtained from a Nanodrop 2000c Spectrophotemeter (Thermoscientific).

Laser Capture Microdissection (LCM) and Quantitative Real-Time PCR.

LCM was performed using a laser microdissection system from PALM Technologies (Zeiss, Jena, Germany). Specific regions of tissue sections, identified based on morphology and/or immunostaining, were cut and captured under a 20× ocular lens. The samples were catapulted into 25 µl of cell direct lysis extraction buffer (Invitrogen). Approximately 1,000,000 µm$^2$ of tissue area was captured into each cap and the lysate was then stored at −80° C. for further processing. qRT-PCR of the LCM samples were performed from cell direct lysis buffer following manufacture's instruction.

Immunohistochemistry and Confocal Microscopy.

Tissue immunostaining was carried out using specific antibodies and standard procedures. Briefly, OCT-embedded tissue was cryosectioned at 10 µm thick, fixed with cold acetone, blocked with 10% normal goat serum and incubated with specific antibodies. Signal was visualized by subsequent incubation with fluorescence-tagged appropriate secondary antibodies (Alexa 488-tagged α-guinea pig, 1:200, Alexa 488-tagged α-rabbit, 1:200; Alexa 568-tagged α-rabbit, 1:200) and counter stained with DAPI. Lectin-based visualization of blood vessels was conducted via tail vein injection of FITC-labeled lectin 30 min prior to tissue. Images were captured by laser scanning confocal microscope (Olympus FV 1000 filter/spectral).

IVIS Imaging.

The animals were imaged under anesthesia using IVIS Lumina II optical imaging system. repTOP™ mitoIRE mice were pre-injected with substrate luciferin (potassium salt of beetle luciferin, Promega) at a dose of 100 mg/kg 5-10 min before imaging. Overlay images with luminescence images were made using Living Image software.

Magnetic Resonance Imaging (MRI) of Stroked Brains.

Magnetic resonance angiography was used to validate our MCAO model in mice and to optimize the occluder size and the internal carotid artery insertion distance for effective MCAO. T2-weighted MRI was performed on anesthetized mice 48 h after MCA-reperfusion using 9.4 T MRI (Bruker Corporation, Bruker BioSpin Corporation, Billerica, Mass., USA). MR images were acquired using a Rapid Acquisition with Relaxation Enhancement (RARE) sequence using the following parameters: field of view (FOV) 30×30 mm, acquisition matrix 256×256, TR 3,500 ms, TE 46.92 ms, slice gap 1.0 mm, rare factor 8, number of averages 3. Resolution of 8.5 pixels per mm. Raw MR images were converted to the standard DICOM format and processed. After appropriate software contrast enhancement of images using Osirix v3.4, digital planimetry was performed by a masked observer to delineate the infarct area in each coronal brain slice. Infarct areas from brain slices were summed, multiplied by slice thickness, and corrected for edema-induced swelling as previously described to determine infarct volume (Khanna S, et al. J Cereb Blood Flow Metab 2013, 33(8): 1197-1206).

Analysis of Muscle Energetics.

Muscle energetics was evaluated NMR spectroscopy measurements on a 9.4 Tesla scanner (Bruker BioSpec) using a volume coil for RF transmission and a 31P coil for reception (Fiedler G B, et al. MAGMA 2015, 28(5): 493-501). In vivo imaging was conducted in a custom-made 1H/31P transceiver coil array. Data were acquired using single pulse sequence. The raw data were windowed for noise reduction and Fourier transformed to spectral domain.

Ultrasound-Based Imaging and Characterization of Blood Vessels.

Blood vessel formation was parallelly monitored via ultrasound imaging. Briefly, a Vevo 2100 system (Visual Sonics, Toronto, ON, Canada) was used to obtain ultrasound images on B-mode with a MS 250 linear array probe (Gnyawali S C, et al. J Vis Exp. 2010 9(41)). Doppler color flow imaging was implemented to monitor and quantify blood flow characteristics under systole and diastole.

GeneChip® Probe Array and Ingenuity Pathway (IPA)® Analyses.

LCM was used to prepare tissue isolates enriched for in vivo-derived iNs from ABM-transfected mouse skin (Roy S, et al. Proc Natl Acad Sci USA 2007, 104(36): 14472-14477; Rink C, et al. J Cereb Blood Flow Metab 2010, 30(7): 1275-1287). Tissue isolated were processed in into lysis buffer from PicoPure® RNA Isolation Kit (ThermoFisher). RNA extraction, target labeling, GeneChip® and data analysis were performed as described previously (Roy S, et al. Proc Natl Acad Sci USA 2007, 104(36): 14472-14477; Rink C, et al. J Cereb Blood Flow Metab 2010, 30(7): 1275-1287; Roy S, et al. Physiol Genomics 2008, 34(2): 162-184). The samples were hybridized to Affymetrix Mouse transcriptome Array 1.0 (MTA1.0). The arrays were washed and scanned with the GeneArray scanner (Affymetrix) at The Ohio State University facilities as described earlier (Roy S, et al. Proc Natl Acad Sci USA 2007, 104(36): 14472-14477; Roy S, et al. Physiol Genomics 2008, 34(2): 162-184). The expression data have been submitted to the Gene Expression Omnibus (GEO; http://www.ncbi.nlm.nih.gov/geo) with the series accession number GSE92413. Raw data were normalized using RMA16 and analyzed using Genespring GX (Agilent, Santa Clara Calif.). Additional processing of data was performed using dChip® software (Harvard University) (Roy S, et al. Proc Natl Acad Sci USA 2007, 104(36): 14472-14477; Roy S, et al. Physiol Genomics 2008, 34(2): 162-184). Functional annotation of the similar genes across groups was performed using IPA® analysis. See Tables 5 and 6.

TABLE 5

IPA analysis: functional annotation of the genes similar between in vitro iNs and in vivo iNs.

| Functions Annotation | p-Value | # Molecules |
| --- | --- | --- |
| Olfactory response | 9.28E−96 | 315 |
| Formation of brain cells | 0.00539 | 13 |
| Production of cortical neurons | 0.00663 | 3 |
| Development of molecular layer of cerebral cortex | 0.00836 | 2 |
| Excitation of retinal ganglion cells | 0.00836 | 2 |
| Excitation of trigeminal ganglion neurons | 0.00836 | 2 |
| Neurogenesis of stem cells | 0.00945 | 6 |
| Localization of neurons | 0.0124 | 3 |
| Abnormal morphology of vertebral body | 0.0185 | 6 |
| Stimulation of sensory neurons | 0.019 | 4 |
| Mechanical nociception | 0.0198 | 5 |
| Lack of cerebellum | 0.0202 | 3 |
| Maturation of granule cells | 0.0236 | 2 |
| Abnormal function of baroreceptor | 0.0301 | 3 |
| Morphology of anterior pituitary cells | 0.0301 | 3 |

TABLE 6

Figure 24A:
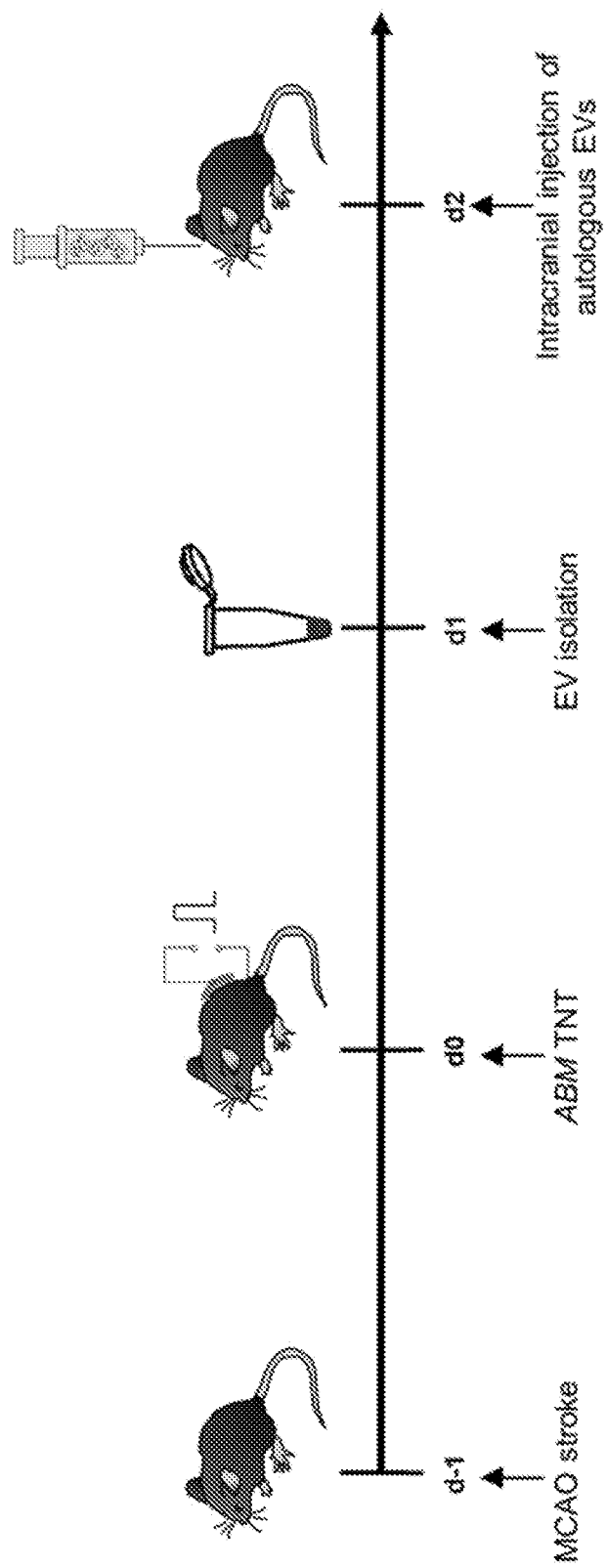
Figure 24B:
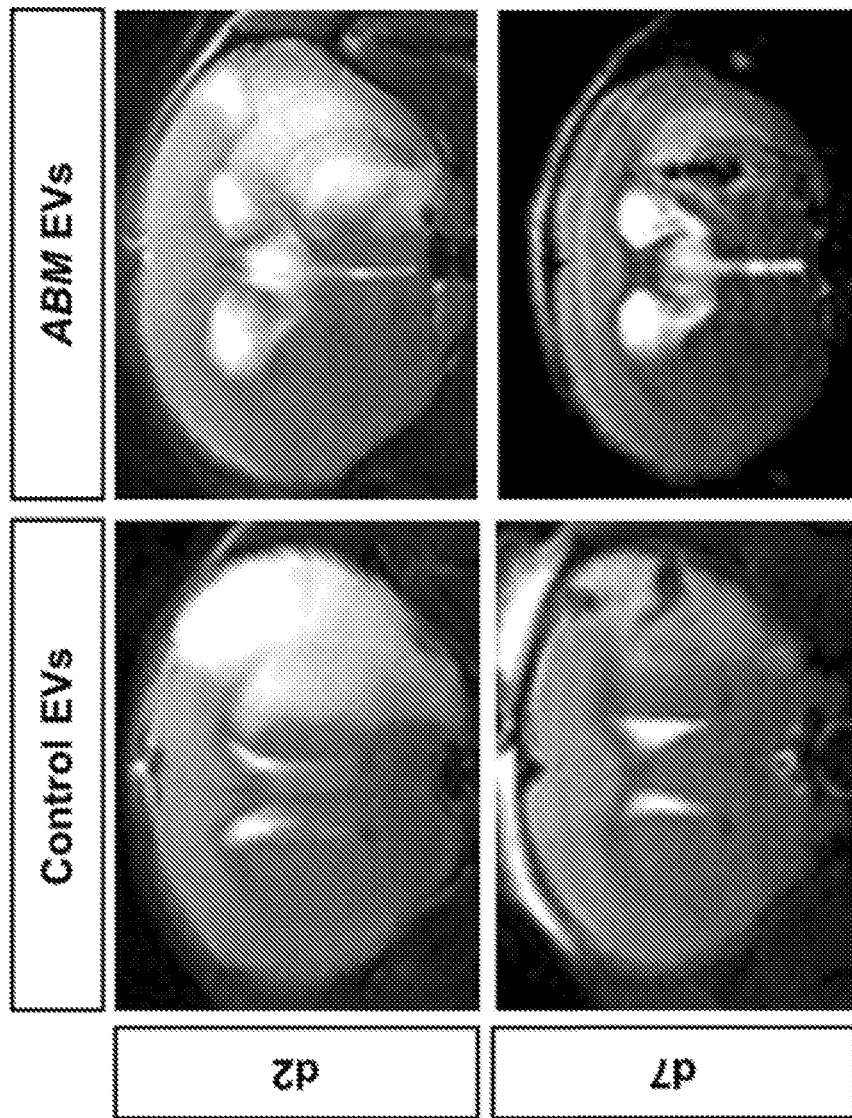
Figure 24C:
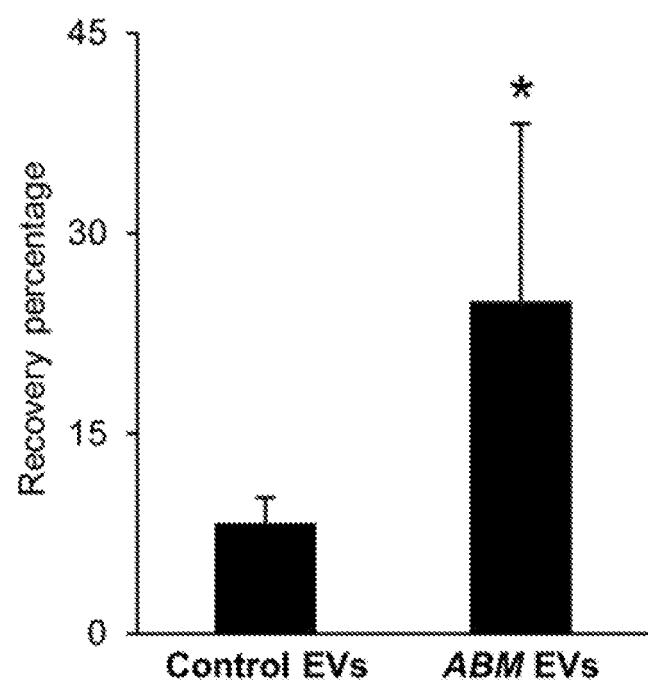
Figure 24D:
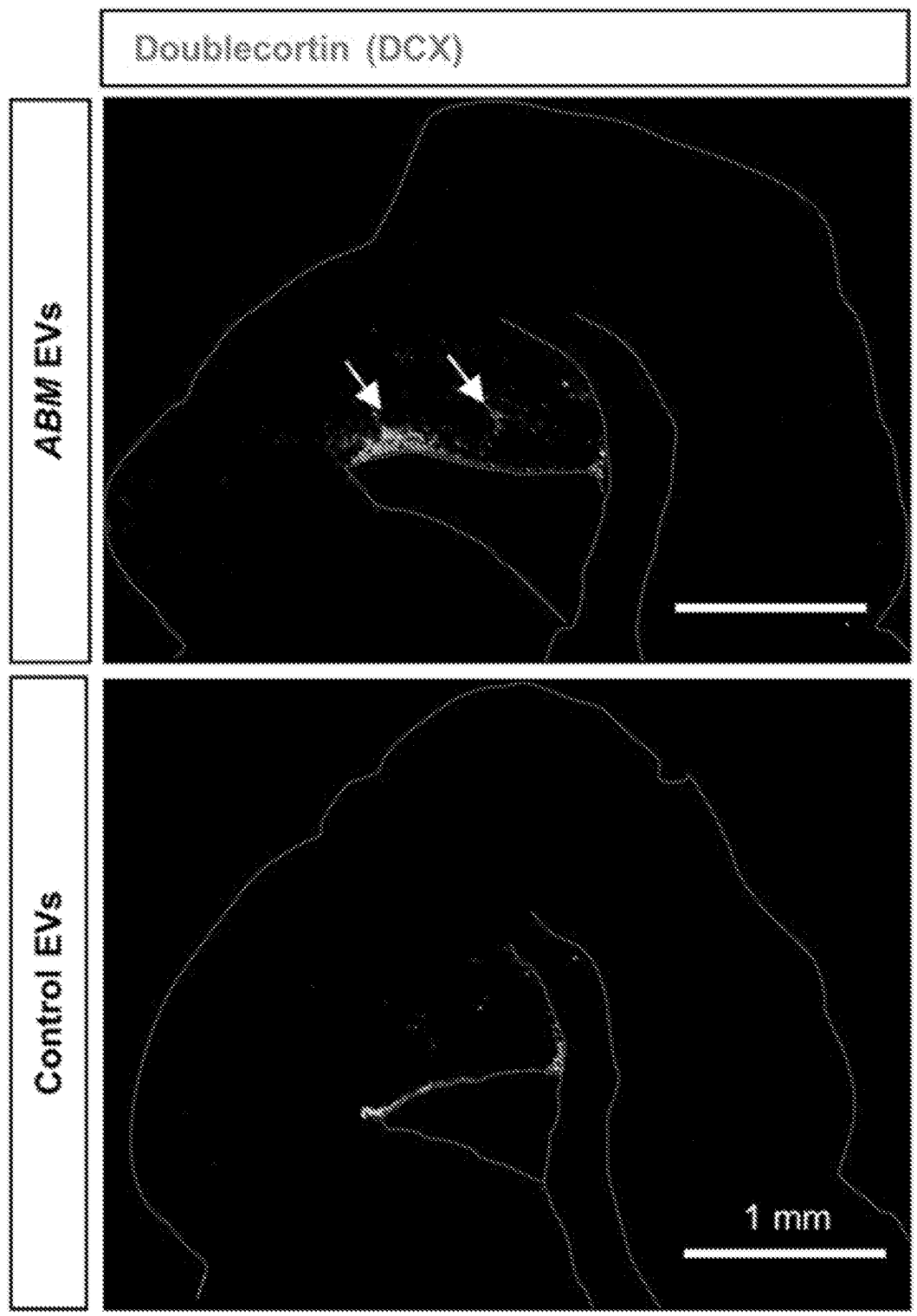

Genes involved in IPA ® analysis shown in FIG. 24b.

| Symbol | Entrez Gene Name | Family | GenBank |
| --- | --- | --- | --- |
| ATOH1 | Atonal bhlh transcription factor 1 | Transcription regulator | NM_007500 |
| BDKRB1 | Bradykinin receptor B1 | G-protein coupled receptor | NM_007539 |
| CALCRL | Calcitonin receptor like receptor | G-protein coupled receptor | NM_018782 |
| CGA | Glycoprotein hormones, alpha polypeptide | Other | NM_009889 |
| CNR1 | Cannabinoid receptor 1 | G-protein coupled receptor | NM_007726 |
| CYP19A1 | Cytochrome P450 family 19 subfamily A member 1 | Enzyme | NM_007810 |
| EGR1 | Early growth response 1 | Transcription regulator | NM_007913 |
| EZR | Ezrin | Other | NM_009510 |
| FGFR3 | Fibroblast growth factor receptor 3 | Kinase | NM_001163215 |
| FKRP | Fukutin related protein | Other | NM_173430 |
| FOXA1 | Forkhead box A1 | Transcription regulator | NM_008259 |
| GLRA2 | Glycine receptor alpha 2 | Ion channel | NM_183427 |
| GLRA3 | Glycine receptor alpha 3 | Ion channel | NM_080438 |
| IFNG | Interferon gamma | Cytokine | NM_008337 |
| IL1RAPL1 | Interleukin 1 receptor accessory protein like 1 | Transmembrane receptor | NM_001160403 |
| IL6 | Interleukin 6 | Cytokine | NM_031168 |
| KLF9 | Kruppel like factor 9 | Transcription regulator | NM_010638 |
| MMP24 | Matrix metallopeptidase 24 | Peptidase | NM_010808 |
| NEUROD6 | Neuronal differentiation 6 | Transcription regulator | NM_009717 |
| NOTCH1 | Notch 1 | Transcription regulator | NM_008714 |
| POU3F2 | POU class 3 homeobox 2 | Transcription regulator | NM_008899 |
| POU3F3 | POU class 3 homeobox 3 | Transcription regulator | NM_008900 |
| PRL | Prolactin | Cytokine | NM_001163530 |
| PRLHR | Prolactin releasing hormone receptor | G-protein coupled receptor | NM_201615 |
| PRNP | Prion protein | Other | NM_011170 |
| PTF1A | Pancreas specific transcription factor, 1a | Transcription regulator | NM_018809 |

TABLE 6-continued

Genes involved in IPA® analysis shown in FIG. 24b.

| Symbol | Entrez Gene Name | Family | GenBank |
| --- | --- | --- | --- |
| SCN9A | Sodium voltage-gated channel alpha subunit 9 | Ion channel | NM_018852 |
| SRC | SRC proto-oncogene, non-receptor tyrosine kinase | Kinase | NM_009271 |
| TRPA1 | Transient receptor potential cation channel subfamily A member 1 | Transporter | NM_177781 |
| VWC2 | von Willebrand factor C domain containing 2 | Other | NM_177033 |
| ZNF423 | Zinc finger protein 423 | Transcription regulator | NM_033327 |

Statistical Analysis.

Samples were coded and data collection was performed in a blinded fashion. Data are reported as mean±standard error of 3-8 biological replicates. Unsuccessful transfections (e.g., due to poor contact between the skin and the nanochannels, or nanochannel clogging, etc.) were excluded from the analysis. Experiments were replicated at least twice to confirm reproducibility. Comparisons between groups were made by analysis of variance (ANOVA). Statistical differences were determined via parametric/non-parametric tests as appropriate with SigmaPlot version 13.0.

Data Availability.

GeneChip expression data can be accessed through the Gene Expression Omnibus. Additional data are available from the corresponding authors upon reasonable request.

In Situ Measurements of Electrophysiological Activity in the Skin.

Efforts were focused on detecting the inherent excitability of induced neurons in vivo, and the general principle of extracellular recording was used to achieve this goal. However, traditional electrophysiological techniques used for extracellular recordings were challenging to implement due to our need to dissect the tissue away from the mouse, identify the induced neurons morphologically, and then place an extracellular electrode in close proximity to the cells of interest. To overcome aforementioned complexities of performing a patch-clamp technique or conventional electrophysiological measurement, chronoamperometric measurements of a conducting polymer electrode placed in the extracellular space were used to detect neuronal excitability. The transfer function for charge ingress and egress in to and out of the polymer is applied to measured data, and poles and residues corresponding to double layer and faradaic response of the conducting polymer are calculated. The residues calculated from transfer function analysis correspond to the changes in cation concentration proximate to the polymer as explained in Venugopal et al (Venugopal V, et al. J Intel Mat Syst Str 2016, 27(12): 1702-1709). By placing the conducting polymer electrode in the ABM-treated area of the mouse as shown in FIG. 25, temporal changes to the residue corresponding to faradic responses are observed, indicating neuronal excitability.

Physics of Operation for Redox-Based Conducting Polymer Cation Sensors.

Polypyrrole doped with dodecylbenzenesulfonate (PPy(DBS)) is a conducting polymer that exchanges cations with a local media at the onset of electrical potentials. The rate of cation ingress is a function of the applied electrical potential, polymer geometry, the current state of the polymer, and concentration of electrolyte (Venugopal V, et al. Sensors and Actuators B: Chemical 2014, 201(0): 293-299). This concentration dependence enables the creation of cation sensors which have been demonstrated to have a linear relationship with NaCl concentrations over the range of 5-100 mM11. Further, PPy(DBS) sensors are nontoxic and redox-mediator free systems capable of determining the local cation concentration of biological material without damaging or affecting their function. Therefore, mesoscale PPy(DBS) sensors have been fabricated into probes capable of residing within the dermal layer to measure in situ cation concentration.

A single oxidation-reduction switch (redox event) of a PPy(DBS) membrane causes both faradaic and double-layer based ion transport. The time-dependent ion transport kinetics are described by the equation below, where $k_1$ and $\tau_1$ values correspond to the total number and rate of ions forming the electrical double layer and the $k_2$ and T2 values correspond to the total number and rate of ions intercalating into the polymer. Based on this, the effects of the double layer capacitor can be neglected leaving the k2 value as the sensitive parameter to cation concentration (Venugopal V, et al. J Intel Mat Syst Str 2016, 27(12): 1702-1709).

$$q(t) = k_1 e^{\frac{t}{\tau_1}} + k_2 e^{\frac{t}{\tau_2}}$$

In order to capture time-dependent changes in cation concentration, multiple redox cycles of PPy(DBS) are required. The frequency of switching should be chosen based on an estimation of the rate of concentration change within the system of interest. In this instance, the rate of electrophysiological activity was unknown, so the redox frequency was chosen to be 5 Hz. At this frequency, the time for each reduction cycle is significantly lesser than the time required for the system to reach a steady state (2.5-10 seconds based on polymer thickness and electrolyte concentration) (Northcutt R G, et al. Physical Chemistry Chemical Physics 2016, 18(26): 17366-17372). This causes the polymer to operate in constant flux between each redox state and creates a condition in which $k_2$ is varied due to the total number of ions that the polymer can accept within a 0.1 second window. The measured $k_2$ is therefore proportional to the local cation concentration. Monitoring changes in $k_2$ over time directly measures changes in cation concentration due to excitability of local cells.

Fabrication of PPy(DBS) Microelectrodes.

Platinum wire (0.025 mm dia., 99.9% pure temper hard from Goodfellow, USA) was inserted through quartz capillaries (75×1 mm, Sutter Instruments) to form a 2 mm protrusion. The protrusion-end was sealed with epoxy, leaving a 1 mm exposed platinum wire as a working electrode (WE). Silver wire (0.5 mm dia., 99.9% pure from Sigma Aldrich) was similarly treated to form a reference electrode (RE) with a 1 mm protrusion. Prior to insertion, the silver wire was soaked for 20 minutes in sodium hypochlorite solution (10-15% chlorine) to form an Ag/AgCl layer. An electropolymerization solution (0.2 mM pyrrole, 98% purity and 0.1 mM sodium dodecylbenzenesulfonate from Sigma Aldrich) was formed and allowed to settle for 30 minutes. The electropolymerization cell consisted of the Pt wire, the Ag/AgCl, and a platinum wire counter electrode (CE). A cyclic voltammetry experiment (CV) was performed to verify the electrochemical connectivity, pyrrole activity, and polymer growth region. A chronoamperometry experiment (CA) was subsequently performed with an applied 0.52 V potential (based on the CV) until 118.5 µC charge was deposited to create a PPy(DBS) membrane with a 0.15 C·cm-2 charge density. The PPy(DBS) tips were then rinsed with DI water and dried under a nitrogen stream.

Equilibration and Calibration of PPy(DBS) Microelectrodes.

After drying under a N2 stream, the PPy(DBS) sensors were equilibrated in a stock solution similar to physiological conditions (125 mM NaCl from Sigma Aldrich in DI water). This was done by CV over 10 cycles to ensure a redundant current response over cycles and increase the sensitivity of the PPy(DBS) tips to cation ingress.

Protocol for Detection of Neuronal Excitability.

Mice were categorized as either ABM, or control and sedated prior to measurement. Two 1 mm perforations were created in the dermal layer (3-5 mm apart). To ensure electrolytic conductivity throughout the epidermis, a physiological 0.9% NaCl solution was injected between the holes. The PPy(DBS) probe and Ag/AgCl probe were then inserted into the injection sites using nanopositioners (Sutter Instruments) such that 1 mm of each probe was exposed to the epidermal layer. A cyclic voltammogram was then recorded to ensure electrochemical connectivity and characterize the noise in the system. Subsequently, a series of chronoamperometric measurements was performed by switching between a reduction and oxidation potential every 0.1 seconds until 100 redox cycles were completed over the course of 20 seconds. The applied reduction and oxidation potential were selected based on the redox peaks observed during the CV (0.2 V lesser than the reduction peak and 0.2 V greater than the oxidation peak). A 5 second equilibration (0 V applied) CA was performed before and after the redox switching. The CA process was repeated 5 to 10 times until the responses were similar between trials, indicating steady state behavior. There were multiple trials recorded at one insertion site, as well as multiple insertion sites. This was done to increase the chances of capturing neuronal cell activity, as the insertion sites were made arbitrarily.

Baseline Characterization of Sensor Response to Concentration Variation.

To further understand the impact of environmental noise on the sensors, cyclic voltammetric and chronoamperometric measurements were performed (using the methods described above) using 0.9% NaCl solution in a 10 mL container. This experiment was used to establish a baseline metric wherein the inherent noise of the system was characterized. This was used to define the "activity" of ABM or control mice. According to this, a 3%+−deviation was considered to be evidence of "excitable" cells. To eliminate transience, the first 25 cycles of the measurement were ignored. Of the remaining 75 redox cycles, only the reduction cycles were considered, to capture the effect of ion ingress while ignoring ion egress. A two-term exponential function was fit to the data using the model described in the first section, and $k_2$ values were obtained. It was noticed that there was a time-dependent bias as well as a substantial offset between electrodes. Consequently, the $k_2$ values were normalized by dividing the k2 values by their average, and subtracting a fifth-order polynomial fit. Using this method gave an objective basis for comparison, independent of electrode used.

Results

Recent advances in nuclear reprogramming in vivo have opened up the possibility for the development of 'on-site', patient-specific cell-based therapies. A novel yet simple to implement non-viral approach was developed to topically and controllably deliver reprogramming factors to tissues through a nanochanneled device (FIG. 17). Such tissue nano-transfection (TNT) approach allows direct cytosolic delivery of reprogramming factors by applying a highly intense and focused electric field through arrayed nanochannels (Gallego-Perez D, et al. Nanomedicine 2016, 12(2): 399-409; Boukany P E, et al. Nat Nanotechnol 2011, 6(11): 747-754), which benignly nanoporates the juxtaposing tissue cell membranes, and electrophoretically drives reprogramming factors into the cells (FIG. 17 a-d). Detailed information regarding the TNT system fabrication process and simulation results can be found in FIGS. 20 and 21. In contrast to current in vivo transfection technologies (e.g., viruses, conventional tissue bulk electroporation or BEP), in which gene delivery is highly stochastic in nature and could lead to adverse side-effects (e.g., inflammatory response, cell death) (Sen C K, et al. Am J Pathol 2015, 185(10): 2629-2640), nanochannel-based transfection enables more focused (FIG. 17 b,c) and ample (FIG. 17d) reprogramming factor delivery at the single cell level, thus making this a powerful tool for deterministic in vivo gene transfection and reprogramming (Gallego-Perez D, et al. Nanomedicine 2016, 12(2): 399-409; Boukany P E, et al. Nat Nanotechnol 2011, 6(11): 747-754).

Figure 17A:
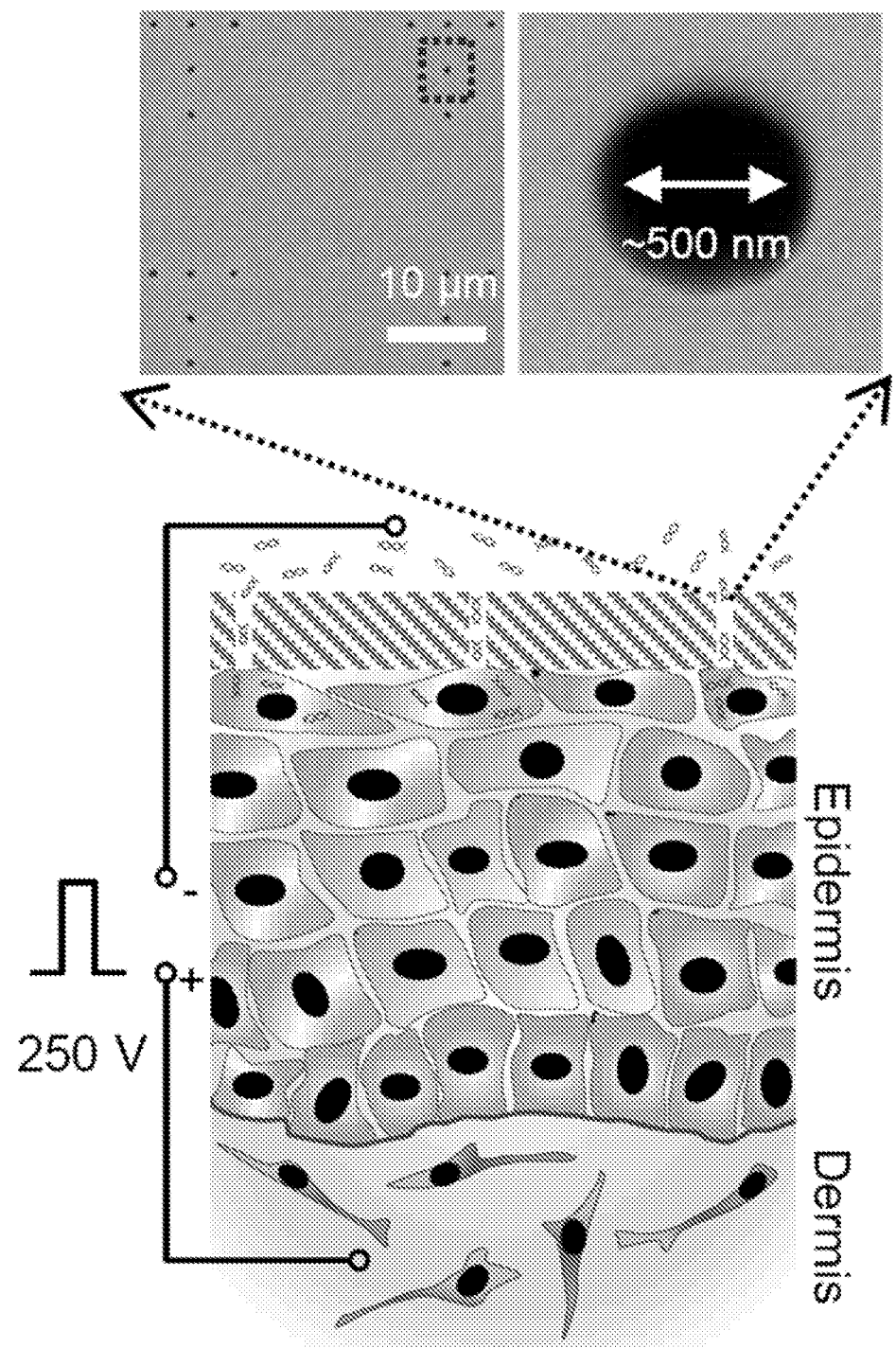
FIG. 17. TNT mediates enhanced reprogramming factor delivery and propagation beyond the transfection boundary. (a) Schematic diagram of the TNT process on exfoliated skin tissue. Exfoliation is required to remove dead cells from the skin surface. The positive electrode is inserted intradermally, while the negative electrode is put in contact with the cargo solution. A pulsed electric field (250 V, 10 ms pulses, 10 pulses) is then applied across the electrodes to nanoporate exposed cell membranes and inject the cargo directly into the cytosol. Scanning electron micrographs (top) of the TNT platform surface showing the nanopore array. (b) Schematic diagram showing the boundary conditions for simulation purposes. Nanochannels are in direct contact with the outermost cell layer. (c) Simulation of the poration profile for different cells (i.e., cells 1, 3 and 5 from panel "b") undergoing TNT (solid lines) vs. BEP (dashed lines). This plot shows that TNT leads to focused poration, while BEP results in widespread poration. (d) ABM expression results for TNT vs. BEP 24 h after transfection (n=5). TNT resulted in superior ABM expression. BEP was conducted via intradermal injection of the ABM plasmids followed by a pulsed electric field. Controls for BEP experiments involved intradermal injections of ABM plasmids with no electric field implementation. (e) Representative IVIS fluorescence and (f) confocal microscopy image of mouse skin after TNT treatment with labeled DNA and the ABM factors, respectively. GFP is the reporter gene in the Ascl1 plasmid. (g) Laser Capture Microdissection (LCM) and qRT-PCR results of gene expression in epidermis and dermis (t=24 h) showing that gene expression propagated beyond the epidermal transfection boundary (n=5-6). (h) Schematic diagram illustrating the concept of EV-mediated transfection propagation from epidermis to dermis. (i) qRT-PCR analysis of the EV cargo showing significant loading of ABM cDNAs/mRNAs (n=6-8). (j) Experimental design to confirm whether EVs are a viable vehicle for propagating transfection and reprogramming. (k) Confocal micrograph showing a mouse embryonic fibroblast (red) that has spontaneously internalized the EVs (green) isolated from TNT-treated skin. (l) MEF cultures showing iNs at day 7 after a 24 h exposure to ABM-laden EVs isolated from ABM-transfected skin. Immunostaining results (week 4) showing increased (m) Tuj1 and (n) Neurofilament (NF) expression in the skin after ABM transfection. (o) Electrophysiological activity shown as a statistically-representative bar plot indicating changes in ionic concentration (quantified as average standard deviations from the norm per insertion site) of the extracellular niche as a result of neuronal cell cluster excitability (n=8, p<0.05, Fisher's exact test). This average was calculated for 5-10 trials (with 100 sequential discrete measurements per trial) for each ABM or control mouse. Activity was defined as changes in ionic concentration in excess to the baseline (dashed line, established as experimental noise measured in physiological saline solution). Each bar shows the results collected on independent mice. *p<0.01 (Dunn's), #p<0.01 (Tukey Test), ##p<0.05 (Holm-Sidak method).
Figure 17B:
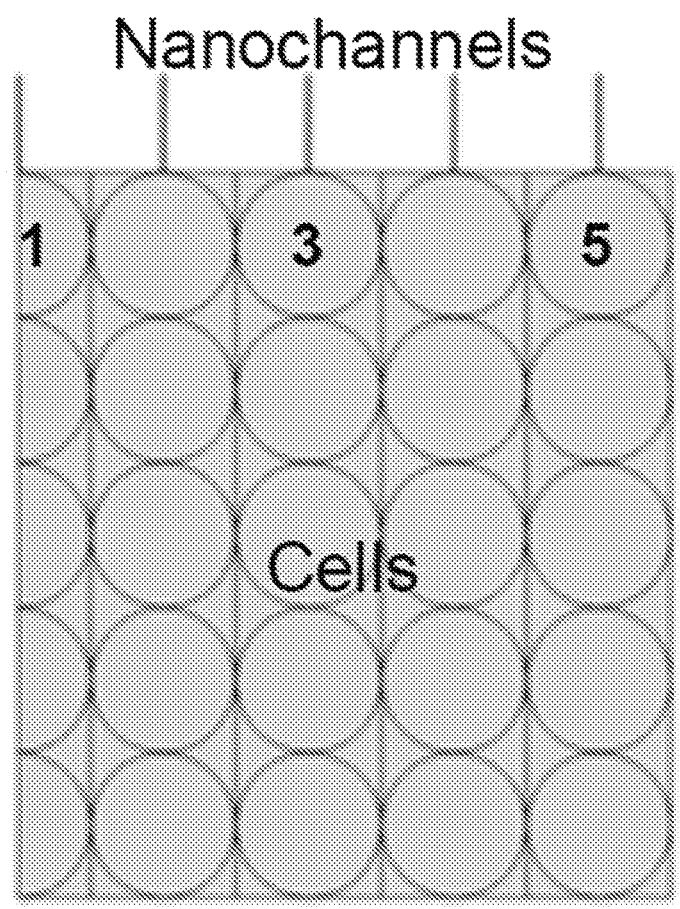
Figure 17C:
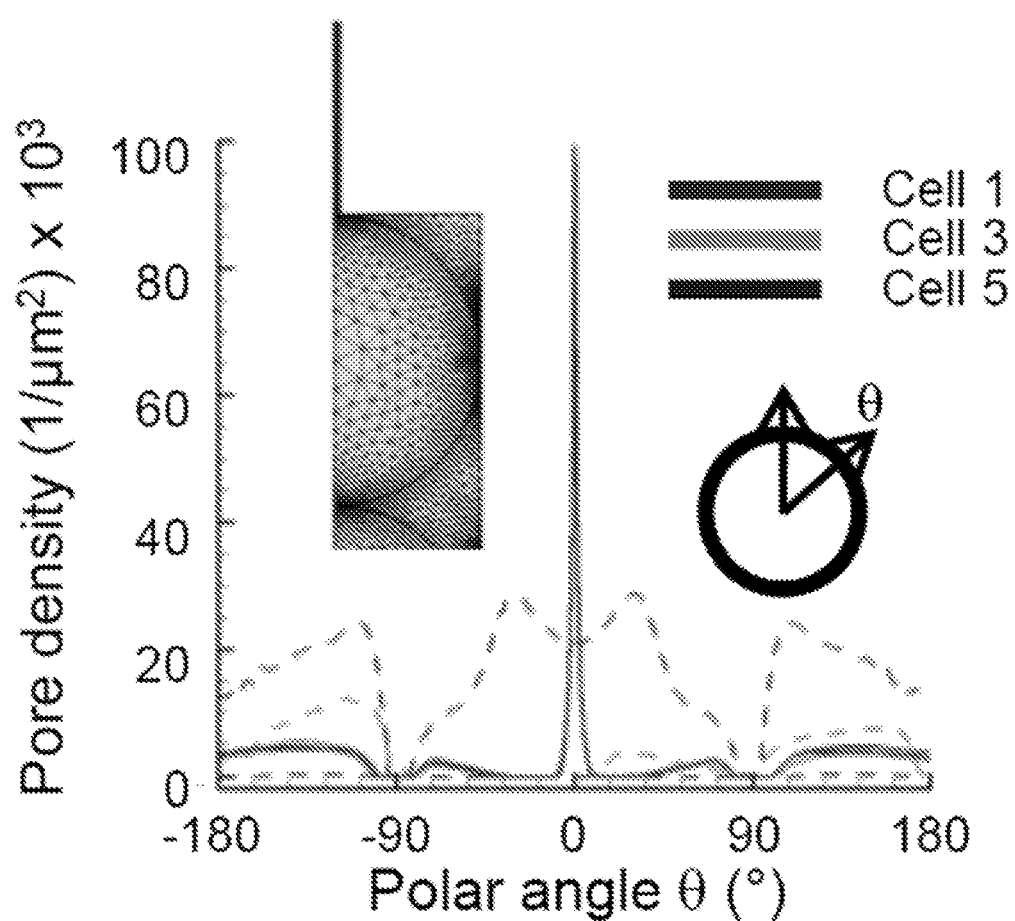
Figure 17D:
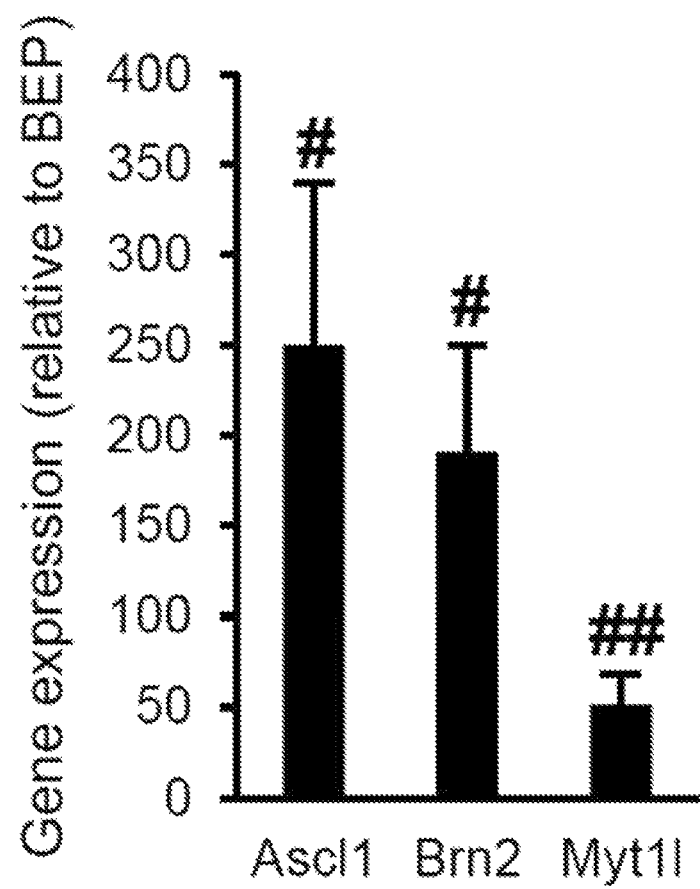
Figure 17E:
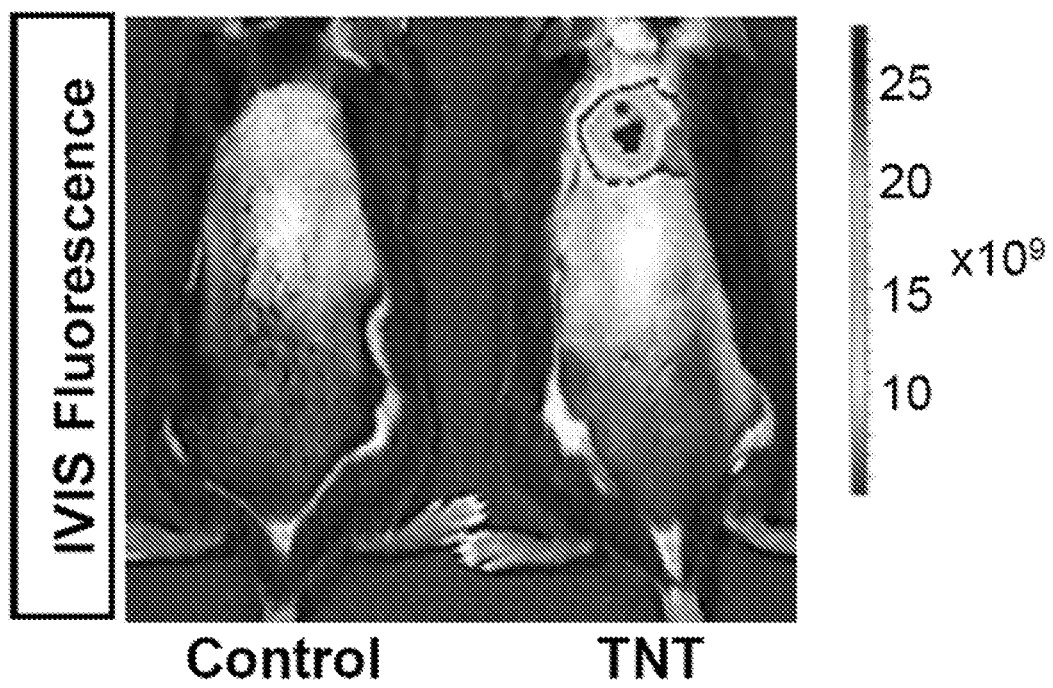
Figure 17F:
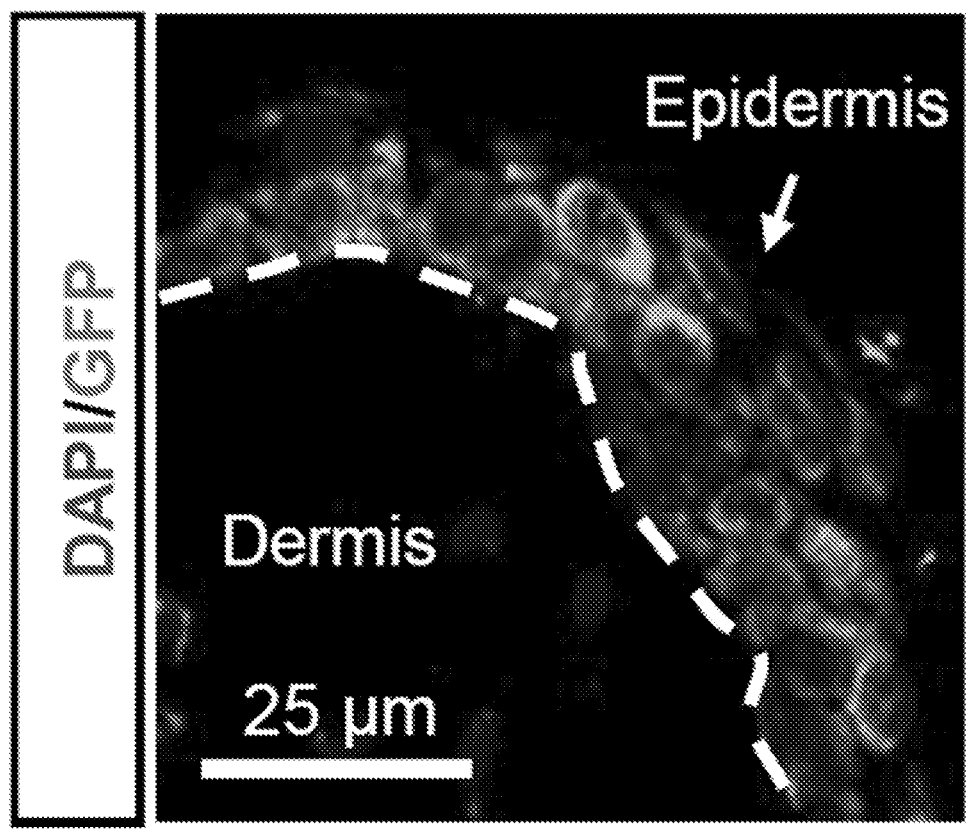
Figure 17G:
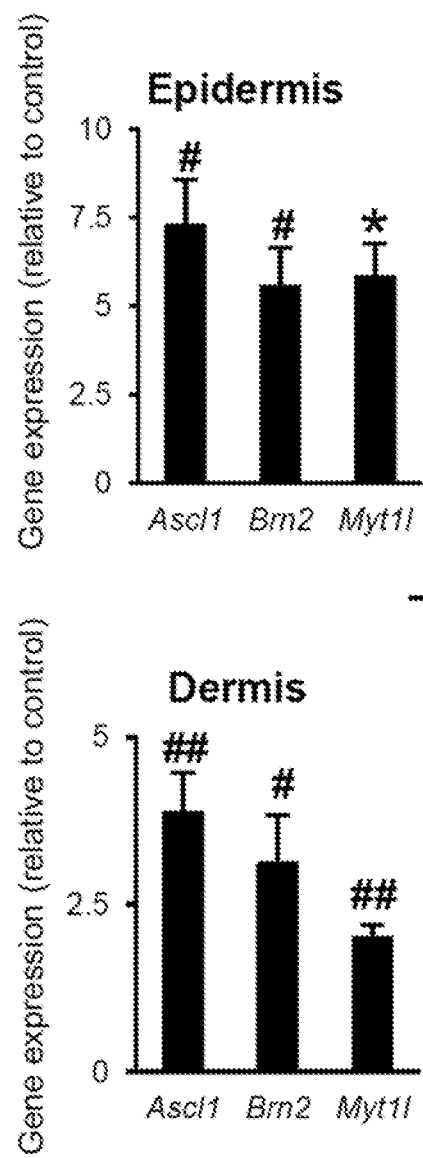
Figure 17H:
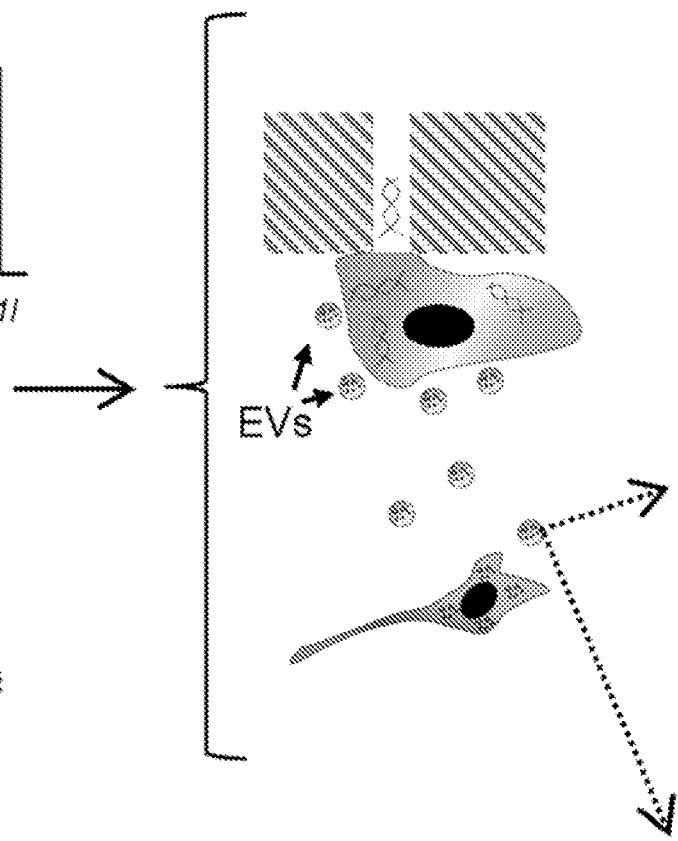
Figure 17I:
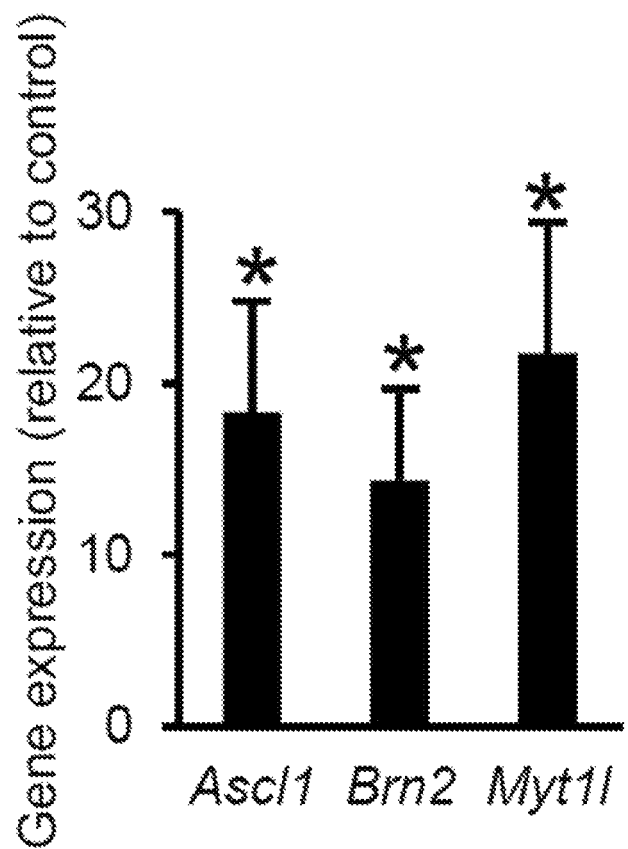
Figure 17J:
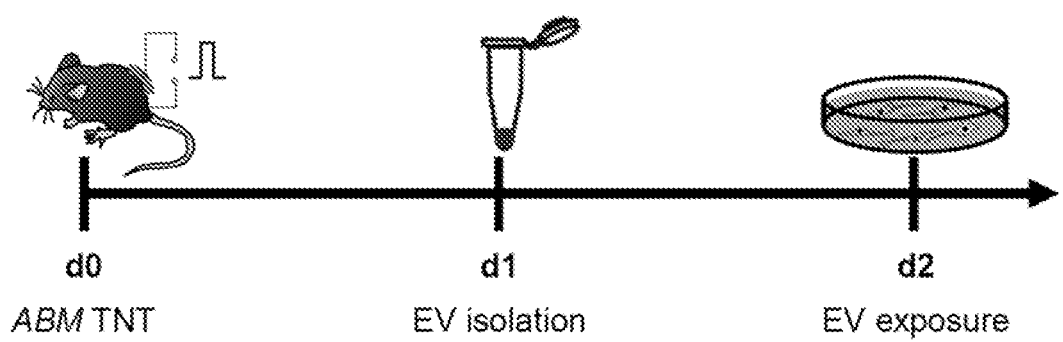
Figure 17N:
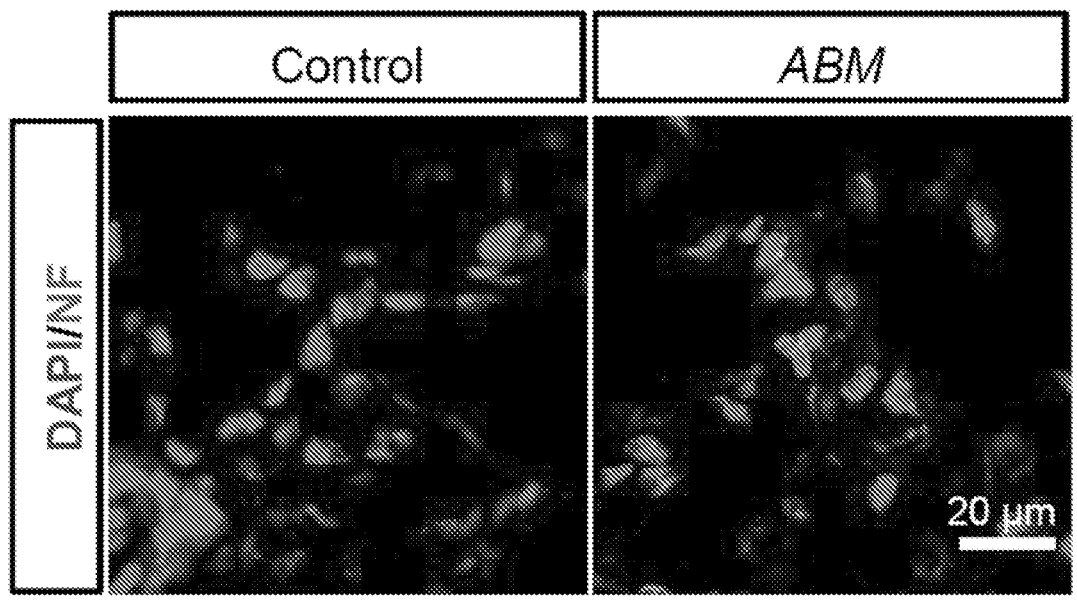
Figure 17O:
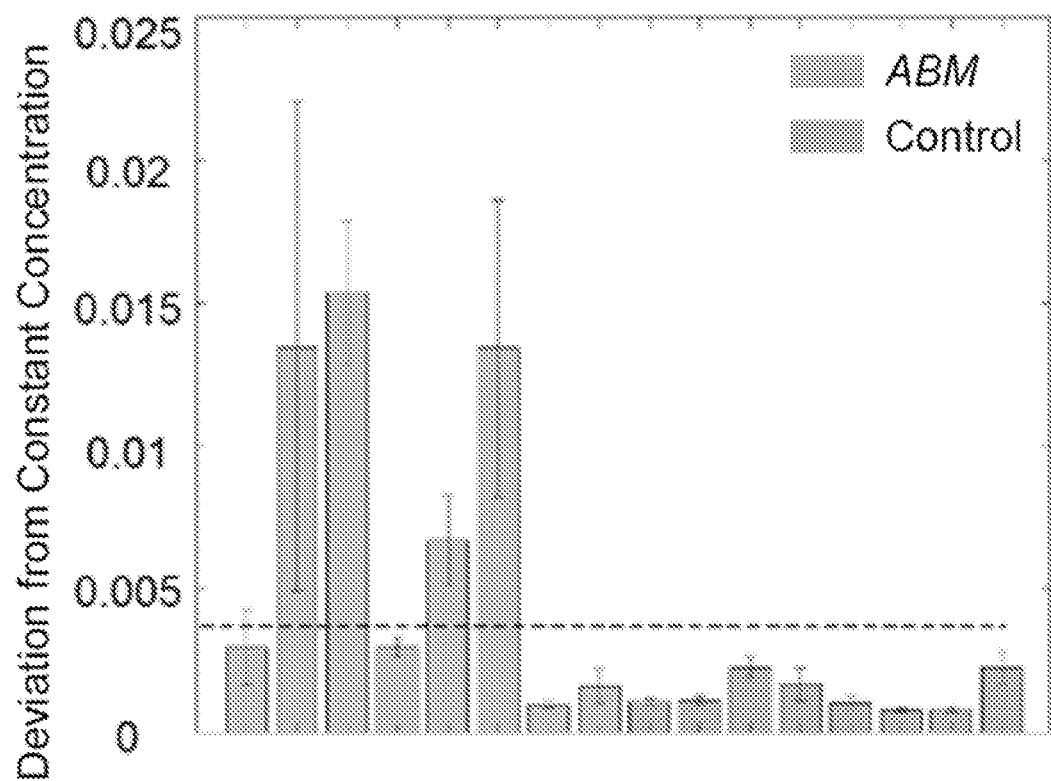

Experiments with FAM-labeled DNA on C57BL/6 mice established that TNT can deliver cargo into the skin in a rapid (<1 second) and non-invasive/topical manner (FIG. 17e). Next, whether TNT-based topical delivery of reprogramming factors could lead to successful skin reprogramming was tested using a robust model where overexpression of Ascl1/Brn2/Myt1I (ABM) is known to directly reprogram fibroblasts into induced neurons (iNs) in vitro (Gallego-Perez D, et al. Nanomedicine 2016, 12(2): 399-409; Vierbuchen T, et al. Nature 2010, 463(7284): 1035-1041). Findings showed that TNT can not only be used for topical delivery of reprogramming factors (FIG. 17f), but it can also orchestrate a coordinated response that results in reprogramming stimuli propagation (i.e. epidermis to dermis) beyond the initial transfection boundary (i.e. epidermis) (FIG. 17g-i) possibly via dispatch of extracellular vesicles (EVs) rich in target gene cDNAs/mRNAs (FIG. 17h,i) (Valadi H, et al. Nat Cell Biol 2007, 9(6): 654-659), among other plausible mechanisms (Davis D M, et al. Nat Rev Mol Cell Biol 2008, 9(6): 431-436). Exposing naïve cells to ABM-loaded EVs isolated from TNT-treated skin (FIG. 17j-l) established that these EVs can be spontaneously internalized by remote cells and trigger reprogramming (FIGS. 17k,l, and 22). Moreover, gene expression analysis indicated that intradermal ABM EV injection triggered changes in the skin consistent with neuronal induction (FIG. 23), as evidenced by increased Tuj1 expression. The neurotrophic effect of skin-derived ABM67 loaded EVs was further confirmed in a middle cerebral artery occlusion (MCAO) stroke mouse model (FIG. 24) (Khanna S, et al. J Cereb Blood Flow Metab 2013, 33(8): 1197-1206).

Successful skin cell reprogramming was verified by immunofluorescence, which showed increased Tuj1 and Neurofilament expression overtime (FIG. 17m,n). Further characterization was conducted via genome-wide transcriptome array analysis comparing in vitro- and in vivo-derived iNs (FIG. 25). Electrophysiological activity, indicative of neuronal excitability, was successfully detected and monitored (in situ) in ~50% of the ABM-transfected mice (FIG. 17O) through a novel polypyrrole (PPy)-based biosensing platform (FIG. 26) (Venugopal V, et al. J Intel Mat Syst Str 2016, 27(12): 1702-1709). No such activity was detected in any of the control mice. Lineage tracing experiments with a K14-Cre reporter mouse model established that the newly-induced neurons partly originated from K14+ skin cells (FIG. 27). Hair follicles also consistently showed marked Tuj1 immunoreactivity, suggesting that follicular cells could participate in the reprogramming process (Hunt D P, et al. Stem Cells 2008, 26(1): 163-172; Higgins C A, et al. J Invest Dermatol 2012, 132(6): 1725-1727). Additional experiments with a Col1A1-eGFP mouse model (FIG. 27), where cells with an active Col1A1 promoter (e.g. dermal fibroblasts) express eGFP, showed a number of collagen/eGFP+ cells in the dermis in a transition phase to Tuj1+, thus suggesting a fibroblastic origin for some of the reprogrammed cells in the skin.

Having validated the TNT platform for successful in vivo reprogramming using iNs as a case study, a robust and simple non-viral methodology was developed that would be capable of reprogramming skin cells into induced endothelial cells (iECs). To this end, a set of reprogramming factors, Etv2, Foxc2, and Fli1 (EFF), were identified and validated (in vitro) to promote more rapid and effective reprogramming of somatic cells into iECs (FIGS. 28 and 29) compared to previous reports (Morita R, et al. Proc Natl Acad Sci USA 2015, 112(1): 160-165). In vitro non-viral transfection and reprogramming experiments (Gallego-Perez D, et al. Nanomedicine 2016, 12(2): 399-409) showed that EFF could reprogram human and mouse primary fibroblasts into iECs rapidly (<1 week) and efficiently (FIG. 28).

Figure 18B:
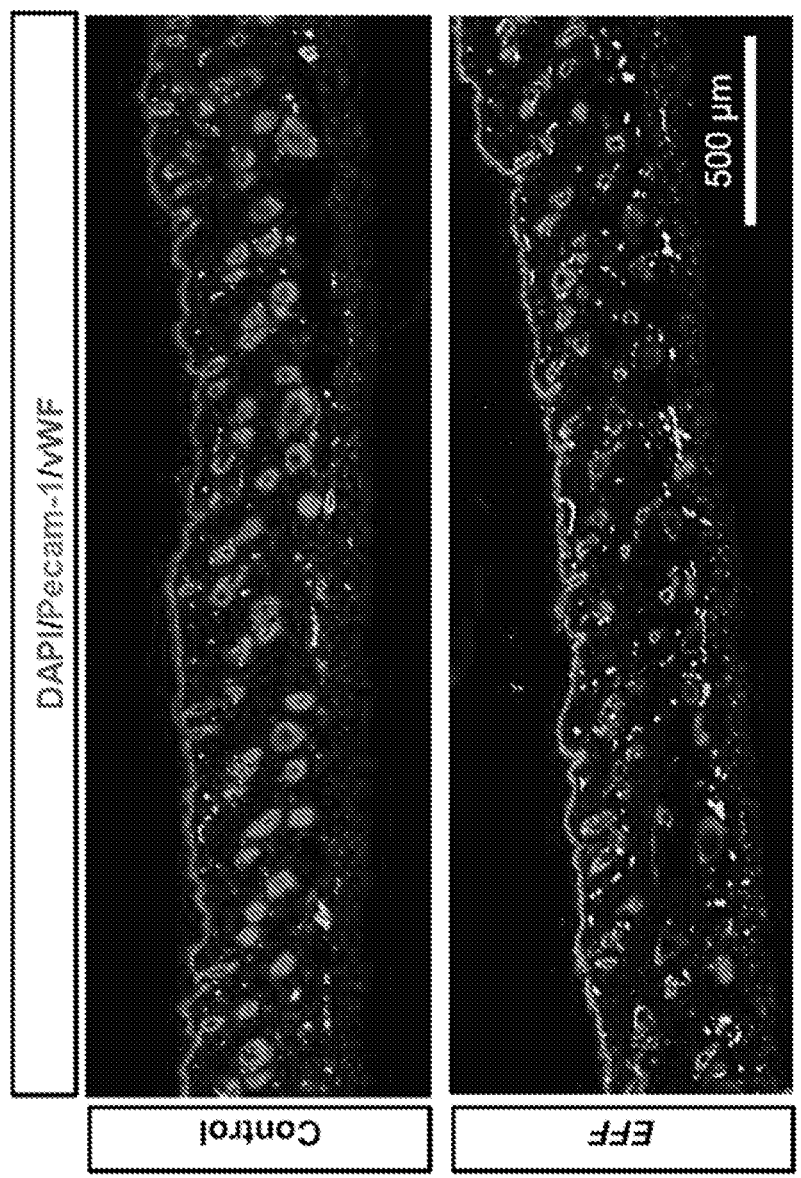
FIG. 18. EFF TNT leads to increased vascularization and rescue of skin tissue under ischemic conditions. (a-c) A one-time treatment of dorsal skin lasting only a few seconds led to increased angiogenesis (Pecam-1, vWF) of skin tissue (day 7) (n=3). (d, e) High resolution laser speckle imaging showed enhanced perfusion to the EFF-treated area over time (n=5). (f) Ultrasound imaging of EFF-treated skin confirmed the presence of superficial blood vessels (dashed circle) with pulsatile behavior, which suggests successful anastomosis with the parent circulatory system. (g) Monopedicle flap experiment showing increased flap necrosis for controls compared to EFF-treated skin. (h) Laser speckle imaging showing increased blood flow to the flapped tissue treated with EFF TNT. (i) Quantification of flap necrosis (n=6). *p<0.05 (t Test), ##p<0.05 (Holm-Sidak method).
Figure 18A:
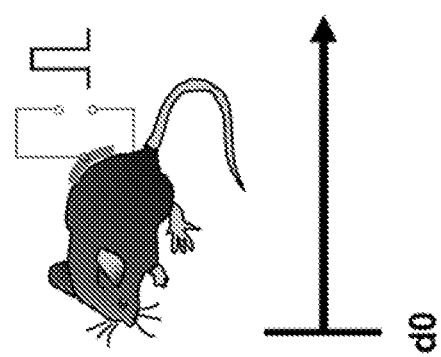
Figure 18C:
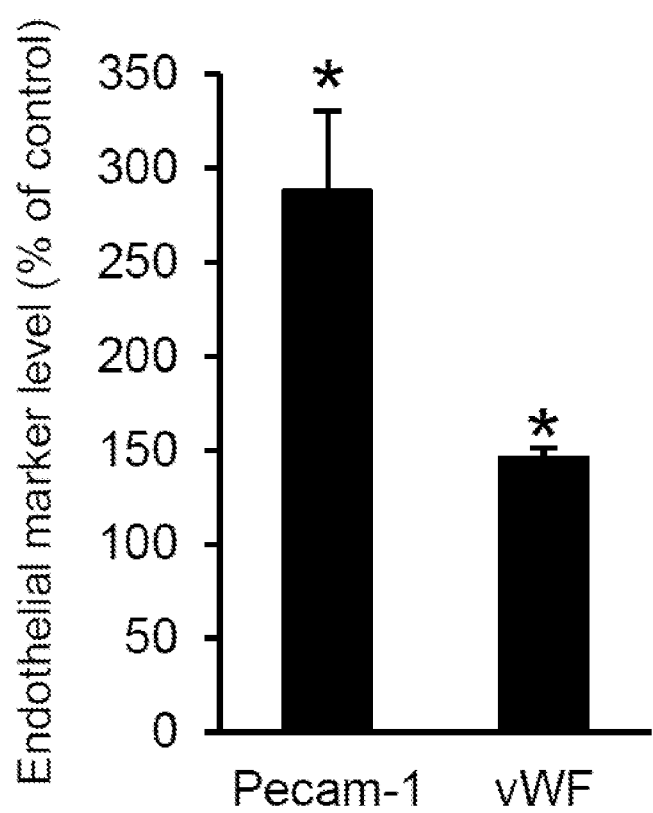
Figure 18D:
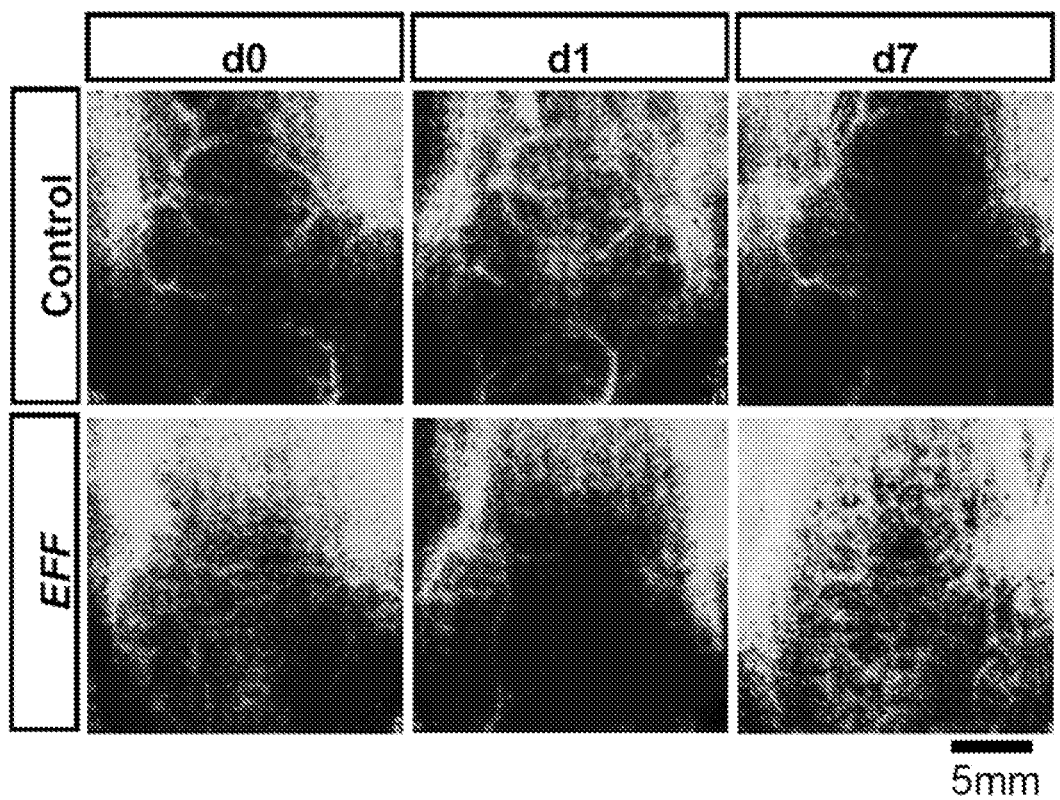
Figure 18E:
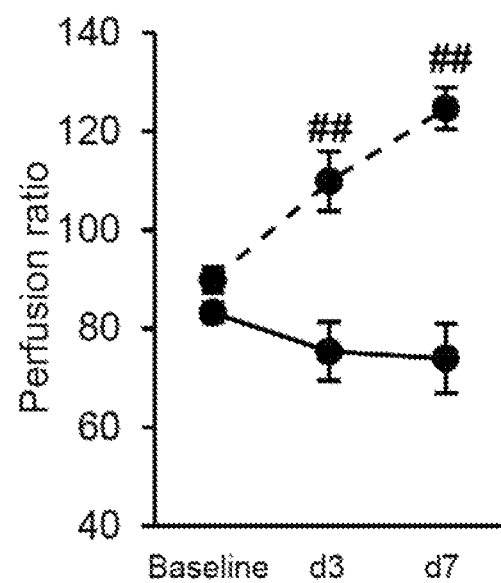
Figure 18F:
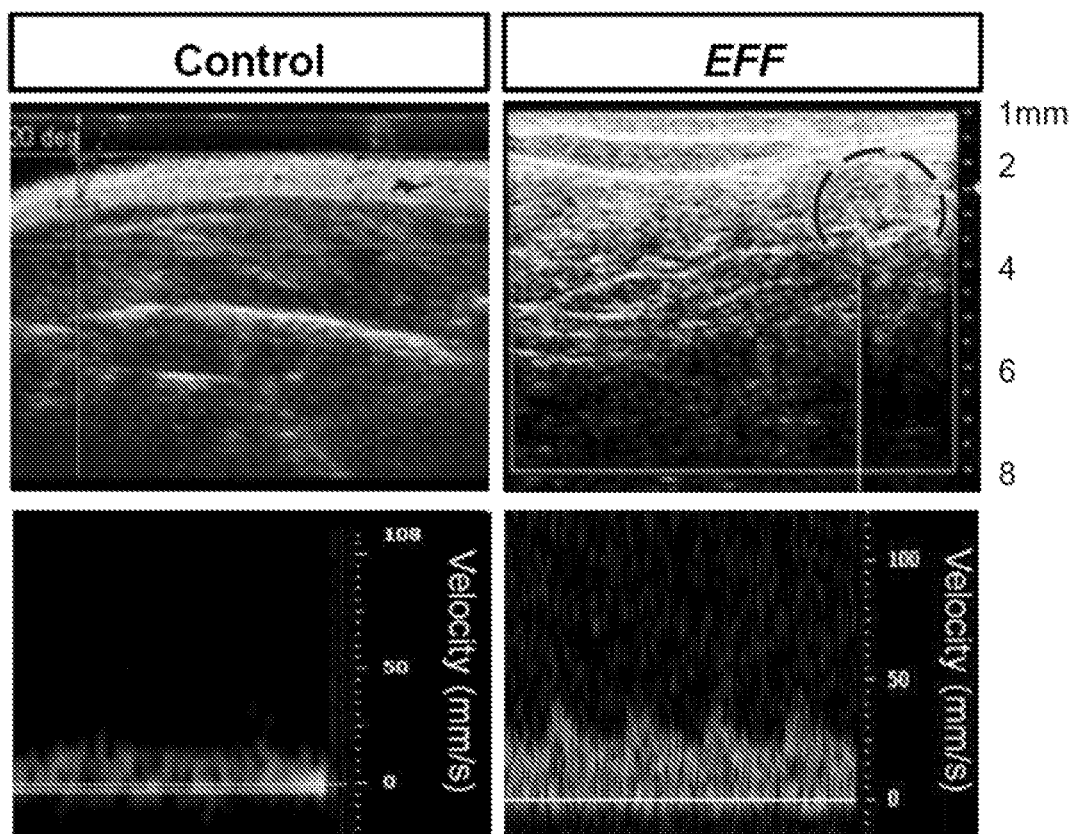

Once the efficacy of EFF to induce direct endothelial cell reprogramming was established in vitro, this paradigm was tested in vivo. Co-transfection of these three genes into dorsal skin of C57BL/6 mice resulted in marked stroma reprogramming within a week, as evidenced by a significant increase in Pecam-1 and vWF expression compared to control skin (FIG. 18a-c), in addition to enhanced proliferative activity (FIG. 30). Experiments with K14-Cre reporter and Col1A1-eGFP mouse models demonstrated that the reprogrammed cell population had for the most part a dermal origin (FIG. 31). High resolution laser speckle (HRLS) imaging of dorsal skin showed that TNT-based delivery of EFF enhanced blood flow to the treated area within 3 days (FIG. 18d, e). Ultrasound imaging detected unexpected pulsatile blood flow only 3 mm away from the surface of the skin (FIG. 18f, right), demonstrating successful anastomosis of the newly formed blood vessels with local functional cutaneous arteries. Note that in control mice, blood vessels were not typically detected near the skin surface (FIG. 18f, left).

Figures 1A, 1B:
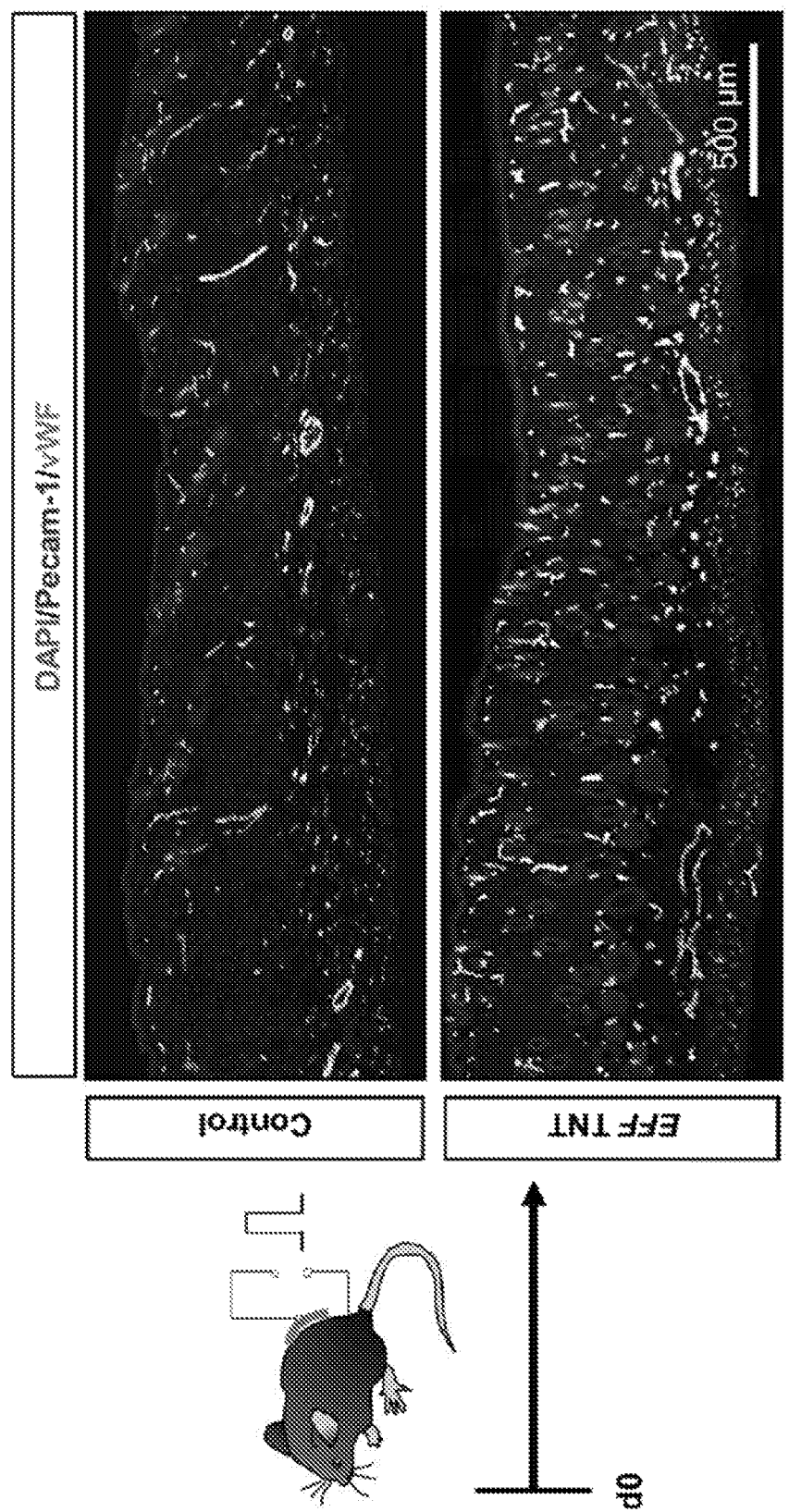
FIGS. 1A to 1I show that EFF TNT leads to increased vascularization and rescue of skin tissue under ischemic conditions.
Figure 1C:
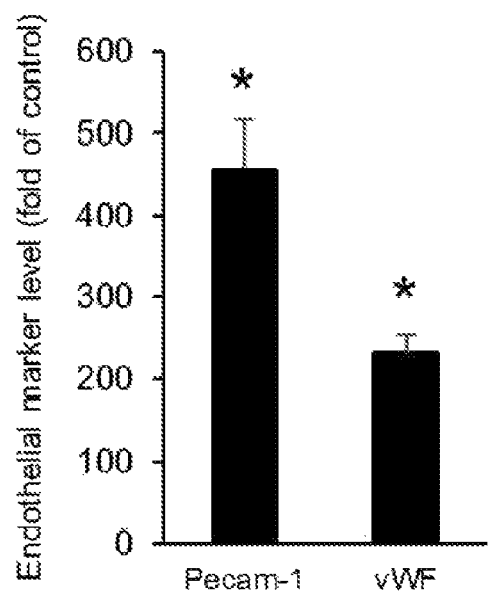
Figure 1D:
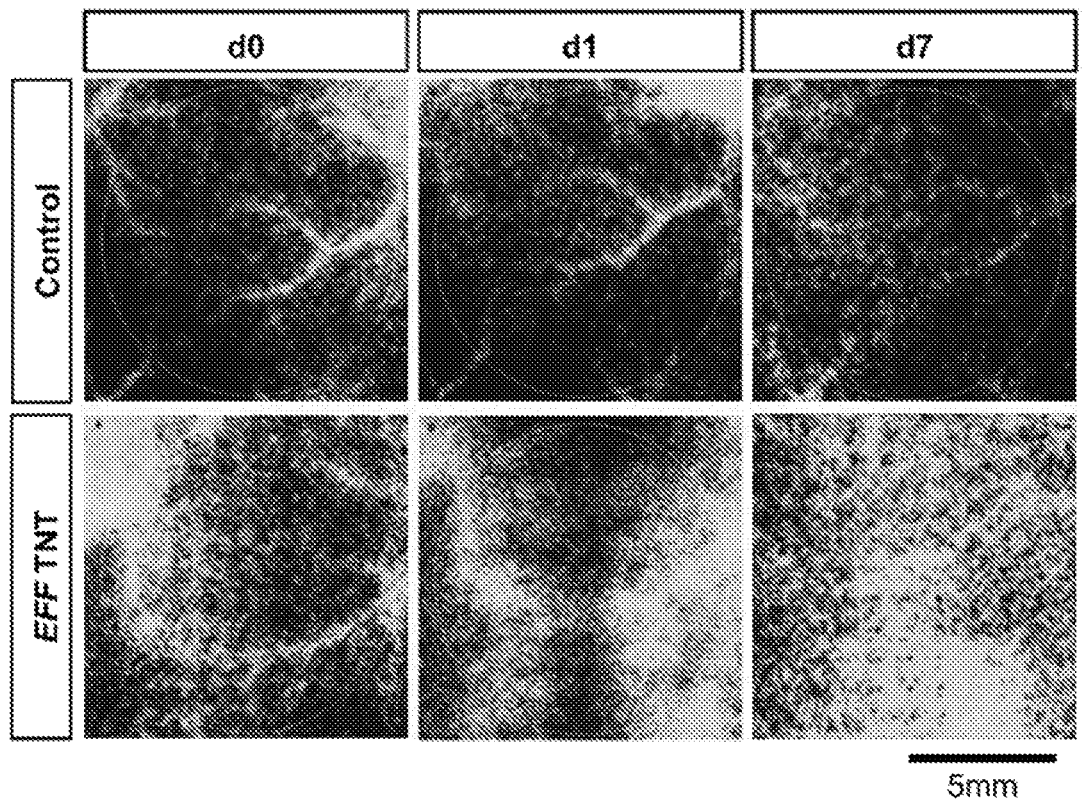
Figure 1E:
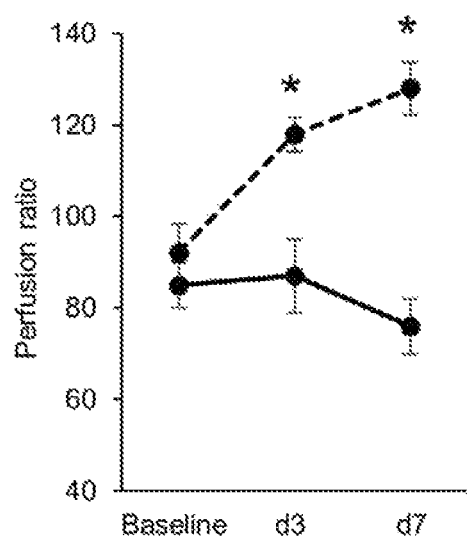
Figure 1F:
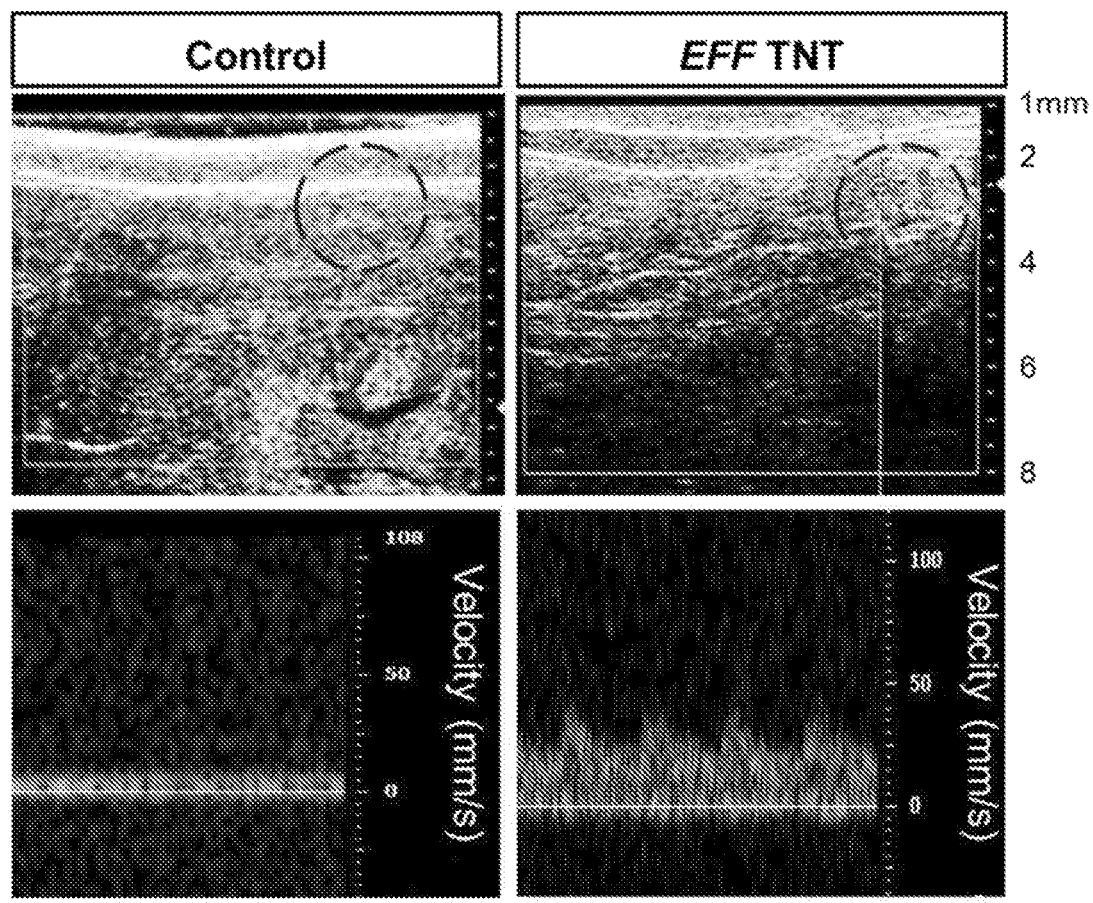
Figure 1G:
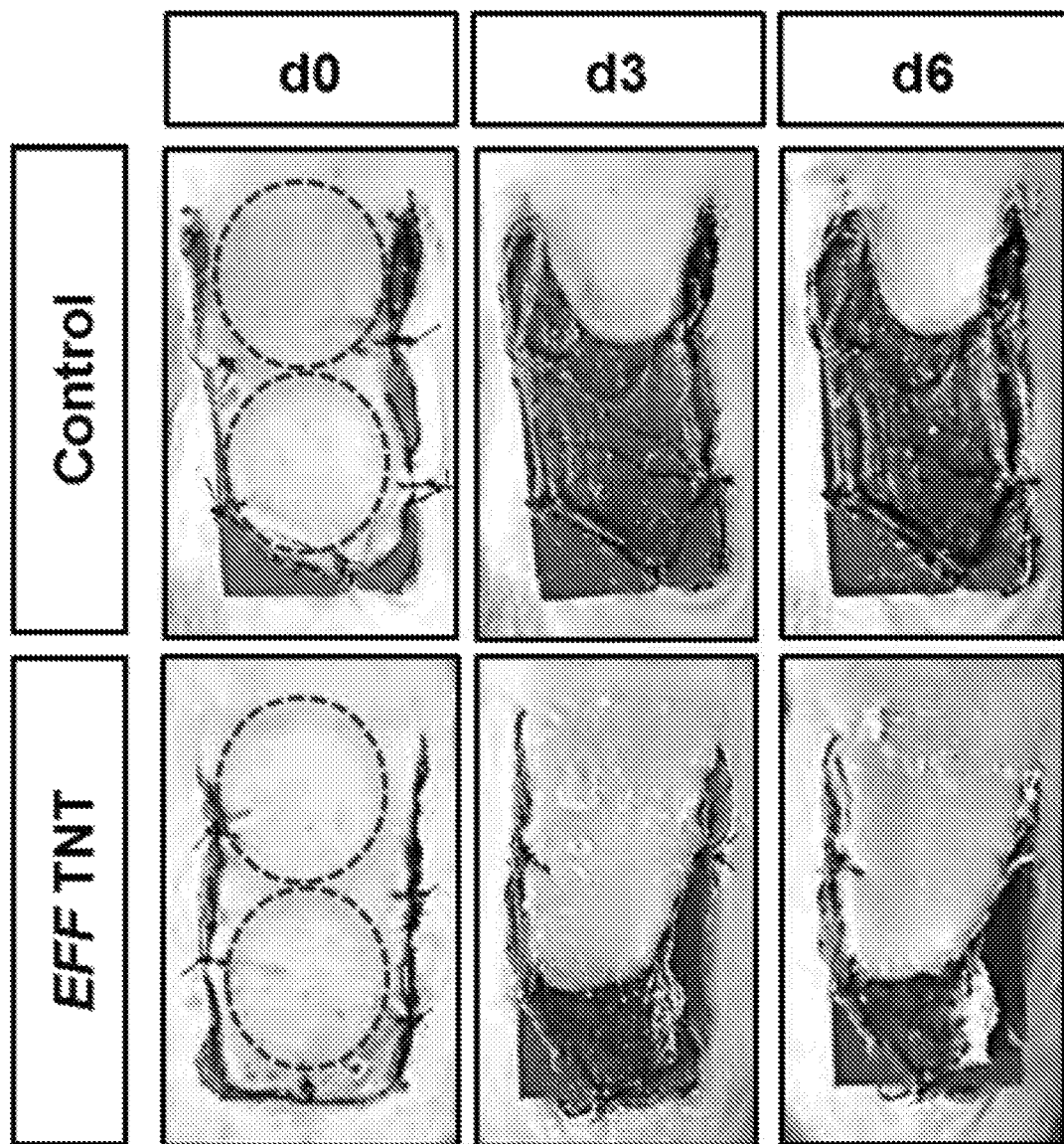
Figure 1H:
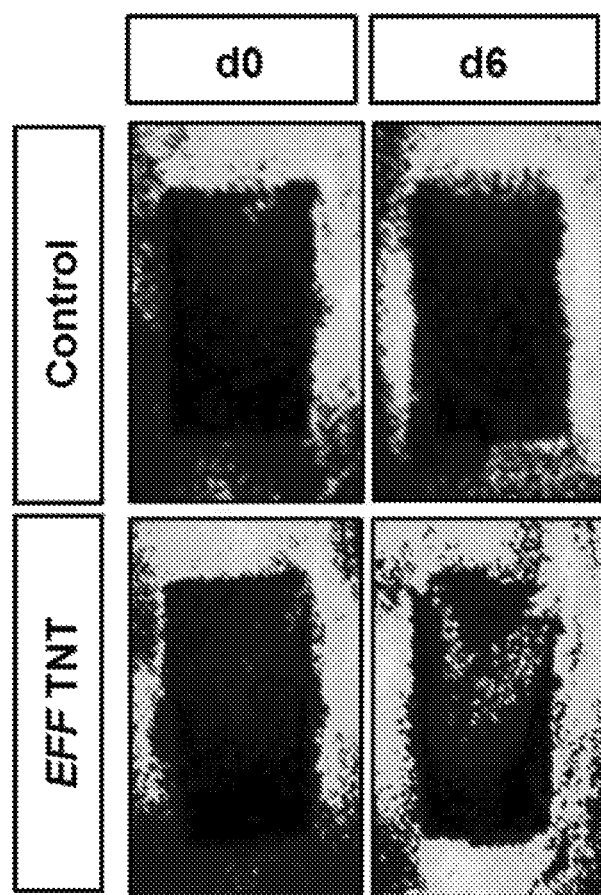
Figure 1I:
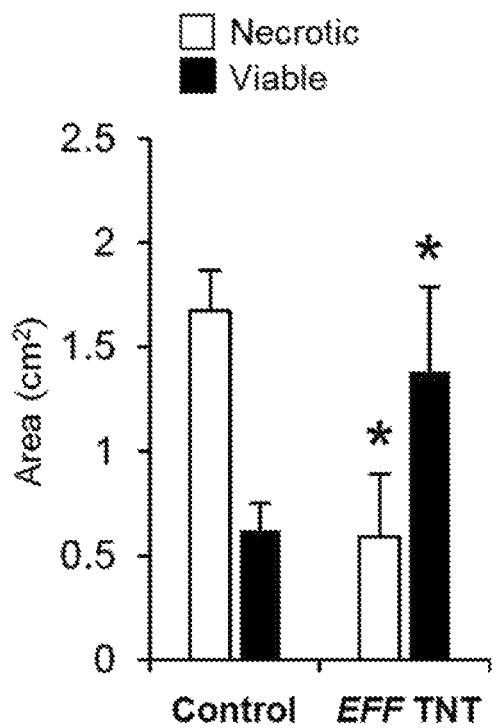
Figure 2A:
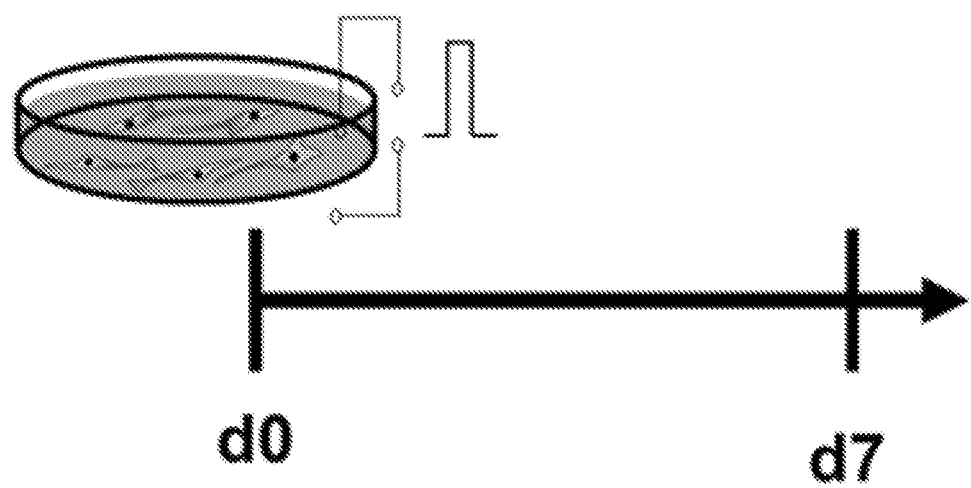
FIGS. 2A to 2I show that the EFF gene cocktail drives faster and more efficient fibroblast reprogramming into induced endothelial cells (iECs).
Figure 2B:
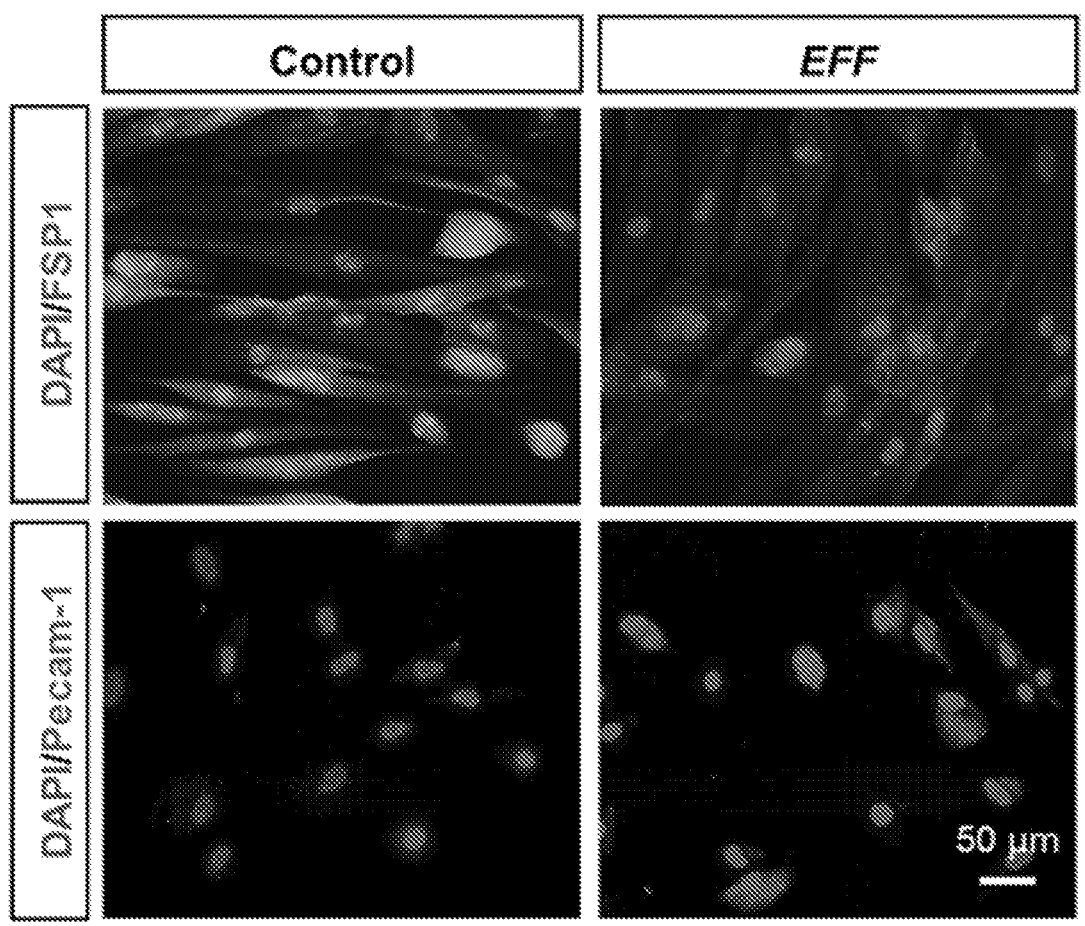
Figure 2C:
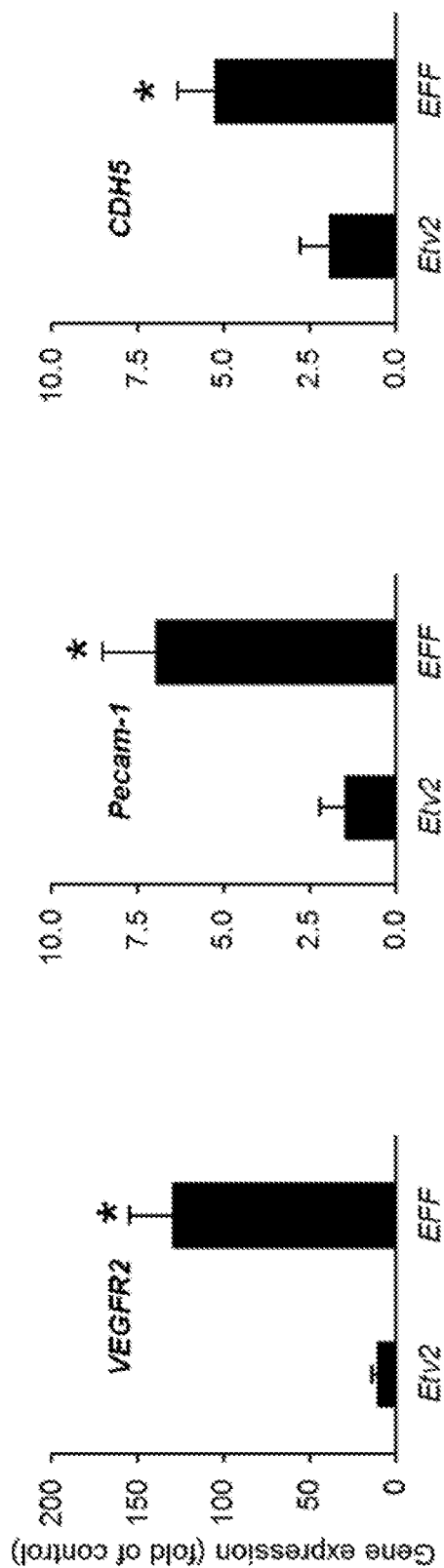
Figure 2D:
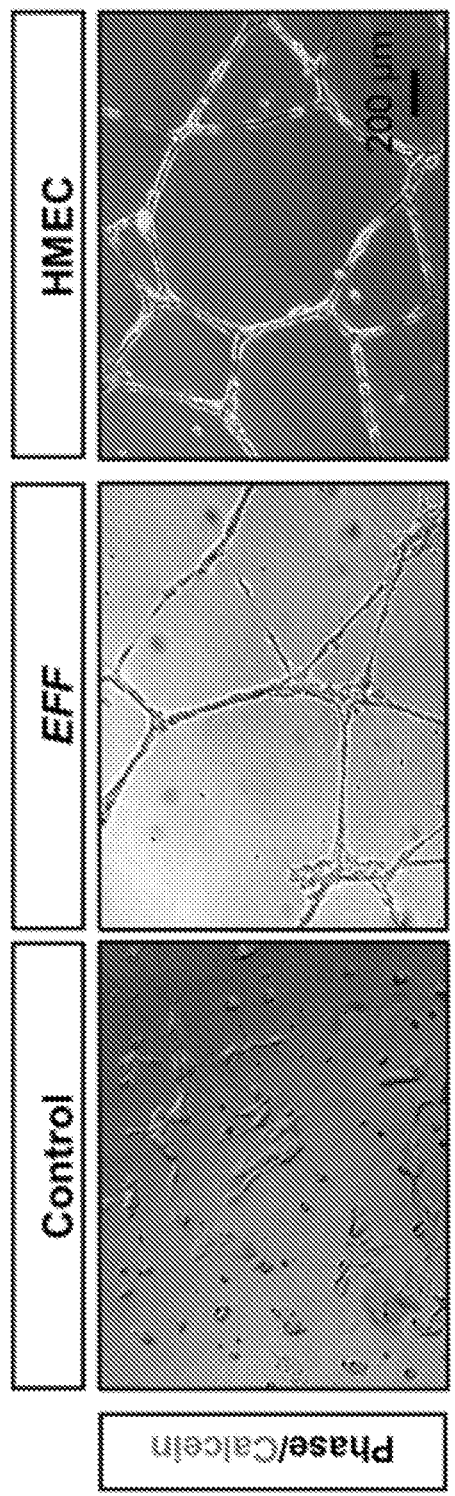
Figure 2E:
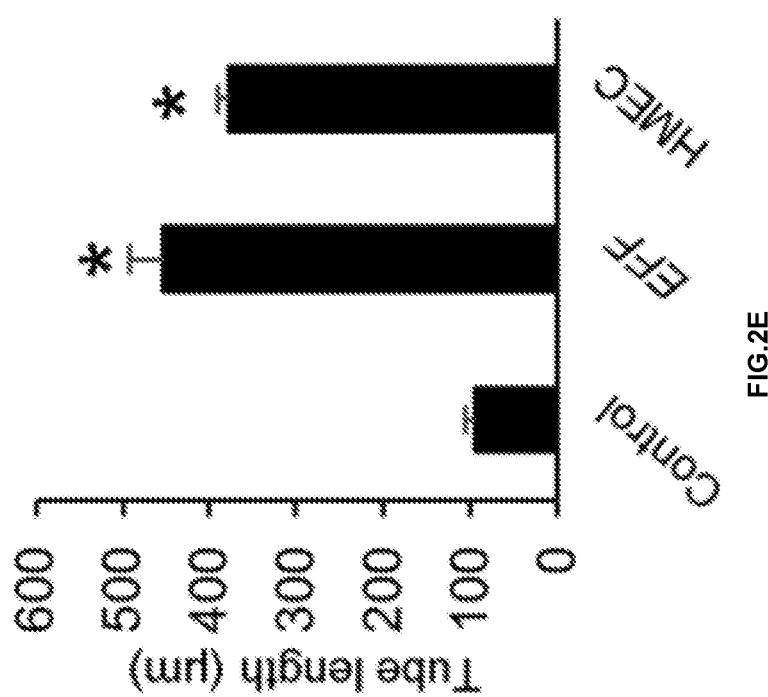
Figure 2F:
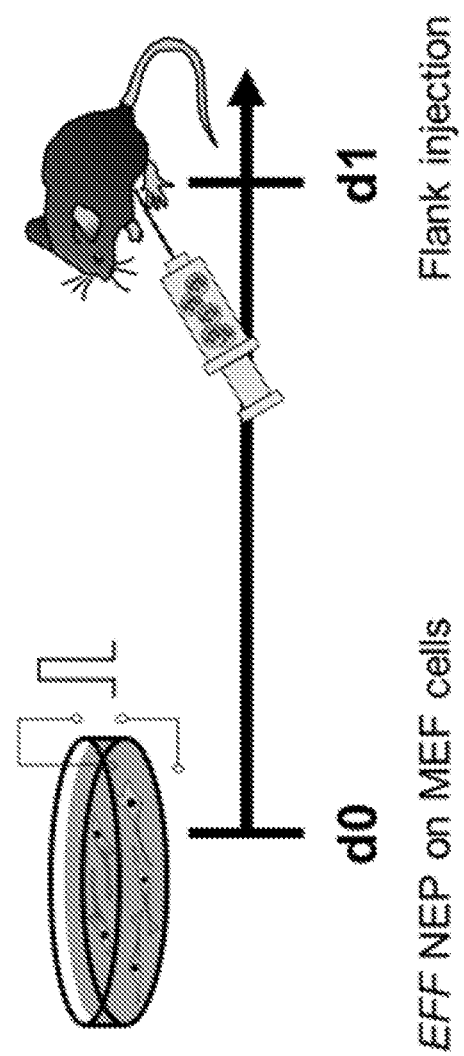
Figure 2G:
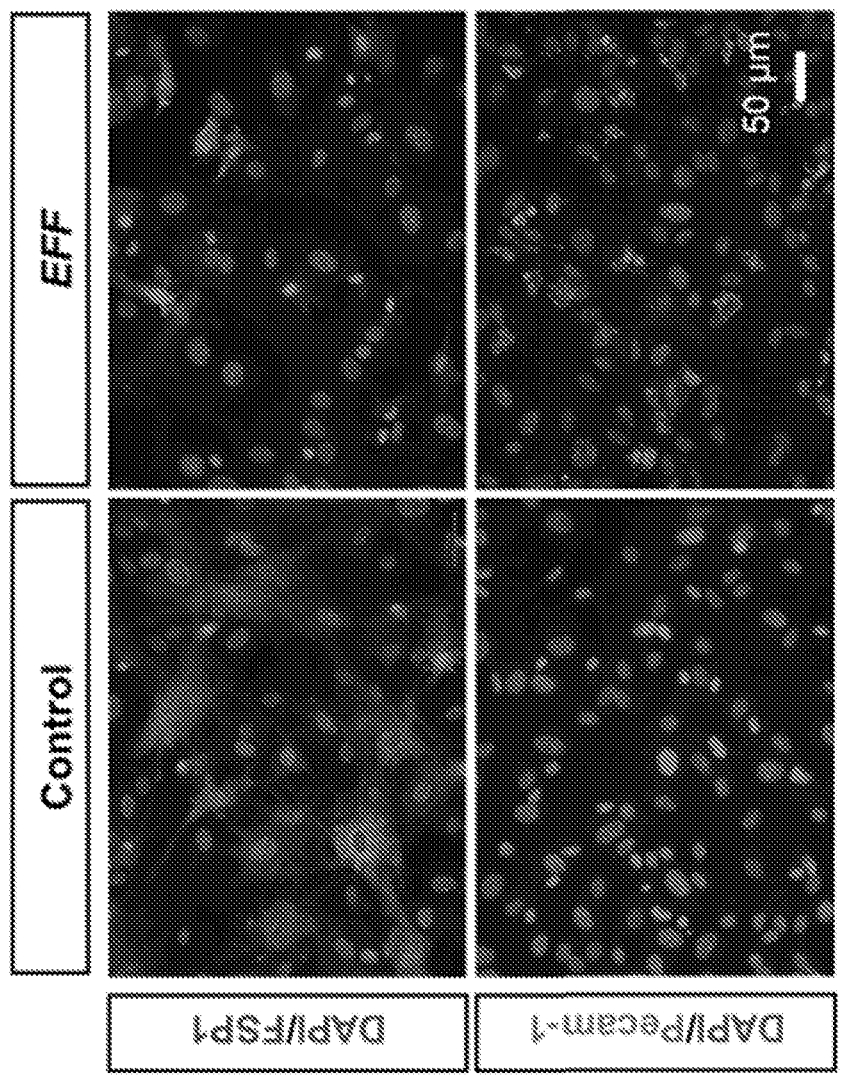
Figure 2H:
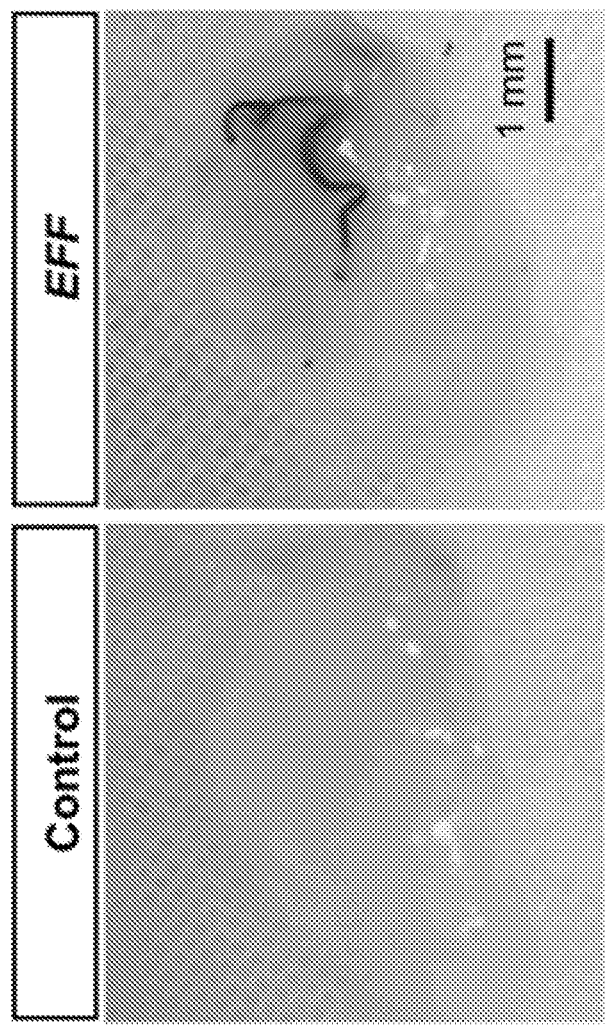
Figure 2I:
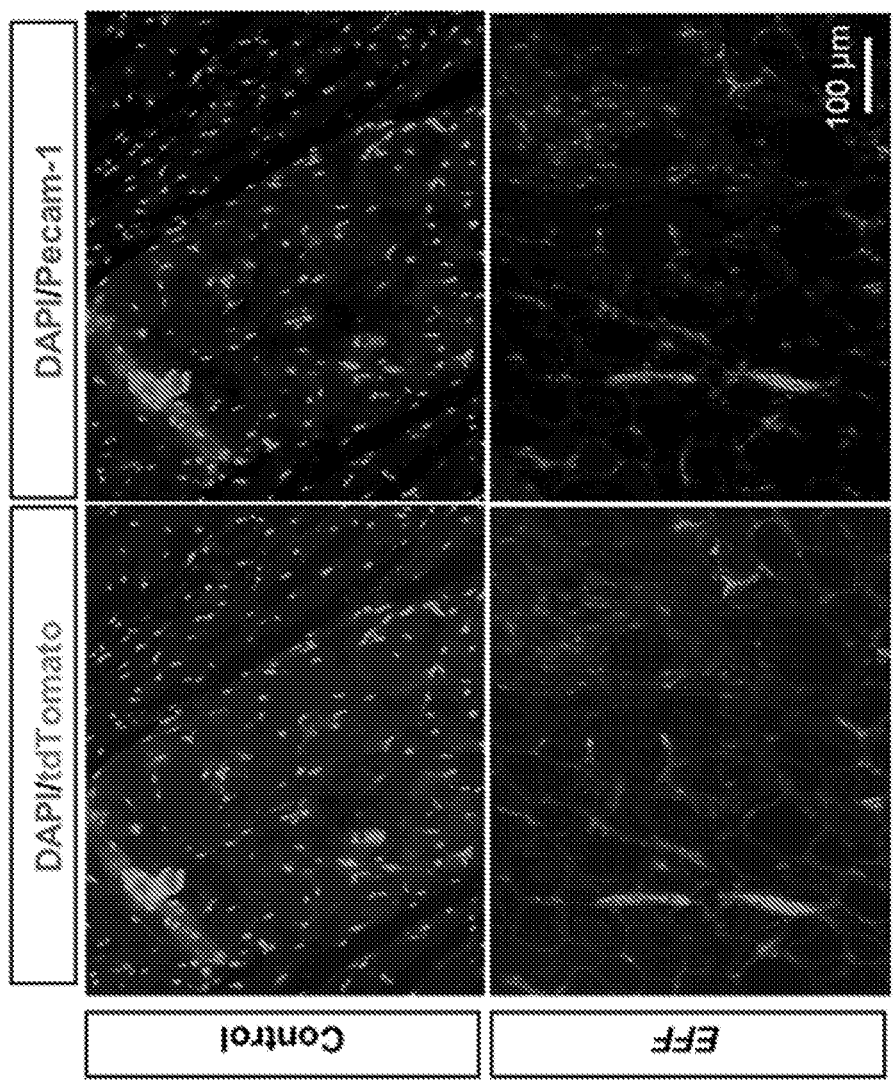
Figure 3A:
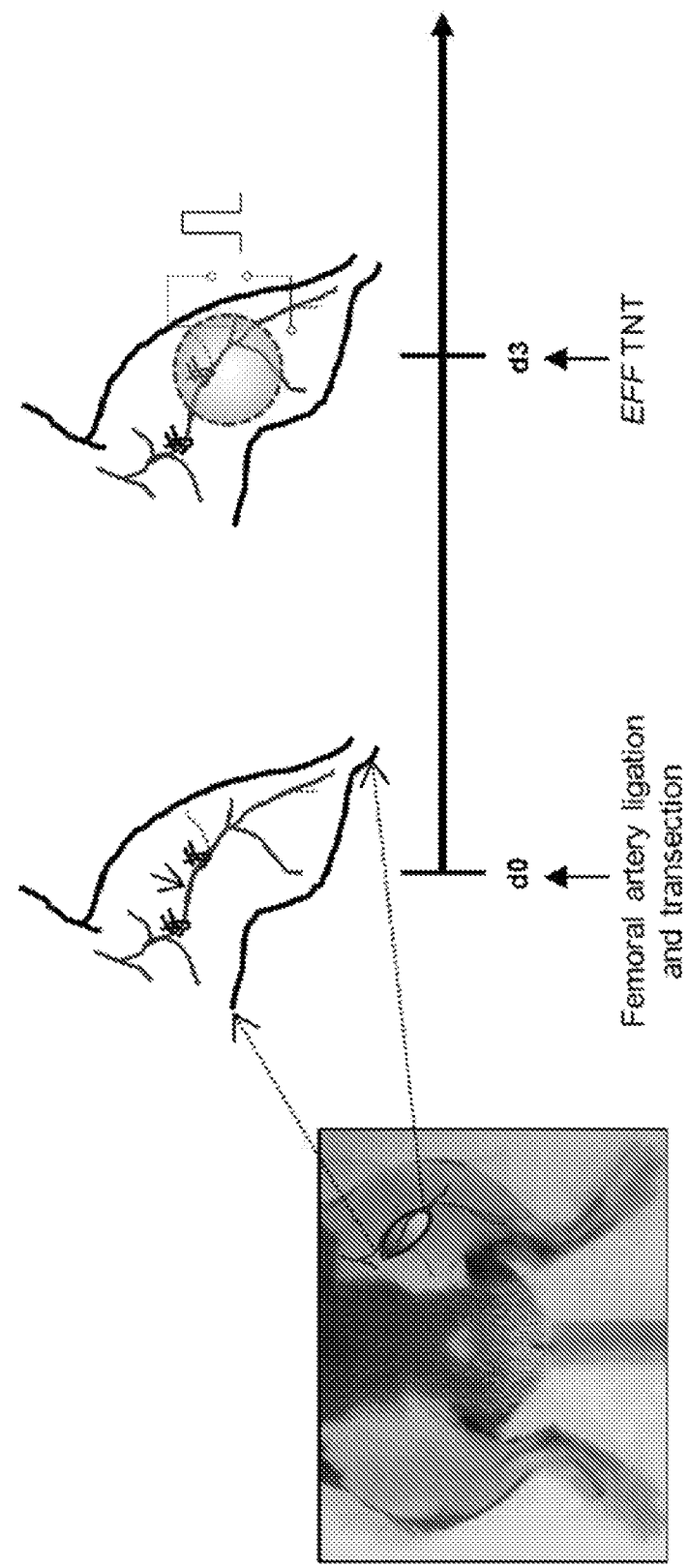
FIGS. 3A to 3F shows that EFF TNT rescues whole limbs from necrotizing ischemia.
Figure 3B:
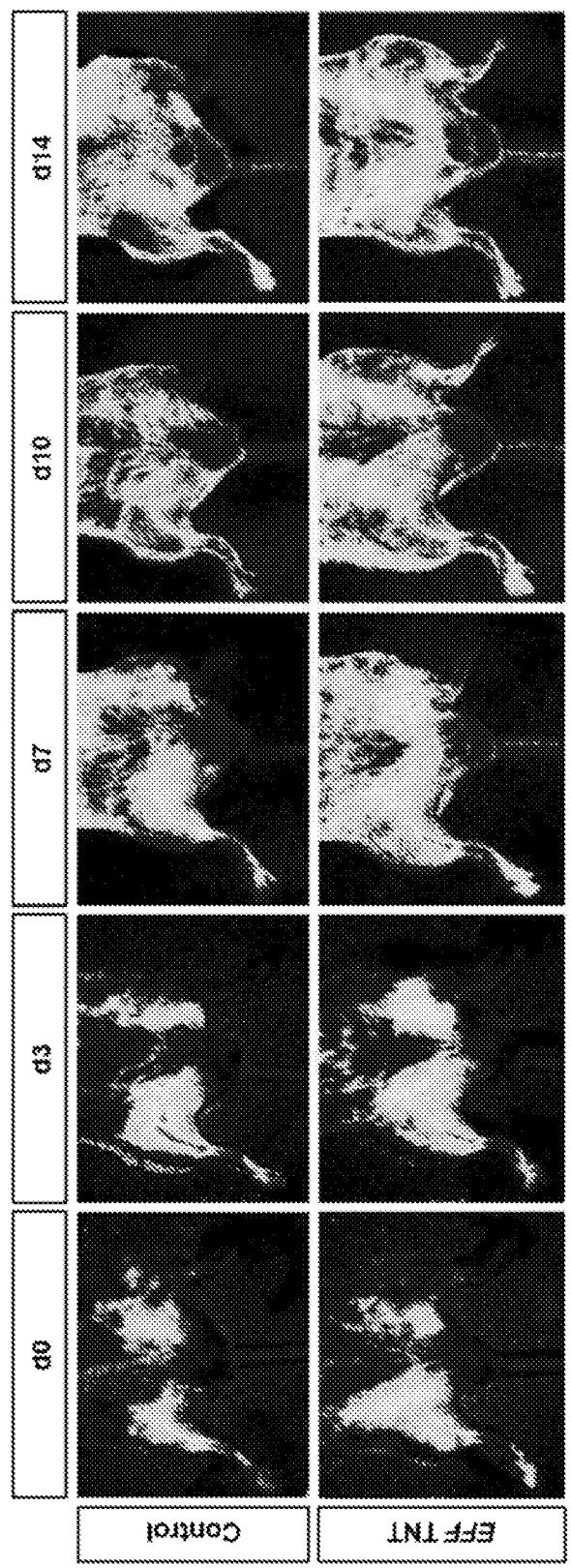
Figure 3C:
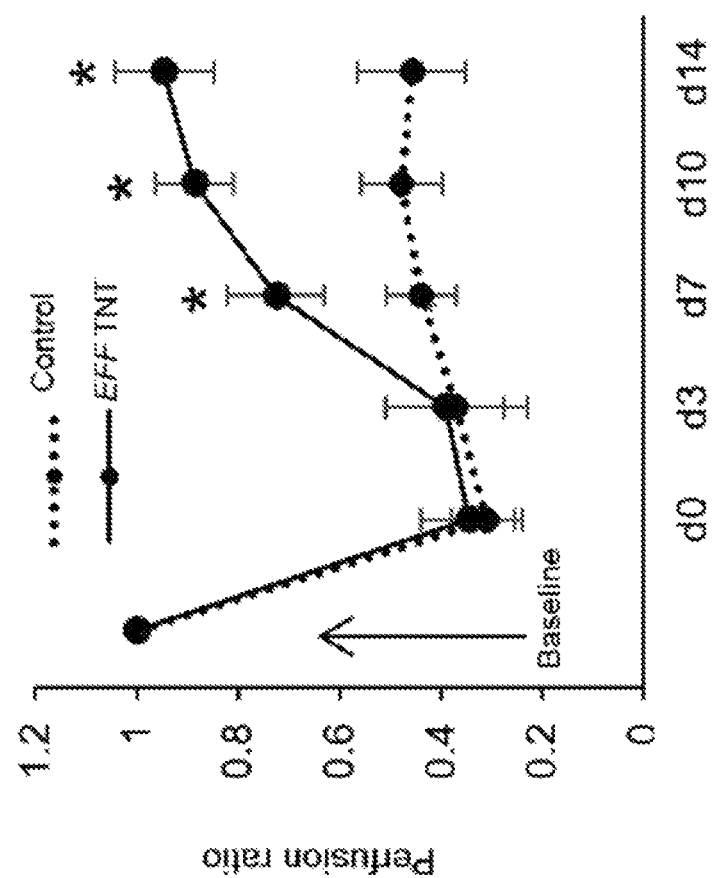
Figure 3D:
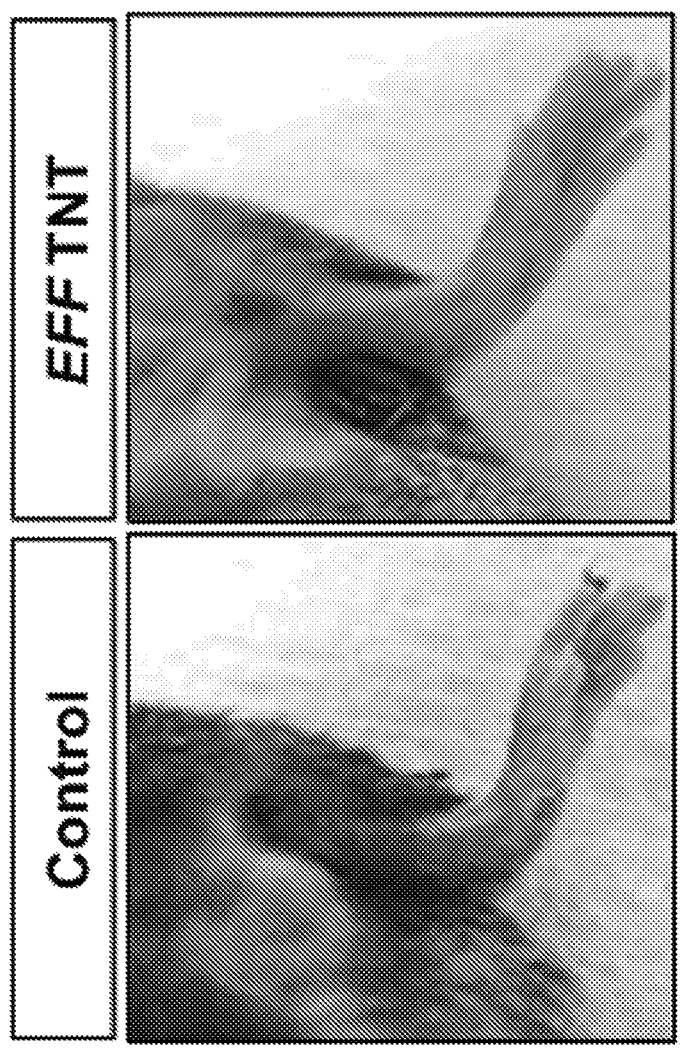
Figure 3E:
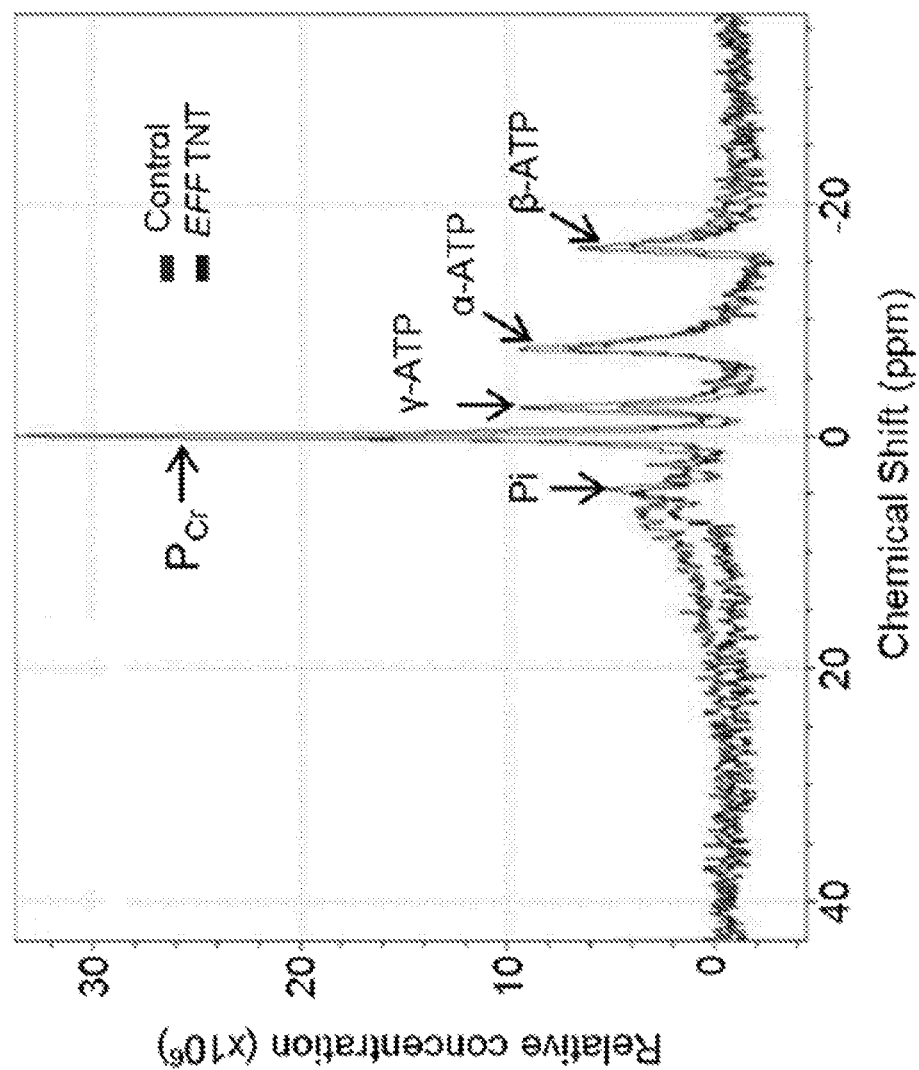
Figure 3F:
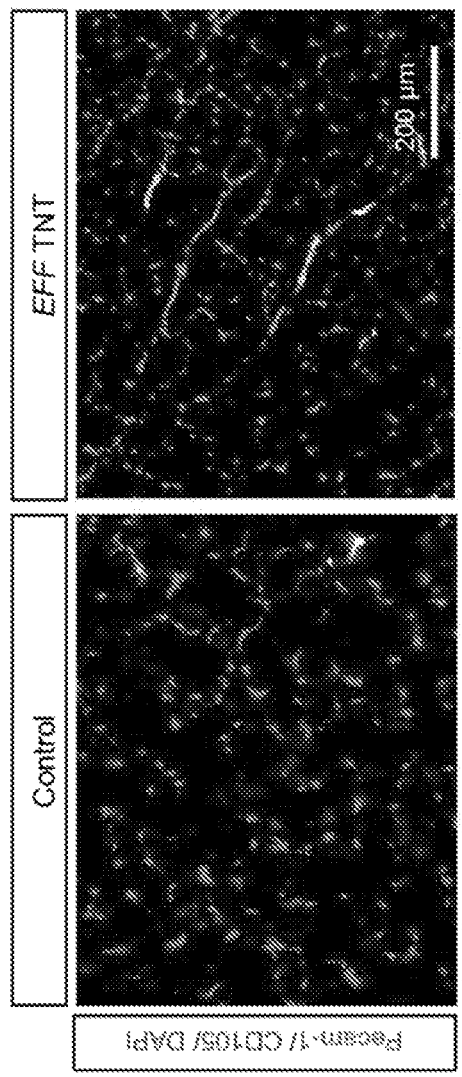
Figure 18G:
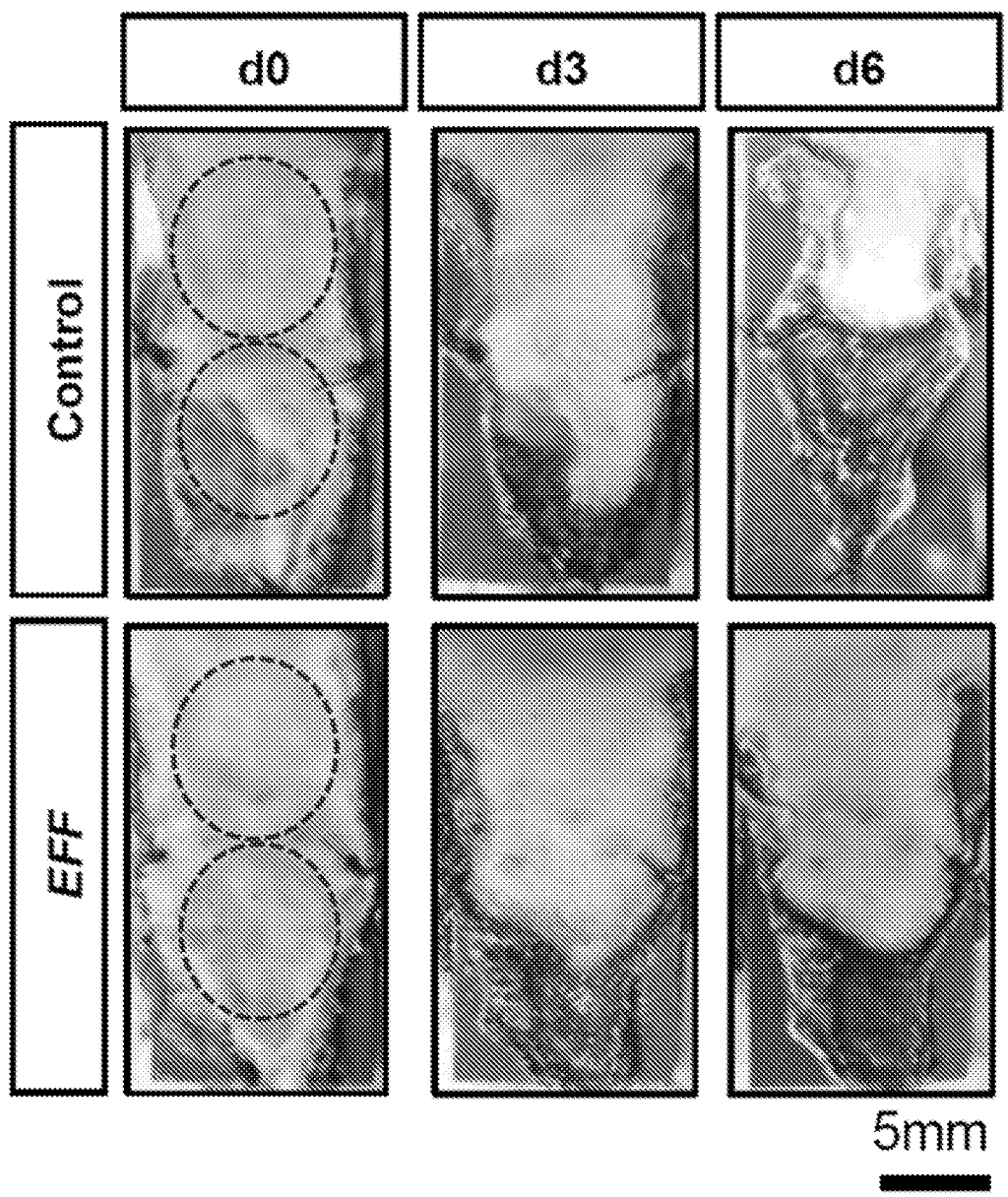
Figure 18H:
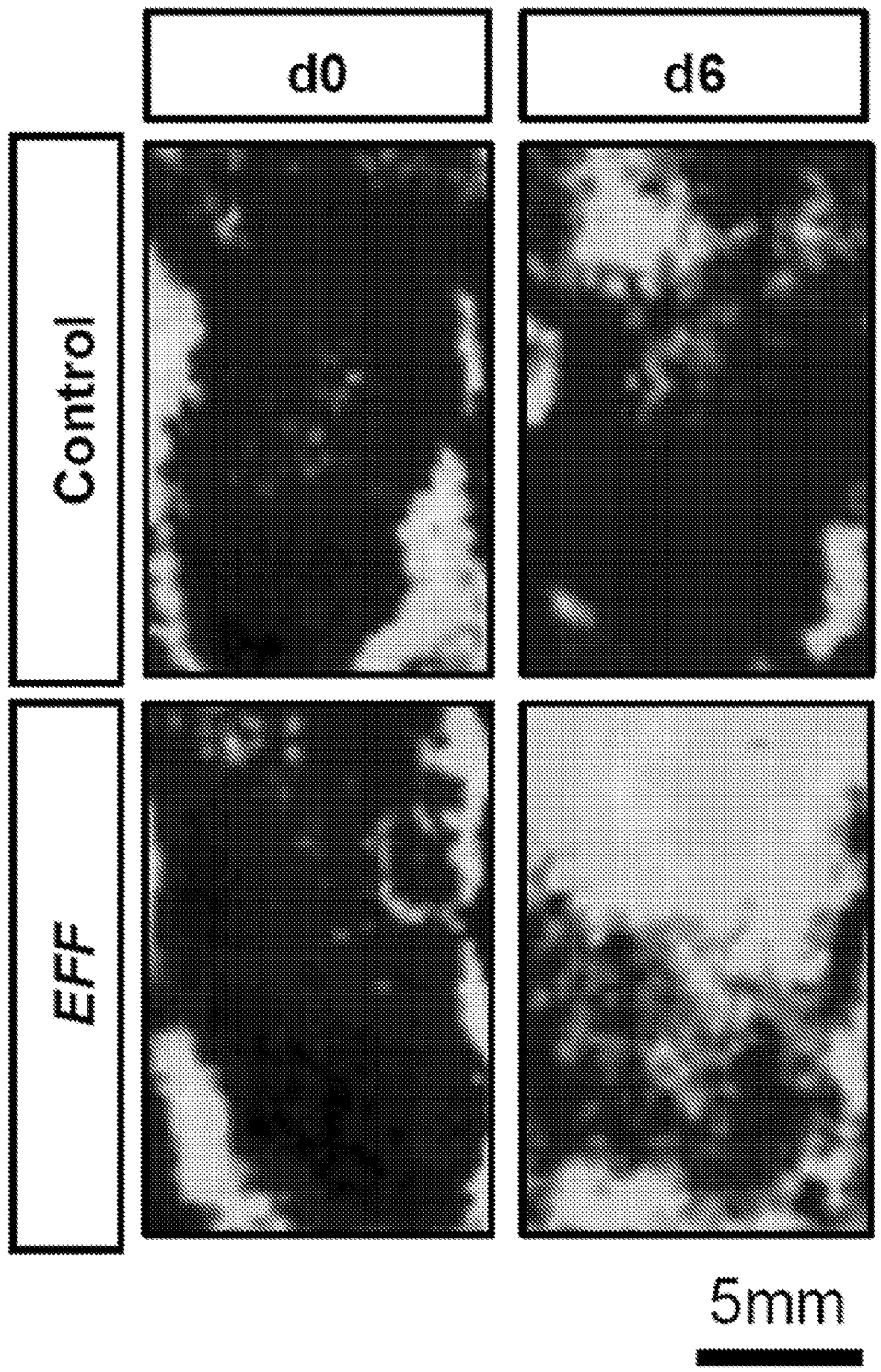
Figure 18I:
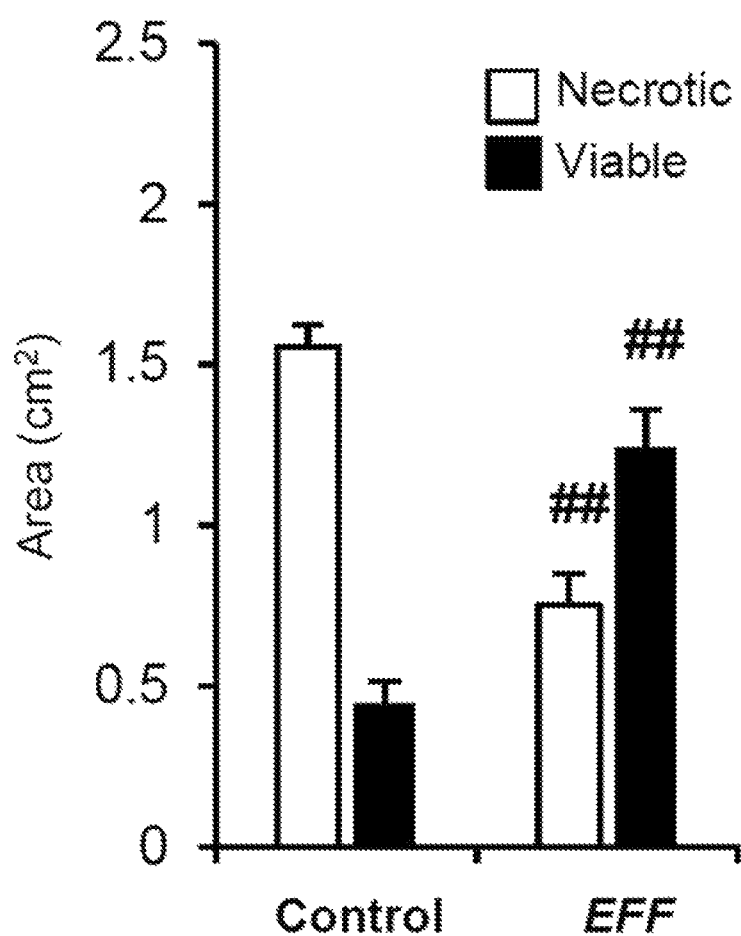

Once the robustness of the EFF cocktail to induce vascular endothelium was demonstrated both in vitro and in vivo, experiments were conducted to study whether EFF TNT-mediated topical skin reprogramming could lead to functional reperfusion of ischemic tissues. This concept was first tested with a full-thickness 2×1 cm2 monopedicle dorsal skin flap in C57BL/6 mice, whereby blood supply to the flapped tissue only came from the cephalad attachment (FIG. 18g). Laser speckle monitoring after EFF treatment showed higher blood perfusion compared to control flaps (FIG. 2h). As expected, control flaps showed significant signs of tissue necrosis (FIG. 18g—top, i). Such tissue damage was significantly limited in response to EFF transfection. Thus, TNT-mediated EFF delivery and subsequent stroma reprogramming effectively counteracted tissue necrosis under ischemic conditions.

Figure 19A:
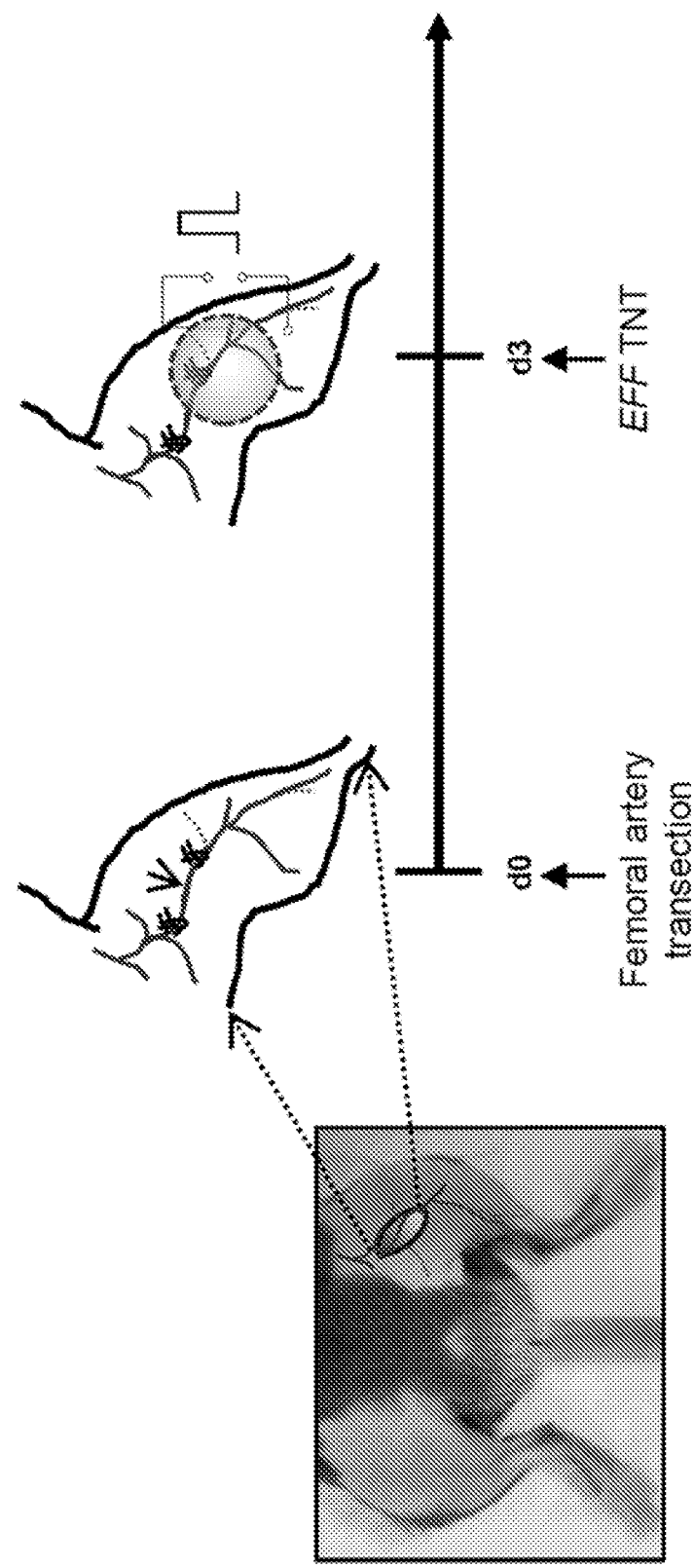
FIG. 19. EFF TNT rescues whole limbs from necrotizing ischemia. (a-c) A one-time treatment of thigh skin lasting only a few seconds led to increased limb reperfusion following transection of the femoral artery. Perfusion was calculated based on the ratio of the ischemic vs. normal/contralateral limb (n=5-7). (d) Control limbs showing more pronounced signs of tissue necrosis compared to EFF-treated limbs (day 14). (e) NMR-based measurements of muscle energetics confirmed increased ATP and PCr levels for EFF-treated limbs compared to controls. (f) Immunofluorescence analysis of the gastrocnemius muscle showing enhanced angiogenesis. ##p<0.05 (Holm-Sidak method).
Figure 19B:
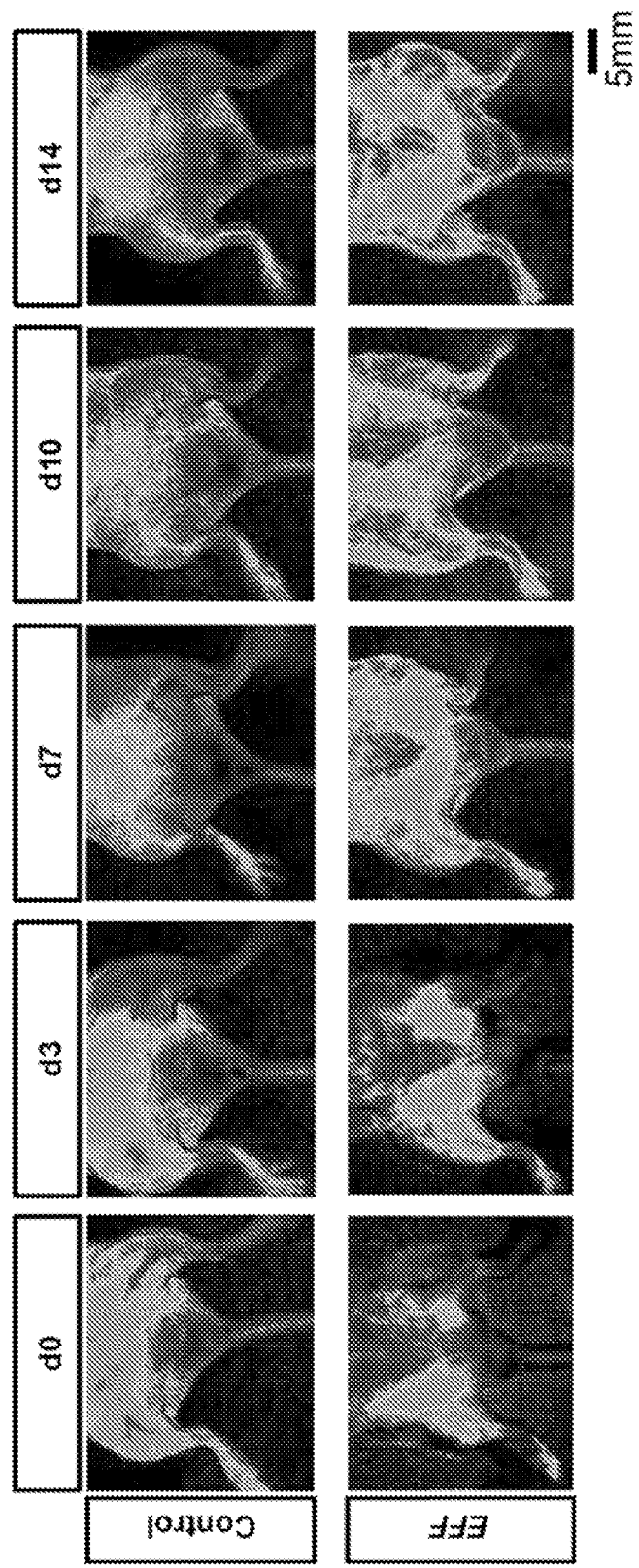
Figure 19C:
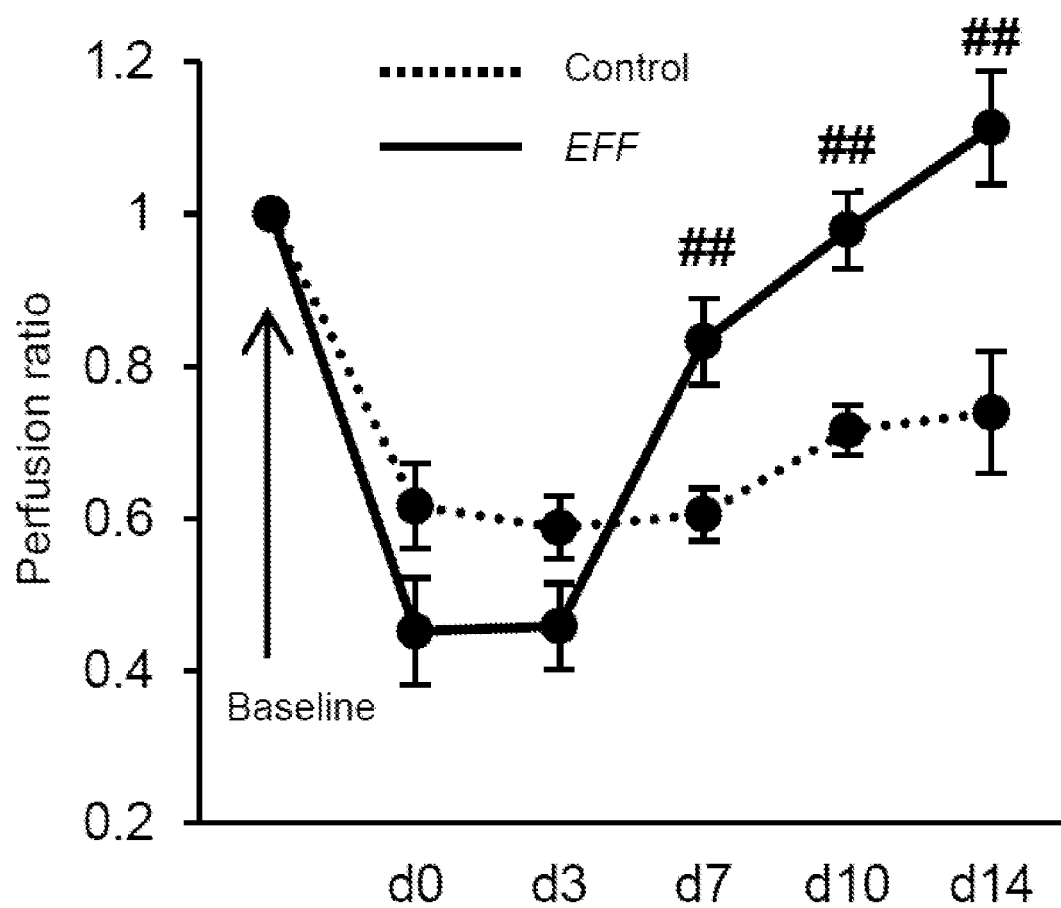
Figure 19D:
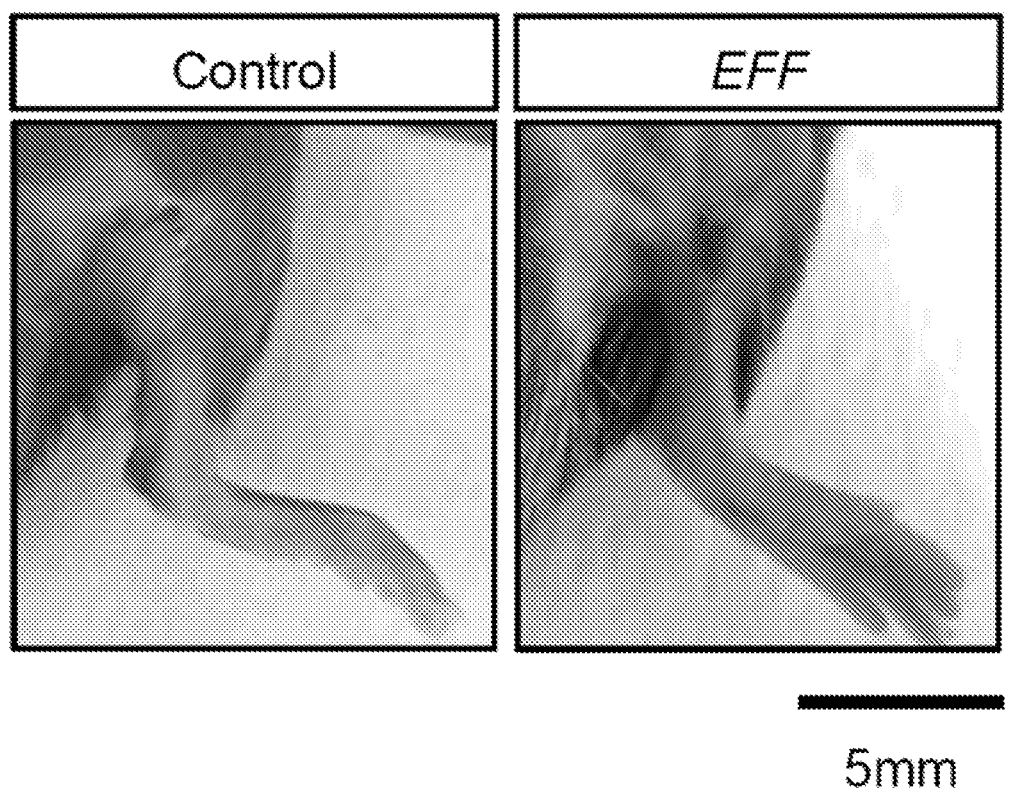
Figure 19E:
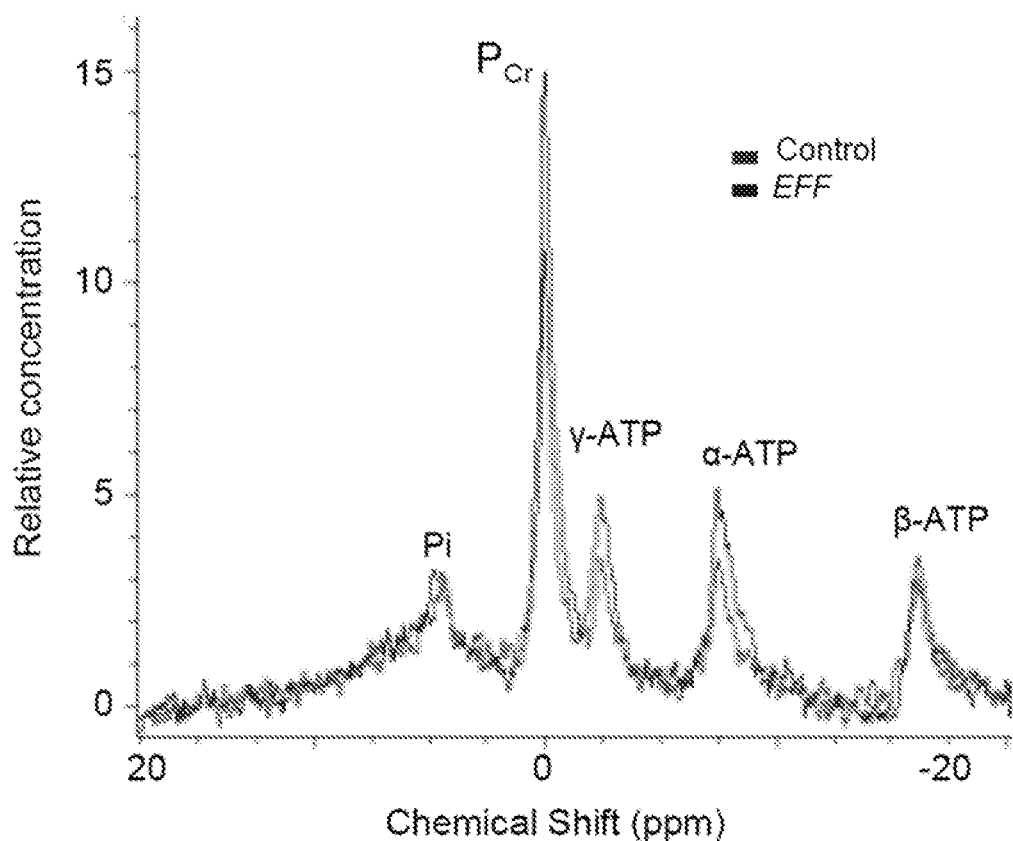
Figure 19F:
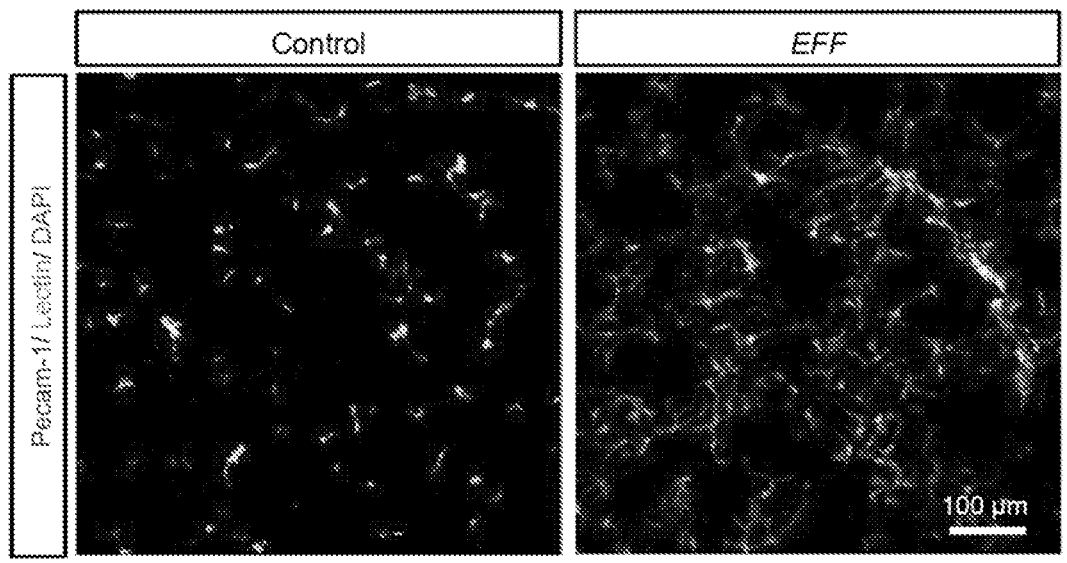
Figures 20A, 20B, 20C, 20D, 20E:
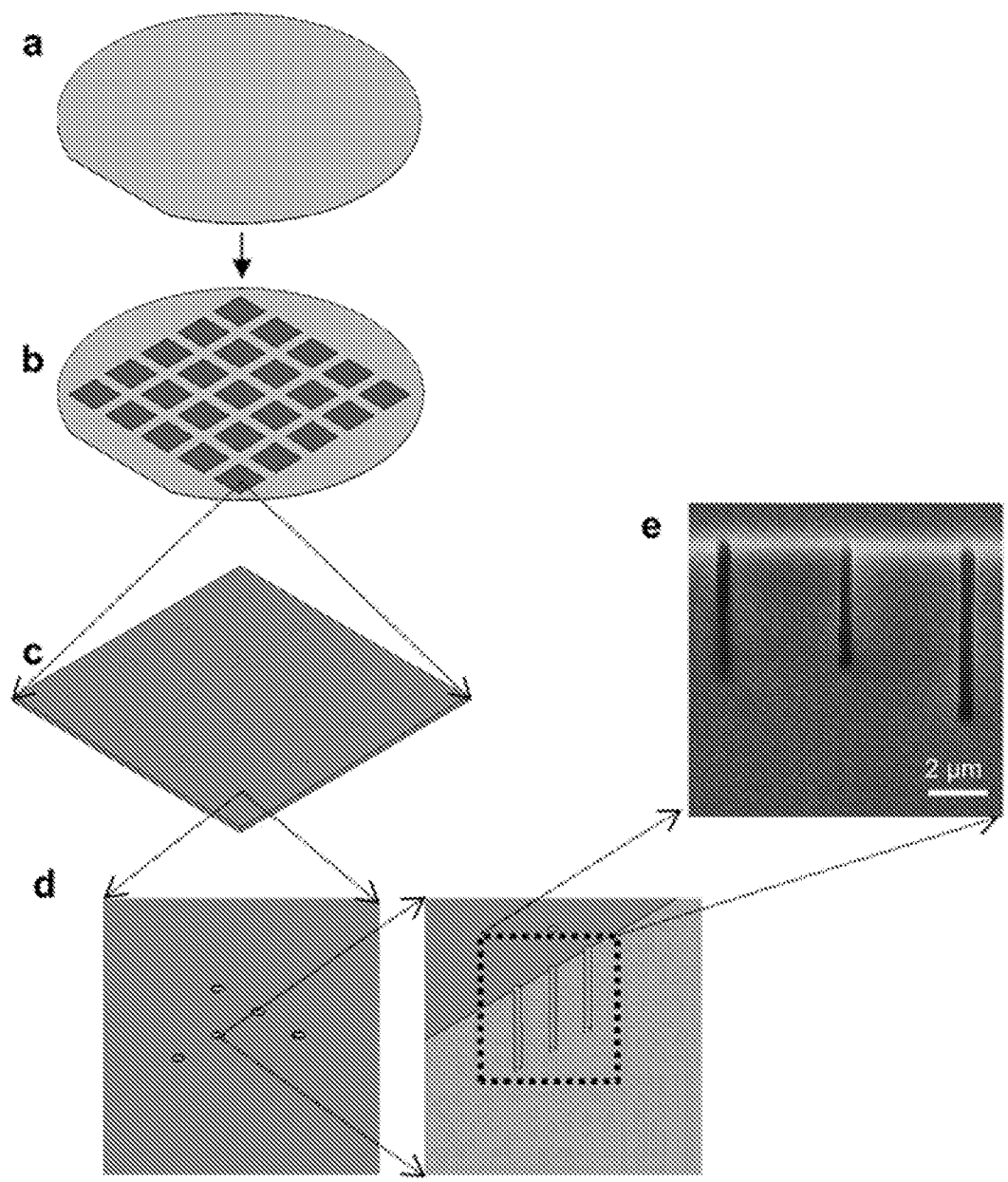
FIG. 20. TNT platform fabrication and nanochannel array simulation. (a) Double side polished silicon wafer. (b-d) Nanochannel patterning and DRIE. (e) Scanning electron microscopy (SEM) image of the etched nanochannels. (f) Back-side etching of microreservoirs. (g) SEM micrographs and (h, i) plots showing etching profiles and etch rates, respectively, under different conditions. (j, k) Simulation results showing field distribution (j1, k1) and heat dissipation profiles (j, k 2-3) for asymmetric (i.e., T-shape) nanochannel arrays vs. symmetric (i.e., cross-shaped) arrays. Bulk electroporation (BEP) is the current gold standard for non-viral gene delivery in vivo. Gene uptake in BEP, however, is a highly stochastic process, which is not only influenced by non-uniform electric fields, but also downstream and/or more passive processes such as endocytosis and diffusion, respectively 1-3. As such, simple approaches that facilitate more active and deterministic gene delivery in vivo are clearly needed. Here cleanroom-based technologies (i.e., projection lithography, contact photolithography, and deep reactive ion etching—DRIE—) were implemented (FIG. 20 a-i)) to fabricate silicon-based TNT devices for active non-viral gene delivery to naturally- (e.g., skin) or surgically-accessible (e.g., skeletal muscle) tissue surfaces in a more deterministic manner. The TNT platforms consisted of a massively-parallel array of clustered nanochannels interconnected to microscale reservoirs that could hold the genetic cargo to be transduced into the tissues. Briefly, arrays of ~400-500 nm channels were first defined on the surface of a ~200 μm thick double-side polished silicon wafer using projection lithography and DRIE. Simulation studies suggest that such asymmetric T-shape array provides some inherent advantages in terms of electric field distribution and heat dissipation compared to a more symmetric nanopore distribution, with asymmetric clusters of nanochannels exhibiting less inactive zones (FIG. 20 j1, k1, red stars), while at the same time reducing by 20-25% the peak and valley temperatures (FIG. 20 j2-3, k2-3). This was then followed by contact lithography-based patterning and DRIE-mediated drilling of an array of microreservoirs juxtaposing the nanochannels. Finally, the platform surface was passivated with a thin insulating layer of silicon nitride.
Figure 20F:
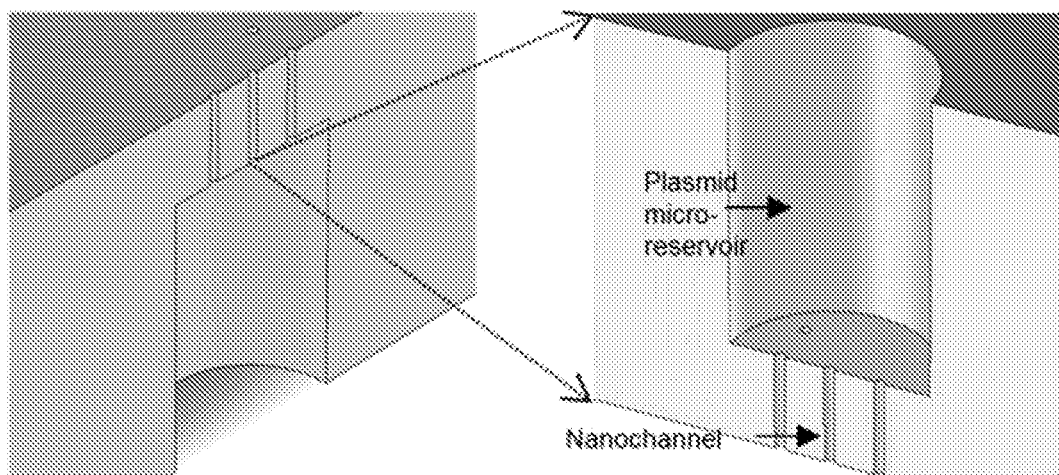
Figure 20G:
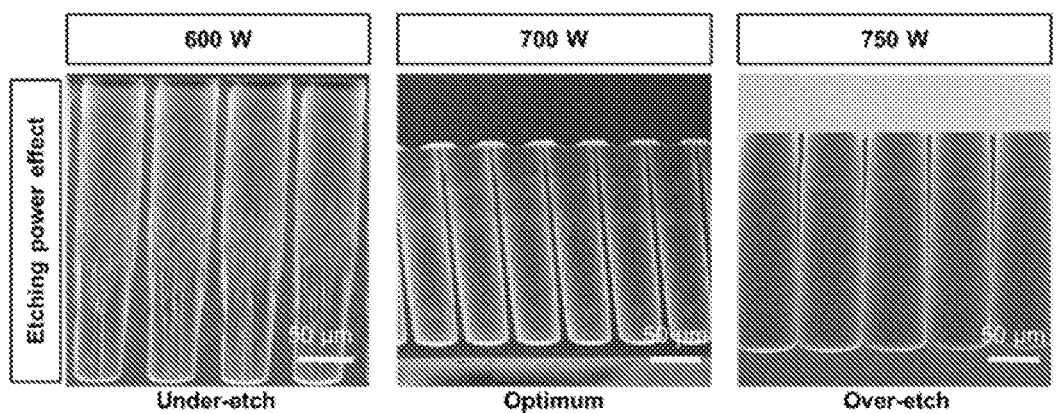
Figure 20H:
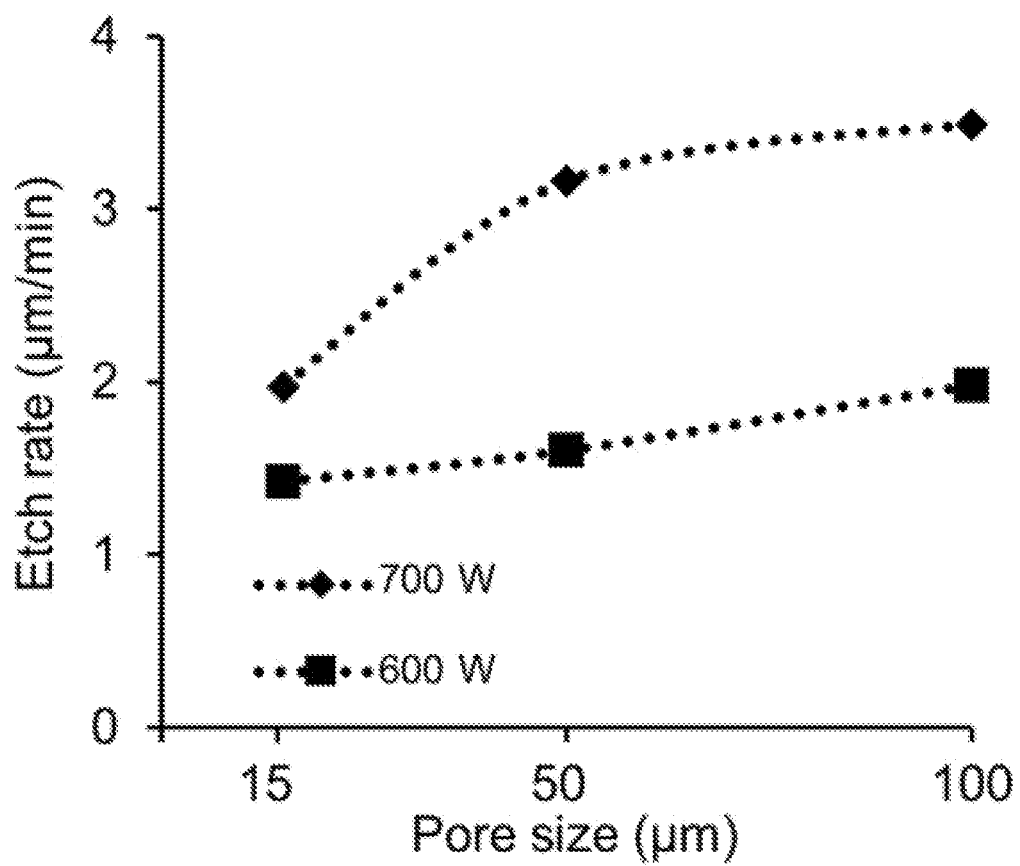
Figure 20I:
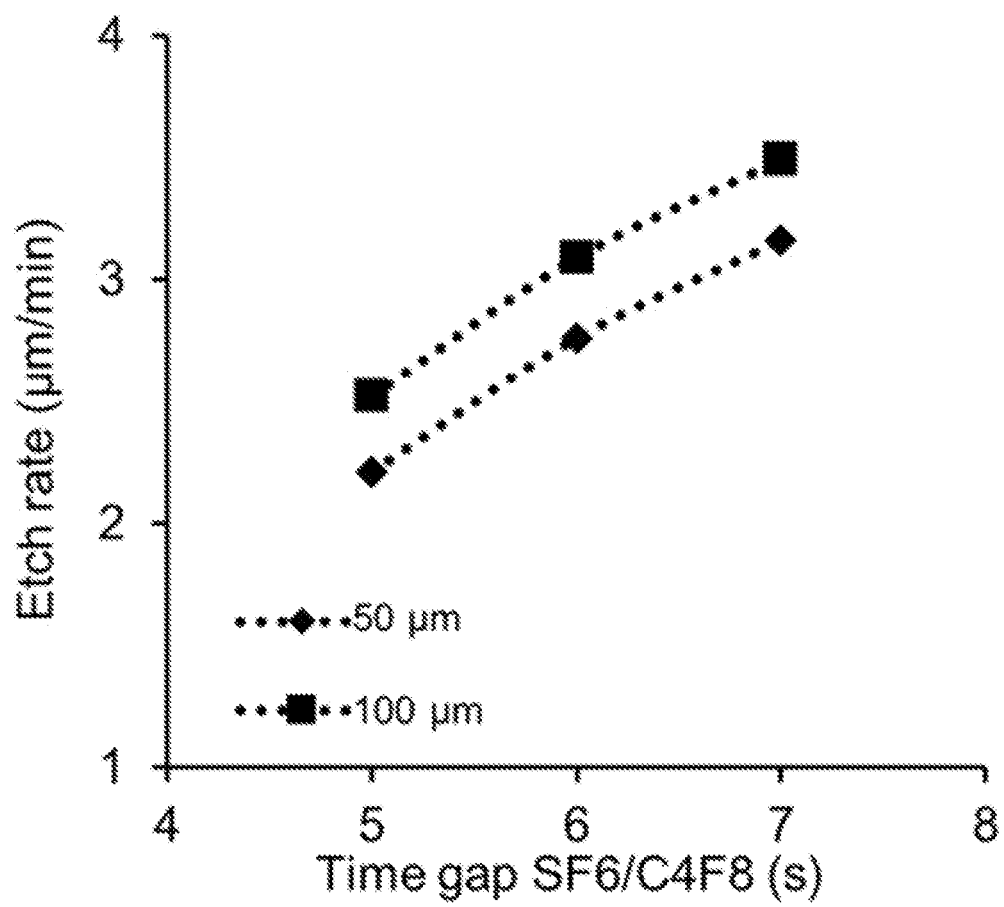
Figure 21A:
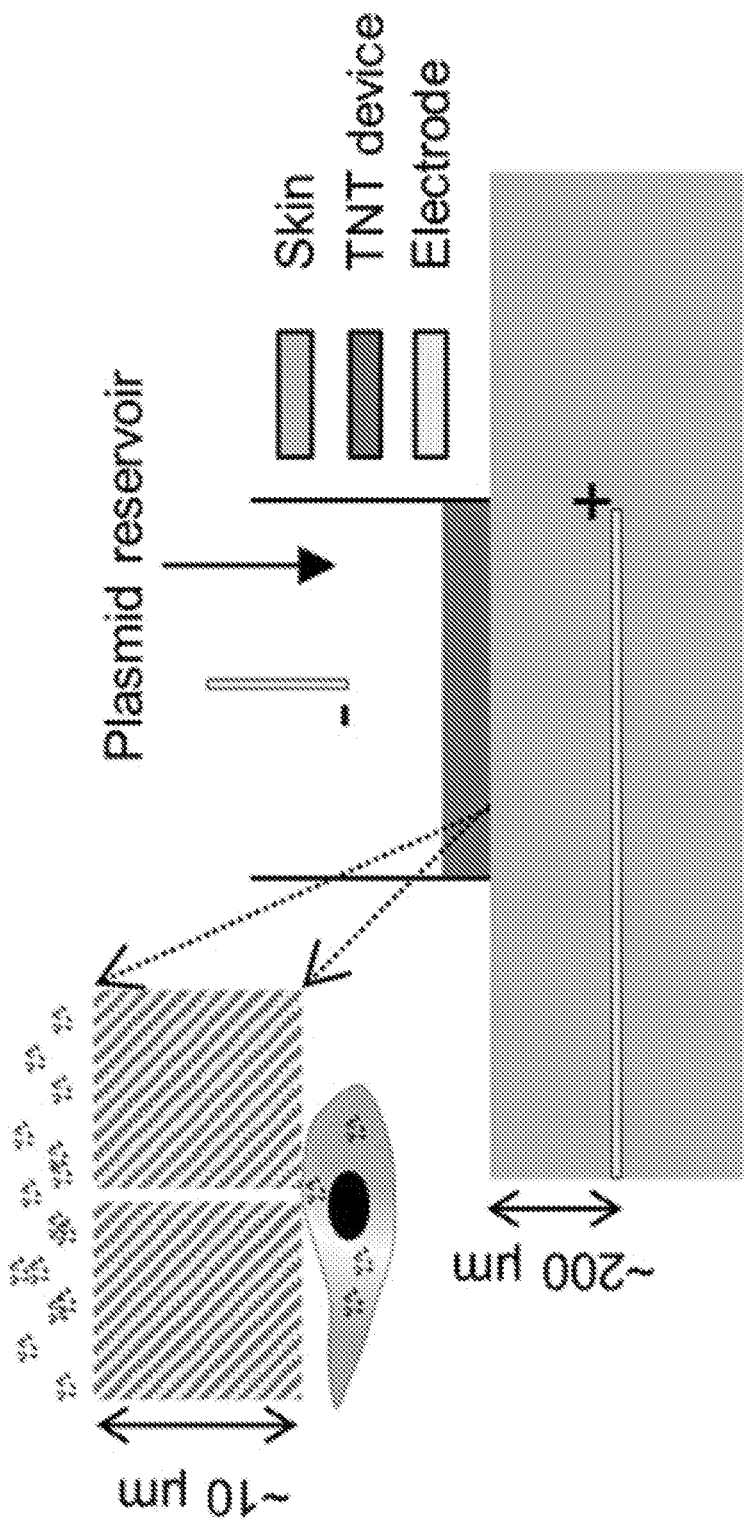
FIG. 21. Simulation results of in vivo nanochannel-based electroporation vs. bulk electroporation (BEP). (a) Schematic diagram illustrating the experimental set-up. (b, c) Simulated voltage distribution under a 250 V stimulation. (d-f) Simulation of transmembrane potential for single-cell bulk electroporation. (g) Poration profile for a cell in direct contact with the nanochannel (cell 1) compared to cells far away from the nanochannels (cell 2 and cell 3). (h) Poration profiles in TNT vs. BEP.
Figure 21C:
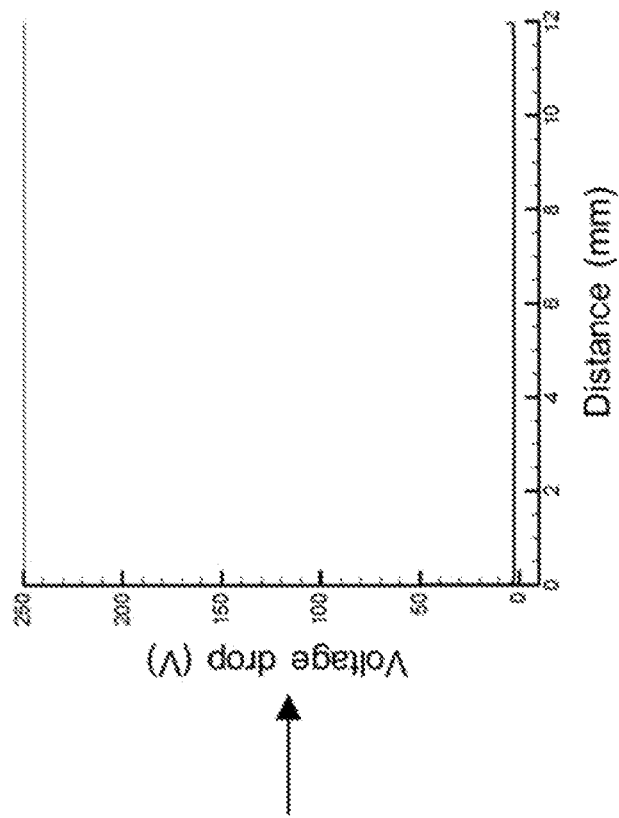
Figure 21B:
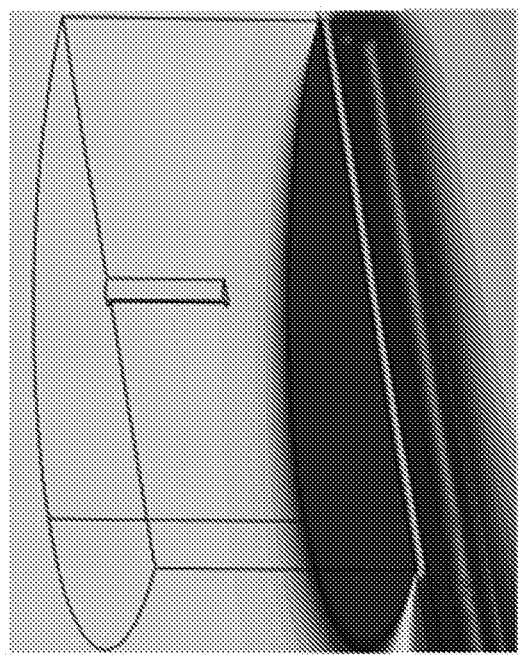
Figure 21E:
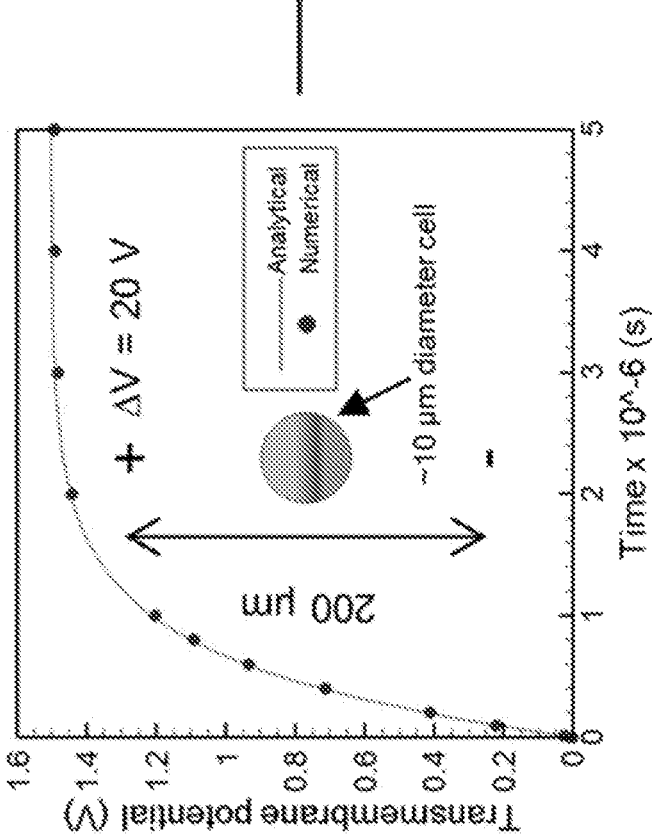
Figure 21D:
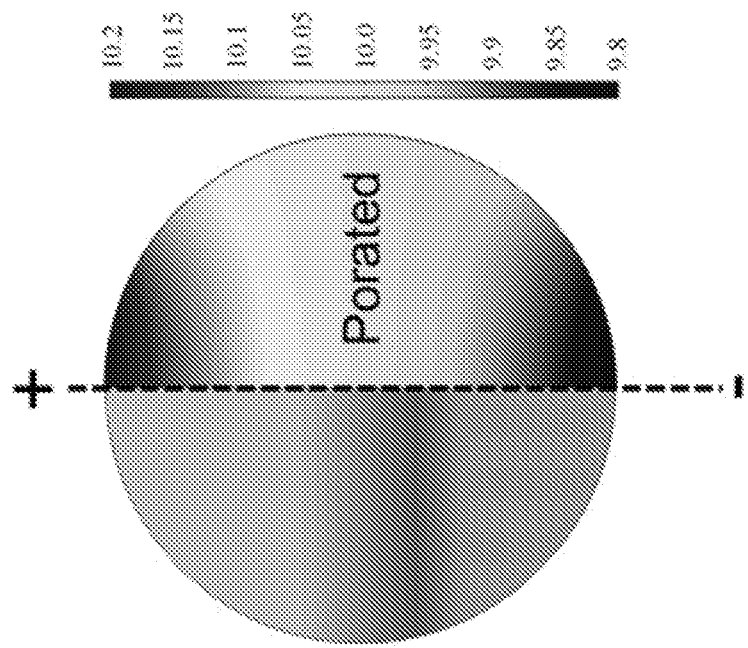
Figure 21F:
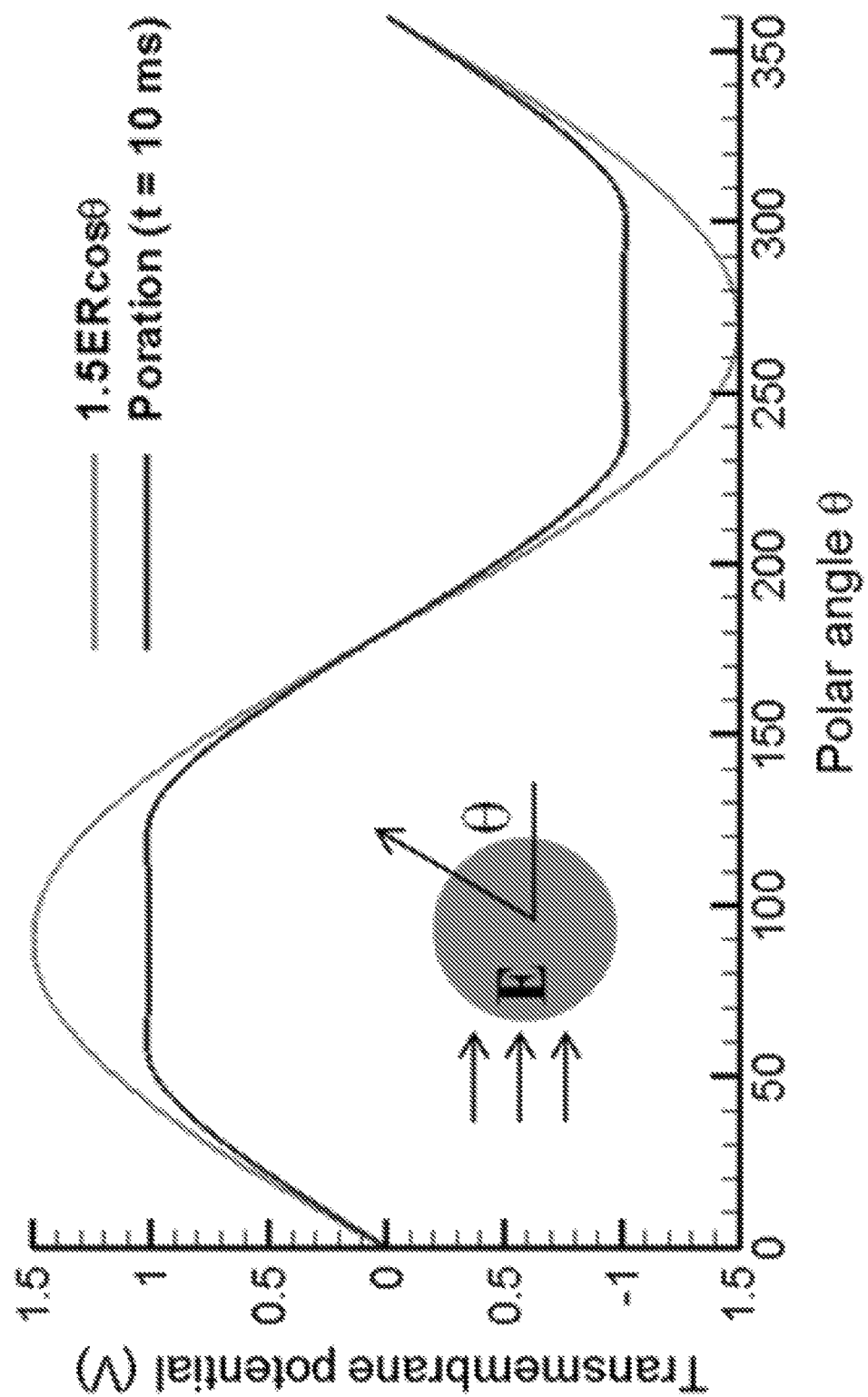
Figure 21G:
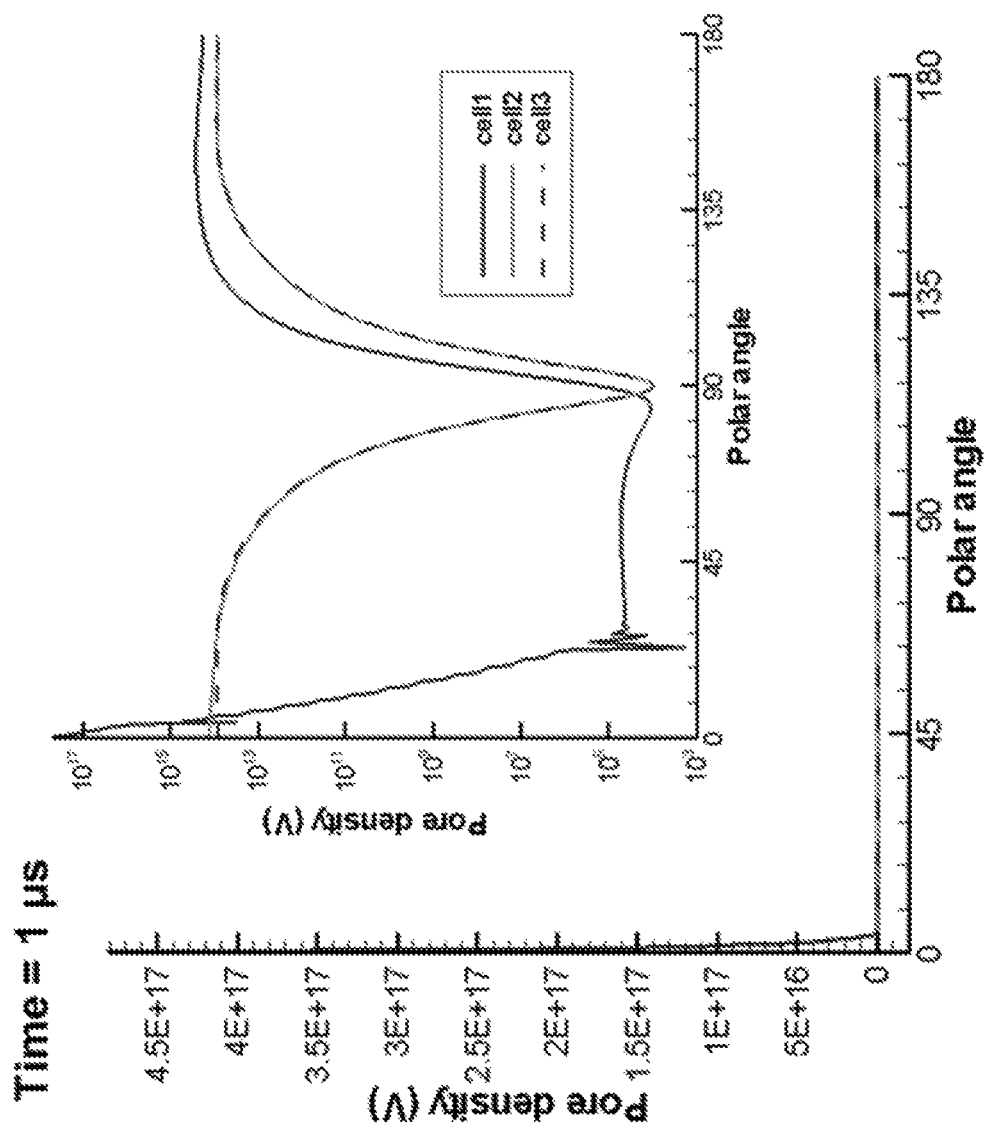
Figure 21H:
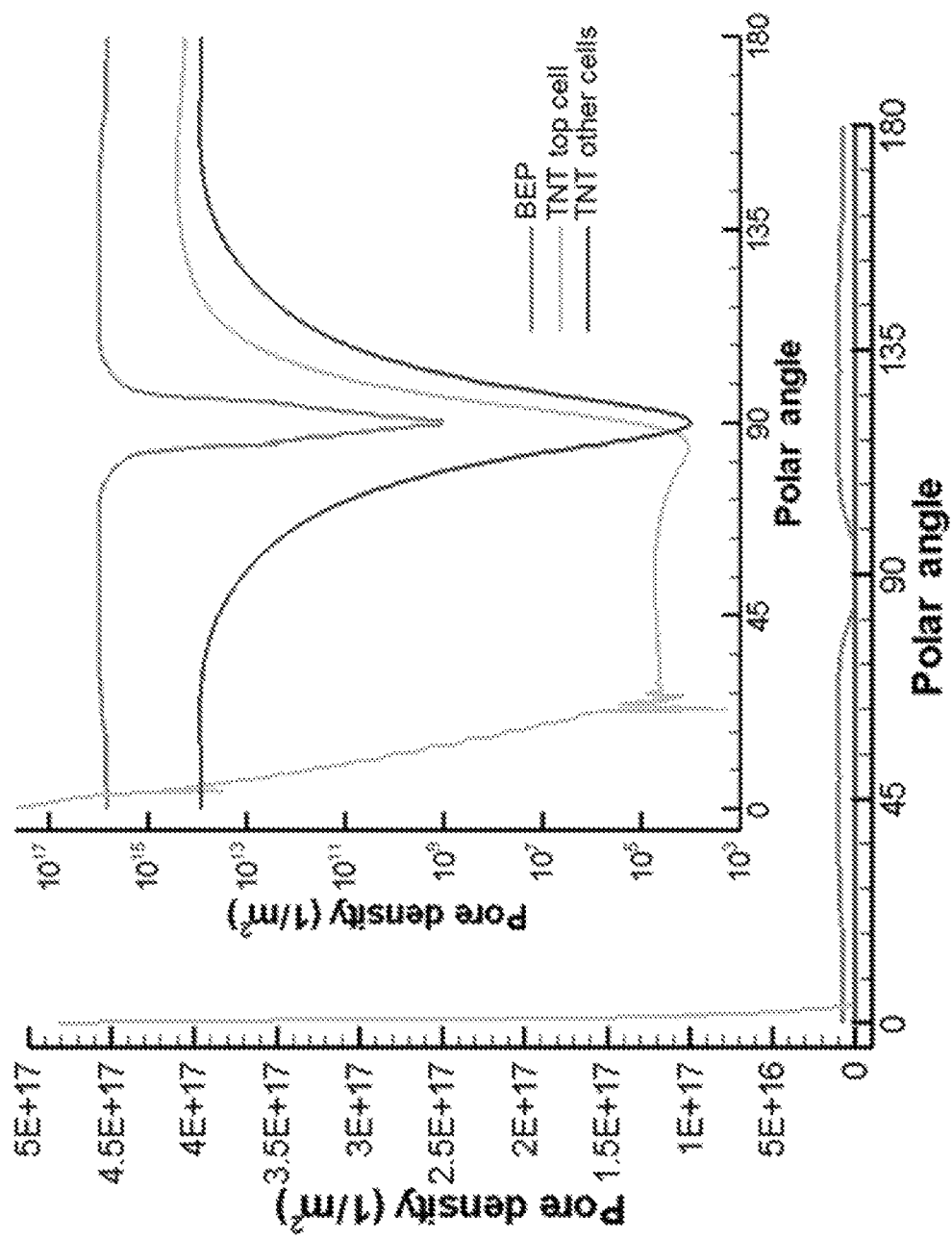
Figure 22A:
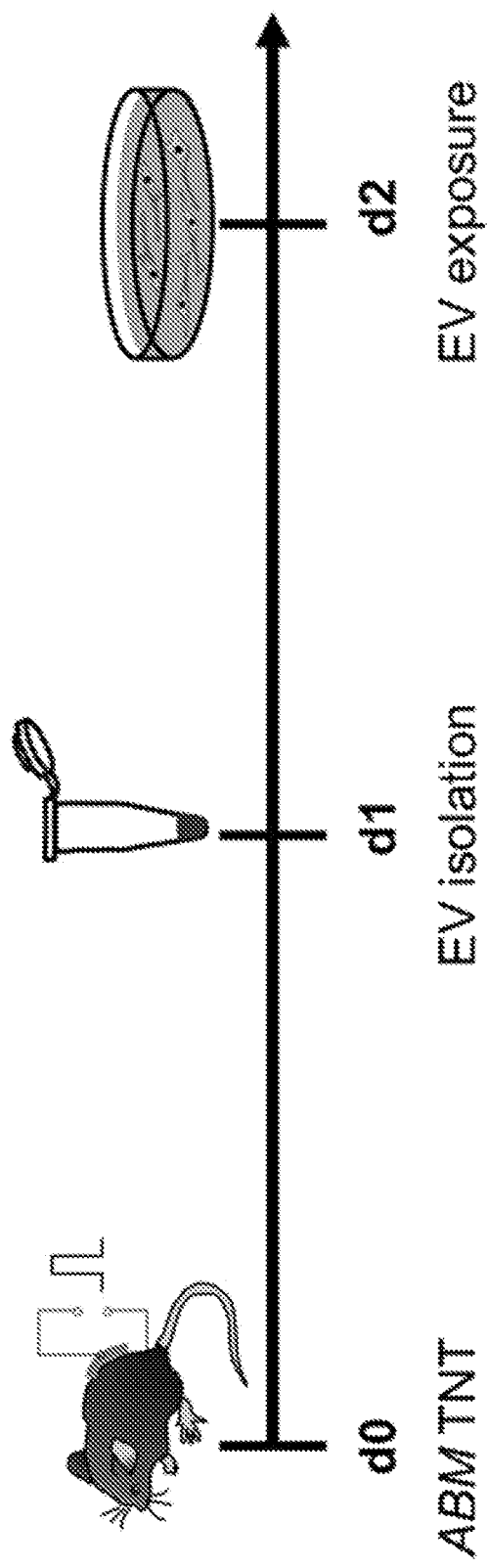
FIG. 22. EV-mediated cellular reprogramming. (a) Schematic diagram illustrating the experimental set-up. EVs are collected from ABM TNT-treated dorsal skin. (b) The ABM copy numbers from the EVs were quantified following a standard procedure, and compared to the gene copy numbers delivered directly through TNT (from skin tissue collected immediately after transfection). Briefly, absolute qPCR quantification was used to assess the copy number of target genes within treated samples by relating the CT value to a standard curve. The standard curve was generated by utilizing a 10-fold-serial dilution series of each gene/plasmid.
Figure 22B:
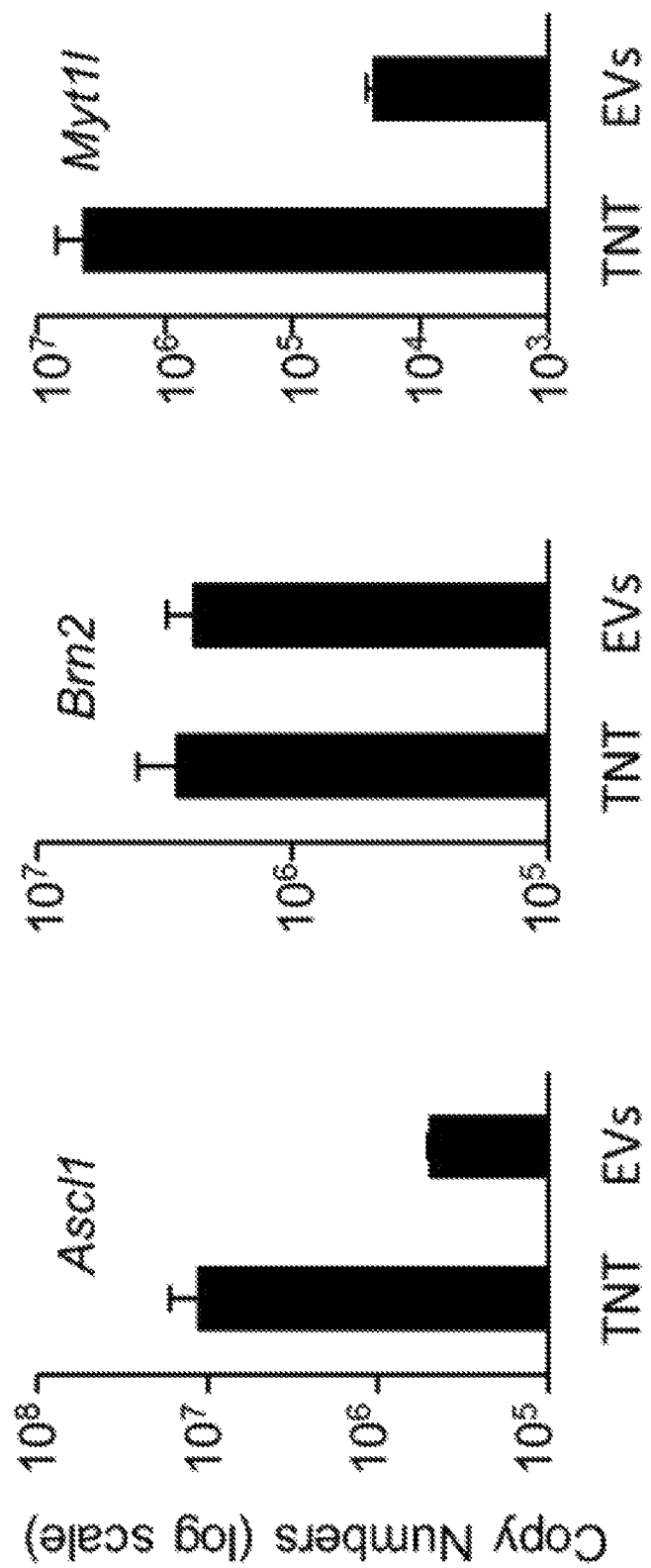
Figure 22C:
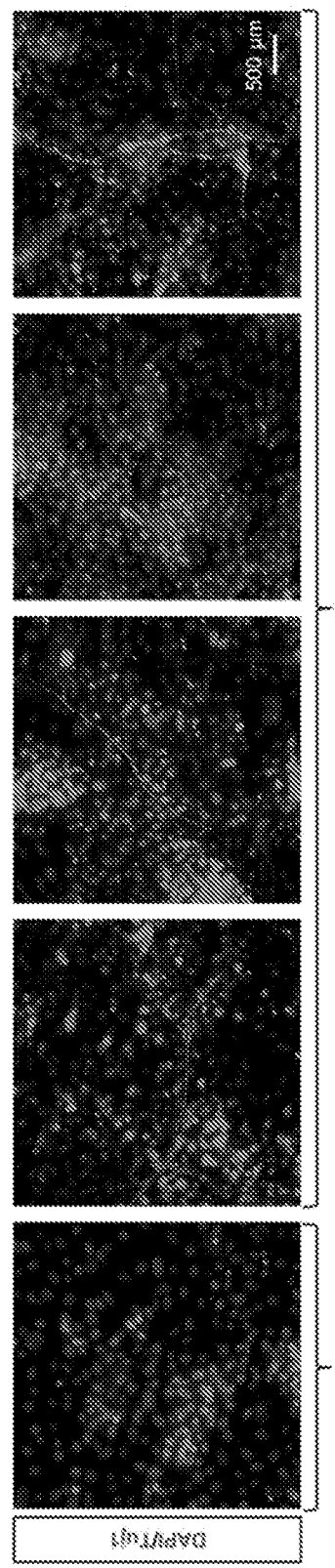

Finally, to verify whether TNT-based delivery of EFF could lead to whole limb rescue, TNT was tested in a hindlimb ischemia C57BL/6 mouse model (FIG. 19a). EFF TNT was conducted on the inner thigh skin three days after transection of the femoral artery. Laser speckle monitoring recorded a significant reduction in blood flow to the limb immediately after surgery (FIG. 19b). Compared to control ischemic limbs, EFF-treated limbs showed improved perfusion as early as day 7 post-TNT (FIG. 19b, c). HRLS imaging demonstrated an increased incidence of small collaterals in the EFF-treated limbs compared to controls (FIG. 32). Macroscopic analysis showed more pronounced signs of tissue necrosis in the control limbs compared to the EFF-treated ones (FIG. 19d). Additional experiments in Balb/c mice, which have a tendency to experience more deleterious side-effects from injury-induced limb ischemia23, 24, showed that EFF transfection also led to successful limb perfusion and minimized incidence of necrosis and auto-amputation (FIG. 33). Muscle energetics testing by nuclear magnetic resonance imaging (NMR) showed increased levels of ATP and phosphocreatine (PCr) in EFF-treated limbs compared to controls (FIG. 19e). Immunofluorescence analysis revealed marked revascularization far beyond the treatment area. Angiogenesis was also induced in more distal locations within the limb, such as the gastrocnemius muscle (FIG. 19f, 34). Although the underlying mechanisms for such response have to be further elucidated, autologous EVs, isolated from EFF-treated dorsal skin, was shown to have the potential to induce blood vessel formation when injected directly into the gastrocnemius muscle in a hindlimb ischemia mouse model (FIG. 35). Parallel in vitro experiments demonstrated that such EVs can induce reprogramming in naïve cells (FIG. 36). It was thus proposed that EVs dispatched from EFF-treated tissue serve as a mediator of propagation of pro-iECs reprogramming signals. PCR analysis revealed that in addition to the transduced EFF cDNAs/mRNAs, these EVs also appeared to be preloaded with pro-angiogenic VEGF and bFGF mRNAs (FIG. 35). This suggests that EVs derived from EFF-treated skin not only represent a viable mechanism for propagating EFF reprogramming signals throughout the target tissue, but may also play a role in niche preconditioning by spreading pro-angiogenic signals within the first hours after transfection.

TNT can therefore be used to deliver reprogramming factors into the skin in a rapid, highly effective, and non-invasive manner. Such TNT delivery leads to tailored skin tissue reprogramming, as demonstrated with well-established and newly developed reprogramming models of iNs and iECs, respectively. TNT-induced skin-derived iECs rapidly formed blood vessel networks that successfully anastomosed with the parent circulatory system and restored tissue and limb perfusion in two murine models of injury-induced ischemia. TNT-based tissue reprogramming has the potential to ultimately enable the use of a patient's own tissue as a prolific immunosurveilled bioreactor to produce autologous cells that can resolve conditions locally/on-site or distally upon harvesting. This simple to implement TNT approach, which elicits and propagates powerfully favorable biological responses through a topical onetime treatment that only lasts seconds, could also find applications beyond plasmid DNA-based reprogramming strategies, including oligo RNA (e.g., miRs, siRNAs)-mediated reprogramming (FIG. 37) (Anokye-Danso F, et al. Cell Stem Cell 2011, 8(4): 376-388), gene modulation, editing, etc.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising two or more nucleic acid sequences encoding proteins selected from the group consisting of ETS Variant 2 (ETV2), Forkhead Box C2 (Foxc2), and Friend Leukemia Integration 1 (FLI1) and a miR-200b inhibitor, wherein the miR-200b inhibitor comprises an antagomir.

2. The composition of claim 1, wherein the two or more nucleic acid sequences are operably linked to an expression control sequence.

3. The composition of claim 2, wherein each of the nucleic acid sequences are operably linked to a single expression control sequence.

4. The composition of claim 2, wherein the nucleic acid sequence is encapsulated in a liposome, microparticle or nanoparticle suitable for intracellular delivery.

* * * * *

SEQUENCE LISTING

```
<160> NUMBER OF SEQ ID NOS: 36

<210> SEQ ID NO 1
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1
uaauacugcc ugguaaugau ga                                              22

<210> SEQ ID NO 2
<211> LENGTH: 335
<212> TYPE: PRT
<213> ORGANISM: Artificial Sequence
<220> FEATURE:
<223> OTHER INFORMATION: Synthetic Construct

<400> SEQUENCE: 2

Met Asp Leu Trp Asn Trp Asp Glu Ala Ser Leu Gln Glu Val Pro Pro
1               5                   10                  15

Gly Asp Lys Leu Thr Gly Leu Gly Ala Glu Phe Gly Phe Tyr Phe Pro
                20                  25                  30

Glu Val Ala Leu Gln Glu Asp Thr Pro Ile Thr Pro Met Asn Val Glu
            35                  40                  45

Gly Cys Trp Lys Gly Phe Pro Glu Leu Asp Trp Asn Pro Ala Leu Pro
        50                  55                  60

His Glu Asp Val Pro Phe Gln Ala Glu Pro Val Ala His Pro Leu Pro
65                  70                  75                  80

Trp Ser Arg Asp Trp Thr Asp Leu Gly Cys Asn Thr Ser Asp Pro Trp
                85                  90                  95

Ser Cys Ala Ser Gln Thr Pro Gly Pro Ala Pro Pro Gly Thr Ser Pro
            100                 105                 110

Ser Pro Phe Val Gly Phe Glu Gly Ala Thr Gly Gln Asn Pro Ala Thr
        115                 120                 125

Ser Ala Gly Gly Val Pro Ser Trp Ser His Pro Pro Ala Ala Trp Ser
    130                 135                 140

Thr Thr Ser Trp Asp Cys Ser Val Gly Pro Ser Gly Ala Thr Tyr Trp
145                 150                 155                 160

Asp Asn Gly Leu Gly Gly Glu Ala His Glu Asp Tyr Lys Met Ser Trp
                165                 170                 175

Gly Gly Ser Ala Gly Ser Asp Tyr Thr Thr Thr Trp Asn Thr Gly Leu
            180                 185                 190

Gln Asp Cys Ser Ile Pro Phe Glu Gly His Gln Ser Pro Ala Phe Thr
        195                 200                 205

Thr Pro Ser Lys Ser Asn Lys Gln Ser Asp Arg Ala Thr Leu Thr Arg
```

```
                210                 215                 220
Tyr Ser Lys Thr Asn His Arg Gly Pro Ile Gln Leu Trp Gln Phe Leu
225                 230                 235                 240

Leu Glu Leu Leu His Asp Gly Ala Arg Ser Ser Cys Ile Arg Trp Thr
                245                 250                 255

Gly Asn Ser Arg Glu Phe Gln Leu Cys Asp Pro Lys Glu Val Ala Arg
            260                 265                 270

Leu Trp Gly Glu Arg Lys Arg Lys Pro Gly Met Asn Tyr Glu Lys Leu
        275                 280                 285

Ser Arg Gly Leu Arg Tyr Tyr Arg Arg Asp Ile Val Leu Lys Ser
    290                 295                 300

Gly Gly Arg Lys Tyr Thr Tyr Arg Phe Gly Gly Arg Val Pro Val Leu
305                 310                 315                 320

Ala Tyr Gln Asp Asp Met Gly His Leu Pro Gly Ala Glu Gly Gln
                325                 330                 335
```

<210> SEQ ID NO 3
<211> LENGTH: 1050
<212> TYPE: DNA
<213> ORGANISM: Artificial Sequence
<220> FEATURE:
<223> OTHER INFORMATION: Synthetic Construct

<400> SEQUENCE: 3

```
agaaccgtca gaacaagcat ccatggacct gtggaactgg gatgaggcgt cactgcagga      60
agtgcctcct gggacaagc tgacaggact gggagcggaa tttggtttct atttccctga     120
agtggctcta caagaggaca caccgatcac accaatgaac gtagaaggct gctggaaagg     180
gttcccagag ctggactgga accccgcttt acctcacgaa gacgtacctt ccaggcgga     240
gcccgttgct cacccccttc cgtggtcgcg agactggaca gacctgggat gcaacacctc     300
ggacccgtgg agctgtgctt cacagacgcc aggccctgcc cctcctggca cgagcccctc     360
cccttcgtc ggctttgaag gggcgaccgg ccagaatcct gccacctcgg caggaggggt     420
ccctcgtgg tcgcaccctc cagctgcctg gagcactacc agctgggact gttctgtggg     480
ccccagtggc gccacctact gggacaatgg cctgggcggg aagcgcatg aggactataa     540
aatgtcatgg ggcgggtctg ccggttcgga ctacaccacc acgtggaata ctgggctgca     600
ggactgcagc atccctttcg aggggcacca gagtccagca ttcaccacgc cctccaaatc     660
gaacaagcag tctgatagag ccacattgac tcgctactcc aaaactaacc accgaggtcc     720
cattcagctg tggcaattcc tcctggagct gctccacgac ggggctcgca gcagctgcat     780
ccgctggacg ggcaatagcc gcgagttcca gctgtgcgac cccaaagagg tggcccggct     840
gtggggcgag cgcaagagga gccgggaat gaattatgag aaactgagtc gaggtctacg     900
ttattattac cgccgcgaca tcgtgctcaa gagtggtggg cgcaagtaca cataccgctt     960
cggggggacgt gtgcctgtcc tcgcctatca ggatgatatg gggcatctgc caggtgcaga    1020
aggccaataa aacaaaaaac aaaaacaaaa                                      1050
```

<210> SEQ ID NO 4
<211> LENGTH: 494
<212> TYPE: PRT
<213> ORGANISM: Artificial Sequence
<220> FEATURE:
<223> OTHER INFORMATION: Synthetic Construct

<400> SEQUENCE: 4

```
Met Gln Ala Arg Tyr Ser Val Ser Asp Pro Asn Ala Leu Gly Val Val
1               5                   10                  15

Pro Tyr Leu Ser Glu Gln Asn Tyr Tyr Arg Ala Ala Gly Ser Tyr Gly
            20                  25                  30

Gly Met Ala Ser Pro Met Gly Val Tyr Ser Gly His Pro Glu Gln Tyr
        35                  40                  45

Gly Ala Gly Met Gly Arg Ser Tyr Ala Pro Tyr His His Gln Pro Ala
50                  55                  60

Ala Pro Lys Asp Leu Val Lys Pro Pro Tyr Ser Tyr Ile Ala Leu Ile
65                  70                  75                  80

Thr Met Ala Ile Gln Asn Ala Pro Glu Lys Lys Ile Thr Leu Asn Gly
                85                  90                  95

Ile Tyr Gln Phe Ile Met Asp Arg Phe Pro Phe Tyr Arg Glu Asn Lys
                100                 105                 110

Gln Gly Trp Gln Asn Ser Ile Arg His Asn Leu Ser Leu Asn Glu Cys
            115                 120                 125

Phe Val Lys Val Pro Arg Asp Asp Lys Lys Pro Gly Lys Gly Ser Tyr
        130                 135                 140

Trp Thr Leu Asp Pro Asp Ser Tyr Asn Met Phe Glu Asn Gly Ser Phe
145                 150                 155                 160

Leu Arg Arg Arg Arg Arg Phe Lys Lys Lys Asp Val Pro Lys Asp Lys
                165                 170                 175

Glu Glu Arg Ala His Leu Lys Glu Pro Pro Ser Thr Thr Ala Lys Gly
                180                 185                 190

Ala Pro Thr Gly Thr Pro Val Ala Asp Gly Pro Lys Glu Ala Glu Lys
            195                 200                 205

Lys Val Val Lys Ser Glu Ala Ala Ser Pro Ala Leu Pro Val Ile
210                 215                 220

Thr Lys Val Glu Thr Leu Ser Pro Glu Gly Ala Leu Gln Ala Ser Pro
225                 230                 235                 240

Arg Ser Ala Ser Ser Thr Pro Ala Gly Ser Pro Asp Gly Ser Leu Pro
                245                 250                 255

Glu His His Ala Ala Ala Pro Asn Gly Leu Pro Gly Phe Ser Val Glu
            260                 265                 270

Thr Ile Met Thr Leu Arg Thr Ser Pro Pro Gly Gly Asp Leu Ser Pro
            275                 280                 285

Ala Ala Ala Arg Ala Gly Leu Val Val Pro Pro Leu Ala Leu Pro Tyr
            290                 295                 300

Ala Ala Ala Pro Pro Ala Ala Tyr Thr Gln Pro Cys Ala Gln Gly Leu
305                 310                 315                 320

Glu Ala Ala Gly Ser Ala Gly Tyr Gln Cys Ser Met Arg Ala Met Ser
                325                 330                 335

Leu Tyr Thr Gly Ala Glu Arg Pro Ala His Val Cys Val Pro Pro Ala
            340                 345                 350

Leu Asp Glu Ala Leu Ser Asp His Pro Ser Gly Pro Gly Ser Pro Leu
            355                 360                 365

Gly Ala Leu Asn Leu Ala Ala Gly Gln Glu Gly Ala Leu Gly Ala Ser
            370                 375                 380

Gly His His His Gln His Gly His Leu His Pro Gln Ala Pro Pro
385                 390                 395                 400

Pro Ala Pro Gln Pro Pro Ala Pro Gln Pro Ala Thr Gln Ala Thr
                405                 410                 415

Ser Trp Tyr Leu Asn His Gly Gly Asp Leu Ser His Leu Pro Gly His
```

```
                420             425             430
Thr Phe Ala Thr Gln Gln Gln Thr Phe Pro Asn Val Arg Glu Met Phe
            435                     440                     445
Asn Ser His Arg Leu Gly Leu Asp Asn Ser Ser Leu Gly Glu Ser Gln
            450                     455                     460
Val Ser Asn Ala Ser Cys Gln Leu Pro Tyr Arg Ala Thr Pro Ser Leu
465                     470                     475                 480
Tyr Arg His Ala Ala Pro Tyr Ser Tyr Asp Cys Thr Lys Tyr
                485                     490
```

<210> SEQ ID NO 5
<211> LENGTH: 2739
<212> TYPE: DNA
<213> ORGANISM: Artificial Sequence
<220> FEATURE:
<223> OTHER INFORMATION: Synthetic Construct

<400> SEQUENCE: 5

```
gaaactttc  ccaatccta  aagggactt  tgcttctttt  tccgggctcg  gccgcgcagc    60
ctctccggac  cctagctcgc  tgacgctgcg  ggctgcagtt  ctcctggcgg  ggccccgaga   120
gccgctgtct  ccttttctag  cactcggaag  ggctggtgtc  gctccacggt  cgcgcgtggc   180
gtctgtgccg  ccagctcagg  gctgccaccc  gccaagccga  gagtgcgcgg  ccagcggggc   240
cgcctgccgt  gcaccttca  ggatgccgat  ccgcccggtc  ggctgaaccc  gagcgccggc   300
gtcttccgcg  cgtggaccgc  gaggctgccc  cgagtcgggg  ctgcctgcat  cgctccgtcc   360
cttcctgctc  tcctgctccg  ggcctcgctc  gccgcgggcc  gcagtcggtg  cgcgcaggcg   420
gcgaccgggc  gtctgggacg  cagcatgcag  gcgcgttact  cggtatcgga  ccccaacgcc   480
ctgggagtgg  taccctattt  gagtgagcaa  aactactacc  gggcggccgg  cagctacggc   540
ggcatggcca  gccccatggg  cgtctactcc  ggccacccgg  agcagtacgg  cgccggcatg   600
ggccgctcct  acgcgcccta  ccaccaccag  cccgcggcgc  caaggacct  ggtgaagccg   660
ccctacagct  atatagcgct  catcaccatg  gcgatccaga  acgcgccaga  gaagaagatc   720
actctgaacg  gcatctacca  gttcatcatg  accgtttcc  ccttctaccg  cgagaacaag   780
cagggctggc  agaacagcat  ccgccacaac  ctgtcactca  atgagtgctt  cgtgaaagtg   840
ccgcgcgacg  acaagaagcc  gggcaagggc  agctactgga  cgctcgaccc  ggactcctac   900
aacatgttcg  agaatggcag  cttcctgcgg  cggcggcggc  gcttcaagaa  gaaggatgtg   960
cccaaggaca  aggaggagcg  ggcccacctc  aaggagccgc  cctcgaccac  ggccaagggc  1020
gctccgacag  ggaccccggt  agctgacggg  cccaaggagg  ccgagaagaa  agtcgtggtt  1080
aagagcgagg  cggcgtcccc  cgcgctgccg  gtcatcacca  aggtggagac  gctgagcccc  1140
gagggagcgc  tgcaggccag  tccgcgcagc  gcatcctcca  cgcccgcagg  ttccccagac  1200
ggctcgctgc  cggagcacca  cgccgcggcg  cctaacgggc  tgcccggctt  cagcgtggag  1260
accatcatga  cgctgcgcac  gtcgcctccg  ggcggcgatc  tgagcccagc  ggccgcgcgc  1320
gccggcctgg  tggtgccacc  gctggcactg  ccatacgccg  cagcgccacc  cgccgcttac  1380
acgcagccgt  gcgcgcaggg  cctggaggct  gcgggctccg  cgggctacca  gtgcagtatg  1440
cgggctatga  gtctgtacac  cggggccgag  cggcccgcgc  acgtgtgcgt  tccgcccgcg  1500
ctggacgagg  ctctgtcgga  ccacccgagc  ggccccggct  cccgctcgg  cgccctcaac  1560
ctcgcagcgg  gtcaggaggg  cgcgttgggg  gcctcgggtc  accaccacca  gcatcacggc  1620
cacctccacc  cgcaggcgcc  accgcccgcc  ccgcagcccc  ctcccgcgcc  gcagcccgcc  1680
```

```
acccaggcca cctcctggta tctgaaccac ggcggggacc tgagccacct ccccggccac   1740
acgtttgcaa cccaacagca aactttcccc aacgtccggg agatgttcaa ctcgcaccgg   1800
ctaggactgg acaactcgtc cctcggggag tcccaggtga gcaatgcgag ctgtcagctg   1860
ccctatcgag ctacgccgtc cctctaccgc cacgcagccc cctactctta cgactgcacc   1920
aaatactgag gctgtccagt ccgctccagc cccaggaccg caccggcttc gcctcctcca   1980
tgggaacctt cttcgacgga gccgcagaaa gcgacggaaa gcgcccctct ctcagaacca   2040
ggagcagaga gctccgtgca actcgcaggt aacttatccg cagctcagtt tgagatctca   2100
gcgagtccct ctaaggggga tgcagcccag caaaacgaaa tacagatttt ttttttaatt   2160 ccttcccccta cccagatgct gcgcctgctc cccttgggc ttcatagatt agcttatgga   2220 ccaaaccccca tagggacccc taatgacttc tgtggagatt ctccacgggc gcaagaggtc   2280
tctccggata aggtgccttc tgtaaacgag tgcggatttg taaccaggct attttgttct   2340
tgcccagagc ctttaatata atatttaaag ttgtgtccac tggataaggt ttcgtcttgc   2400
ccaactgtta ctgccaaatt gaattcaaga aacgtgtgtg ggtcttttct ccccacgtca   2460
ccatgataaa ataggtccct ccccaaactg taggtctttt acaaaacaag aaaataattt   2520
atttttttgt tgttgttgga taacgaaatt aagtatcgga tacttttaat ttaggaagtg   2580
catggctttg tacagtagat gccatctggg gtattccaaa aacacaccaa aagactttaa   2640
aatttcaatc tcacctgtgt ttgtcttatg tgatctcagt gttgtattta ccttaaaata   2700
aacccgtgtt gttttctgc ccaaaaaaaa aaaaaaaa                            2739
```

```
<210> SEQ ID NO 6
<211> LENGTH: 452
<212> TYPE: PRT
<213> ORGANISM: Artificial Sequence
<220> FEATURE:
<223> OTHER INFORMATION: Synthetic Construct

<400> SEQUENCE: 6

Met Asp Gly Thr Ile Lys Glu Ala Leu Ser Val Val Ser Asp Asp Gln
1               5                   10                  15

Ser Leu Phe Asp Ser Ala Tyr Gly Ala Ala His Leu Pro Lys Ala
                20                  25                  30

Asp Met Thr Ala Ser Gly Ser Pro Asp Tyr Gly Gln Pro His Lys Ile
            35                  40                  45

Asn Pro Leu Pro Pro Gln Gln Glu Trp Ile Asn Gln Pro Val Arg Val
        50                  55                  60

Asn Val Lys Arg Glu Tyr Asp His Met Asn Gly Ser Arg Glu Ser Pro
65                  70                  75                  80

Val Asp Cys Ser Val Ser Lys Cys Asn Lys Leu Val Gly Gly Gly Glu
                85                  90                  95

Ala Asn Pro Met Asn Tyr Asn Ser Tyr Met Asp Glu Lys Asn Gly Pro
            100                 105                 110

Pro Pro Pro Asn Met Thr Thr Asn Glu Arg Arg Val Ile Val Pro Ala
        115                 120                 125

Asp Pro Thr Leu Trp Thr Gln Glu His Val Arg Gln Trp Leu Glu Trp
    130                 135                 140

Ala Ile Lys Glu Tyr Gly Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175
```

Arg Ala Thr Ser Ala Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
        195                 200                 205

Asp Gln Ser Ser Arg Leu Asn Val Lys Glu Asp Pro Ser Tyr Asp Ser
    210                 215                 220

Val Arg Arg Gly Ala Trp Asn Asn Met Asn Ser Gly Leu Asn Lys
225                 230                 235                 240

Ser Pro Leu Leu Gly Gly Ser Gln Thr Met Gly Lys Asn Thr Glu Gln
                245                 250                 255

Arg Pro Gln Pro Asp Pro Tyr Gln Ile Leu Gly Pro Thr Ser Ser Arg
                260                 265                 270

Leu Ala Asn Pro Gly Ser Gly Gln Ile Gln Leu Trp Gln Phe Leu Leu
            275                 280                 285

Glu Leu Leu Ser Asp Ser Ala Asn Ala Ser Cys Ile Thr Trp Glu Gly
        290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
        355                 360                 365

Leu Gln Pro His Pro Thr Glu Thr Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Ser His Pro Ser Ser Met Pro Val Thr Ser Ser Ser Phe Phe
                405                 410                 415

Gly Ala Ala Ser Gln Tyr Trp Thr Ser Pro Thr Ala Gly Ile Tyr Pro
            420                 425                 430

Asn Pro Ser Val Pro Arg His Pro Asn Thr His Val Pro Ser His Leu
        435                 440                 445

Gly Ser Tyr Tyr
    450

<210> SEQ ID NO 7
<211> LENGTH: 3184
<212> TYPE: DNA
<213> ORGANISM: Artificial Sequence
<220> FEATURE:
<223> OTHER INFORMATION: Synthetic Construct

<400> SEQUENCE: 7
aaagtgaagt cacttcccaa aattagctga aaaaaagttt catccggtta actgtctctt       60
tttcgatccg ctacaacaac aaacgtgcac aggggagcga gggcagggcg ctcgcagggg      120
gcactcagag agggcccagg gcgccaaaga ggccgcgccg ggctaatctg aagggggctac    180 gaggtcaggc tgtaaccggg tcaatgtgtg gaatattggg gggctcggct gcagacttgg     240
ccaaatggac gggactatta aggaggctct gtctgtggtg agtgacgatc agtccctttt     300
tgattcagca tacggagcgg cagcccatct ccccaaggca gatatgactg cttcggggag     360
tcctgactac gggcagcccc acaaaatcaa ccccctgcca ccgcagcagg agtggatcaa     420

-continued

```
ccagccagtg agagtcaatg tcaagcggga gtatgaccac atgaatggat ccagggagtc    480
tccggtggac tgcagtgtca gcaaatgtaa caagctggtg ggcggaggcg aagccaaccc    540
catgaactat aatagctaca tggatgagaa gaacggcccc cctcctccca acatgaccac    600
caacgaacgg agagtcattg tgcctgcaga ccccacactg tggacacagg agcacgttcg    660
acagtggctg gagtgggcta taaaggaata cggattgatg gagattgaca cttccttctt    720
ccagaacatg gatggcaagg aattgtgtaa aatgaacaag gaggacttcc tccgagccac    780
ctccgcctac aacacagaag tgctgttgtc gcacctcagt tacctcaggg aaagttcact    840
gctggcctat aacacaacct cccatacaga ccagtcctca cgactgaatg tcaaggaaga    900
cccttcttat gactctgtca ggagaggagc atggaacaat aatatgaact ctggcctcaa    960
caaaagtcct ctccttggag gatcacagac catgggcaag aacactgagc agcggcccca   1020
gccagatcct tatcagatcc tggggccaac cagcagccgc ctagcaaacc ctgggagtgg   1080
gcagatccag ctgtggcagt ttctcctgga actactgtcc gacagcgcca acgccagctg   1140
tatcacctgg gaggggacca acgggagtt caaaatgacg gaccctgatg aggtggccag   1200
gcgctgggga gagcggaaga gcaagcccaa catgaattat gacaagctga gccgggccct   1260
ccgatactac tatgacaaaa acattatgac caaagtgcat ggcaaaaggt atgcctacaa   1320
gtttgacttc catggcattg cccaggccct gcagccacat ccaacagaga catccatgta   1380
caagtatccc tctgatatct cctacatgcc ttcctaccat gcccatcaac agaaggtgaa   1440
ctttgtcccg tctcacccat cctccatgcc tgtcacctcc tccagcttct ttggagcagc   1500
atcacaatac tggacctccc ccactgctgg gatctatcca acccagtg tcccccgcca   1560 tcctaacacc cacgtgcctt cacacttagg cagctactac tagaactaac accagttggc   1620
cttctggctg aagttccagc tctcactta ctggatactc tggactctaa aaggcacagt   1680
agccttgaag agataagaaa actggatgtt ctttctttg gatagaacct ttgtatttgt   1740
tcttctaaaa aaattattat ttttatgtta aaaactttg tttcctctac ctgaaaaaa   1800 aaaaagatca ttccatgagc cagtccacca gtttggattc tcaacctcct atcatcgaat   1860
gagttaaata tttaggttac tggaacggtt tataccatga ttctgagaaa ggagtacgca   1920
ttttctttac tcttttttt tatgaccaaa gcagtttctt atcagcacac gggtctcatc   1980
attgtaggat tccctacgat catgaatcat ggacttgacc agggttggtc tggtttgaga   2040
cttagtaaaa gtcaaggcag gatgtttata atcttatctt cggaggactc aattcagtgg   2100
atggcaactg gaacactggc tctgaggcca gtgaagttt ttgcccaact ggaatttaaa   2160
agatgtgtgt ctatgtgtgt atttaagaag ccattattat tacaaaattc ctcacaatgg   2220
gcagtatgtg tttgggtgac tcttctcccc agaaatagtc agaatatgaa caaagaaagt   2280
ttaacacaaa ctcagacact cctgacgggc agaggattaa ataacatttt tttggagggt   2340
ttaataacat ttttggaggg gttttttgt ttgttttgt ttttggggt ttttttgtt   2400 tgttttttgt ttttggttt ttggtttttt tttgtttttt tttttttttt ggttttgatt   2460
tttaatgaca gtgagtccca gaactttgaa aagtcatggg gatttctaaa ctcagattcg   2520
caaacgctgt gcgtttgtca gaccaccaga ccaaggtcaa acaatcagaa ggcaactaac   2580
tgtataaatt atgcagagtt attttcctat atctcacagt attaaaaaaa taataatta   2640 aaaattaaag aataagtaaa cgagttgacc tcggtcacaa atgcagtttt actatcaaat   2700
caatcattgt tatttttta aaatataatt tgtacatctt tgtcaatctg tacatttggg   2760
ctatttgtac gttttttgtaa ctgttttttt ttaataagca taatgtgact attgaaaacg   2820
```

```
aggagttaaa agtcactgag tttttaggaa gaaaaaccta aaaatacagt tatttaacac    2880
gcatgcccaa acaagatctg tttagaccta caacgcttta gaaatgtttg taaataacag    2940
agttgcaata acctgaaaag gacaaacaaa cttttctctg tgcacacgag gcactctcct    3000
gctctatata tgcaatatat ttttagatgt gcaaatatat atataatttt tcaggtaatc    3060
gtgacttttt aaacgatatt gttaaggtga caactcttag tccactgaag actaagttgt    3120
aaaataattt gaccttaata aattgtgcct tcttctttt cttcttctct cagaaaaaaa     3180
aaaa                                                                 3184
```

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
ctctgctgcc tcctggcttc t                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
cgaggcggat cacaagcaat a                                              21

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
tcaatgggcg ggggtcgtt                                                 19

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

<400> SEQUENCE: 11
gcggtctggc agtaaaaact atc                                            23

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
gtgaaacagc attgctgtca ctt                                            23

<210> SEQ ID NO 13
<211> LENGTH: 19
<212> TYPE: DNA

```
<213> ORGANISM: Artificial Sequence
<220> FEATURE:
<223> OTHER INFORMATION: Synthetic Construct

<400> SEQUENCE: 13
cgacgaggga tcctacgac                                                  19

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
cttcctctgc cctcgaac                                                   18

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
ggtggagttc aagtccatct ac                                              22

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tggcgtccac gtagtagtag                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
cgcgagttcc agctgtgcga                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
ggcgaggaca ggcacacgtc                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
gggctgggct gcagacttgg                                                 20
```

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
ggggctgccc gtagtcagga                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
tacgcgccct accaccacca                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
gccctgcttg ttctcgcggt                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
ggaccagtcc ccgaagcagc                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
agtggagcag ctggcctgga                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
agcgctgtga acgcttgcct                                          20

<210> SEQ ID NO 26
<211> LENGTH: 20
<212> TYPE: DNA
<213> ORGANISM: Artificial Sequence
<220> FEATURE:

<223> OTHER INFORMATION: Synthetic Construct

<400> SEQUENCE: 26
catgagaggc cctcccggct                                                    20

<210> SEQ ID NO 27
<211> LENGTH: 17
<212> TYPE: DNA
<213> ORGANISM: Artificial Sequence
<220> FEATURE:
<223> OTHER INFORMATION: Synthetic Construct

<400> SEQUENCE: 27
ccgtccagct cgaccag                                                       17

<210> SEQ ID NO 28
<211> LENGTH: 18
<212> TYPE: DNA
<213> ORGANISM: Artificial Sequence
<220> FEATURE:
<223> OTHER INFORMATION: Synthetic Construct

<400> SEQUENCE: 28
gatcacatgg tcctgctg                                                      18

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
gtgcaacgag cagggcgagt                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
ggagccaccg cgcacagaat                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
gctggtgcag agcggcaaga                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
agacggcggt aggtggcgat                                                    20

```
<210> SEQ ID NO 33
<211> LENGTH: 24
<212> TYPE: DNA
<213> ORGANISM: Artificial Sequence
<220> FEATURE:
<223> OTHER INFORMATION: Synthetic Construct

<400> SEQUENCE: 33
gtgtgatggg attccctgga ccta                                              24

<210> SEQ ID NO 34
<211> LENGTH: 24
<212> TYPE: DNA
<213> ORGANISM: Artificial Sequence
<220> FEATURE:
<223> OTHER INFORMATION: Synthetic Construct

<400> SEQUENCE: 34
cctgagctcc agcttctcca tctt                                              24

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
gtgcagtgcc agcctcgtcc                                                   20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
gcaccggcct caccccattt                                                   20
```